United States Patent
Goodacre et al.

(10) Patent No.: US 8,486,950 B2
(45) Date of Patent: Jul. 16, 2013

(54) JANUS KINASE INHIBITOR COMPOUNDS AND METHODS

(75) Inventors: Simon Charles Goodacre, Flex Meadow (GB); Yingjie Lai, Cupertino, CA (US); Jun Liang, Palo Alto, CA (US); Steven R. Magnuson, Dublin, CA (US); Kirk D. Robarge, San Francisco, CA (US); Mark S. Stanley, Pacifica, CA (US); Vickie Hsiao-Wei Tsui, Burlingame, CA (US); Karen Williams, Flex Meadow (GB); Birong Zhang, Union City, CA (US); Aihe Zhou, San Jose, CA (US)

(73) Assignee: F. Hoffmann-La Roche AG, Basel (CH)

( * ) Notice: Subject to any disclaimer, the term of this patent is extended or adjusted under 35 U.S.C. 154(b) by 147 days.

(21) Appl. No.: 12/813,142

(22) Filed: Jun. 10, 2010

(65) Prior Publication Data
US 2010/0317643 A1 Dec. 16, 2010

Related U.S. Application Data

(60) Provisional application No. 61/186,322, filed on Jun. 11, 2009.

(51) Int. Cl.
*C07D 401/12* (2006.01)
*C07D 213/75* (2006.01)
*A61K 31/4439* (2006.01)

(52) U.S. Cl.
USPC ........... 514/256; 514/352; 514/353; 544/328; 546/308; 546/309

(58) Field of Classification Search
USPC .................. 544/328; 546/308, 309; 514/256, 514/352, 353
See application file for complete search history.

(56) References Cited

U.S. PATENT DOCUMENTS

| | | | |
|---|---|---|---|
| 3,317,534 A | 5/1967 | Nitta et al. | |
| 5,958,944 A | 9/1999 | Arita et al. | |
| 7,456,175 B2 | 11/2008 | Nettekoven et al. | |
| 7,612,076 B2 | 11/2009 | Nettekoven et al. | |
| 2002/0183371 A1 | 12/2002 | Gordeev et al. | |
| 2003/0134859 A1* | 7/2003 | Amemiya et al. | 514/247 |
| 2004/0102324 A1 | 5/2004 | Annis et al. | |
| 2005/0197364 A1 | 9/2005 | Kelly et al. | |
| 2009/0163516 A1 | 6/2009 | Dunkel et al. | |
| 2009/0163545 A1 | 6/2009 | Goldfarb | |
| 2009/0298830 A1 | 12/2009 | Mann et al. | |
| 2011/0009447 A1 | 1/2011 | Huth et al. | |

FOREIGN PATENT DOCUMENTS

| | | |
|---|---|---|
| DE | 102005060449 | 6/2007 |
| EP | 0757038 A1 | 2/1997 |
| EP | 1195372 A1 | 4/2002 |
| EP | 1314712 A1 | 5/2003 |
| GB | 2406856 | 4/2005 |
| JP | 62158252 A * | 7/1987 |
| JP | 11001456 A * | 1/1999 |
| JP | 2003-73357 A * | 3/2003 |
| WO | 96/15111 | 5/1996 |
| WO | 01/81311 A1 | 11/2001 |
| WO | 2005/082367 A1 | 9/2005 |
| WO | 2006/007378 | 1/2006 |
| WO | 2006/040645 A1 | 4/2006 |
| WO | 2006/067446 A1 | 6/2006 |
| WO | 2006/101977 A2 | 9/2006 |
| WO | 2007/089768 A2 | 8/2007 |
| WO | 2008/017696 A1 | 2/2008 |
| WO | 2008/055068 A2 | 5/2008 |
| WO | 2009/012283 A1 | 1/2009 |
| WO | 2009/051822 A1 | 4/2009 |
| WO | 2009/087238 A9 | 7/2009 |

OTHER PUBLICATIONS

Levine et al., Myeloproliferative Disorders, Blood, vol. 112, No. 6, pp. 2190-2198 (2008).*
Borie et al., JAK3 inhibition, a viable new modality of immunosuppression for solid organ translpants, Trends in Molecular Medicine, vol. 10, No. 11, pp. 532-541, 2004.*
Versotovsek, Therapeutic potential of JAK2 inhibitors, Hematology, American Society of Hematology Education Program Book, pp. 636-642, 2009.*
Robinson, Medical Therapy of Inflammatory Bowel Disease for the 21st century, Eur. J. Surg. 164, Suppl. 582, pp. 90-98, (1998).*

(Continued)

*Primary Examiner* — Deepak Rao
(74) *Attorney, Agent, or Firm* — Tamara Kale; Genentech, Inc.

(57) ABSTRACT

The invention provides compounds of Formula I, stereoisomers or pharmaceutically acceptable salts thereof, wherein A, B, D, $R^1$, $R^2$, $R^4$ and $R^5$ are defined herein, a pharmaceutical composition that includes a compound of Formula I and methods of use thereof.

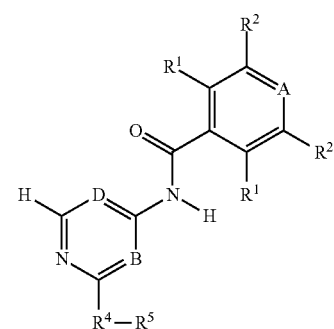

19 Claims, No Drawings

OTHER PUBLICATIONS

Harkiolaki et al., T Cell-Mediated Autoimmune Disease Due to Low-Affinity Crossreactivity to Common Microbial Peptides, Immunity 30, pp. 348-357, 2009.*

Getts et al., Current landscape for T-cell targeting in autoimmunity and transplantation, Immunotherapy, 3(7), pp. 853-870, 2011.*

Aliagas-Martin et al., "A class of 2,4-bisanilinopyrimidine Aurora A inhibitors with unusually high selectivity against Aurora B" *J Med Chem.* 52:3300-7 (May 2009).

Baslund et al., "Targeting interleukin-15 in patients with rheumatoid arthritis: a proof-of-concept study" *Arthritis Rheum.* 52(9):2686-92 (Sep. 2005).

Changelian et al., "Prevention of organ allograft rejection by a specific Janus kinase 3 inhibitor" *Science* 302:875-8 (Oct. 2003).

Clemence Francois et al., "New benzamide derivatives, their salts, process of preparation, application as medicaments and compositions containing them" Abstract of FR 2607812 (A1) (Jun. 10, 1988).

Eliel and Wilen, "7-3. Chemical Separation of Enantiomers Via Diastereomers" *Stereochemistry of Organic Compounds,* New York:John Wiley & Sons, Inc. pp. 322-381 (1994).

Firmbach-Kraft et al., "tyk2, prototype of a novel class of non-receptor tyrosine kinase genes" *Oncogene* 5:1329-36 (1990).

From the International Searching Authority, "PCT/EP2010/058128",(2010).

Grozinger et al., "Synthesis of five nevirapine metabolites" *Journal of Heterocyclic Chemistry* 37(2):229-39 (2000).

Guo et al., "Genistein modulates splenic natural killer cell activity, antibody-forming cell response, and phenotypic marker expression in F(0) and F(1) generations of Sprague-Dawley rats" *Toxicol Appl Pharmacol.* 181(3):219-27 (Jun. 2002).

Holsapple, "6 The Plaque-Forming Cell (PFC) Response in Immunotoxicology: An Approach to Monitoring the Primary Effector Function of B Lymphocytes" *Modern Methods in Immunotoxicology,* Burleson, Dean and Munson, New York, NY:Wiley-Liss Publishers vol. 1:71-108 (1995).

House, "Theory and practice of cytokine assessment in immunotoxicology" *Methods* 19(1):17-27 (Sep. 1999).

Hubbard, "Effects of xenobiotics on macrophage function: evaluation in vitro" *Methods* 19(1):8-16 (Sep. 1999).

Jacob, "Resolution of (+/−)-5-Bromonornicitine. Synthesis of (R)- and (S)-Nornicotine of High Enantiomeric Purity" *J. Org. Chem.* 47:4165-67 (1982).

Kisseleva et al., "Signaling through the JAK/STAT pathway, recent advances and future challenges" *Gene* 285:1-24 (2002).

Krueger et al., "A human interleukin-12/23 monoclonal antibody for the treatment of psoriasis" *N Engl J Med.* 356(6):580-92 (Feb. 2007).

Lebrec et al., "Th(1)/Th(2) responses to drugs" *Toxicology* 158:25-9 (Feb. 2001).

Levy et al., "Stats: transcriptional control and biological impact" *Nat Rev Mol Cell Biol.* 3:651-62 (Sep. 2002).

Lochmuller and Souter, "Chromatographic resolution of enantiomers selective review" *J Chromatogr.* 113(3):283-302 (Oct. 1975).

Mannon et al., "Anti-interleukin-12 antibody for active Crohn's disease" *N Engl J Med.* 351(20):2069-79 (Nov. 2004).

Miller et al., "Developmental exposure to lead causes persistent immunotoxicity in Fischer 344 rats" *Toxicol Sci.* 42(2):129-35 (Apr. 1998).

Minegishi et al., "Human tyrosine kinase 2 deficiency reveals its requisite roles in multiple cytokine signals involved in innate and acquired immunity" *Immunity* 25:745-55 (Nov. 2006).

Mirek and Dydula, "Thin-layer chromatography of anilides of pyridinecarboxylic acids and benzamidopyridines" *Journal of Chromatography* 171(462-5) (Apr. 1979).

Moffett et al., "Antiulcer agents. p-Aminobenzamido aromatic compound" *J. Med. Chem.* 14(10):963ι8 (1971).

Morrison, "Kinetics of the reversible inhibition of enzyme-catalysed reactions by tight-binding inhibitors" *Biochimica Et Biophysica Acta* 185:269-286 (1969).

O'Shea et al., "Cytokine Signaling in 2002: New Surprises in the Jak/Stat Pathway" *Cell* 109:S121-S131(Apr. 2002).

Okamoto, "Optical resolution of dihydropyridine enantiomers by high-performance liquid chromatography using phenylcarbamates of polysaccharides as a chiral stationary phase" *J. of Chromatogr.* 513:375-378 (1990).

Park et al., "Photoreaction of 2-halo-N-pyridinylbenzamide: intramolecular cyclization mechanism of phenyl radical assisted with n-complexation of chlorine radical" *J Org Chem.* 66(7):2197-206 (Apr. 2001).

Rastetter et al., "Rituximab: expanding role in therapy for lymphomas and autoimmune diseases" *Annual Review of Medicine* 55:477-503 (2004).

Reich et al., "Ustekinumab" *Nat Rev Drug Discov.* 8(5):355-6 (May 2009).

Sakakibara Kazumasa et al., "4-Aminopyridinebenzamide Derivative" Abstract of JP 62158252 A (Jul. 14, 1987).

Saltzman et al., "Cloning and characterization of human Jak-2 kinase: high mRNA expression in immune cells and muscle tissue" *Biochem Biophys Res Commun.* 246:627-33 (May 1998).

Scheinecker et al., "Tocilizumab" *Nat Rev Drug Discov.* 8(4):273-4 (Apr. 2009).

Schindler et al., "JAK-STAT signaling: from interferons to cytokines" *J Biol Chem.* 282(28):20059-63 (Jul. 2007).

Smialowicz et al., "The effects of perinatal/juvenile heptachlor exposure on adult immune and reproductive system function in rats" *Toxicol Sci.* 61(1):164-75 (May 2001).

Stella and Himmelstein, "Prodrugs: A Chemical Approach to Targeted Drug Delivery" *Directed Drug Delivery,* Borchardt et al., Humana Press pp. 247-267 (1985) .

Thompson, "JAK protein kinase inhibitors" *Drug News Perspect* 18(5):305-10 (Jun. 2005).

Uehata Masayoshi et al., "Rho Kinase Inhibitor Comprising Amide Compound" Abstract of JP 2003073357 (A) (Mar. 12, 2003).

Watford and O'Shea, "Human tyk2 kinase deficiency: another primary immunodeficiency syndrome" *Immunity* 25:695-7 (Nov. 2006).

Wilks, "Two putative protein-tyrosine kinases identified by application of the polymerase chain reaction" *Proc. Natl. Acad. Sci. USA* 86:1603-1607 (1989).

Wilman, D.E., "Prodrugs in Cancer Chemotherapy" *Biochemical Society Transactions* (615th Meeting, Belfast) 14:375-382 (1986).

Asano et al., "Synthesis and Biological Evaluation of Benzamides and Benzamidines: Structal Requirement of a Pyrimidine Ring for Inhibition of EGFR Tyrosine Kinase" *Bioorganic & Medicinal Chemistry Letters,* vol. 14, No. 9, pp. 2299-2302 (2004).

Fink et al., "Preparation of 3-(4-Pyridinylamino)-1,2-Benzisoxazoles via a Nucleophilic Armatic Substitution Reaction" *Tetrahedron Letters,* vol. 37, No. 7, pp. 995-998 (1996).

White et al., "Substituted Benzanilides: Structural Variation and Inhibition of Complex II Activity in Mitochondria from a Wild-Type Strain and a Carboxin-Selected Mutant Strain of *Ustilago maydis*" Pesticide Biochemistry and Physiology, vol. 27, No. 3, pp. 249-260 (1987).

* cited by examiner

JANUS KINASE INHIBITOR COMPOUNDS AND METHODS

CROSS-REFERENCE TO RELATED APPLICATIONS

This application claims the benefit under 35 U.S.C. §119(e) of U.S. Provisional Application Ser. No. 61/186,322, filed Jun. 11, 2009, which is incorporated herein by reference in its entirety for all purposes.

FIELD OF THE INVENTION

Compounds of Formula I, which are inhibitors of TYK2 kinase, as well as compositions containing these compounds, and methods of use including, but not limited to, in vitro, in situ and in vivo diagnosis or treatment of mammalian cells.

BACKGROUND OF INVENTION

Cytokine pathways mediate a broad range of biological functions, including many aspects of inflammation and immunity Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFNgamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). JAK1 knockout mice die perinatally due to defects in LIF receptor signaling (Kisseleva et al., 2002, gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

Biochemical and genetic studies have shown an association between JAK2 and single-chain (e.g., EPO), IL-3 and interferon gamma cytokine receptor families (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders (MPDS) in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and Il-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

SUMMARY OF INVENTION

One embodiment includes a compound of Formula I:

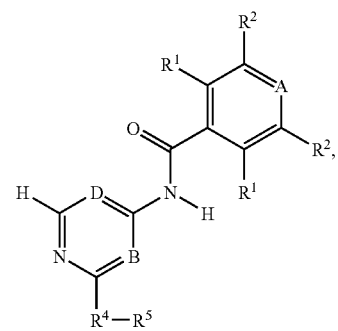

stereoisomers or pharmaceutically acceptable salts thereof, wherein A, B, D, $R^1$, $R^2$, $R^4$ and $R^5$ are defined herein.

Another embodiment includes a pharmaceutical composition that includes a compound of Formula I and a pharmaceutically acceptable carrier, adjuvant or vehicle.

Another embodiment includes a method of treating or lessening the severity of a disease or condition responsive to the inhibition of a Janus kinase activity in a patient. The method includes administering to the patient a therapeutically effective amount of a compound of Formula I.

Another embodiment includes a method of treating or lessening the severity of a disease or condition responsive to the inhibition of TYK2 kinase activity in a patient. The method includes administering to the patient a therapeutically effective amount of a compound of Formula I.

Another embodiment includes a method of treating an immunological disease in a patient. The method includes administering to the patient a therapeutically effective amount of a compound of Formula I.

Another embodiment includes a compound of Formula I for use in therapy.

Another embodiment includes a compound of Formula I for use in treating immunological diseases.

Another embodiment includes a compound of Formula I for use in treating inflammatory diseases.

Another embodiment includes a compound of Formula I for use in treating psoriasis or inflammatory bowel disease.

Another embodiment includes use of a compound of Formula I in the manufacture of a medicament for the treatment of immunological diseases.

Another embodiment includes use of a compound of Formula I in the manufacture of a medicament for the treatment of psoriasis or inflammatory bowel disease.

Another embodiment includes a method of manufacturing a compound of Formula I, comprising reacting a compound having formula iii:

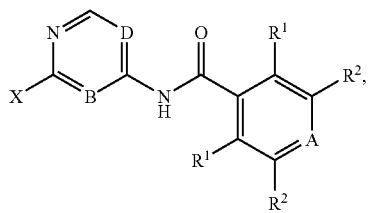

wherein X is halogen or leaving group; with a compound of the formula Y—$R^4$-$R^5$, wherein Y is H or is absent, under conditions sufficient to form a compound of Formula I.

Another embodiment includes a kit for treating a disease or disorder responsive to the inhibition of a Janus kinase. The kit includes a first pharmaceutical composition comprising a compound of Formula I and instructions for use.

Another embodiment includes a kit for treating a disease or disorder responsive to the inhibition of TYK2 kinase. The kit includes a first pharmaceutical composition comprising a compound of Formula I and instructions for use.

DETAILED DESCRIPTION OF THE INVENTION

Reference will now be made in detail to certain embodiments, examples of which are illustrated in the accompanying structures and formulas. While the invention will be described in conjunction with the enumerated embodiments, the invention is intended to cover all alternatives, modifications, and equivalents, which may be included within the scope of the present invention as defined by the claims. One skilled in the art will recognize methods and materials similar or equivalent to those described herein, which could be used in the practice of the present invention.

Definitions

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The term $C_0$ refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl and 1-octyl.

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_4$, $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_9$. In another example, the aryl group is a $C_6$ aryl group. Aryl includes bicyclic groups comprising an aromatic ring with a fused non-aromatic or partially saturated ring. Example aryl groups include, but are not limited to, phenyl, naphthalenyl, anthracenyl, indenyl, indanyl, 1,2-dihydronapthalenyl and 1,2,3,4-tetrahydronapthyl. In one example, aryl includes phenyl. In one embodiment, optional substituents on aryl are selected from halogen (F, Cl, Br, I), hydroxy, cyano, nitro, alkyl (for example $C_1$-$C_6$ alkyl), —O($C_1$-$C_6$ alkyl), benzyloxy, carboxy, carboxymethyl, hydroxymethyl, aminomethyl, trifluoromethyl, alkylsulfonylamino, alkylsulfonylaminoalkyl, arylsulfonylamino, arylsulfonylaminoalkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2-chloro-6-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl, 2,6-dichloro-4-cyanophenyl, 2-chloro-4-cyano-6-fluorophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups include the 2-chlorophenyl, 2,6-dichlorophenyl, 2-chloro-6-fluorophenyl, 2,6-dichloro-4-cyanophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Halo" or "halogen" refers to F, Cl, Br or I.

The terms "heterocycle," "heterocyclyl" and "heterocyclic ring" are used interchangeably herein and refer to: (i) a saturated or partially unsaturated cyclic group (i.e., having one or more double and/or triple bonds within the ring) ("heterocycloalkyl"), or (ii) an aromatic cyclic group ("heteroaryl"), and in each case, which at least one ring atom is a heteroatom independently selected from nitrogen, oxygen, phosphorus and sulfur, the remaining ring atoms being carbon.

The heterocyclyl group may be optionally substituted with one or more substituents described below. In one embodiment, heterocyclyl includes monocycles or bicycles having 1 to 9 carbon ring members ($C_1$-$C_9$) with the remaining ring atoms being heteroatoms selected from N, O, S and P. In other examples, heterocyclyl includes monocycles or bicycles having $C_1$-$C_5$, $C_3$-$C_5$ or $C_4$-$C_5$, with the remaining ring atoms being heteroatoms selected from N, O, S and P. In another embodiment, heterocyclyl includes 3-7-membered rings or 3-6 membered rings, containing one or more heteroatoms independently selected from N, O, S and P. In other examples, heterocyclyl includes monocyclic 3-, 4-, 5-, 6- or 7-membered rings, containing one or more heteroatoms independently selected from N, O, S and P. In another embodiment, heterocyclyl includes bi- or polycyclic or bridged 4-, 5-, 6-, 7-, 8- and 9-membered ring systems, containing one or more heteroatoms independently selected from N, O, S and P. Examples of bicycle systems include, but are not limited to, [3,5], [4,5], [5,5], [3,6], [4,6], [5,6], or [6,6] systems. Examples of bridged ring systems include, but are not limited to [2.2.1], [2.2.2], [3.2.2] and [4.1.0] arrangements, and having 1 to 3 heteroatoms selected from N, O, S and P. In another embodiment, heterocyclyl includes spino groups having 1 to 4 heteroatoms selected from N, O, S and P. The heterocyclyl group may be a carbon-linked group or heteroatom-linked group. "Heterocyclyl" includes a heterocyclyl group fused to a cycloalkyl group.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, oxazepanyl, diazepanyl, 1,4-diazepanyl, diazepinyl, thiazepinyl, thiazepanyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyco[3.1.0] hexanyl, 3,6-diazabicyclo[3.1.1] heptanyl, 6-azabicyclo[3.1.1]heptanyl, 3-azabicyclo[3.1.1] heptanyl, 3-azabicyclo[4.1.0] heptanyl and azabicyclo[2.2.2] hexanyl. Examples of a heterocyclyl group wherein a ring atom is substituted with oxo (=O) are pyrimidinonyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

The term "heteroaryl" refers to an aromatic carbocyclic radical in which at least one ring atom is a heteroatom independently selected from nitrogen, oxygen and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include 5-6-membered rings, or monocyclic aromatic 5-, 6- and 7-membered rings containing one or more heteroatoms independently selected from nitrogen, oxygen, and sulfur. In another embodiment, exemplary heteroaryl groups include fused ring systems of up to 9 carbon atoms wherein at least one aromatic ring contains one or more heteroatoms independently selected from nitrogen, oxygen, and sulfur. "Heteroaryl" includes heteroaryl groups fused with an aryl, cycloalkyl or other heterocyclyl group. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "leaving group" refers to a portion of a first reactant in a chemical reaction that is displaced from the first reactant by a second reactant in the chemical reaction. Examples of leaving groups include, but are not limited to, halogen atoms and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)). Additional examples of leaving groups are well known to one of ordinary skill in the art.

"Treat" and "treatment" includes both therapeutic treatment and prophylactic or preventative measures, wherein the object is to prevent or slow down (lessen) an undesired physiological change or disorder, such as the development or spread of cancer or inflammation. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, remission and sustaining remission (whether partial or total), whether detectable or undetectable. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer.

To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In the case of immunological disease, the therapeutic effective amount is an amount sufficient to decrease or alleviate an allergic disorder, the symptoms of an autoimmune and/or inflammatory disease (e.g. psoriasis or inflammatory bowel disease), or the symptoms of an acute inflammatory reaction (e.g. asthma). In some embodiments, a therapeutically effective amount is an amount of a chemical entity described herein sufficient to significantly decrease the activity or number of B-cells.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is an agent useful in the treatment of a given disorder, for example, cancer or inflammatory disorders. Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF inhibitors (e.g., ANGIOZYME®) and (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents; (x) ACTEMRA® (tocilizumab) and (xi) pharmaceutically acceptable salts, acids and derivatives of any of the above.

Humanized monoclonal antibodies with therapeutic potential as agents in combination with the Janus kinase inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Liposome" refers to a vesicle composed of one or more lipids, phospholipids and/or surfactants, which is useful for delivery of a drug (such as a compound of Formula I and, optionally, a chemotherapeutic agent) to a mammal. The components of the liposome can be in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include diastereomers, enantiomers, conformers and the like.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound of Formulas I-VII. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of Formulas I-VII. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "compound of this invention," and "compounds of the present invention", and "compounds of Formulas I", "compounds of Formulas I-VII", unless otherwise indicated, include compounds of Formula I, IIa, IIb, IIc, IId, IIe, IIf, IIg, IIh, IIi, IIj, IIk, III, IIIa, IIIb, IIIc, IIId, IIIe, IIIf, IVa, IVb, V, Va, Vb, VIa, VIIb, VIIc, VIId, VIIa, VIIb, VIIc and/or VIId, and stereoisomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula I, IIa, IIb, IIc, IId, IIe, IIf, IIg, IIh, IIi, IIj, IIk, III, IIIa, IIIb, IIIc, IIId, IIIe, IIIf, IVa, IVb, V, Va, VIa, VIIb, VIIc, VIId, VIIa, VIIb, VIIc and/or VIId, wherein one or more hydrogen atoms are replaced deuterium or tritium, or one or more carbon atoms are replaced by a $^{13}$C- or $^{14}$C-enriched carbon are within the scope of this invention.

Janus Kinase Inhibitor Compounds

In one embodiment, a compound of Formula I, and pharmaceutical formulations thereof, are provided that are useful in the treatment of diseases, conditions and/or disorders responsive to the inhibition of Janus kinases.

In another embodiment, a compound of Formula I, and pharmaceutical formulations thereof, are provided that are useful in the treatment of diseases, conditions and/or disorders responsive to the inhibition of TYK2 kinase.

Another embodiment includes compounds of Formula I:

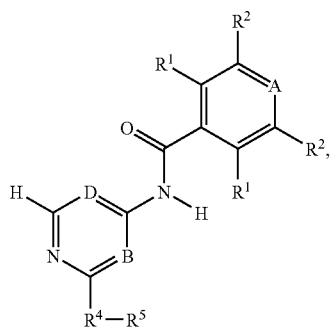

I stereoisomers or a pharmaceutically acceptable salt thereof, wherein:

A is $CR^3$ or N;

B and D are independently $CR^{15}$ or N, wherein B and D cannot be N at the same time;

$R^1$ is independently H, halogen, $C_1$-$C_3$ alkyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein both $R^1$ cannot be H at the same time, and wherein said alkyl and cycloalkyl are optionally substituted by halogen, $OR^6$, —$NR^6R^7$ or phenyl;

$R^2$ and $R^3$ are independently H, $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)$OR^8$, —($C_0$-$C_3$ alkyl)$SR^8$, —($C_0$-$C_3$ alkyl)$NR^8R^9$, —($C_0$-$C_3$ alkyl)$CF_3$, —O($C_0$-$C_3$ alkyl)$CF_3$, —($C_0$-$C_3$ alkyl)$NO_2$, —($C_0$-$C_3$ alkyl)$C(O)R^8$, —($C_0$-$C_3$ alkyl)$C(O)OR^8$, —($C_0$-$C_3$ alkyl)$C(O)NR^8R^9$, —($C_0$-$C_3$ alkyl)$NR^8C(O)R^9$, —($C_0$-$C_3$ alkyl)$S(O)_{1-2}R^8$, —($C_0$-$C_3$ alkyl)$NR^8S(O)_{1-2}R^9$, —($C_0$-$C_3$ alkyl)$S(O)_{1-2}NR^8R^9$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)(5-6-membered heteroaryl) or —($C_0$-$C_3$ alkyl)phenyl, wherein $R^2$ and $R^3$ are independently optionally substituted by $R^{10}$;

$R^4$ is H, halogen, —($C_0$-$C_1$ alkyl)$NH_2$, —($C_0$-$C_1$ alkyl)$NH_2$, —($C_0$-$C_1$ alkyl)OH, —($C_0$-$C_1$ alkyl)SH, —($C_0$-$C_1$ alkyl)$NR^6R^7$, —($C_0$-$C_1$ alkyl)$NR^6C(O)$—, —($C_0$-$C_1$ alkyl)$NR^6C(O)O$—, —($C_0$-$C_1$ alkyl)$NR^6C(O)NR^7$—, —($C_0$-$C_1$ alkyl)$NR^6S(O)_{1-2}$— or —($C_0$-$C_1$ alkyl)$NR^6S(O)_{1-2}NR^7$—;

$R^5$ is absent, $C_1$-$C_6$ alkyl, $C_3$-$C_6$ cycloalkyl, phenyl, 3-7-membered heterocyclyl or 5-6-membered heteroaryl, wherein $R^5$ is optionally substituted by $R^{10}$;

$R^6$ and $R^7$ are each independently H or $C_1$-$C_3$ alkyl, optionally substituted by halogen, oxo or —$NR^{11}R^{12}$; or $R^6$ and $R^7$ are independently taken together with the atom to which they are attached to form a 3-6 membered heterocyclyl, optionally substituted by halogen, oxo, —$NR^{11}R^{12}$ or $C_1$-$C_3$ alkyl;

$R^8$ and $R^9$ are each independently H, $C_1$-$C_3$ alkyl, $C_3$-$C_6$ cycloalkyl, phenyl, 3-6-membered heterocyclyl or 5-6-membered heteroaryl, optionally substituted by $R^{10}$; or $R^8$ and $R^9$ are independently taken together with the atom to which they are attached to form a 3-6 membered heterocyclyl, optionally substituted by halogen, oxo, —$NR^{11}R^{12}$ or $C_1$-$C_3$ alkyl;

$R^{10}$ is independently H, oxo, $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$CF_3$, —($C_0$-$C_3$ alkyl)$NO_2$, —($C_0$-$C_3$ alkyl)$C(O)R^{11}$, —($C_0$-$C_3$ alkyl)$C(O)OR^{11}$, —($C_0$-$C_3$ alkyl)$C(O)NR^{11}R^{12}$, —($C_0$-$C_3$ alkyl)$NR^{11}C(O)R^{12}$, —($C_0$-$C_3$ alkyl)$S(O)_{1-2}R^{11}$, —($C_0$-$C_3$ alkyl)$NR^{11}S(O)_{1-2}R^{12}$, —($C_0$-$C_3$ alkyl)$S(O)_{1-2}NR^{11}R^{12}$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)$C(O)$(3-6-membered heterocyclyl), —($C_0$-$C_3$ alkyl)(5-6-membered heteroaryl) or —($C_0$-$C_3$ alkyl)phenyl, wherein $R^{10}$ is independently optionally substituted by halogen, $C_1$-$C_3$ alkyl, oxo, —$CF_3$, —($C_0$-$C_3$ alkyl)$OR^{13}$, —($C_0$-$C_3$ alkyl)$NR^{13}R^{14}$, —($C_0$-$C_3$ alkyl)$C(O)R^{13}$ or —($C_0$-$C_3$ alkyl)$S(O)_{1-2}R^{13}$;

$R^{11}$ and $R^{12}$ are independently H, $C_1$-$C_6$ alkyl, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)(5-6-membered heteroaryl) or —($C_0$-$C_3$ alkyl)phenyl, optionally substituted by halogen, oxo, —$OR^{13}$, —$SR^{13}$, —$NR^{13}R^{14}$, $C_1$-$C_3$ alkyl, —($C_0$-$C_3$ alkyl)($C_3$-$C_6$ cycloalkyl), —($C_0$-$C_3$ alkyl)phenyl, —($C_0$-$C_3$ alkyl)(3-6-membered heterocyclyl) or —($C_0$-$C_3$ alkyl)(5-6-membered heteroaryl); or $R^{11}$ and $R^{12}$ are taken together with the atom to which they attached to form a 3-6 membered heterocyclyl, optionally substituted by halogen, oxo, —$NR^{13}R^{14}$ or $C_1$-$C_3$ alkyl;

$R^{13}$ and $R^{14}$ are independently H, $C_1$-$C_6$ alkyl, OH or $OCH_3$, optionally substituted by halogen, —$NH_2$, —$N(CH_3)_2$, phenyl or oxo, wherein said phenyl is optionally substituted by halogen, $C_1$-$C_6$ alkyl, $CF_3$, —$NR^aR^b$ or $OR^a$ or $R^{13}$ and $R^{14}$ are taken together with the atom to which they are attached to form a 3-6 membered heterocyclyl, optionally substituted by halogen, oxo, —$NH_2$, —$N(CH_3)_2$ or $C_1$-$C_3$ alkyl;

$R^{15}$ is independently H, halogen, $C_1$-$C_3$ alkyl, $C_1$-$C_3$ alkenyl, $C_1$-$C_3$ alkynyl, $C_3$-$C_4$ cycloalkyl, —$CF_3$, —$OR'$, —$SR^a$, —CN, —$NO_2$, —$NR^aSO_2R^b$, —$NR^aC(O)R^b$ or —$NR^aR^b$; and $R^a$ and $R^b$ are independently H or $C_1$-$C_6$ alkyl optionally substituted by halogen or oxo; or $R^a$ and $R^b$ are taken together with the atom to which they are attached to form a 3-6 membered heterocyclyl, optionally substituted by halogen, oxo or $C_1$-$C_3$ alkyl.

Another embodiment includes compounds of Formula I:

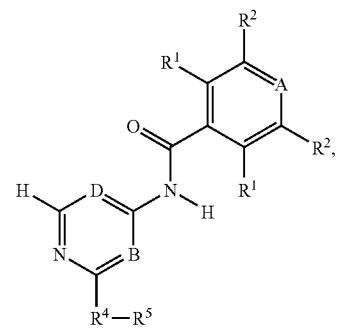

I stereoisomers or a pharmaceutically acceptable salt thereof, wherein:

A is $CR^3$ or N;

B and D are independently CH or N, wherein B and D cannot be N at the same time;

$R^1$ is independently H, halogen, $C_1$-$C_3$ alkyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein both $R^1$ cannot be H at the same time, and wherein said alkyl and cycloalkyl are optionally substituted by halogen, $OR^6$, —$NR^6R^7$ or phenyl;

$R^2$ and $R^3$ are independently H, $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)$OR^8$, —($C_0$-$C_3$ alkyl)$SR^8$, —($C_0$-$C_3$ alkyl)$NR^8R^9$, —($C_0$-$C_3$ alkyl)$CF_3$, —O($C_0$-$C_3$ alkyl)$CF_3$, —($C_0$-$C_3$ alkyl)$NO_2$, —($C_0$-$C_3$ alkyl)C(O)$R^8$, —($C_0$-$C_3$ alkyl)C(O)$OR^8$, —($C_0$-$C_3$ alkyl)C(O)$NR^8R^9$, —($C_0$-$C_3$ alkyl)$NR^8C(O)R^9$, —($C_0$-$C_3$ alkyl)$S(O)_{1-2}R^8$, —($C_0$-$C_3$ alkyl)$NR^8S(O)_{1-2}R^9$, —($C_0$-$C_3$ alkyl)$S(O)_{1-2}NR^8R^9$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)(5-6-membered heteroaryl) or —($C_0$-$C_3$ alkyl)phenyl, wherein $R^2$ and $R^3$ are independently optionally substituted by $R^{10}$;

$R^4$ is H, halogen, —($C_0$-$C_1$ alkyl)$NH_2$, —($C_0$-$C_1$ alkyl)NH—, —($C_0$-$C_1$ alkyl)OH, —($C_0$-$C_1$ alkyl)SH, —($C_0$-$C_1$ alkyl)$NR^6R^7$, —($C_0$-$C_1$ alkyl)$NR^6C(O)$—, —($C_0$-$C_1$ alkyl)$NR^6C(O)O$—, —($C_0$-$C_1$ alkyl)$NR^6C(O)NR^7$—, —($C_0$-$C_1$ alkyl)$NR^6S(O)_{1-2}$— or —($C_0$-$C_1$ alkyl)$NR^6S(O)_{1-2}NR^7$—;

$R^5$ is absent, $C_1$-$C_6$ alkyl, $C_3$-$C_6$ cycloalkyl, phenyl, 3-7-membered heterocyclyl or 5-6-membered heteroaryl, wherein $R^5$ is optionally substituted by $R^{10}$;

$R^6$ and $R^7$ are each independently H or $C_1$-$C_3$ alkyl, optionally substituted by halogen, oxo or —$NR^{11}R^{12}$; or $R^6$ and $R^7$ are independently taken together with the atom to which they are attached to form a 3-6 membered heterocyclyl, optionally substituted by halogen, oxo, —$NR^{11}R^{12}$ or $C_1$-$C_3$ alkyl;

$R^8$ and $R^9$ are each independently H, $C_1$-$C_3$ alkyl, $C_3$-$C_6$ cycloalkyl, phenyl, 3-6-membered heterocyclyl or 5-6-membered heteroaryl, optionally substituted by $R^{10}$; or $R^8$ and $R^9$ are independently taken together with the atom to which they are attached to form a 3-6 membered heterocyclyl, optionally substituted by halogen, oxo, —$NR^{11}R^{12}$ or $C_1$-$C_3$ alkyl;

$R^{10}$ is independently H, oxo, $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$CF_3$, —($C_0$-$C_3$ alkyl)$NO_2$, —($C_0$-$C_3$ alkyl)C(O)$R^{11}$, —($C_0$-$C_3$ alkyl)C(O)$OR^{11}$, —($C_0$-$C_3$ alkyl)C(O)$NR^{11}R^{12}$, —($C_0$-$C_3$ alkyl)$NR^{11}C(O)R^{12}$, —($C_0$-$C_3$ alkyl)$S(O)_{1-2}R^{11}$, —($C_0$-$C_3$ alkyl)$NR^{11}S(O)_{1-2}R^{12}$, —($C_0$-$C_3$ alkyl)$S(O)_{1-2}NR^{11}R^{12}$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), —($C_0$-$C_3$ alkyl)(5-6-membered heteroaryl) or —($C_0$-$C_3$ alkyl)phenyl, wherein $R^{10}$ is independently optionally substituted by halogen, $C_1$-$C_3$ alkyl, oxo, —$CF_3$, —($C_0$-$C_3$ alkyl)$OR^{13}$, —($C_0$-$C_3$ alkyl)$NR^{13}R^{14}$, —($C_0$-$C_3$ alkyl)C(O)$R^{13}$ or —($C_0$-$C_3$ alkyl)$S(O)_{1-2}R^{13}$;

$R^{11}$ and $R^{12}$ are independently H, $C_1$-$C_6$ alkyl or —($C_0$-$C_3$ alkyl)phenyl, optionally substituted by halogen, oxo, $OR^{13}$, —$NR^{13}R^{14}$, $C_1$-$C_3$ alkyl, —($C_0$-$C_3$ alkyl)($C_3$-$C_6$ cycloalkyl), —($C_0$-$C_3$ alkyl)phenyl, —($C_0$-$C_3$ alkyl)(3-6-membered heterocyclyl) or —($C_0$-$C_3$ alkyl)(5-6-membered heteroaryl); or $R^{11}$ and $R^{12}$ are taken together with the atom to which they attached to form a 3-6 membered heterocyclyl, optionally substituted by halogen, oxo, —$NR^{13}R^{14}$ or $C_1$-$C_3$ alkyl; and $R^{13}$ and $R^{14}$ independently H, $C_1$-$C_6$ alkyl, OH or $OCH_3$, optionally substituted by halogen, —$NH_2$, —$N(CH_3)_2$ or oxo; or $R^{13}$ and $R^{14}$ are taken together with the atom to which they attached to form a 3-6 membered heterocyclyl, optionally substituted by halogen, oxo, —$NH_2$, —$N(CH_3)_2$ or $C_1$-$C_3$ alkyl.

In one embodiment of Formula I, A is $CR^3$. In another embodiment of Formula I, A is $CR^3$, and B and D are CH. In another embodiment of Formula I, A is $CR^3$, B is CH and D is N.

In another embodiment of Formula I, A is $CR^3$, B is N and D is CH.

In certain embodiments, A is $CR^3$ and B and D are $CR^{15}$. In certain embodiments, A is $CR^3$, B is N and D is $CR^{15}$. In certain embodiments, A is $CR^3$, B is $CR^{15}$ and D is N.

In one embodiment of Formula I, A is N. In one embodiment of Formula I, A is N, and B and D are CH. In another embodiment of Formula I, A is N, B is CH and D is N. In another embodiment of Formula I, A and B are N, and D is CH.

In certain embodiments, A is N and B and D are $CR^{15}$. In certain embodiments, A is N, B is N and D are $CR^{15}$. In certain embodiments, A is N, B is $CR^{15}$ and D is N.

In one embodiment of Formula I, $R^1$ is independently halogen. In another embodiment of Formula I, one $R^1$ is halogen and the other $R^1$ is H, halogen, $C_1$-$C_3$ alkyl, $C_3$-$C_4$ cycloalkyl, —$CF_3$, —OH, —O($C_1$-$C_3$ alkyl), —SH, —S($C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl. In another embodiment of Formula I, one $R^1$ is halogen and the other $R^1$ is halogen, $C_1$-$C_3$ alkyl, $C_3$-$C_4$ cycloalkyl, —$CF_3$, —OH, —O($C_1$-$C_3$ alkyl), —SH, —S($C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl. In another embodiment of Formula I, $R^1$ is independently F or Cl. In another embodiment of Formula I, $R^1$ is Cl.

In another embodiment of Formula I, $R^1$ is independently halogen, $C_1$-$C_3$ alkyl, $C_3$-$C_4$ cycloalkyl, —$CF_3$, —OH, —O($C_1$-$C_3$ alkyl), —SH, —S($C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl.

In another embodiment of Formula I, $R^1$ is independently H, F, Cl, Br, —$NO_2$, —$CF_3$, —$CH_3$, —$OCH_3$, —$NH_2$, —$NHC(O)CH_3$, —$NHSO_2CH_3$ or —$OCH_2$-phenyl, wherein both $R^1$ cannot be H at the same time. In another embodiment of Formula I, $R^1$ is independently H, F, Cl, Br, —$OCH_3$, —$NH_2$, —$CF_3$ or —$CH_3$, wherein both $R^1$ cannot be H at the same time. In another embodiment of Formula I, $R^1$ is independently F, Cl, Br, —$OCH_3$, —$NH_2$, —$CF_3$ or —$CH_3$. In another embodiment of Formula I, $R^1$ is independently H, F or Cl, wherein both $R^1$ cannot be H at the same time.

In one embodiment of Formula I, $R^2$ and $R^3$ are independently H, halogen, —CN, —$NH_2$, —$CH_2NH_2$, —NHCOCH$_3$, —$CONH_2$, —$CH_2OH$, methyl, ethyl, ethenyl, —C(O)H, —$NO_2$, -(ethynyl)$CH_2OH$, pyrrazolyl, —$SCH_3$, —OH, —OMe, —$CF_3$ or —$NHSO_2CH_3$. In one embodiment of Formula I, $R^2$ is independently H, F, Cl, methyl, ethyl, —$NHSO_2CH_3$, —$NO_2$, —$NH_2$ or —$NHCOCH_3$. In one embodiment of Formula I, $R^2$ is independently H, F, Cl, methyl or ethyl. In one embodiment of Formula I, $R^2$ is independently H, F or Cl. In one embodiment of Formula I, $R^2$ is independently H. In one embodiment of Formula I, $R^2$ is independently Cl or F.

In one embodiment of Formula I, $R^4$ is H, halogen, —$NH_2$, —NH—, —OH, —SH, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—. In another embodiment of Formula I, $R^4$ is halogen, —$(C_0$-$C_1$ alkyl)$NH_2$, —$(C_0$-$C_1$ alkyl)$NH$—, —$(C_0$-$C_1$ alkyl)$OH$, —$(C_0$-$C_1$ alkyl)$SH$, —$(C_0$-$C_1$ alkyl)$NR^6R^7$, —$(C_0$-$C_1$ alkyl)$NR^6C(O)$—, —$(C_0$-$C_1$ alkyl)$NR^6C(O)O$—, —$(C_0$-$C_1$ alkyl)$NR^6C(O)NR^7$—, —$(C_0$-$C_1$ alkyl)$NR^6S(O)_{1-2}$— or —$(C_0$-$C_1$ alkyl)$NR^6S(O)_{1-2}NR^7$—. In another embodiment of Formula I, $R^4$ is halogen, —$NH_2$, —NH—, —OH, —SH, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—.

In another embodiment of Formula I, $R^4$ is H, —$NH_2$, —NH—, —$NR^6R^7$, —$NR^6C(O)$—, —$NR^6C(O)O$—, —$NR^6C(O)NR^7$—, —$NR^6S(O)_{1-2}$— or —$NR^6S(O)_{1-2}NR^7$—. In another embodiment of Formula I, $R^4$ is —$NH_2$, —NH—, —$NR^6R^7$, —$NR^6C(O)$—, —$NR^6C(O)O$— or —$NR^6C(O)NR^7$—. In another embodiment of Formula I, $R^4$ is —NH—, —$NR^6C(O)$—, —$NR^6C(O)O$— or —$NR^6C(O)NR^7$—. In another embodiment of Formula I, $R^4$ is —NH— or —$NR^6C(O)$—.

In certain embodiments, $R^4$ is H, —$NH_2$, —NH—, —OH, —SH, —$NR^6C(O)$—, —$NR^6C(O)O$—, —$NR^6C(O)NR^7$—, —$NR^6S(O)_{1-2}$— or —$NR^6S(O)_{1-2}NR^7$—. In certain embodiments, $R^4$ is —$NH_2$, —NH—, —$NR^6C(O)$—, —$NR^6C(O)O$— or —$NR^6C(O)NR^7$—.

In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NHSO_2CH_3$, —$NHC(O)R^7$ or —$NR^6R^7$, wherein said alkyl and cycloalkyl are optionally substituted by halogen, $OR^8$, —$NR^8R^9$ or phenyl; and $R^4$ is halogen, —$(C_0$-$C_1$ alkyl)$NH_2$, —$(C_0$-$C_1$ alkyl)$NH$—, —$(C_0$-$C_1$ alkyl)$OH$, —$(C_0$-$C_1$ alkyl)$SH$, —$(C_0$-$C_1$ alkyl)$NR^6R^7$, —$(C_0$-$C_1$ alkyl)$NR^6C(O)$—, —$(C_0$-$C_1$ alkyl)$NR^6C(O)O$—, —$(C_0$-$C_1$ alkyl)$NR^6C(O)NR^7$—, —$(C_0$-$C_1$ alkyl)$NR^6S(O)_{1-2}$— or —$(C_0$-$C_1$ alkyl)$NR^6S(O)_{1-2}NR^7$—.

In one embodiment of Formula I, $R^1$ is independently halogen, A is $CR^3$ and D and B are CH. In another embodiment of Formula I, $R^1$ is independently halogen, A is $CR^3$, B is N and D is CH. In another embodiment of Formula I, $R^1$ is independently halogen, A is $CR^3$, B is CH and D is N. In another embodiment of Formula I, $R^1$ is independently halogen, A is N, and D and B are CH. In another embodiment of Formula I, $R^1$ is independently halogen, A and B are N and D is CH. In another embodiment of Formula I, $R^1$ is independently halogen, A and D are N and B is CH.

In one embodiment of Formula I, $R^1$ is independently halogen, A is $CR^3$ and D and B are $CR^{15}$.

In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A is $CR^3$ and D and B are CH. In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A is $CR^3$, B is N and D is CH. In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A is $CR^3$, B is CH and D is N. In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A is N, and D and B are CH. In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A and B are N and D is CH. In another embodiment of Formula I, $R^1$ is independently halogen, $C_1$-$C_3$ alkyl, $C_3$-$C_4$ cycloalkyl, —$CF_3$, —OH, —$O(C_1$-$C_3$ alkyl), —SH, —$S(C_1$-$C_3$ alkyl), —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^8$, —$NR^8R^9$ or phenyl, A and D are N and B is CH.

In another embodiment of Formula I, when $R^4$ is —OH, $R^5$ is absent, and one of B and D are N and the other is CH, then the portion of Formula I having the structure:

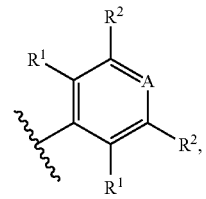

is other than

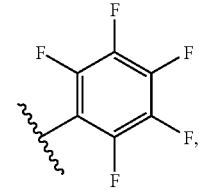

wherein the wavy lines represent the point of attachment in Formula I.

In another embodiment of Formula I, when the portion of Formula I having the structure:

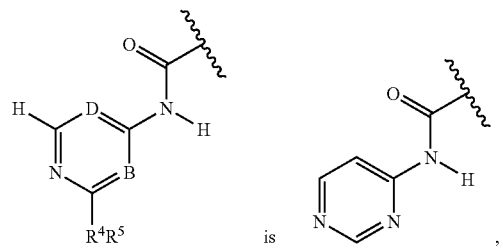

is then the portion of Formula I having the structure:

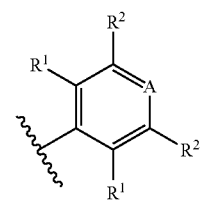

is other than the following:
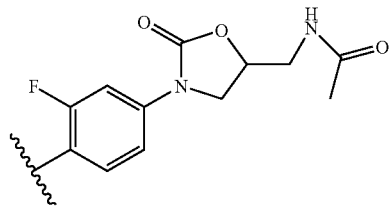
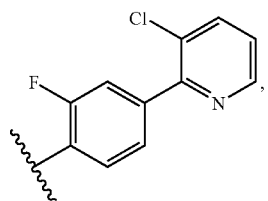
wherein the wavy lines represent the point of attachment in Formula I.
In another embodiment of Formula I, when the portion of Formula I having the structure:
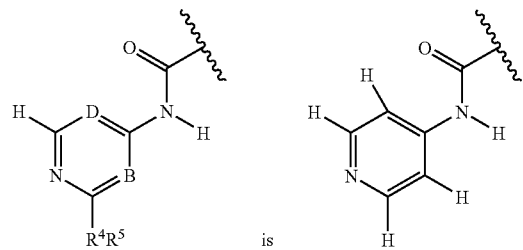
is
then the portion of Formula I having the structure:
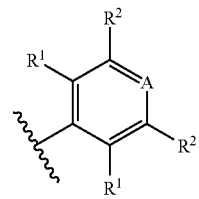
is other than the following:
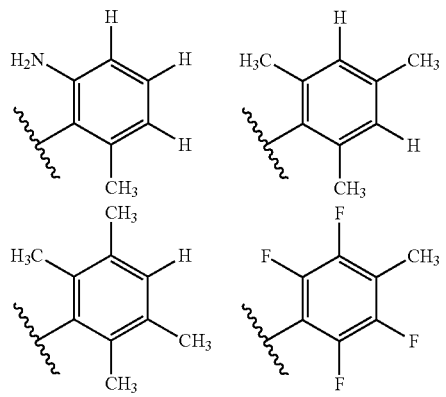
-continued
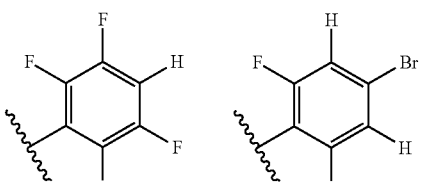
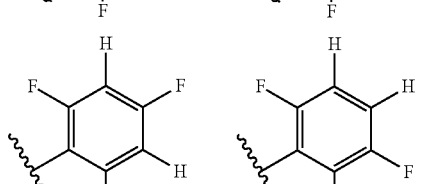
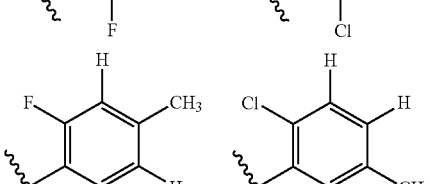
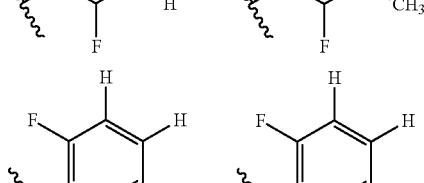
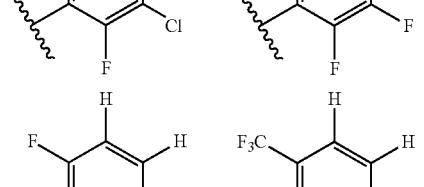
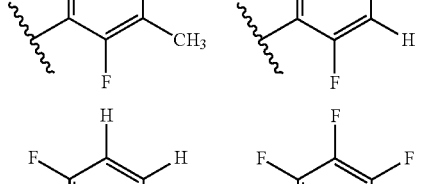
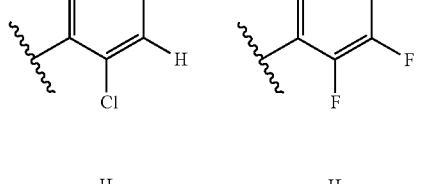
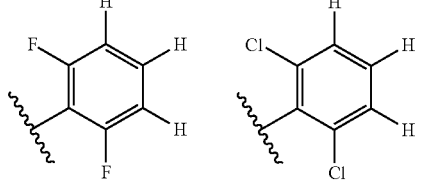
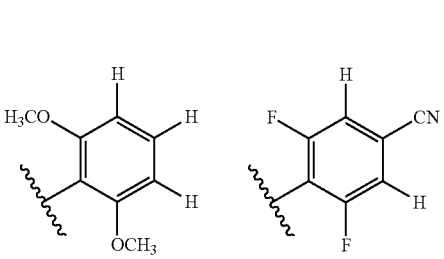

-continued

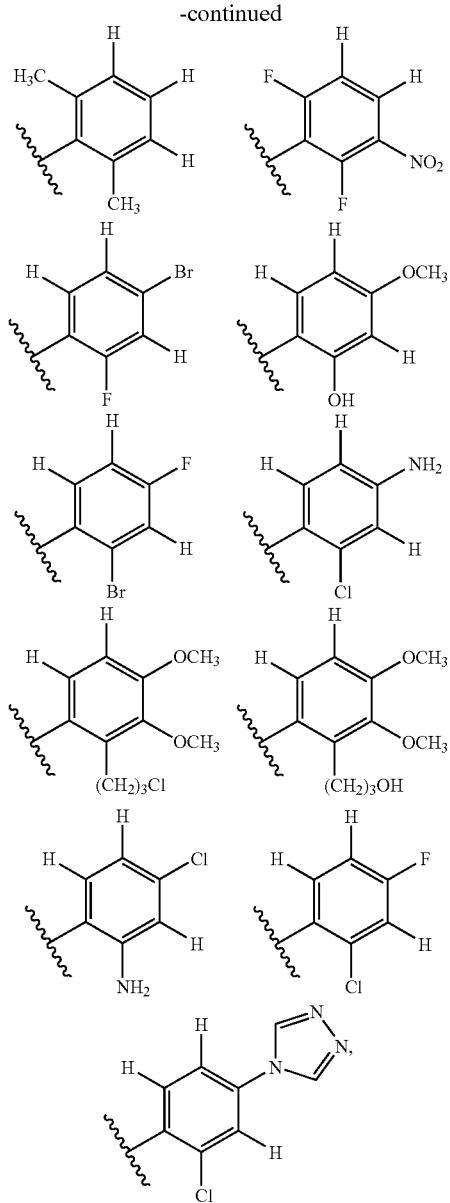

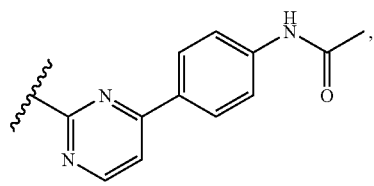 [SMILES: *c1nccc(-c2ccc(NC(C)=O)cc2)n1 ; ","]

wherein the wavy lines represent the point of attachment in Formula I.

In another embodiment of Formula I, when A is $CR^3$, B is CH, D is N, $R^1$ is $C^1$, $R^2$ and $R^3$ are H, $R^4$ is —NH—, $R^5$ is other than the structure:

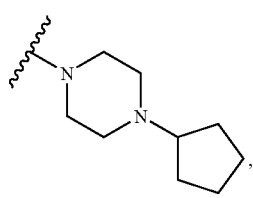 [SMILES: *N1CCN(C2CCCC2)CC1 ; ","]

wherein the wavy line represents the point of attachment in Formula I.

In another embodiment of Formula I, when A is $CR^3$, B and D are CH, one $R^1$ is F or —OCH$_3$, and the other $R^1$ is H, $R^2$ and $R^3$ are H, —$R^4$-$R^5$ is other than the structure:

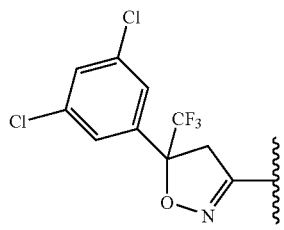

wherein the wavy line represents the point of attachment in Formula I.

In another embodiment of Formula I, when A is $CR^3$, B and D are CH, or B is CH and D is N, one $R^1$ is —CH$_3$ and the other $R^1$ is H, $R^2$ is H, $R^4$ is H or Cl; $R^5$ is absent; $R^3$ is other than the structure:

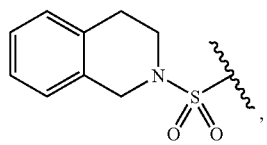 [SMILES: *S(=O)(=O)N1CCc2ccccc2C1 ; ","]

wherein the wavy line represents the point of attachment in Formula I.

In another embodiment of Formula I, when A is $CR^3$, B and D are CH, one $R^1$ is Cl and the other $R^1$ is H; $R^3$ is H, $R^4$ is Cl; $R^5$ is absent; $R^2$ is other than the structure:

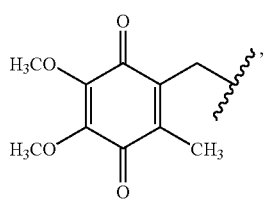 [SMILES: *CC1=C(C)C(=O)C(OC)=C(OC)C1=O ; ","]

wherein the wavy line represents the point of attachment in Formula I.

In another embodiment of Formula I, when A is $CR^3$, B and D are CH, one $R^1$ is —OH and the other $R^1$ is H; $R^3$ is H, $R^4$ is Cl; $R^5$ is absent; $R^2$ is other than the structure:

wherein the wavy line represents the point of attachment in Formula I.

In another embodiment of Formula I, when A is $CR^3$, B and D are CH, one $R^1$ is F and the other $R^1$ is H, $R^2$ is H, $R^4$ is H or Cl; $R^5$ is absent; $R^3$ is other than 3-chloropyridin-2-yl.

In another embodiment of Formula I, when A is $CR^3$, B is CH, D is N; one $R^1$ is Cl; $R^2$ and $R^3$ are H, $R^4$ is Cl; $R^5$ is absent; the other $R^1$ is other than H.

In another embodiment of Formula I, when A is $CR^3$, B is N; D is CH, one $R^1$ is —CH$_3$ and the other $R^1$ is H; $R^2$ and $R^3$ are H; $R^5$ is absent; $R^4$ is other than OH.

In another embodiment of Formula I, a compound is selected from Formulas IIa-III:
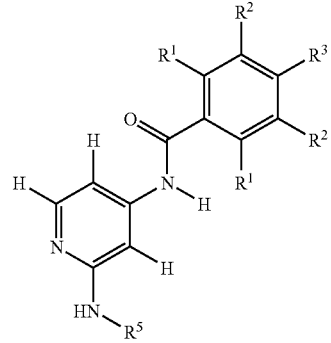
IIa
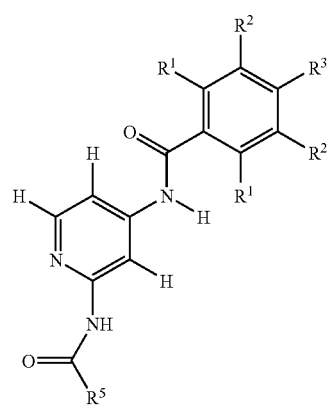
IIb
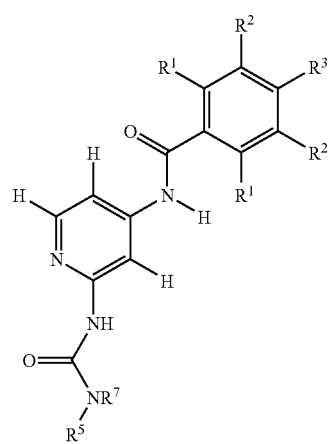
IIc
-continued
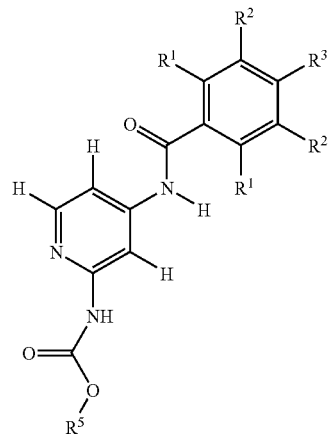
IId
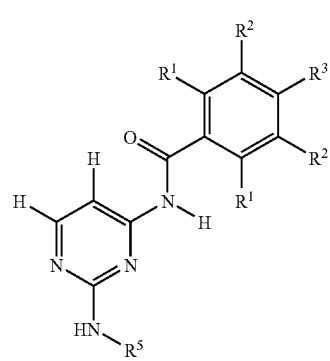
IIe
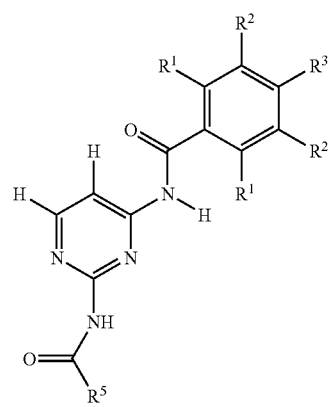
IIf
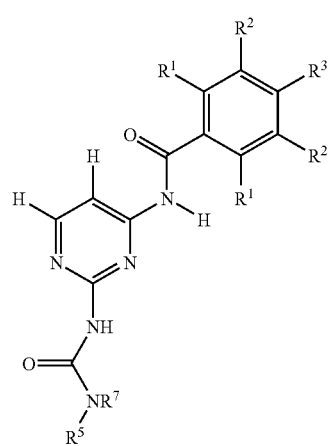
IIg

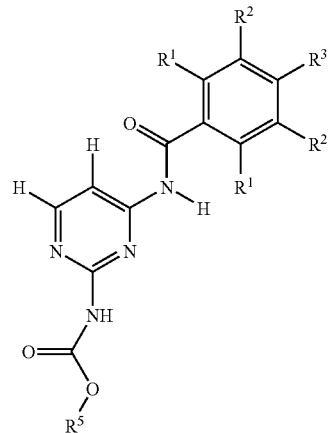

IIh

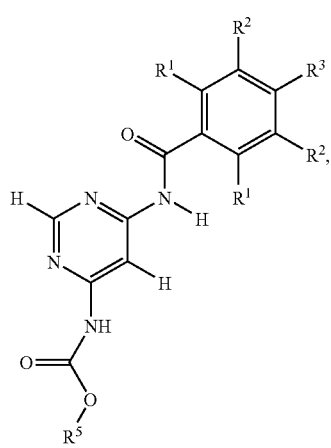

III

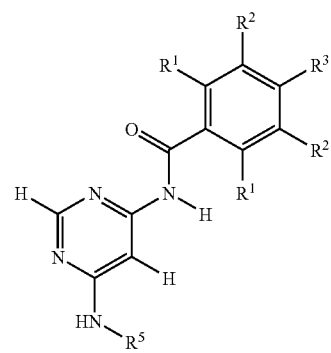

IIi including stereoisomers and pharmaceutically acceptable salts thereof, wherein $R^1$-$R^3$, and $R^5$-$R^{14}$ are independently as defined in any embodiment of Formula I.

In one embodiment of Formulas IIa-III, $R^1$ is independently H or halogen, wherein both $R^1$ are not H at the same time. In one embodiment of Formulas IIa-III, one $R^1$ is Cl and the other $R^1$ is H or halogen.

In another embodiment of Formula I, a compound is selected from Formulas IIIa-IIf:

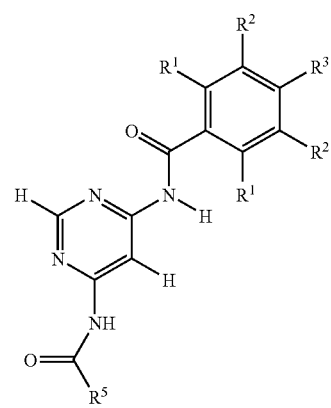

IIj

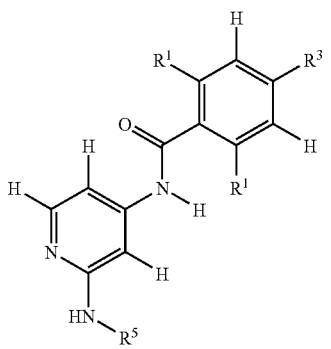

IIIa

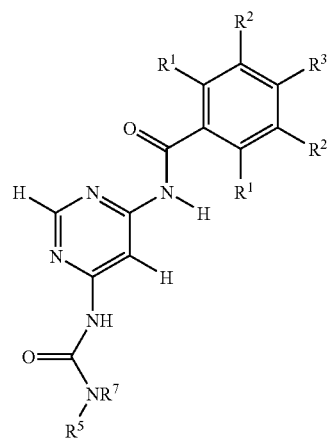

IIk

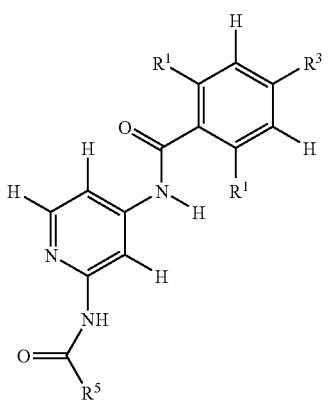

IIIb

-continued

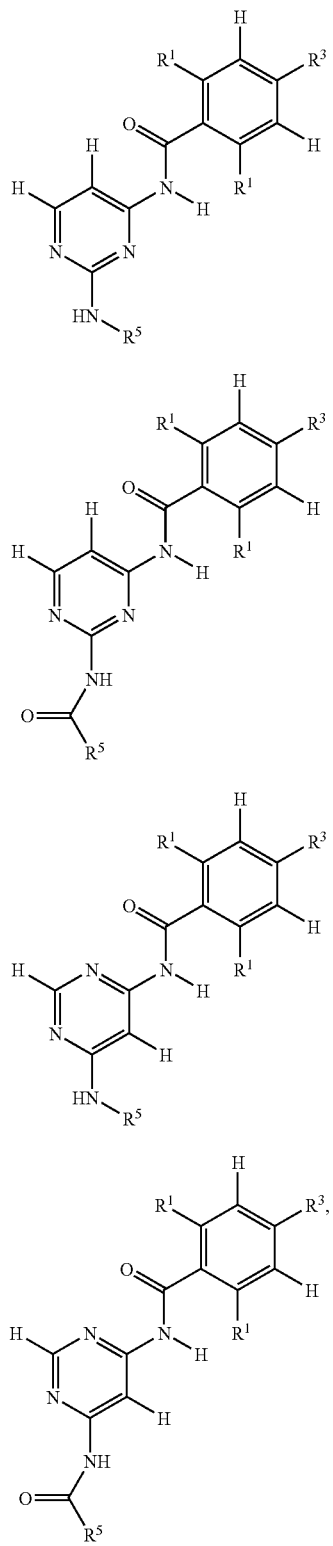

including stereoisomers and pharmaceutically acceptable salts thereof, wherein $R^1$, $R^3$, and $R^5$-$R^{14}$ are independently as defined in any embodiment of Formula I.

In one embodiment of Formulas IIIa-IIIf, $R^1$ is independently H or halogen, wherein both $R^1$ are not H at the same time. In one embodiment of Formulas IIIa-IIIf, one $R^1$ is Cl and the other $R^1$ is H or halogen.

In one embodiment of Formula I, a compound is selected from Formulas IVa-IVb:

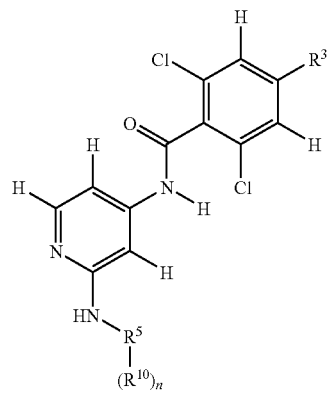

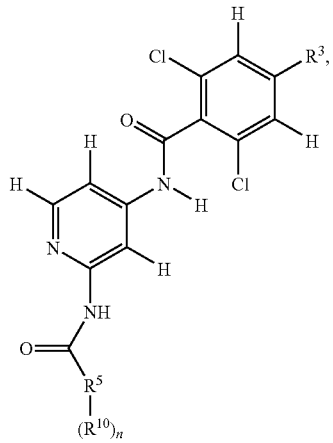

stereoisomers or a pharmaceutically acceptable salt thereof, wherein n is 0, 1, 2, 3 or 4, and $R^3$ and $R^5$-$R^{14}$ are independently as defined in any embodiment of Formula I.

In another embodiment of Formula I, a compound is selected from Formula V:

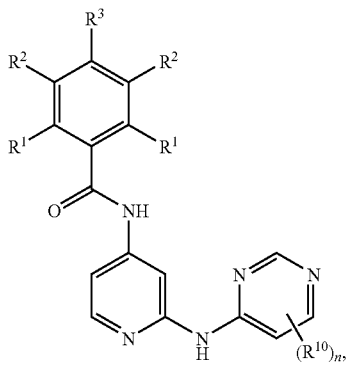

stereoisomers or a pharmaceutically acceptable salt thereof, wherein n is 0, 1, 2 or 3, and $R^1$-$R^{14}$ are as defined in any of the embodiments for Formula I. In one example of Formula V, $R^1$ is independently H or halogen, wherein both R¹ are not H at the same time. For example, a compound is selected from Formula Va:

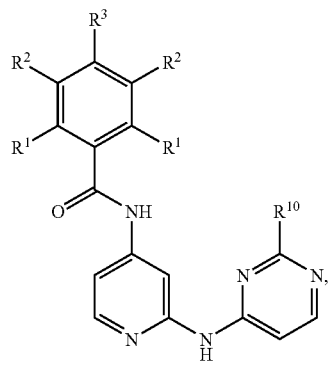

Va stereoisomers or a pharmaceutically acceptable salt thereof, wherein R¹-R³ and R⁶-R¹⁴ are as defined in any of the embodiments for Formula I. In an example of Formula Va, R¹ is independently halogen. In another example of Formula Va, R¹ is halogen and R² and R³ are hydrogen. In another example of Formula Va, R¹ is halogen, R² and R³ are hydrogen, and R¹⁰ is C₁-C₆ alkyl, halogen, —CN, —OR¹¹, —SR¹¹, —NR¹¹R¹², —CF₃, —C(O)R¹¹, —C(O)OR¹¹, —C(O)NR¹¹R¹², —NR¹¹C(O)R¹², —S(O)₁₋₂R¹¹, —NR¹¹S(O)₁₋₂R¹², —S(O)₁₋₂NR¹¹R¹², C₃-C₆ cycloalkyl, 3-6-membered heterocyclyl, —C(O)(3-6-membered heterocyclyl), 5-6-membered heteroaryl or phenyl, wherein R¹⁰ is independently optionally substituted by halogen, C₁-C₃ alkyl, oxo, —CF₃, —OR¹³, —NR¹³R¹⁴, —C(O)R¹³ or —S(O)₁₋₂R¹³.

In another example, a compound is selected from Formula Vb:

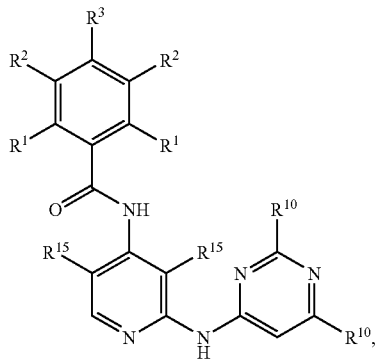

Vb stereoisomers or a pharmaceutically acceptable salt thereof, wherein R¹-R³ and R⁶-R¹⁴ are as defined in any of the embodiments for Formula I. In an example of Formula Vb, R¹ is independently halogen. In another example of Formula Vb, R¹ is independently halogen, R² is hydrogen and R³ is hydrogen, C₁-C₃ alkyl, halogen, —CN, —OH, or —NH₂. In another example of Formula Vb, R¹ is independently halogen, R² is hydrogen, R³ is hydrogen, C₁-C₃ alkyl, halogen, —CN, —OH, or —NH₂, R¹⁰ is independently C₁-C₆ alkyl, halogen, —CN, —OR¹¹, —SR¹¹, —NR¹¹R¹², —CF₃, —C(O)R¹¹, —C(O)OR¹¹, —C(O)NR¹¹R¹², —NR¹¹C(O)R¹², —S(O)₁₋₂R¹¹, —NR¹¹S(O)₁₋₂R¹², —S(O)₁₋₂NR¹¹R¹², C₃-C₆ cycloalkyl, 3-6-membered heterocyclyl, —C(O)(3-6-membered heterocyclyl), 5-6-membered heteroaryl or phenyl, wherein R¹⁰ is independently optionally substituted by halogen, C₁-C₃ alkyl, oxo, —CF₃, —OR¹³, —NR¹³R¹⁴, —C(O)R¹³ or —S(O)₁₋₂R¹³, and R¹⁵ is independently H, halogen, C₁-C₃ alkyl, C₁-C₃ alkenyl, C₁-C₃ alkynyl, C₃-C₄ cycloalkyl, —CF₃, —OR%, —SRᵃ, —CN, —NO₂ or —NRᵃRᵇ.

In another embodiment of Formula I, a compound is selected from Formulas VIa-VId:

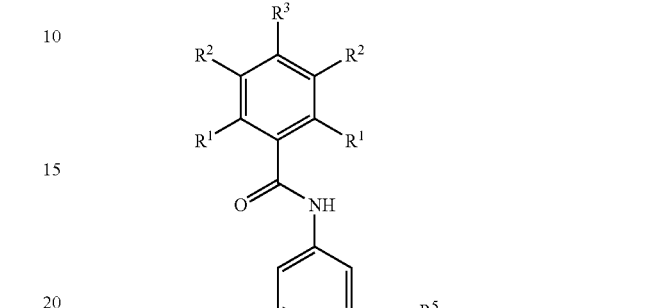

VIa

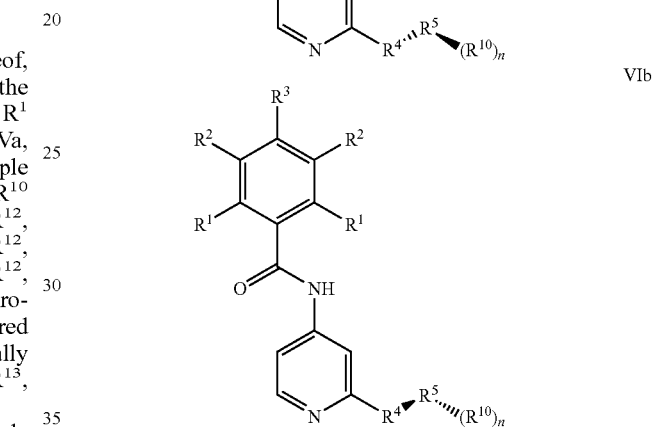

VIb

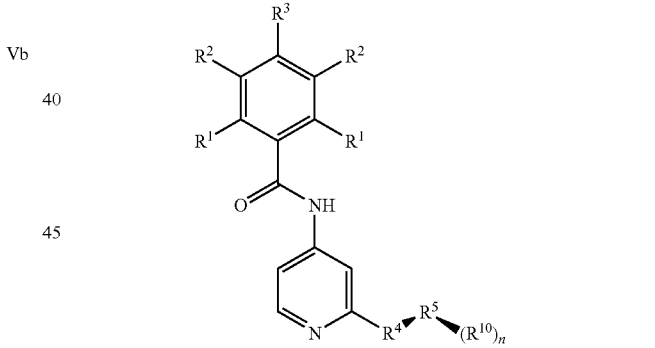

VIc

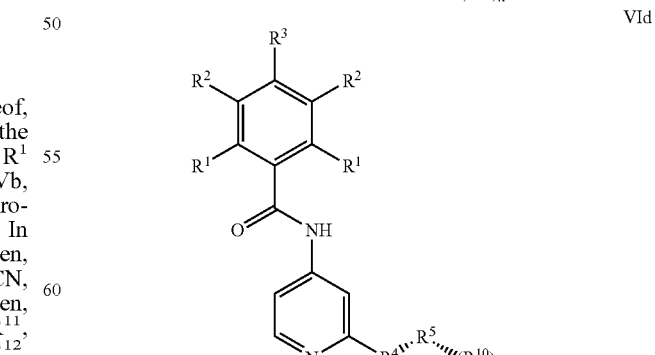

VId stereoisomers or a pharmaceutically acceptable salt thereof, wherein n is 0, 1, 2 or 3 and R¹-R¹⁴ are as defined in any of the embodiments for Formula I.

In an embodiment of Formulas VIa-VId, $R^5$ is 3-6 membered heterocycloalkyl, $C_3$-$C_6$ cycloalkyl or $C_1$-$C_6$ alkyl.

Another embodiment includes a compound of Formulas VIIa-d:

VIIa
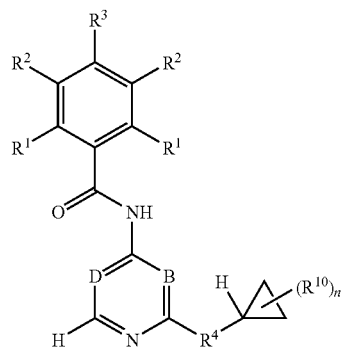

VIIb
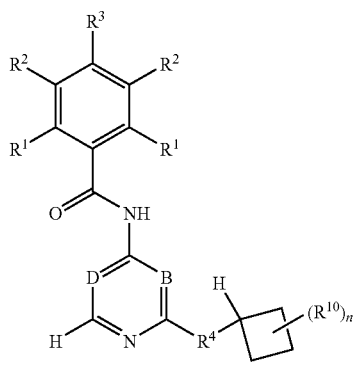

VIIc
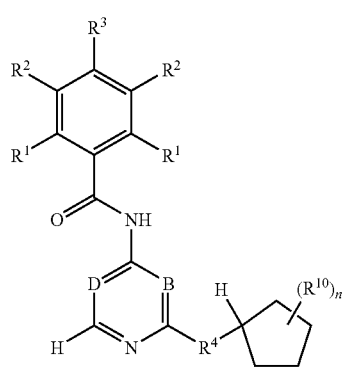

VIId
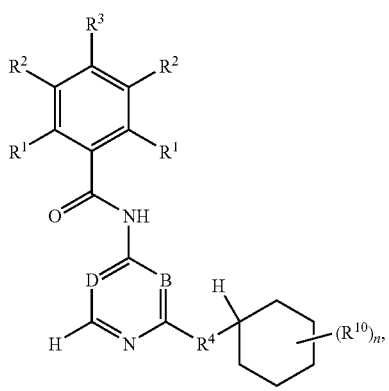

stereoisomers or a pharmaceutically acceptable salt thereof, wherein n is 0, 1, 2 or 3 and $R^1$-$R^{15}$ are as defined in any of the embodiments for Formula I. In one example of Formulas VII, D and B are independently $CR^{15}$. In another example, D and B are independently $CR^{15}$ and $R^1$ is independently H or halogen, wherein both $R^1$ are not H at the same time. In another example, D and B are independently $CR^{15}$, $R^1$ is independently H or halogen, wherein both $R^1$ are not H at the same time, $R^2$ is H, $R^3$ is hydrogen, $C_1$-$C_3$ alkyl, halogen, —CN, —OH, or —NH$_2$, $R^4$ is —NH— or —NHC(O)— and $R^{10}$ is oxo, $C_1$-$C_6$ alkyl, halogen, —CN, —OR$^{11}$, —SR$^{11}$, —NR$^{11}$R$^{12}$, —CF$_3$, —C(O)R$^{11}$, —C(O)OR$^{11}$, —C(O)NR$^{11}$R$^{12}$, —NR$^{11}$C(O)R$^{12}$, —S(O)$_{1-2}$R$^{11}$, —NR$^{11}$S(O)$_{1-2}$R$^{12}$, —S(O)$_{1-2}$NR$^{11}$R$^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —CF$_3$, —OR$^{13}$, —NR$^{13}$R$^{14}$, —C(O)R$^{13}$ or —S(O)$_{1-2}$R$^{13}$.

In another embodiment, in Formulas I-III and V-VI, the portion of Formula I having the structure:

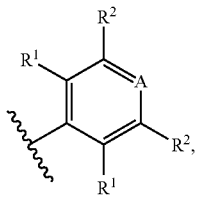

or the portion of Formulas IIa-III, V-Va or VIa-VIb having the structure

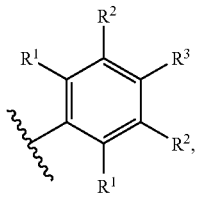

or the portion of Formulas IIIa-IIIb having the structure

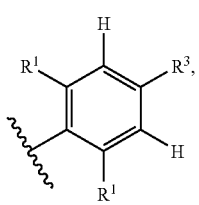

is selected from:

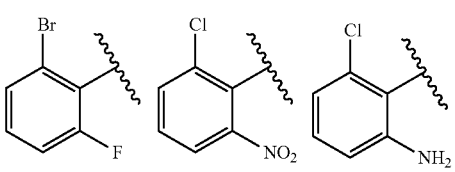

-continued

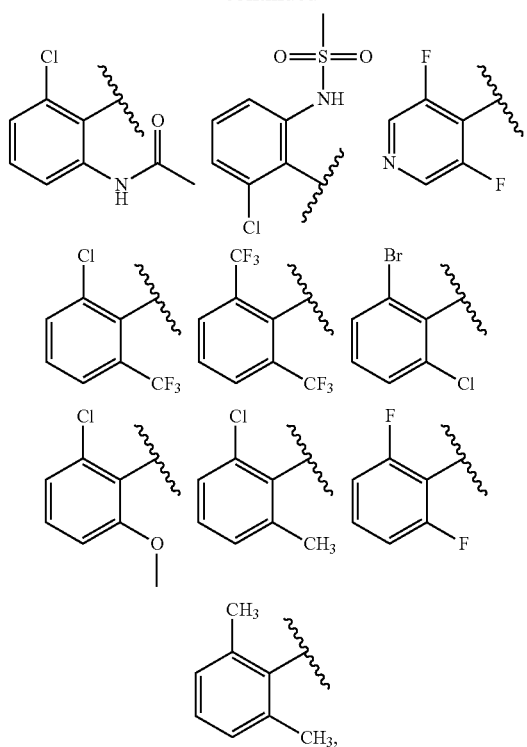

wherein the wavy lines represent the point of attachment in Formulas I-III. In another embodiment, such portion is selected from:

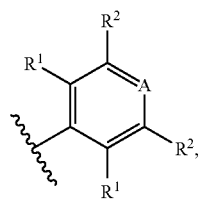

In another embodiment, in Formulas I-VI, the portion of Formula I having the structure:

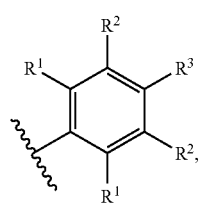

or the portion of Formulas IIa-III, V-Va or VIa-VIb having the structure

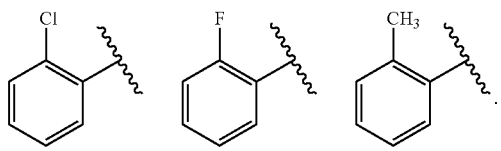

or the portion of Formulas IIIa-IIIb having the structure

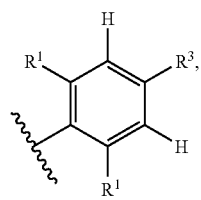

or the portion of Formulas IVa-IVb having the structure

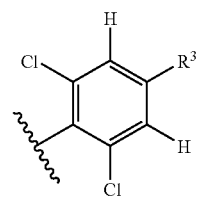

is selected from:

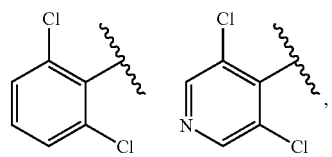 [SMILES: *c1c(Cl)cccc1Cl ; *c1c(Cl)cncc1Cl ; ","]

wherein the wavy lines represent the point of attachment in Formulas I-IV.

In another embodiment, in Formulas I-VI, the portion of Formula I having the structure:

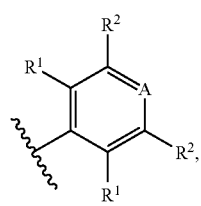

or the portion of Formulas IIa-III, V-Va or VIa-VIb having the structure

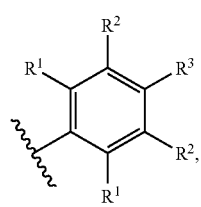

or the portion of Formulas IIIa-IIIb having the structure
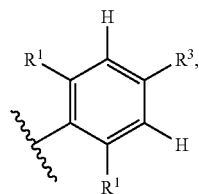
or the portion of Formulas IVa-IVb having the structure
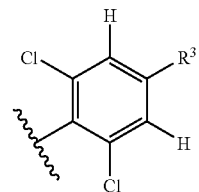
is selected from:
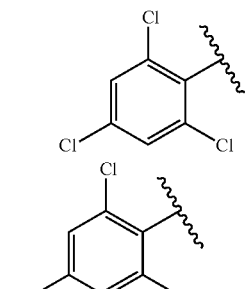 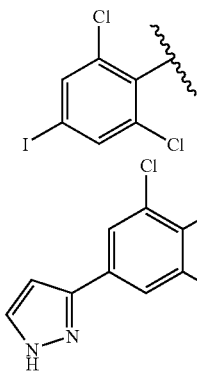
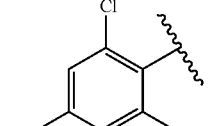 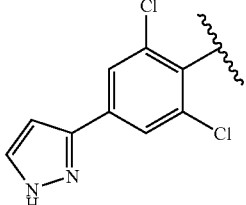
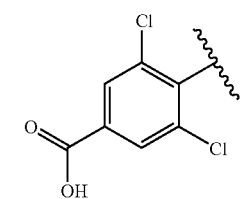 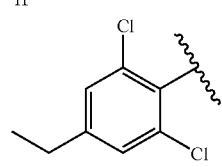
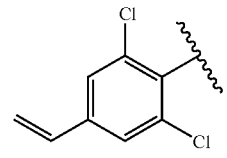 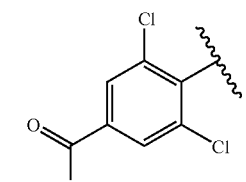
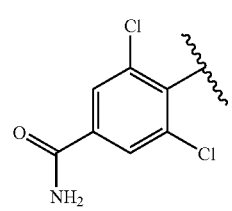 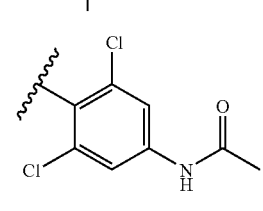
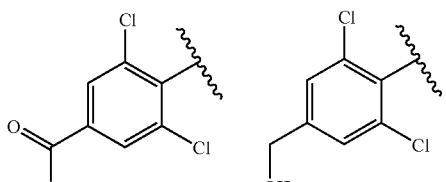 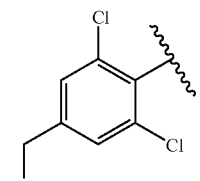
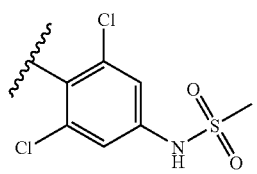 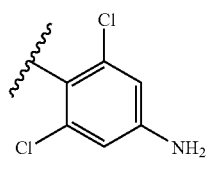
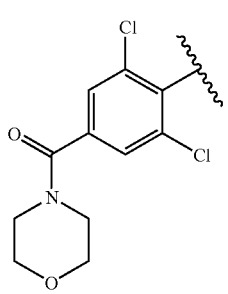 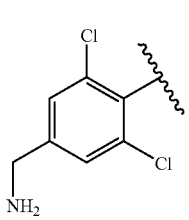
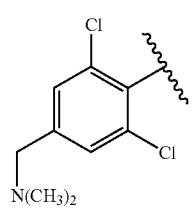 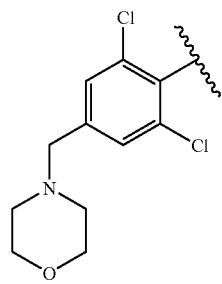
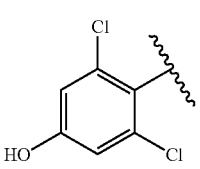 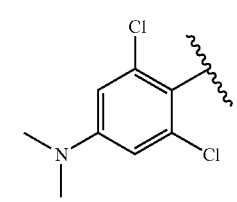
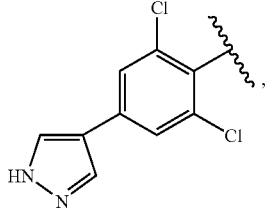
wherein the wavy lines represent the point of attachment in Formulas I-IV.

In another embodiment, in Formulas I-II and V-VI, the portion of Formula I having the structure:

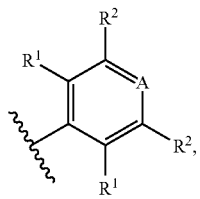

or the portion of Formulas IIa-III, V-Va or VIa-VIb having the structure

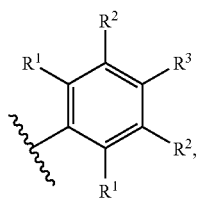

is selected from:

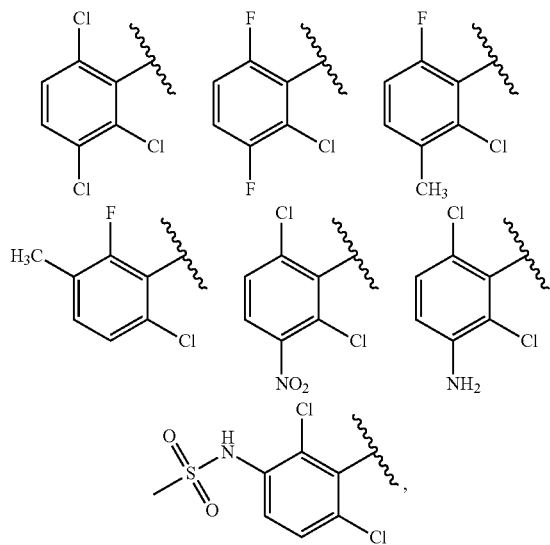

wherein the wavy lines represent the point of attachment in Formulas I-II.

In certain embodiments, $R^1$ is independently H, Cl, F, Br, —$NO_2$, —$CF_3$, —$CH_3$, —$OCH_2$-phenyl, —$NHSO_2CH_3$, —$OCH_3$, —OH, —$OCF_3$, wherein both $R^1$ cannot be H at the same time.

In certain embodiments, $R^1$ is independently halogen.
In certain embodiments, $R^2$ is H.
In certain embodiments, $R^2$ is independently H or halogen.
In certain embodiments, $R^2$ is independently H or $C_1$-$C_3$ alkyl.
In certain embodiments, $R^2$ is independently H or —$NR^8R^9$.
In certain embodiments, $R^2$ is independently H or —$OR^8$.
In certain embodiments, $R^2$ is independently H, F, Cl, methyl, ethyl, —$NHSO_2CH_3$, —$NO_2$, —$NH_2$, —NHCOCH$_3$, —$SCH_3$, —OH, —$OCH_3$ In another embodiment, in Formulas I-VI, $R^3$ is H, $C_1$-$C_6$ alkyl, $C_2$-$C_6$ alkenyl, $C_2$-$C_6$ alkynyl, halogen, —CN, —$OR^8$, —$SR^8$, —$NR^8R^9$, —$CF_3$, —$OCF_3$, —$NO_2$, —$C(O)R^8$, —$C(O)OR^8$, —$C(O)NR^8R^9$, —$NR^8C(O)R^9$, —$S(O)_{1-2}R^8$, —$NR^8S(O)_{1-2}R^9$, —$S(O)_{1-2}NR^8R^9$, $C_3$-$C_6$ cycloalkyl, 3-6-membered heterocyclyl, 5-6-membered heteroaryl or phenyl, wherein $R^3$ is independently optionally substituted by 0, 1, 2 or 3 $R^{10}$. In another embodiment, in Formulas I-VI, $R^3$ is H, halogen, —CN, —$NR^8R^9$, —$NR^8COR^9$, —$CONR^8R^9$, $C_1$-$C_6$ alkyl, 3-6-membered heterocyclyl, 5-6-membered heteroaryl, phenyl, —$SR^8$, —$OR^9$, —$CF_3$ or —$NR^8SO_2R^9$. In another embodiment, in Formulas I-VI, $R^3$ is H, halogen, —CN, —$NH_2$, —$CH_2NH_2$, —$NHCOCH_3$, —$CONH_2$, —$CH_2OH$, methyl, ethyl, ethenyl, —C(O)H, —$NO_2$, -(ethynyl)$CH_2OH$, pyrrazolyl, —$SCH_3$, —OH, —OMe, —$CF_3$ or —$NHSO_2CH_3$. In another embodiment, in Formulas I-VI, $R^3$ is H, F, Cl, —CN, —$NH_2$, —$NHCOCH_3$, —$CONH_2$, —$CH_2OH$, methyl, ethyl, ethenyl, pyrrazolyl, —$SCH_3$, —OH, —$OCH_3$, —$CF_3$ or —$NHSO_2CH_3$.

In certain embodiments, $R^3$ is H.
In certain embodiments, $R^3$ is halogen. In certain embodiments, $R^3$ is F, Cl or I.
In certain embodiments, $R^3$ is $C_1$-$C_6$ alkyl, $C_2$-$C_6$ alkenyl, $C_2$-$C_6$ alkynyl, optionally substituted by 1-3 $R^{10}$. In certain embodiments, $R^3$ is methyl, ethyl, ethenyl, 1-hydroxyethyl, 1-hydroxy-1-methylethyl, —C≡CCH$_2$OH, —$CH_2F$ or —$CF_3$.

In certain embodiments, $R^3$ is —($C_0$-$C_3$ alkyl)$OR^8$ optionally substituted by 1-3 $R^{10}$. In certain embodiments, $R^3$ is —OH, —$OCH_3$, —$OCF_3$, 1-hydroxyethyl or 1-hydroxy-1-methylethyl.

In certain embodiments, $R^3$ is —($C_0$-$C_3$ alkyl)$NR^8R^9$ optionally substituted by 1-3 $R^{10}$. In certain embodiments, $R^3$ is —$NH_2$, —NHC(O)CH$_3$, —NHC(O)O (t-butyl), —$CH_2NH_2$, $CH_2N(CH_3)_2$, —$CH_2NHCH_3$, —$CH_2NHCH_2CH_3$, —$CH_2NHCH_2CH_2OH$, —$CH_2NHCH_2CH_2CH_3$, —$CH_2NHCH(CH_3)_2$, —$CH_2NHcyclopropyl$, —$CH_2NHCH_2cyclopropyl$, —$CH_2NHC(CH_3)_3$, morpholinyl, pyrrolidinonyl or —$CH_2$-morpholinyl.

In certain embodiments, $R^3$ is —($C_0$-$C_3$ alkyl)$CF_3$ optionally substituted by 1-3 $R^{10}$. In certain embodiments, $R^3$ is —$CF_3$.

In certain embodiments, $R^3$ is —($C_0$-$C_3$ alkyl)CN optionally substituted by 1-3 $R^{10}$. In certain embodiments, $R^3$ is —CN.

In certain embodiments, $R^3$ is —($C_0$-$C_3$ alkyl)$NO_2$ optionally substituted by 1-3 $R^{10}$. In certain embodiments, $R^3$ is —$NO_2$.

In certain embodiments, $R^3$ is —$C(O)R^8$ optionally substituted by 1-3 $R^{10}$. In certain embodiments, $R^3$ is —$C(O)R^8$, wherein $R^8$ is H or $C_1$-$C_6$ alkyl optionally substituted by 1-3 $R^{10}$. In certain embodiments, $R^3$ is —C(O)H or —C(O)CH$_3$. In certain embodiments, $R^3$ is —C(O)(3-6 membered heterocyclyl) optionally substituted by 1-3 halogen, oxo or $C_1$-$C_3$ alkyl. In certain embodiments, $R^3$—C(O)morpholinyl or —C(O)(N-methylpiperizinyl).

In certain embodiments, $R^3$ is —($C_0$-$C_3$ alkyl)$C(O)OR^8$ optionally substituted by 1-3 $R^{10}$.

In certain embodiments, $R^3$ is —$CO_2H$.

In certain embodiments, $R^3$ is —($C_0$-$C_3$ alkyl)$C(O)NR^8R^9$ optionally substituted by 1-3 $R^{10}$. In certain embodiments, $R^3$ is —$CONH_2$ or —$CONMe_2$.

In certain embodiments, $R^3$ is —($C_0$-$C_3$ alkyl)$NR^8C(O)R^9$ optionally substituted by 1-3 $R^{10}$. In certain embodiments, $R^3$ is —NHCOMe.

In certain embodiments, $R^3$ is —($C_0$-$C_3$ alkyl)S(O)$_{1-2}R^8$ optionally substituted by 1-3 $R^{10}$.

In certain embodiments, $R^3$ is —SO$_2$CH$_3$.

In certain embodiments, $R^3$ is —($C_0$-$C_3$ alkyl)NR$^8$S(O)$_{1-2}R^9$ optionally substituted by 1-3 $R^{10}$. In certain embodiments, $R^3$ is —NHSO$_2$CH$_3$.

In certain embodiments, $R^3$ is —($C_0$-$C_3$ alkyl)(3-6-membered heterocyclyl) optionally substituted by 1-3 $R^{10}$. In certain embodiments, $R^3$ is morpholinyl, pyrrolidinonyl, oxazolidinonyl or —CH$_2$-morpholinyl.

In certain embodiments, $R^3$ is —($C_0$-$C_3$ alkyl)(3-6-membered heteroaryl) optionally substituted by 1-3 $R^{10}$. In certain embodiments, $R^3$ is pyrazolyl or triazolyl.

In certain embodiments, $R^3$ is H, F, Cl, I methyl, ethyl, ethenyl, 1-hydroxyethyl, 1-hydroxy-1-methylethyl, —C≡CCH$_2$OH, —CH$_2$F, —CF$_3$—OH, —OCH$_3$, —OCF$_3$—NH$_2$, —NHC(O)CH$_3$, —NHC(O)O(t-butyl), —CH$_2$NH$_2$, —CH$_2$N(CH$_3$)$_2$, —CH$_2$NHCH$_3$, —CH$_2$NHCH$_2$CH$_3$, —CH$_2$NHCH$_2$CH$_2$OH, —CH$_2$NHCH$_2$CH$_2$CH$_3$, —CH$_2$NHCH(CH$_3$)$_2$, —CH$_2$NHcyclopropyl, —CH$_2$NHCH$_2$cyclopropyl, —CH$_2$NHC(CH$_3$)$_3$, —CH$_2$-morpholinyl, —CN, —NO$_2$—C(O)H, —C(O)CH$_3$, —C(O)morpholinyl, —C(O)(N-methylpiperizinyl), —CO$_2$H, —CONH$_2$, —CONMe$_2$, —NHCOMe, —SO$_2$CH$_3$, —NHSO$_2$CH$_3$, morpholinyl, pyrrolidinonyl, oxazolidinonyl, —CH$_2$-morpholinyl, pyrazolyl or triazolyl.

In certain embodiments, $R^4$ is H, —NH$_2$, —NH—, —NHC(O)—, —NHC(O)O— or NHC(O)NR$^7$—. In certain embodiments, $R^4$ is H. In certain embodiments, $R^4$ is —NH$_2$, —NH— or —NHC(O)—. In certain embodiments, $R^4$ is —NHC(O)—.

In another embodiment, in Formulas I-IV and VI, $R^5$ is methyl, ethyl, propyl, iso-propyl, tert-butyl, cyclopropyl, cyclobutyl, cyclopentyl, cyclohexyl, azetidinyl, oxetanyl, tetrahydrofuranyl, diazepanyl, pyrrolidinyl, phenyl, pyridinyl, pyrimidinyl, pyridazinyl, pyrazinyl, triazinyl, thienyl, pyrazolyl, pyranyl, triazolyl, isoxazolyl, oxazolyl, imidazolyl, thiazolyl or thiadiazolyl, wherein $R^5$ is optionally substituted by 1, 2 or 3 $R^{10}$.

In another embodiment, in Formulas I-IV and $V^1$, $R^5$ is $C_1$-$C_6$ alkyl or $C_3$-$C_6$ cycloalkyl, wherein $R^5$ is optionally substituted by $R^{10}$, wherein $R^{10}$ is oxo, $C_1$-$C_6$ alkyl, halogen, —CN, —OR$^{11}$, —SR$^{11}$, —NR$^{11}R^{12}$, —CF$_3$, —C(O)R$^{11}$, —C(O)OR$^{11}$, —C(O)NR$^{11}R^{12}$, —NR$^{11}$C(O)R$^{12}$, —S(O)$_{1-2}R^{11}$, —NR$^{11}$S(O)$_{1-2}R^{12}$, —S(O)$_{1-2}$NR$^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —CF$_3$, —OR$^{13}$, —NR$^{13}R^{14}$, C(O)R$^{13}$ or —S(O)$_{1-2}R^{13}$. In an example, $R^5$ is methyl, ethyl, propyl, iso-propyl, tert-butyl, cyclopropyl, cyclobutyl, cyclopentyl or cyclohexyl, wherein $R^5$ is optionally substituted by 1, 2 or 3 $R^{10}$. In an example, $R^5$ is sec-butyl optionally substituted by 1, 2 or 3 $R^{10}$. In one embodiment, $R^5$ is cyclopropyl optionally substituted by halogen, CH$_2$OH, methyl, CH$_2$NH$_2$, CF$_3$ or C(O)OH. In an example, $R^5$ is 2-fluorocycloprop-1-yl. In an example, $R^5$ is 3-fluorocyclobut-1-yl.

In another embodiment, in Formulas I-IV and VI, $R^5$ or —$R^5$—($R^{10}$)$_n$ is selected from:

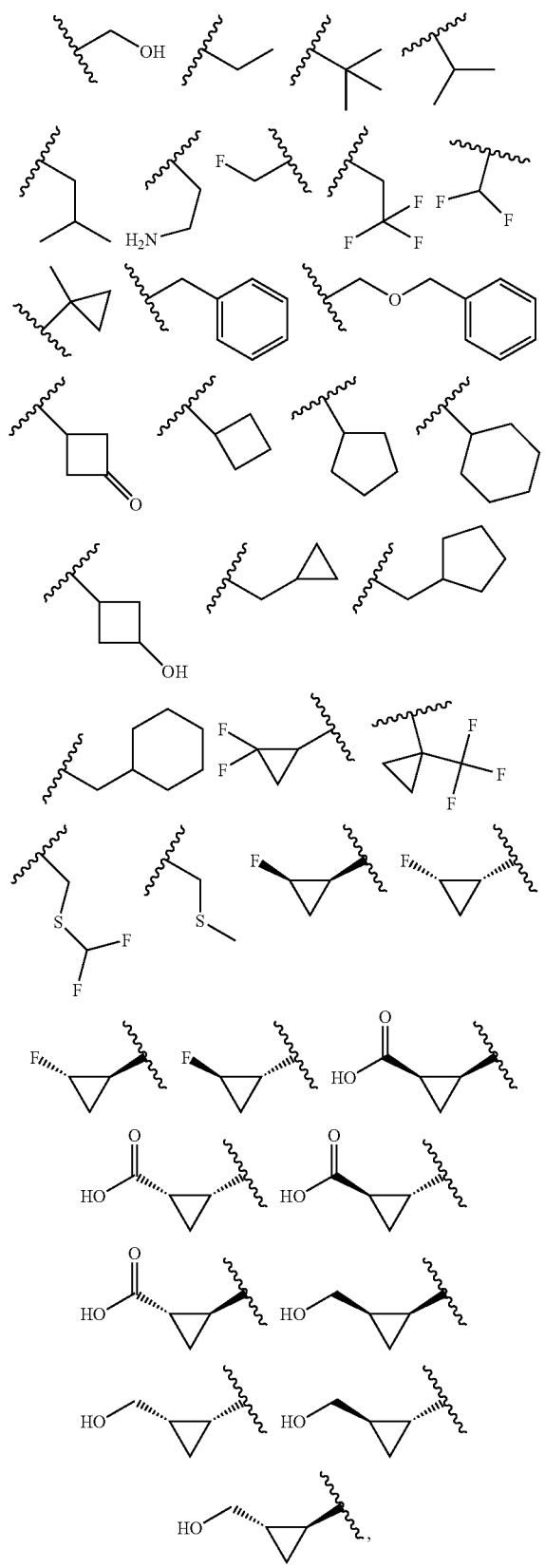

wherein the wavy lines represent the point of attachment in Formulas I-IV.

In another embodiment, in Formulas I-IV and VI, $R^5$ or $—R^5—(R^{10})_n$ is selected from:
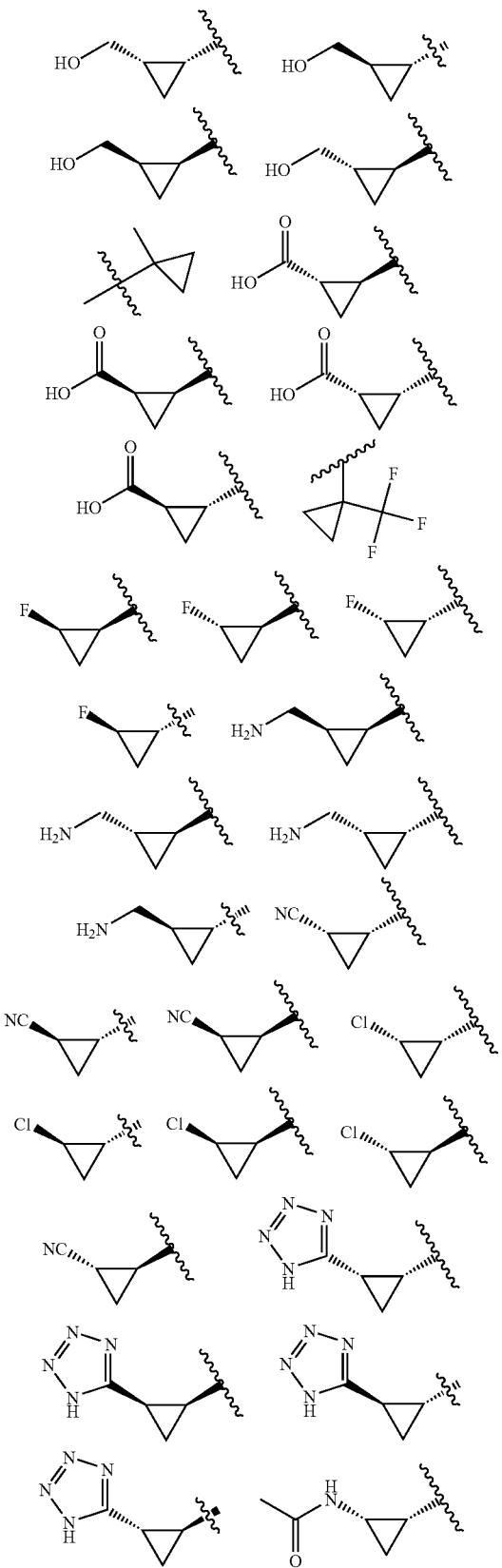
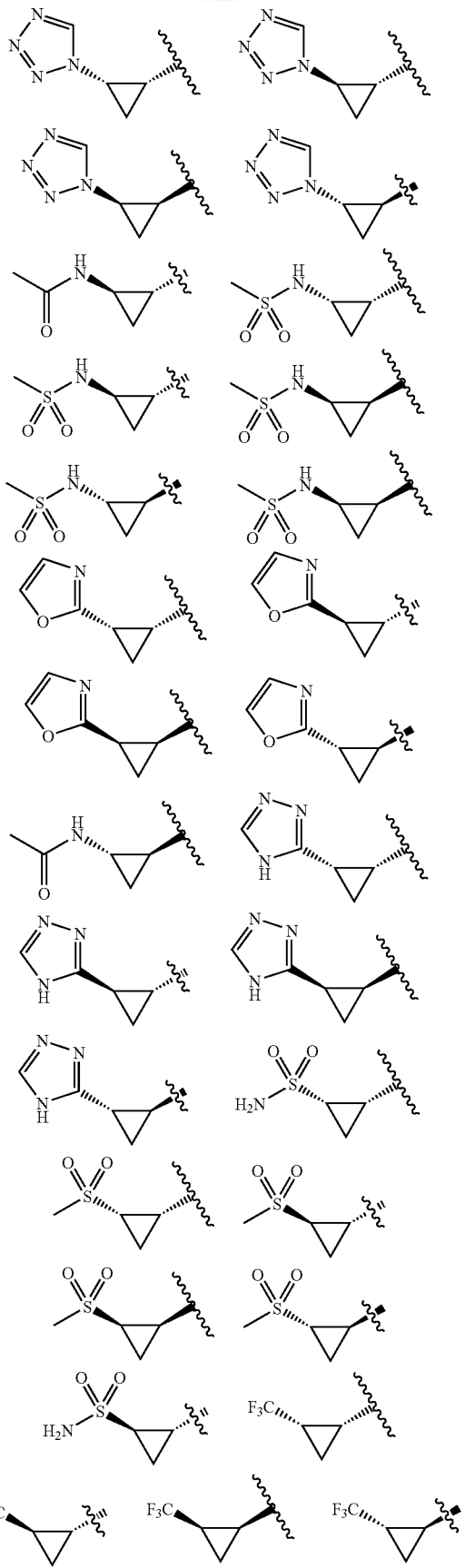

-continued

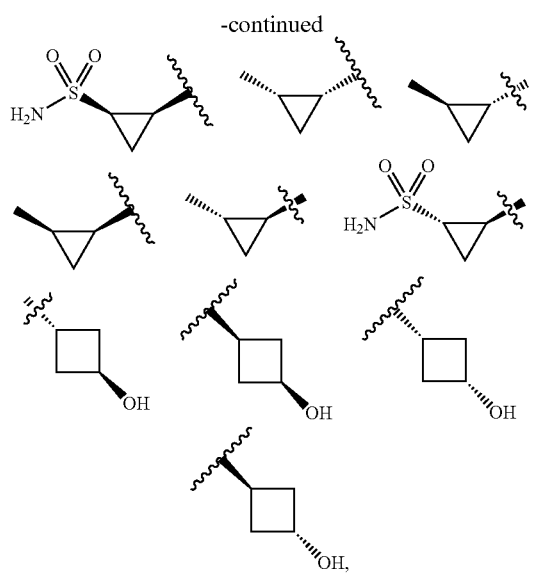

wherein the wavy lines represent the point of attachment in Formulas I-IV.

In another embodiment, in Formulas I-IV and $V^1$, $R^5$ or —$R^5$—$(R^{10})_n$ is selected from:

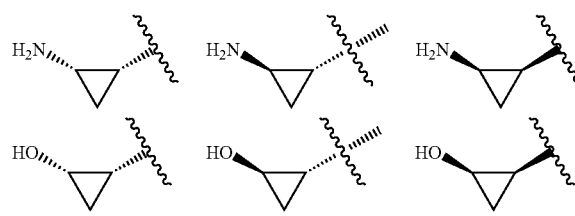

wherein the wavy lines represent the point of attachment in Formulas I-IV.

In another embodiment, in Formulas I-IV and $V^1$, $R^5$ or —$R^5$—$(R^{10})_n$ is selected from:

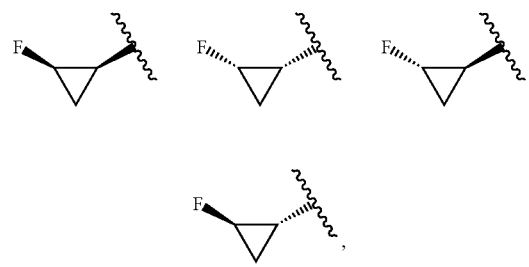

wherein the wavy lines represent the point of attachment in Formulas I-IV.

In another embodiment, in Formulas I-IV and VI, $R^5$ is 3-7-membered heterocyclyl, wherein $R^5$ is optionally substituted by $R^{10}$, wherein $R^{10}$ is oxo, $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$. In an example, $R^5$ is azetidinyl, tetrahydrofuranyl, diazepanyl, oxetanyl or pyrrolidinyl, wherein $R^5$ is optionally substituted by 1, 2 or 3 $R^{10}$. In an example, $R^5$ is tetrahydropyranyl, 1,1-dioxotetrahydrothienyl, pyrimidinonyl or dihydrooxazolyl, wherein $R^5$ is optionally substituted by 1, 2 or 3 $R^{10}$.

In another embodiment, in Formulas I-IV and VI, $R^5$ or —$R^5$—$(R^{10})_n$ is selected from:

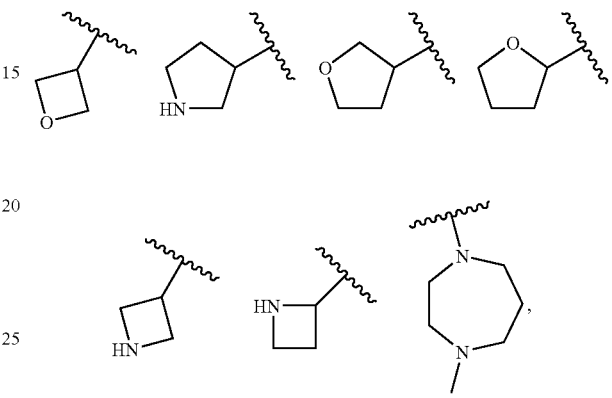

wherein the wavy lines represent the point of attachment in Formulas I-IV.

In another embodiment, in Formulas I-IV and VI, $R^5$ or —$R^5$—$(R^{10})_n$ is selected from:

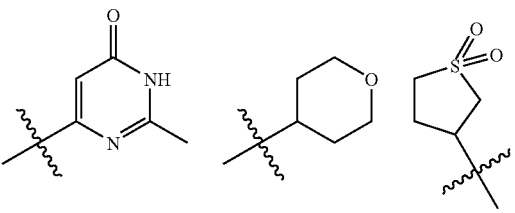

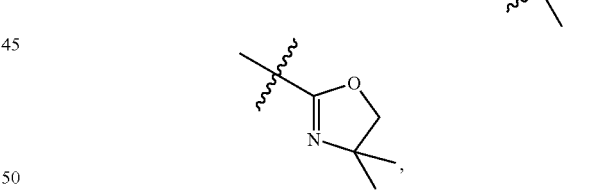

wherein the wavy lines represent the point of attachment in Formulas I-IV.

In another embodiment, in Formulas I-IV, $R^5$ is phenyl, wherein $R^5$ is optionally substituted by $R^{10}$, wherein $R^{10}$ is $C_1$-$C_6$ alkyl, halogen, —CN, —$OR^{11}$, —$SR^{11}$, —$NR^{11}R^{12}$, $CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$. In another embodiment, $R^5$ is phenyl, optionally substituted by 1, 2 or 3 $R^{10}$.

In another embodiment, in Formulas I-IV, $R^5$ or —$R^5$—$(R^{10})_n$ is selected from:

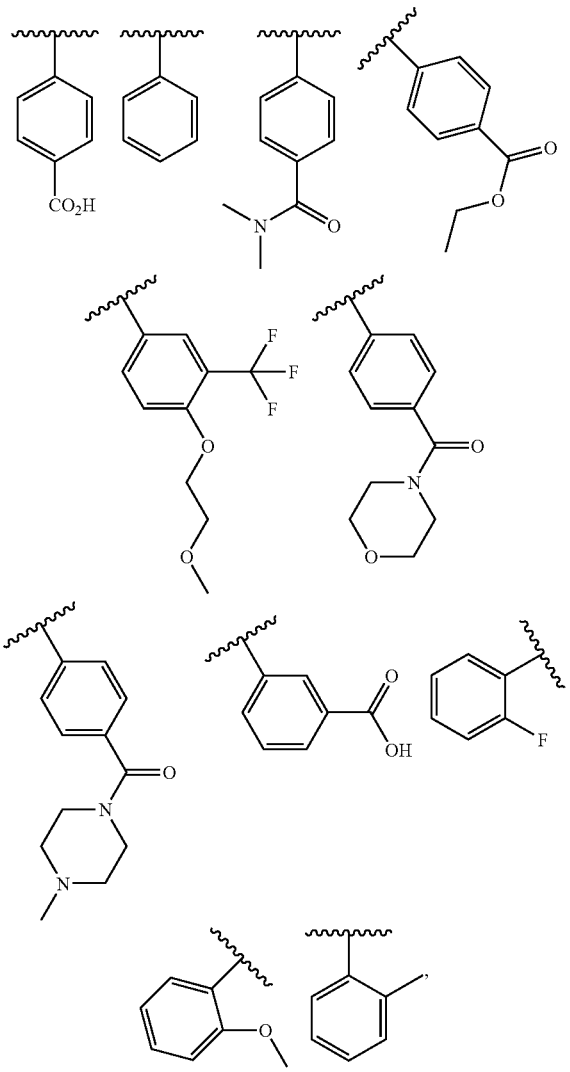

wherein the wavy lines represent the point of attachment in Formulas I-IV.

In another embodiment, in Formulas I-IV, $R^5$ is 5-6-membered heteroaryl, wherein $R^5$ is optionally substituted by $R^{10}$, wherein $R^{10}$ is $C_1$-$C_6$ alkyl, halogen, —CN, —$OR^{11}$, —$SR^{11}$, —$NR^{11}R^{12}$, —$CF_3$, —$C(O)R^{11}$—$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cyclo alkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$. In an example, $R^5$ is pyridinyl, pyrimidinyl, pyridazinyl, pyrazinyl, triazinyl, thienyl, pyrazolyl, pyranyl, triazolyl, isoxazolyl, oxazolyl, imidazolyl, thiazolyl or thiadiazolyl, wherein $R^5$ is optionally substituted by 1, 2 or 3 $R^{10}$. In an example, $R^5$ is quinolinyl, isoquinolinyl, wherein $R^5$ is optionally substituted by 1, 2 or 3 $R^{10}$.

In another embodiment, in Formulas I-IV, $R^5$ is pyridinyl, optionally substituted by $R^{10}$, wherein $R^{10}$ is $C_1$-$C_6$ alkyl, $C_2$-$C_6$ alkenyl, $C_2$-$C_6$ alkynyl, halogen, —$(C_0$-$C_3$ alkyl)CN, —$(C_0$-$C_3$ alkyl)$OR^{11}$, —$(C_0$-$C_3$ alkyl)$SR^{11}$, —$(C_0$-$C_3$ alkyl)$NR^{11}R^{12}$, —$(C_0$-$C_3$ alkyl)$CF_3$, —$(C_0$-$C_3$ alkyl)$NO_2$, —$(C_0$-$C_3$ alkyl)$C(O)R^{11}$, —$(C_0$-$C_3$ alkyl)$C(O)OR^{11}$, —$(C_0$-$C_3$ alkyl)$C(O)NR^{11}R^{12}$, —$(C_0$-$C_3$ alkyl)$NR^{11}C(O)R^{12}$, —$(C_0$-$C_3$ alkyl)$S(O)_{1-2}R^{11}$, —$(C_0$-$C_3$ alkyl)$NR^{11}S(O)_{1-2}R^{12}$, —$(C_0$-$C_3$ alkyl)$S(O)_{1-2}NR^{11}R^{12}$, —$(C_0$-$C_3$ alkyl)$(C_3$-$C_6$ cycloalkyl), —$(C_0$-$C_3$ alkyl)(3-6-membered heterocyclyl), —$(C_0$-$C_3$ alkyl)$C(O)$(3-6-membered heterocyclyl), —$(C_0$-$C_3$ alkyl)(5-6-membered heteroaryl) or —$(C_0$-$C_3$ alkyl)phenyl, wherein $R^{10}$ is independently optionally substituted by halogen, $C_1$-$C_3$ alkyl, oxo, —$CF_3$, —$(C_0$-$C_3$ alkyl)$OR^{13}$, —$(C_0$-$C_3$ alkyl)$NR^{13}R^{14}$, —$(C_0$-$C_3$ alkyl)$C(O)R^{13}$ or —$(C_0$-$C_3$ alkyl)$S(O)_{1-2}R^{13}$. In an example, $R^5$ is pyridinyl, optionally substituted by 1, 2 or 3 $R^{10}$, and wherein $R^{10}$ is $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$.

In another embodiment, in Formulas I-IV, $R^5$ or —$R^5$—$(R^{10})$— is selected from:

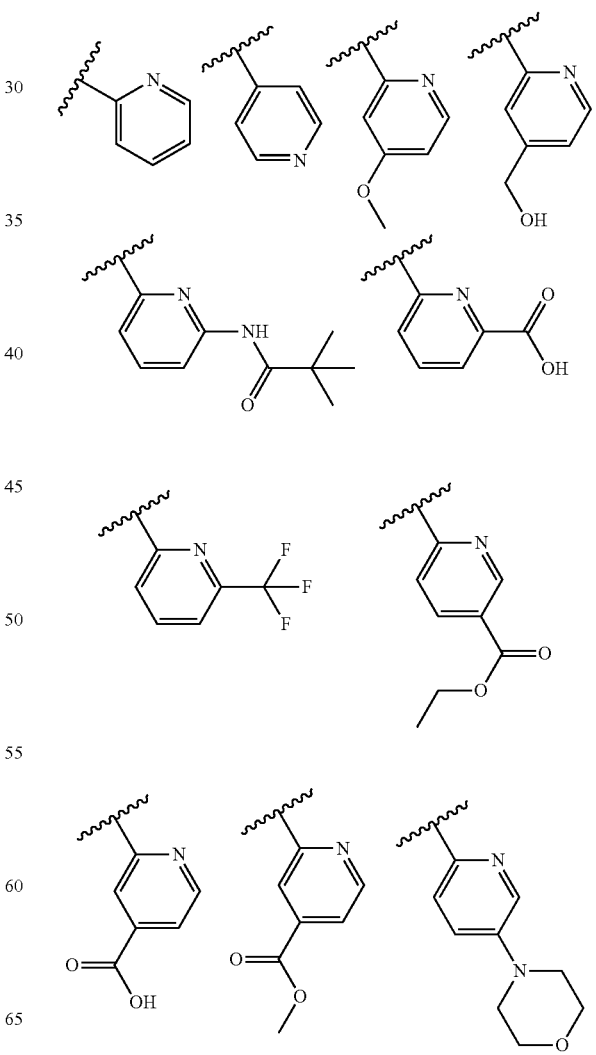

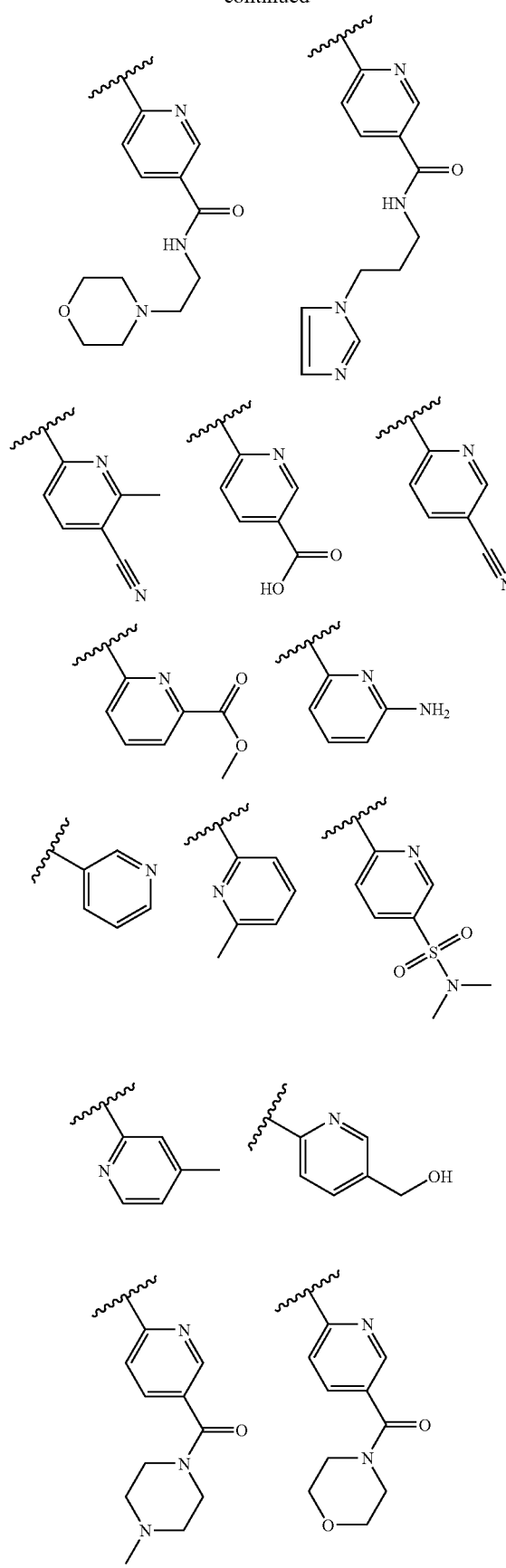
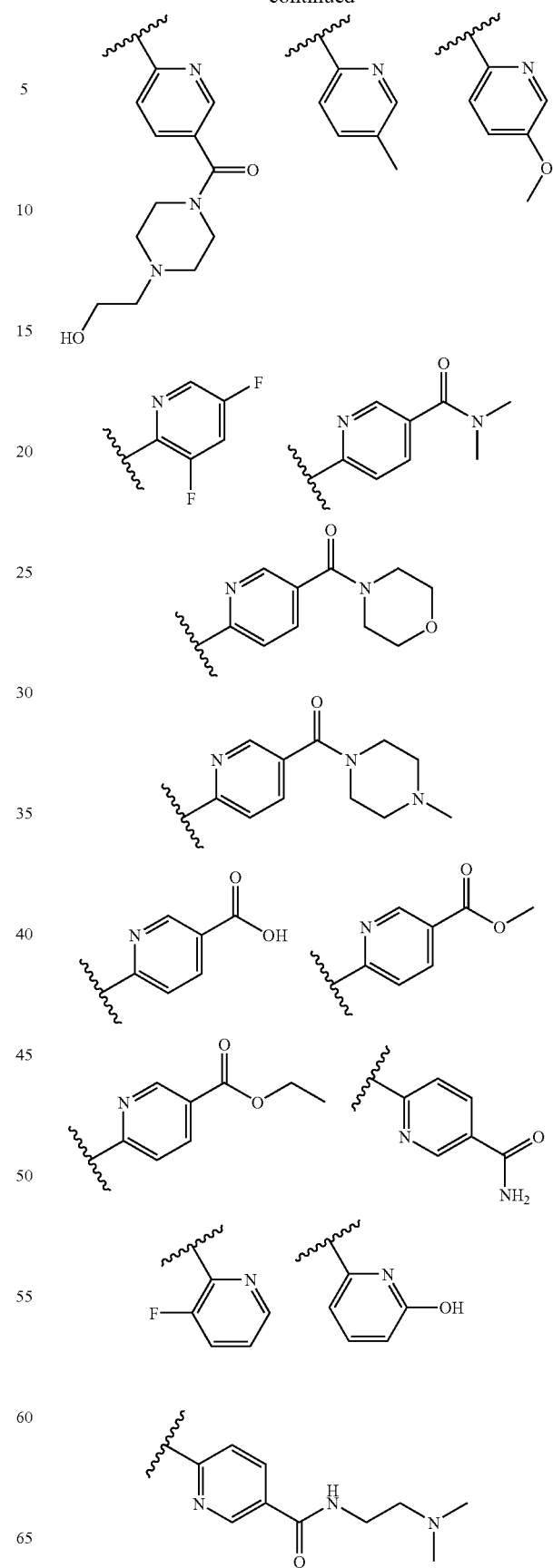

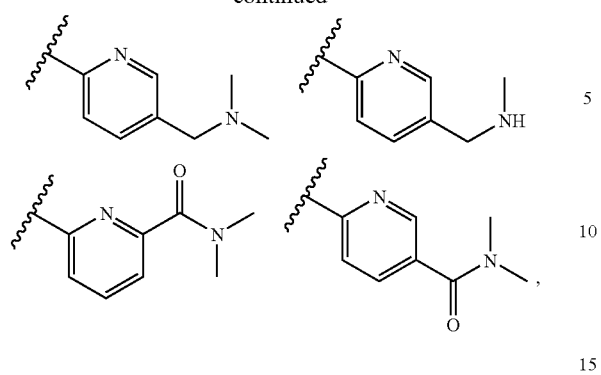

wherein the wavy lines represent the point of attachment in Formulas I-IV.

In another embodiment, in Formulas I-IV, $R^5$ is pyrimidinyl, pyridazinyl, or pyrazinyl, optionally substituted by $R^{10}$, wherein $R^{10}$ is $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)OR$^{11}$, —($C_0$-$C_3$ alkyl)SR$^{11}$, —($C_0$-$C_3$ alkyl)NR$^{11}$R$^{12}$, —($C_0$-$C_3$ alkyl) CF$_3$, —($C_0$-$C_3$ alkyl)NO$_2$, —($C_0$-$C_3$ alkyl)C(O)R$^{11}$, —($C_0$-$C_3$ alkyl)C(O)OR$^{11}$, —($C_0$-$C_3$ alkyl)C(O)NR$^{11}$R$^{12}$, —($C_0$-$C_3$ alkyl)NR$^{11}$C(O)R$^{12}$, —($C_0$-$C_3$ alkyl) S(O)$_{1-2}$R$^{11}$, —($C_0$-$C_3$ alkyl)NR$^{11}$S(O)$_{1-2}$R$^{12}$, —($C_0$-$C_3$ alkyl)S(O)$_{1-2}$NR$^{11}$R$^{12}$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), —($C_0$-$C_3$ alkyl)(5-6-membered heteroaryl) or —($C_0$-$C_3$ alkyl)phenyl, wherein $R^{10}$ is independently optionally substituted by halogen, $C_1$-$C_3$ alkyl, oxo, —CF$_3$, —($C_0$-$C_3$ alkyl)OR$^{13}$, —($C_0$-$C_3$ alkyl) NR$^{13}$R$^{14}$, —($C_0$-$C_3$ alkyl)C(O)R$^{13}$ or —($C_0$-$C_3$ alkyl) S(O)$_{1-2}$R$^{13}$. In an example, $R^5$ is pyrimidinyl, pyridazinyl, or pyrazinyl, optionally substituted by 1, 2 or 3 $R^{10}$, and wherein $R^{10}$ is $C_1$-$C_6$ alkyl, halogen, —CN, —OR$^{11}$, —SR$^{11}$, —NR$^{11}$R$^{12}$, —CF$_3$, —C(O)R$^{11}$, —C(O)OR$^{11}$, —C(O) NR$^{11}$R$^{12}$, —NR$^{11}$C(O)R$^{12}$, —S(O)$_{1-2}$R$^{11}$, —NR$^{11}$ S(O)$_{1-2}$R$^{12}$, —S(O)$_{1-2}$NR$^{11}$R$^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —CF$_3$, —OR$^{13}$, —NR$^{13}$R$^{14}$, —C(O)R$^{13}$ or —S(O)$_{1-2}$R$^{13}$.

In another embodiment, in Formulas I-IV, $R^5$ or —$R^5$—($R^{10}$)$_n$ is selected from:

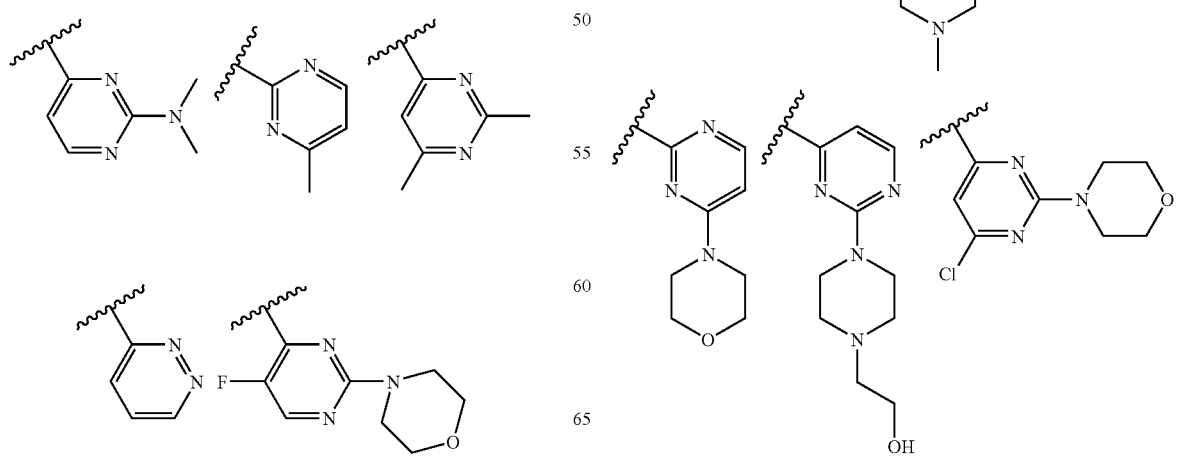

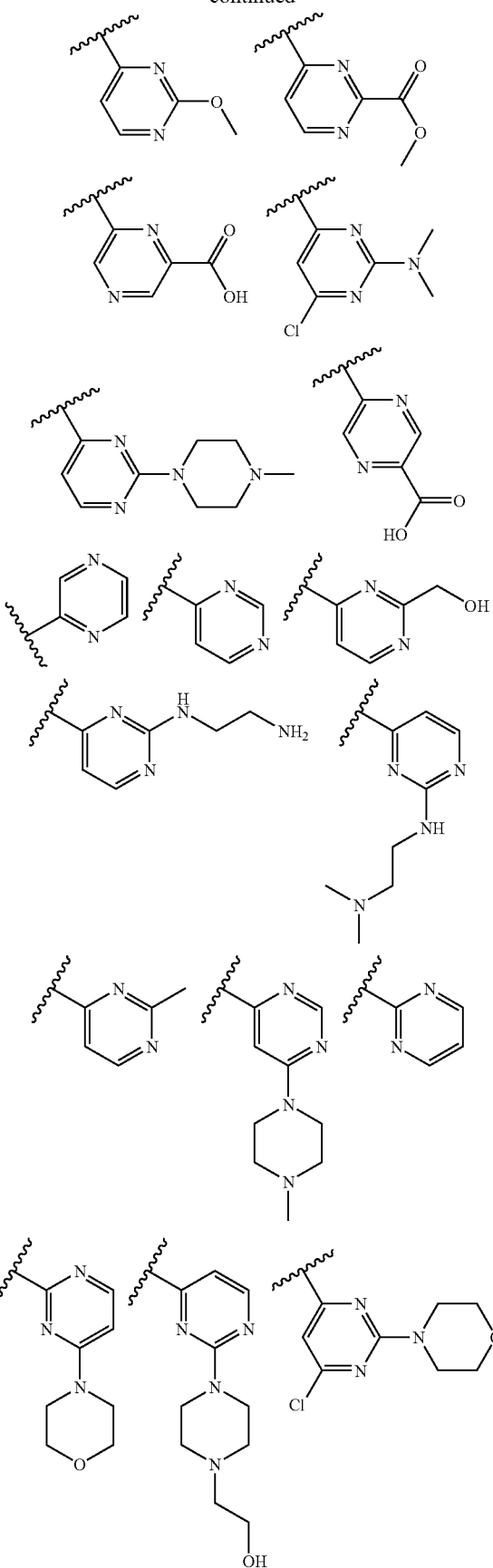

-continued
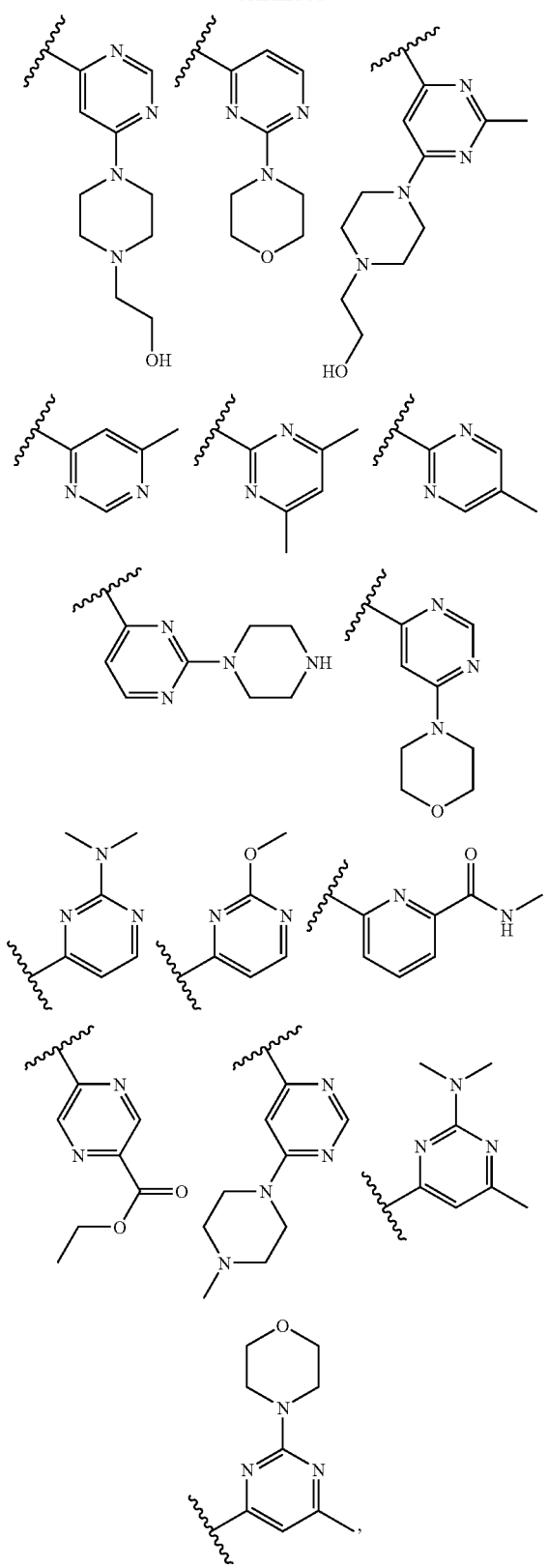
wherein the wavy lines represent the point of attachment in Formulas I-IV.
In certain embodiments, $R^5$ or $—R^5—(R^{10})_n$ is selected from:
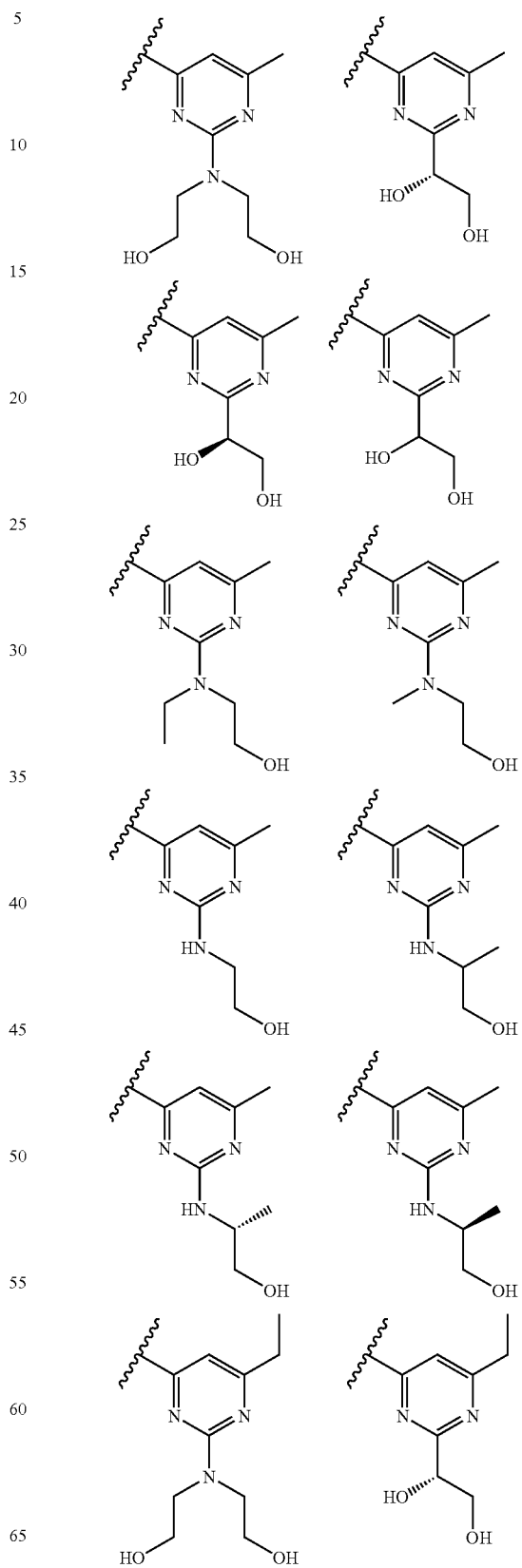

55
-continued
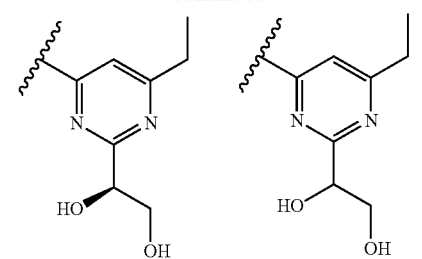
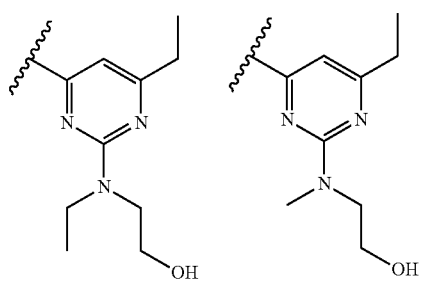
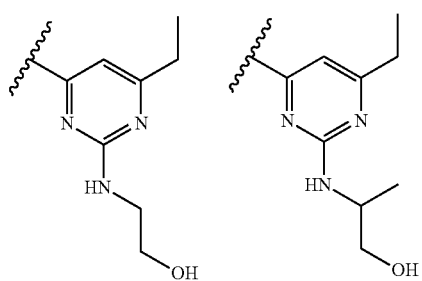
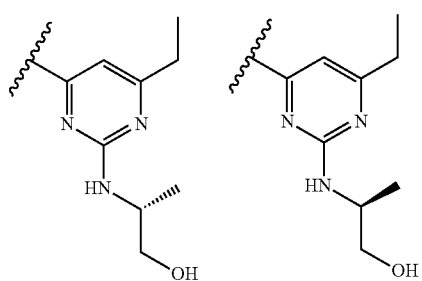
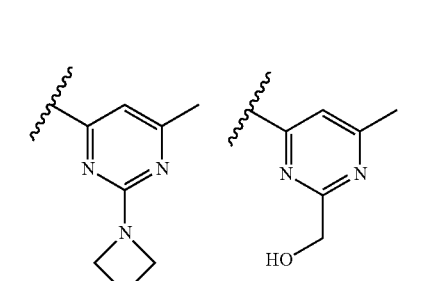
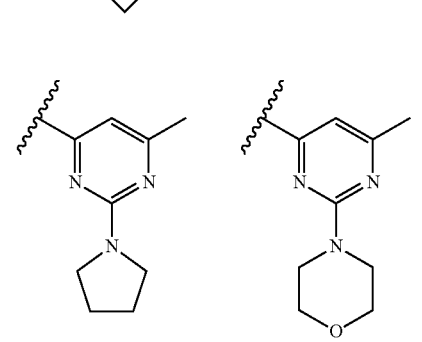
56
-continued
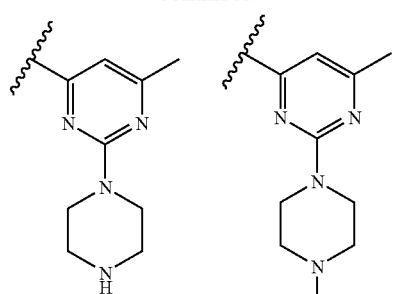
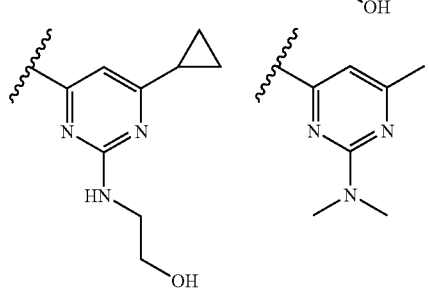
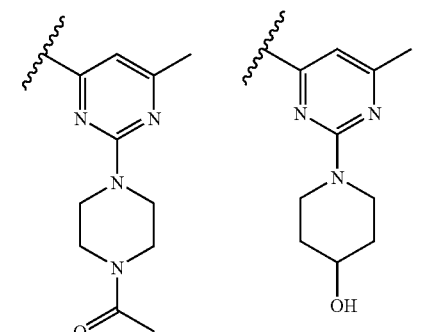
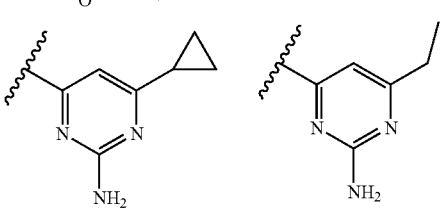
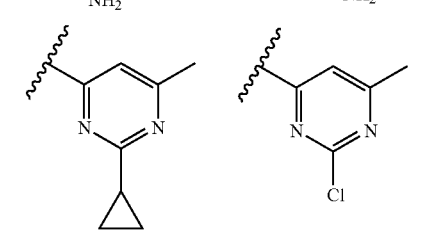
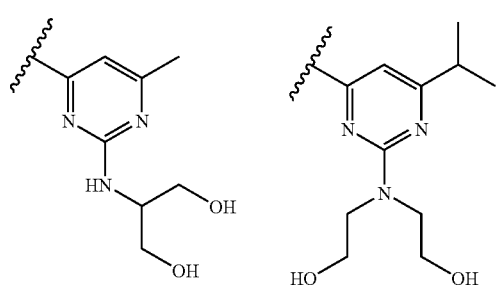

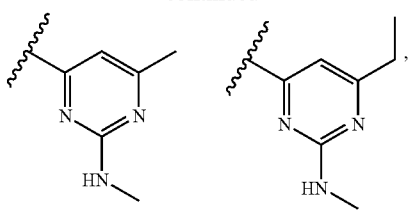
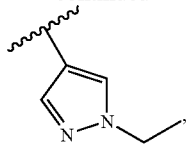

wherein the wavy lines represent the point of attachment in Formulas I-IV.

In another embodiment, in Formulas I-IV, $R^5$ is thienyl, pyrazolyl, pyranyl, triazolyl, isoxazolyl, oxazolyl, imidazolyl, thiazolyl or thiadiazolyl, wherein $R^5$ is optionally substituted by $R^{10}$, wherein $R^{10}$ is $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$.

In another embodiment, in Formulas I-IV, $R^5$ or —$R^5$—$(R^{10})_n$ is selected from:

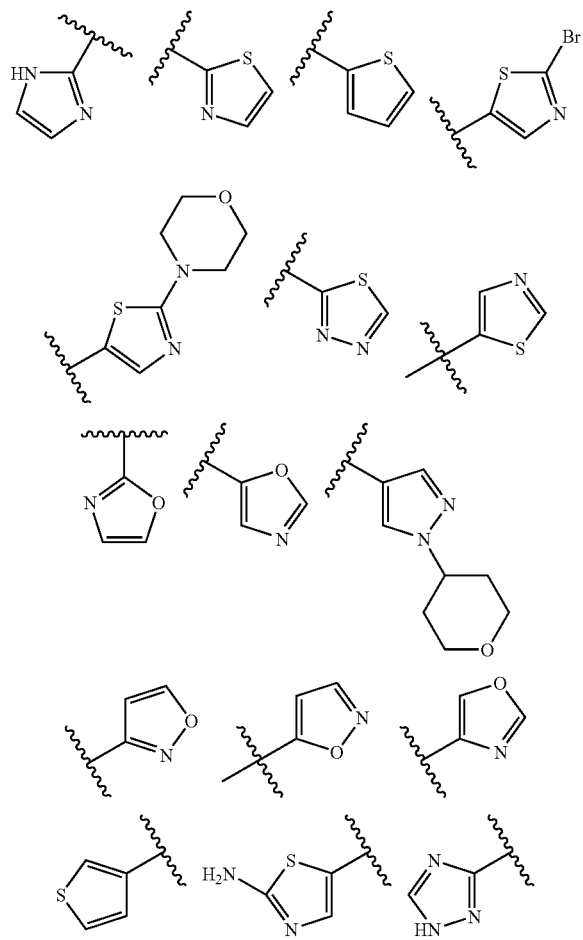

wherein the wavy lines represent the point of attachment in Formulas I-IV.

In another embodiment, in Formulas I-VII, $R^{10}$ is a 3-9-membered heterocyclyl, optionally substituted by $C_1$-$C_3$ alkyl, halogen, oxo, —$CF_3$, —$OR^{11}$, —$S(O)_{1-2}R^{11}$, —$S(O)_{1-2}NR^{11}R^{12}$, —$C(O)R^{11}$, —$C(O)OR^{11}$ or —$C(O)NR^{11}R^{12}$. In an example, $R^{10}$ is azetidinyl, oxetanyl, diazepanyl, tetrahydrofuranyl or pyrrolidinyl, piperazinyl, imidazolidinyl, 3-azabicyco[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl or azabicyclo[2.2.2]hexanyl, optionally substituted by $C_1$-$C_3$ alkyl, halogen, oxo, —$CF_3$, —$OR^{11}$, —$S(O)_{1-2}R^{11}$, —$S(O)_{1-2}NR^{11}R^{12}$, —$C(O)R^{11}$, —$C(O)OR^{11}$ or —$R^{12}$. In an example, $R^{10}$ is morpholinyl optionally substituted by $C_1$-$C_3$ alkyl.

In another embodiment, in Formulas I-VII, $R^{10}$ is a $C_1$-$C_6$ alkyl optionally substituted by 1-3 substituents independently selected from halogen, oxo, —$CF_3$, —$OR^{11}$, —$S(O)_{1-2}R^{11}$, —$S(O)_{1-2}NR^{11}R^{12}$, —$C(O)R^{11}$, —$C(O)OR^{11}$ and —$C(O)NR^{11}R^{12}$.

In another embodiment, in Formulas I-VII, $R^{10}$ is a —($C_0$-$C_3$ alkyl)$NR^{11}R^{12}$ optionally substituted by 1-3 substituents independently selected from halogen, oxo, —$CF_3$, —$OR^{11}$, —$S(O)_{1-2}R^{11}$, —$S(O)_{1-2}NR^{11}R^{12}$, —$C(O)R^{11}$, —$C(O)OR^{11}$ and —$C(O)NR^{11}R^{12}$.

In certain embodiments, $R^{10}$ is halogen. In certain embodiments, $R^{10}$ is fluoro.

In certain embodiments, $R^{11}$ and $R^{12}$ are independently H, $C_1$-$C_6$ alkyl, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)(5-6-membered heteroaryl) or —($C_0$-$C_3$ alkyl)phenyl, optionally substituted by halogen, oxo, —$OR^{13}$, —$NR^{13}R^{14}$, $C_1$-$C_3$ alkyl, —($C_0$-$C_3$ alkyl)($C_3$-$C_6$ cycloalkyl), —($C_0$-$C_3$ alkyl) phenyl, —($C_0$-$C_3$ alkyl)(3-6-membered heterocyclyl) or —($C_0$-$C_3$ alkyl)(5-6-membered heteroaryl).

In certain embodiments, $R^{11}$ and $R^{12}$ are independently H or $C_1$-$C_6$ alkyl.

In certain embodiments, $R^{11}$ and $R^{12}$ are taken together with the atom to which they attached to form a 3-6 membered heterocyclyl, optionally substituted by halogen, oxo, —$NR^{13}R^{14}$ or $C_1$-$C_3$ alkyl.

In certain embodiments, $R^{13}$ and $R^{14}$ are independently H, $C_1$-$C_6$ alkyl, OH or $OCH_3$, optionally substituted by halogen, —$NH_2$, —$N(CH_3)_2$, phenyl or oxo, wherein said phenyl is optionally substituted by halogen, $C_1$-$C_6$ alkyl, $CF_3$, —$NR^aR^b$ or $OR^a$.

In certain embodiments, $R^{13}$ and $R^{14}$ are independently H or $C_1$-$C_6$ alkyl.

In certain embodiments, $R^{13}$ and $R^{14}$ are taken together with the atom to which they are attached to form a 3-6 membered heterocyclyl, optionally substituted by halogen, oxo, —$NH_2$, —$N(CH_3)_2$ or $C_1$-$C_3$ alkyl;

In certain embodiments, $R^{15}$ is independently H, halogen, $C_1$-$C_3$ alkyl, $C_1$-$C_3$ alkenyl, $C_1$-$C_3$ alkynyl, $C_3$-$C_4$ cycloalkyl, —$CF_3$, —$OR^a$, —$SR^a$, —CN, —$NO_2$, —$NR^aSO_2R^b$, —$NR^aC(O)R^b$ or —$NR^aR^b$.

In certain embodiments, $R^{15}$ is independently H, halogen, —$NO_2$, $C_1$-$C_3$ alkyl or —$NR^aR^b$.

In certain embodiments, $R^{15}$ is independently H, F, Cl, —$CH_3$, —$NO_2$ or —$NH_2$.

In certain embodiments, $R^{15}$ is independently H or F.

In certain embodiments, $R^{15}$ is independently H.

In certain embodiments, $R^a$ and $R^b$ are independently H or $C_1$-$C_6$ alkyl optionally substituted by halogen or oxo.

In certain embodiments, $R^a$ and $R^b$ are taken together with the atom to which they are attached to form a 3-6 membered heterocyclyl, optionally substituted by halogen, oxo or $C_1$-$C_3$ alkyl.

In another embodiment, in Formula I, A is $CR^3$; B and D are CH; $R^1$ is H, —$OCH_3$, —$CF_3$, —$CH_3$, Cl or F, wherein both $R^1$ cannot be H at the same time; $R^2$ is H; $R^3$ is H, halogen, $C_1$-$C_3$ alkyl optionally substituted by —$OR^{11}$, or —CN; $R^4$ is —NH—, NHC(O)—, NHC(O)NH— or —NHC(O)O—; and $R^5$ is methyl, cyclopropyl, cyclobutyl, pyrimidinyl, pyridinyl, pyridazinyl, pyrazinyl, pyrazolyl, oxazolyl, thienyl or phenyl.

Another embodiment includes a compound selected from Examples 1-618, stereoisomers or a pharmaceutically acceptable salt thereof. Another embodiment includes a compound selected from Examples 1-11, 14-20, 22, 24, 26-54, 56, 58-65, 68-70, 72, 74-80, 82-165, 168, 173-185, 188-196 and 198-618, stereoisomers or a pharmaceutically acceptable salt thereof.

The compounds of Formulas I-VII may contain asymmetric or chiral centers, and, therefore, exist in different stereoisomeric forms. It is intended that all stereoisomeric forms of the compounds of Formulas I-VII, including but not limited to: diastereomers, enantiomers, and atropisomers as well as mixtures thereof such as racemic mixtures, form part of the present invention. In addition, the present invention embraces all geometric and positional isomers. For example, if a compound of Formulas I-VII incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of Formulas I-VII (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of Formulas I-VII may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of Formulas I-VII, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of Formulas I-VII include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of Formulas I-VII (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of Formulas I-VII can generally be prepared by following procedures analogous to those disclosed in the Schemes and/or in the Examples herein below, by substituting an isotopically labeled reagent for a non-isotopically labeled reagent.

Synthesis of Janus Kinase Inhibitor Compounds

Compounds of Formulas I-VII may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984.

Compounds of Formulas I-VII may be prepared singly or as compound libraries comprising at least 2, for example 5 to 1,000 compounds, or 10 to 100 compounds of Formulas I-VII. Libraries of compounds of Formulas I-VII may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formulas I-VII, enantiomers, diasteriomers or pharmaceutically acceptable salts thereof.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from commercially available starting materials using the general methods illustrated herein.

For illustrative purposes, reaction Schemes 1-7 depicted below provide routes for synthesizing the compounds of Formulas I-VII, as well as key intermediates. For a more detailed description of the individual reaction steps, see the Examples section below. Those skilled in the art will appreciate that other synthetic routes may be available and used to synthesize compounds of Formulas I-VII. Although specific starting materials and reagents are depicted in the Schemes and discussed below, other starting materials and reagents may be available for substitution to provide a variety of derivatives and/or reaction conditions. In addition, many of the compounds prepared by the methods described below can be further modified in light of this disclosure using conventional chemistry well known to those skilled in the art.

SCHEME 1

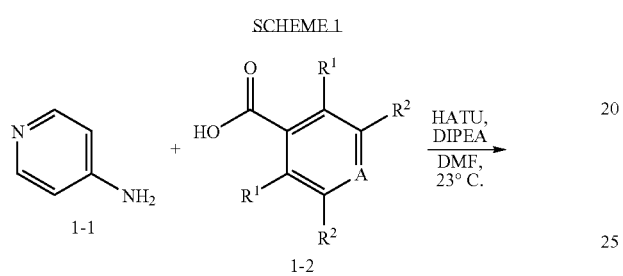

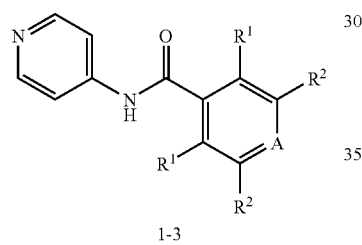

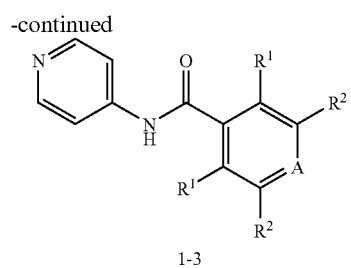

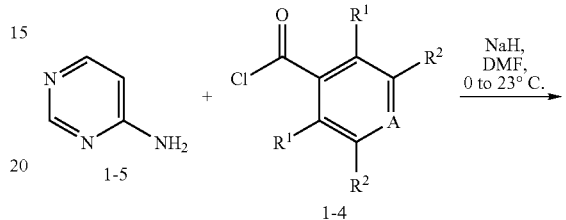

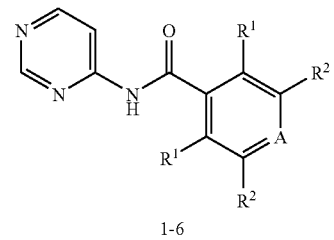

Compounds of Formulas I-VII can be synthesized as shown in Reaction Scheme 1. For example, commercially available compounds 4-aminopyridine (1-1) and a carboxylic acid (1-2) can be coupled together using HATU (O-(7-azabenzotriazol-1-yl)-N,N,N',N'-tetramethyluronium hexafluorophosphate) in DMF (dimethylformamide) to give amides (1-3). Alternatively, 4-aminopyridine (1-1) can be treated with sodium hydride in DMF, followed by reaction with acid chlorides (1-4), either neat or as a dilute solution, to give amides (1-3). Additionally, 4-aminopyrimidine (1-5) can be treated with sodium hydride in DMF, followed by reaction with acid chlorides (1-4), either neat or as a dilute solution, to give pyrimidine amides (1-6).

SCHEME 2

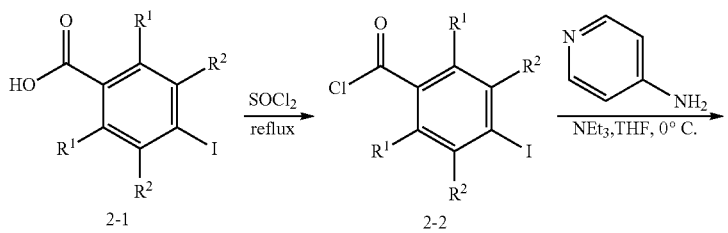

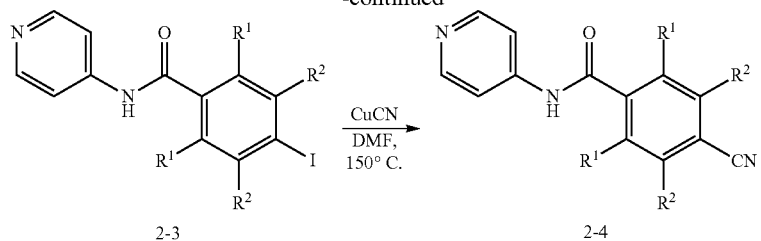

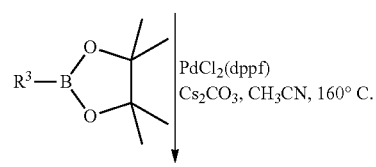

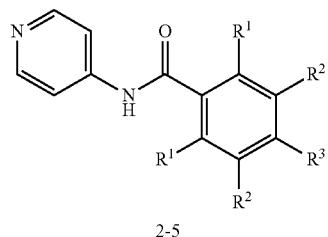

Compounds of Formulas I-VII can be synthesized as shown in Reaction Scheme 2. For example, a 4-iodo carboxylic acid (2-1) can be converted to the acid chloride (2-2) by refluxing in thionyl chloride. The acid chloride (2-2) is subsequently coupled to 4-aminopyridine in the presence of a base, such as triethylamine, to give amide (2-3). The iodide group in the amide (2-3) can then be converted to many other functional groups using chemistry known to one of ordinary skill in the art. For example, the iodide (2-3) can be converted to the nitrile (2-4) by reacting with cuprous cyanide in DMF. The iodide (2-3) can also be coupled to a borate, or a boronic acid, via palladium-catalyzed Suzuki reaction, to give a variety of different compounds (2-5) (including those where $R^3$ is phenyl or substituted phenyl, heteroaryl or substituted heteroaryl).

SCHEME 3

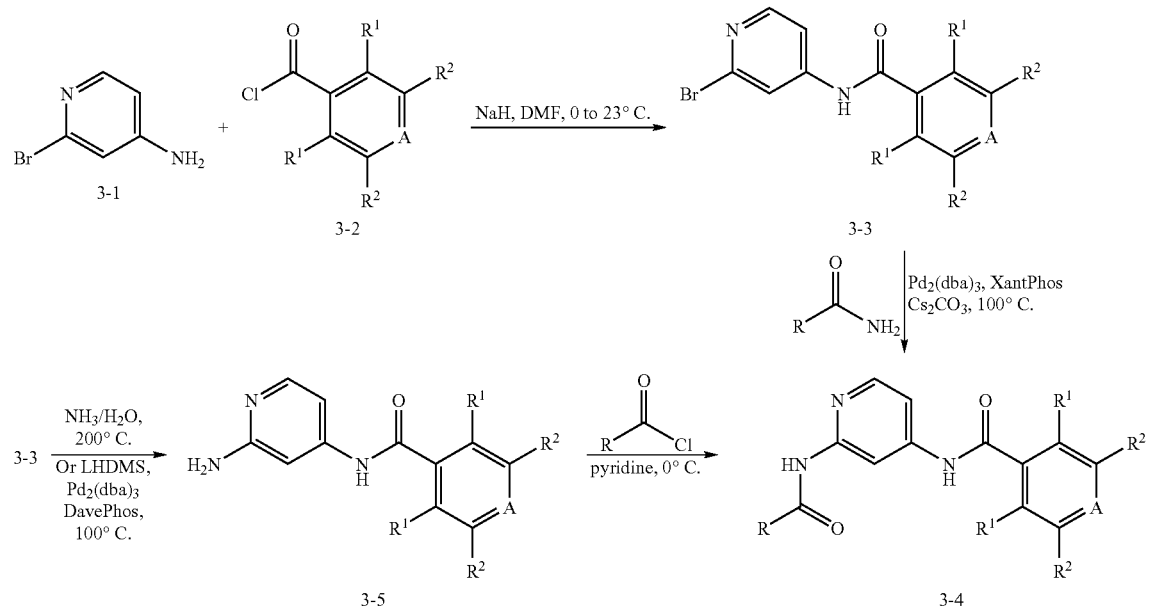

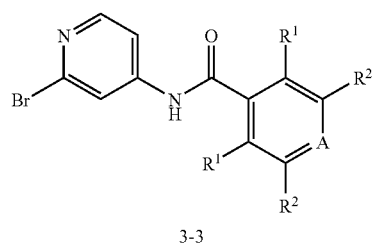 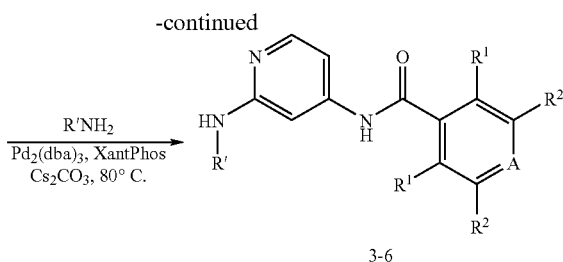

Compounds of Formulas I-VII can be synthesized as shown in Reaction Scheme 3. For example, 4-amino-2-bromopyridine (3-1) can be coupled with acid chlorides (3-2) using sodium hydride in DMF to give amides (3-3). The bromo-amides (3-3) can be converted to amines (3-5) by heating with aqueous concentrated ammonia at 200° C. Alternatively, bromo-amides (3-3) can be converted to amine-amides (3-5) via palladium-catalyzed Buchwald coupling reactions. The amine-amides (3-5) can be converted to amides (3-4) by reacting with an acid chloride in a solvent such as pyridine. Bromo-amides (3-3) can also be converted directly to amides (3-4) via palladium-catalyzed coupling reactions. In a similar manner, bromo-amides (3-3) can be coupled with amines using Buchwald coupling conditions to give amines (3-6).

SCHEME 4

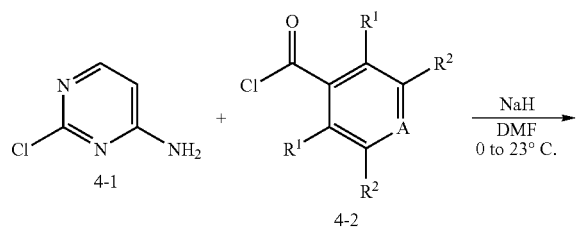

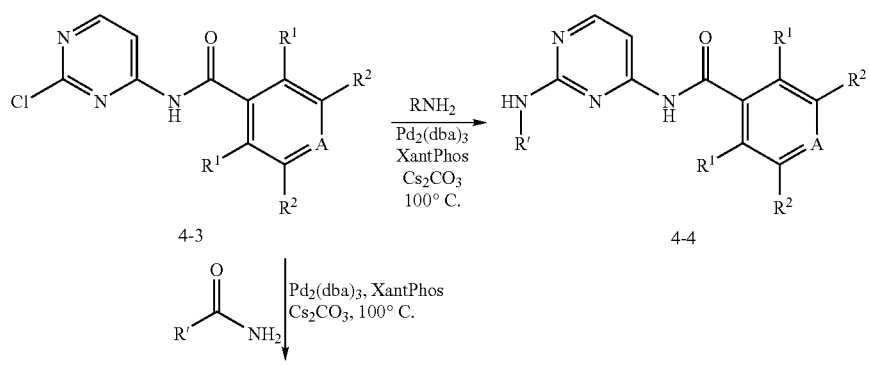

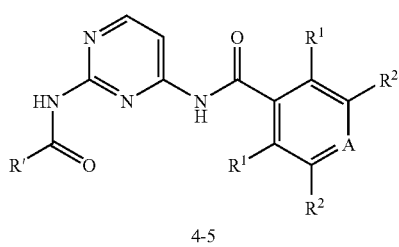

Compounds of Formulas I-VII can be synthesized as shown in Reaction Scheme 4. For example, 4-amino-2-chloropyrimidine (4-1) is coupled with an acid chloride (4-2) in DMF to give chloro-amides (4-3). Chloro-amides (4-3) can be converted to amines (4-4) via a palladium-catalyzed Buchwald reaction. Alternatively, chloro-amides (4-3) can be converted to amides (4-5) by a palladium-catalyzed coupling reaction.

SCHEME 5

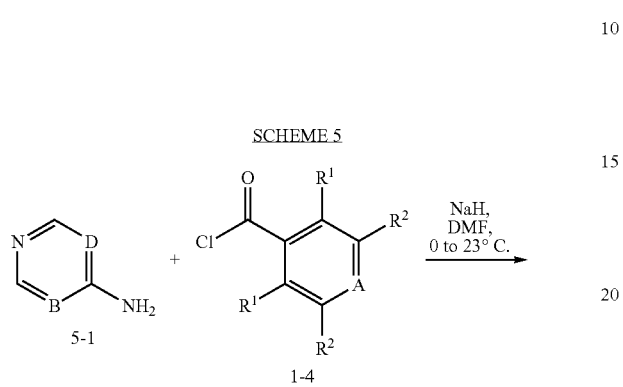

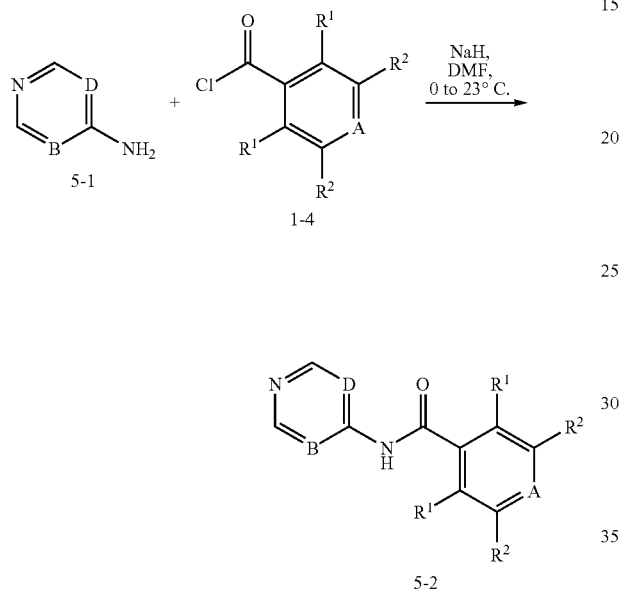

Compounds of Formulas I-VII can be synthesized as shown in Reaction Scheme 5. For example, commercially available heteroaryl amines (5-1) (for example 4-aminopyridine and 4-aminopyrimidine) can be treated with sodium hydride in DMF, followed by reaction with acid chlorides (1-4), either neat or as a dilute solution, to give amides (5-2).

SCHEME 6

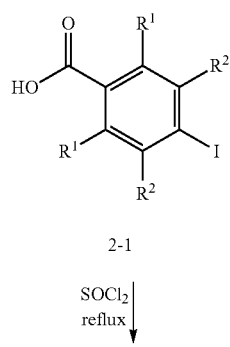

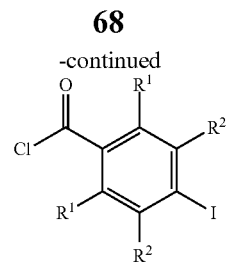

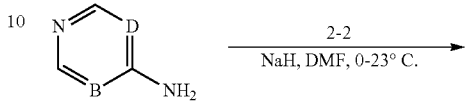

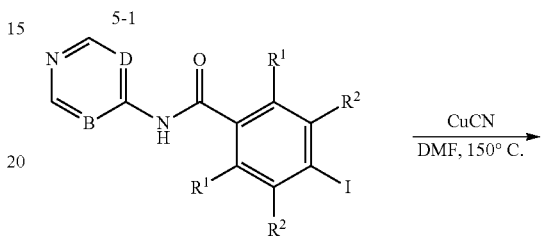

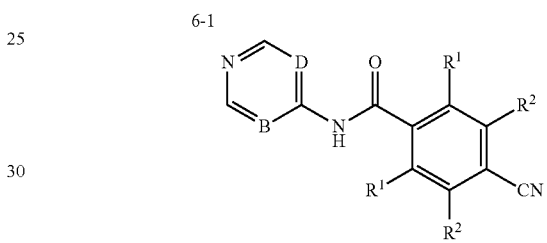

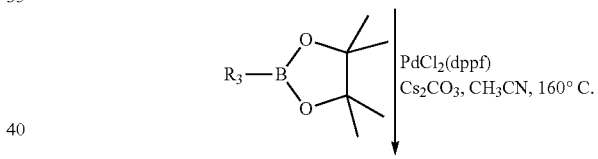

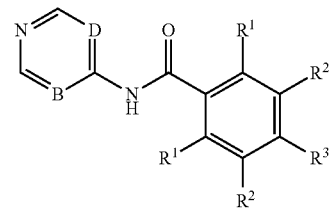

Compounds of Formulas I-VII can be synthesized as shown in Reaction Scheme 6. For example, a 4-iodo carboxylic acid (2-1) can be converted to the acid chloride (2-2) by refluxing in thionyl chloride. The acid chloride (2-2) is subsequently coupled to a heteroarylamine (5-1) (for example 4-aminopyridine or 4-aminopyrimidine) in the presence of a base, such as sodium hydride, to give amide (6-1). The iodide group in the amide (6-1) can then be converted to many other functional groups using chemistry known to one of ordinary skill in the art. For example, the iodide (6-1) can be converted to the nitrile (6-2) by reacting with cuprous cyanide in DMF. The iodide (6-1) can also be coupled to a borate, or a boronic acid, via palladium-catalyzed Suzuki reaction, to give a variety of different compounds (6-3).

SCHEME 7

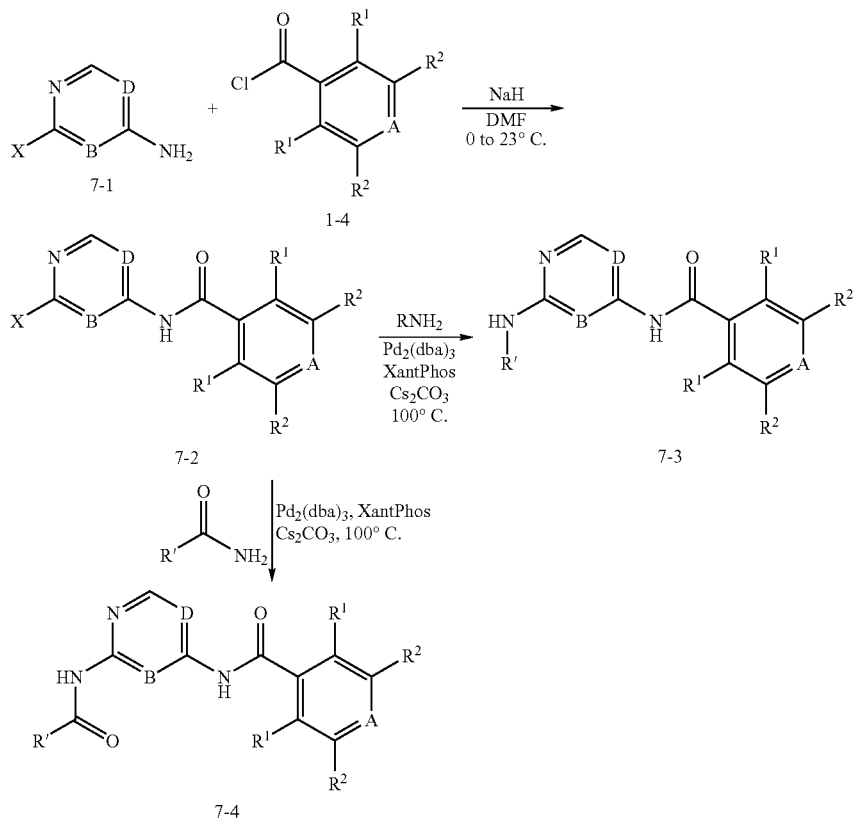

Compounds of Formulas I-VII can be synthesized as shown in Reaction Scheme 7. For example, halogenated heteroarylamines (7-1) (for example 4-amino-2-bromopyridine) can be coupled with acid chlorides (1-4) using sodium hydride in DMF to give amides (7-2). The amide (7-1) can be converted to amines (7-3) via a palladium-catalyzed Buchwald coupling reaction. In a similar manner, amides (7-1) can be coupled to an amides via palladium-catalyzed Buchwald coupling reaction to give products such as (7-4).

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (e.g. —NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N═C═O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH═CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

Positional isomers, for example E and Z forms, of compounds of Formulas I-VII, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Biological Evaluation

Previous studies have shown that the isolated kinase domains of human JAK1, JAK2, JAK3 or TYK2 phosphorylate peptide substrates in in vitro kinase assays (Saltzman et al., *Biochem. Biophys. Res. Commun.* 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP_004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., *Biochem. Biophys. Res. Commun.* 246:627-633 (2004)). The activity of the JAK1, JAK2, JAK3 or TYK2 kinase domains was measured in vitro by monitoring phosphorylation of JAK3 derived peptides using the Caliper LabChip technology (see Examples).

The compounds of the present invention are tested for their capacity to inhibit a Janus kinase activity and activation (primary assays) and for their biological effects on growing cells (secondary assays) as described herein. The compounds having $IC_{50}$ of less than 10 µM (preferably less than 5 µM, more preferably less than 1 µM, most preferably less than 0.5 µM) in the appropriate Janus kinase activity and activation assay (see Examples A and B), and $EC_{50}$ of less than 20 µM (preferably less than 10 µM, more preferably less than 5 µM, most preferably less than 1 µM) in the appropriate cellular assays (see Example C) are useful as Janus kinase inhibitors.

Administration of Janus Kinase Inhibitor Compounds

The compounds of the invention inhibit TYK2 kinase activity. Accordingly, the compounds of the invention are useful for reducing, blocking and/or interfering type I interferon, IL-6, IL-10, IL-12 and/or IL-23 signaling in particular cells and tissue. Compounds of the invention are useful for inhibiting TYK2 kinase activity in cells that overexpress TYK2 kinase. More broadly, the compounds can be used for the treatment of diseases which overexpress TYK2 kinase, e.g. autoimmune or inflammatory diseases.

Another embodiment includes a method of treating or lessening the severity of a disease or condition responsive to the inhibition of a Janus kinase activity in a patient. The method includes the step of administering to a patient a therapeutically effective amount of a compound of Formulas I-VII.

Another embodiment includes a method of treating or lessening the severity of a disease or condition responsive to the inhibition of TYK2 kinase activity in a patient. The method includes the step of administering to a patient a therapeutically effective amount of a compound of Formulas I-VII.

Another embodiment includes a compound of Formulas I-VII for use in therapy.

Another embodiment includes a compound of Formulas I-VII for use in treating immunological diseases.

Another embodiment includes a compound of Formulas I-VII for use in treating inflammatory diseases.

Another embodiment includes a compound of Formulas I-VII for use in treating psoriasis or inflammatory bowel disease.

Another embodiment includes use of a compound of Formulas I-VII in the manufacture of a medicament for the treatment of immunological diseases.

Another embodiment includes use of a compound of Formulas I-VII in the manufacture of a medicament for the treatment of psoriasis or inflammatory bowel disease.

In one embodiment, a compound of Formulas I-VII is administered to a patient in a therapeutically effective amount to treat or lessen the severity of a disease or condition responsive to the inhibition of a Janus kinase activity, and said compound is at least 15 fold, alternatively 10 fold, alternatively 5 fold or more selective in inhibiting one Janus kinase activity over inhibiting each of the other Janus kinase activities.

In one embodiment, a compound of Formulas I-VII is administered to a patient in a therapeutically effective amount to treat or lessen the severity of a disease or condition responsive to the inhibition of TYK2 kinase activity, and said compound is at least 5 fold, alternatively 10 fold or more selective in inhibiting TYK2 kinase activity over inhibiting JAK1, JAK2 and JAK3 kinase activities.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory disease is inflammatory bowel disease, rheumatoid arthritis, psoriasis, contact dermatitis or delayed hypersensitivity reactions.

In one embodiment, the inflammatory disease is inflammatory bowel disease, Crohn's disease, ulcerative colitis, rheumatoid arthritis, psoriasis, contact dermatitis or delayed hypersensitivity reactions.

In one embodiment, the autoimmune disease is lupus or multiple sclerosis.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology*, Vol. 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through one or more of the Janus kinase pathways in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 68). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 69) determines the ability of compounds to inhibit the production of CD69 by B lymphocytes in human whole blood activated by crosslinking surface IgM with goat F(ab')$_2$ anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern*

*Methods in Immunotoxicology*, Volume 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

A compound of Formulas I-VII may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound of Formulas I-VII is administered orally, it may be formulated as a pill, capsule, tablet, etc. with a pharmaceutically acceptable carrier or excipient. Where the compound of Formulas I-VII is administered parenterally, it may be formulated with a pharmaceutically acceptable parenteral vehicle and in a unit dosage injectable form, as detailed below.

A dose to treat human patients may range from about 10 mg to about 1000 mg of a compound of Formulas I-VII. A typical dose may be about 100 mg to about 300 mg of a compound of Formulas I-VII. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Pharmaceutical Formulations of Janus Kinase Inhibitor Compounds

Another embodiment includes a pharmaceutical composition that includes a compound of Formulas I-VII and a pharmaceutically acceptable carrier, adjuvant or vehicle.

In one embodiment, the pharmaceutical composition also includes an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

In one embodiment, a compound of Formulas I-VII is present in a pharmaceutical formulation in an amount to detectably inhibit Janus kinase activity and a pharmaceutically acceptable carrier, adjuvant or vehicle.

In one embodiment, a compound of Formulas I-VII is present in a pharmaceutical formulation in an amount to detectably inhibit TYK2 kinase activity and a pharmaceutically acceptable carrier, adjuvant or vehicle.

In one embodiment, a compound of Formulas I-VII is present in a pharmaceutical formulation in an amount to detectably inhibit a Janus kinase activity and is at least 15 fold, alternatively 10 fold, or 5 fold or more selective in inhibiting one Janus kinase activity over inhibiting each of the other JAK1, JAK2, JAK3 and/or Tyk-2 activity.

In one embodiment, a compound of Formulas I-VII is present in a pharmaceutical formulation in an amount to detectably inhibit TYK2 kinase activity and is at least 5 fold, alternatively 10 fold or more selective in inhibiting TYK2 kinase activity over inhibiting JAK1, JAK2 and JAK3 activity.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of a compound of Formulas I-VII may be prepared for various routes and types of administration. A compound of Formulas I-VII having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

In an embodiment, the compound of Formulas I-VII for use in a pharmaceutical composition is substantially sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing a compound of Formulas I-VII, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formulas I-VII suitable for oral administration may be prepared as discrete units such as pills, capsules, cachets or tablets each containing a predetermined amount of the compound of Formulas I-VII.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a compound of Formulas I-VII intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of a compound of Formulas I-VII may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas I-VII may be employed alone or in combination with other therapeutic agents for the treatment of a disease or disorder described herein, such as an immunologic disorder (e.g. psoriasis or inflammation) or a hyperproliferative disorder (e.g., cancer). In certain embodiments, a compound of Formulas I-VII is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be a NSAID or other anti-inflammatory agent. The second therapeutic agent may be a chemotherapeutic agent. The second therapeutic agent of the pharmaceutical combination formulation or dosing regimen preferably has complementary activities to the compound of Formulas I-VII such that they do not adversely affect each other. Such compounds are suitably present in combination in amounts that are effective for the purpose intended. In one embodiment, a composition of this invention comprises a compound of Formulas I-VII, or a stereoisomer, geometric isomer, tautomer, solvate, metabolite, or pharmaceutically acceptable salt or prodrug thereof, in combination with a therapeutic agent such as an NSAID.

Another embodiment, therefore, includes a method of treating or lessening the severity of a disease or condition responsive to the inhibition of a Janus kinase in a patient, comprising administering to said patient a therapeutically effective amount of a compound of Formulas I-VII, and further comprising, administering a second therapeutic agent.

Another embodiment, therefore, includes a method of treating or lessening the severity of a disease or condition responsive to the inhibition of TYK2 kinase in a patient, comprising administering to said patient a therapeutically effective amount of a compound of Formulas I-VII, and further comprising, administering a second therapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In a particular embodiment of therapy, a compound of Formulas I-VII, or a stereoisomer, geometric isomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formulas I-VII, or a stereoisomer, geometric isomer, tautomer, solvate, metabolite, or pharmaceutically acceptable salt or prodrug thereof, and the use of at least one other cancer treatment method, or immunological disorder method. The amounts of the compound(s) of Formulas I-VII and the other pharmaceutically active immunologic or chemotherapeutic agent(s) and the relative timings of administration will be selected in order to achieve the desired combined therapeutic effect.

Metabolites of the Janus Kinase Inhibitor Compounds

Another embodiment includes in vivo metabolic products of an administered compound of Formulas I-VII. Such products may result for example from the oxidation, reduction, hydrolysis, amidation, deamidation, esterification, deesterification, enzymatic cleavage, and the like, of the administered compound.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of a compound of Formulas I-VII.

Methods and Articles of Manufacture

Another embodiment includes a method of manufacturing a compound of Formula I. The method includes: (a) reacting a compound of formula i:

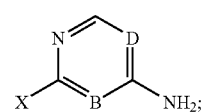

wherein X is independently hydrogen, halogen or a leaving group, and B and D are as defined for Formula I, with a compound of formula II:

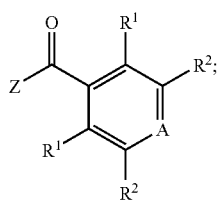

wherein Z is halogen or a leaving group, $R^1$, $R^2$ and A are as defined for Formula I, to prepare a compound of formula iii:

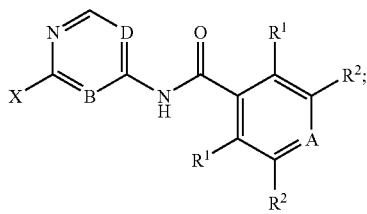

and (b) optionally reacting a compound of formula iii with a compound of formula Y-$R^4$-$R^5$, wherein Y is H or is absent, under conditions sufficient to form a compound of Formula I:

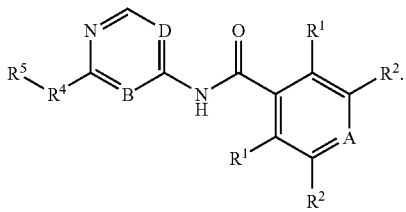

In one example, a compound of formula iii is reacted with a compound of the formula Y—$R^4$-$R^5$, under basic conditions, for example, in the presence of an amine (e.g. ammonia or alkyl-amine such as triethyl- or trimethyl-amine). In a further example, a compound of formula iii is reacted with a compound of the formula Y-$R^4$-$R^5$, under basic conditions and at elevated temperatures (e.g. greater than about 50° C., alternatively in the range of about 50-250° C.). In one example, a compound of formula iii, wherein X is Br, is reacted with ammonia at an elevated temperature in the range of about 50-250° C. to form a compound of Formula I, wherein $R^4$ is —$NH_2$ and $R^5$ is absent.

In another example, a compound of formula iii is reacted with a compound of the formula Y-$R^4$-$R^5$, under transition metal-catalyzed coupling conditions, for example, in the presence of a copper, palladium, platinum (or some combination thereof) catalyst. In one example, a compound of formula iii is reacted with a compound of the formula Y-$R^4$-$R^5$, in the presence of a palladium (II) salt, and optionally in the presence of a phosphine or bisphosphine ligand.

In another example, a compound of formula iii, wherein X is halogen (e.g. Br) is reacted with a compound of the formula Y-$R^4$-$R^5$, wherein Y is H, $R^4$ is —NH—, —$NR^6R^7$, —$NR^6C(O)$—, —$NR^6C(O)O$—, —$NR^6C(O)NR^7$—, —$NR^6S(O)_{1-2}$— or —$(C_0$-$C_1$ alkyl)$NR^6S(O)_{1-2}NR^7$—, in the presence of a palladium (II) salt (e.g. $Pd_2(dba)_3$) and optionally in the presence of a phosphine or bisphosphine ligand (e.g. 4,5-bis(diphenylphosphino)-9,9-dimethylxanthene), under conditions sufficient (e.g. optionally in the presence of a base, such as carbonate bases, for example $Cs_2CO_3$) to form a compound of Formula I, wherein $R^1$, $R^2$ and $R^5$ are defined in any embodiment of Formula I.

Another embodiment includes a kit for treating a disease or disorder responsive to the inhibition of a Janus kinase. The kit includes:

(a) a first pharmaceutical composition comprising a compound of Formulas I-VII; and (b) instructions for use.

In another embodiment, the kit further includes:

(c) a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of Formulas I-VII or formulation thereof which is effective for treating the condition and may have a sterile access port (for example the container may be an intravenous solution bag or a vial having a stopper pierceable by a hypodermic injection needle). The container includes a composition comprising at least one compound of Formulas I-VII. The label or package insert indicates that the composition is used for treating the condition of choice, such as cancer. In one embodiment, the label or package inserts indicates that the composition comprising the compound of Formulas I-VII can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of Formulas I-VII contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of Formulas I-VII, and alternative methods for preparing the compounds of Formulas I-VII are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

Compounds of Formulas I-VII may be assayed for the ability to modulate the activity of Janus protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formulas I-VII to bind to kinases and may be measured either by radiolabelling the compound of Formulas I-VII prior to binding, isolating the compound of Formulas I-VII/kinase complex and determining the amount of radiolabel bound, or by running a competition experiment where a compound of Formulas I-VII is incubated with known radiolabeled ligands. These and other useful in vitro assays are well known to those of skill in the art.

In an embodiment, the compounds of Formulas I-VII can be used to control, modulate or inhibit tyrosine kinase activity, for example Janus protein kinase (e.g. TYK2) activity, additional serine/threonine kinases, and/or dual specificity kinases. Thus, they are useful as pharmacological standards for use in the development of new biological tests, assays and in the search for new pharmacological agents.

Example A

JAK1, JAK2 and TYK2 Inhibition Assay Protocol

The activity of the isolated JAK1, JAK2 or TYK2 kinase domain was measured by monitoring phosphorylation of a peptide derived from JAK3 (SEQ ID NO:1 Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-618, compounds were diluted serially in DMSO and added to 50 uL kinase reactions containing 1.5 nM JAK1, 0.2 nM purified JAK2 or 1 nM purified TYK2 enzyme, 100 mM Hepes pH7.2, 0.015% Brij-35, 1.5 uM peptide substrate, 25 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example B

JAK3 Inhibition Assay Protocol

The activity of the isolated JAK3 kinase domain was measured by monitoring phosphorylation of a peptide derived from JAK3 (SEQ ID NO:2 Leu-Pro-Leu-Asp-Lys-Asp-Tyr-Tyr-Val-Val-Arg) fluorescently labeled on the N-terminus with 5-carboxyfluorescein using the Caliper LabChip technology (Caliper Life Sciences, Hopkinton, Mass.). To determine the inhibition constants (Ki) of Examples 1-618, compounds were diluted serially in DMSO and added to 50 uL kinase reactions containing 5 nM purified JAK3 enzyme, 100 mM Hepes pH7.2, 0.015% Brij-35, 1.5 uM peptide substrate, 5 uM ATP, 10 mM $MgCl_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.*, 63:437-467 (1979).

Example C

Cell-based Pharmacology Assays

The activities of compounds I-618 were determined in cell-based assays that are designed to measure Janus kinase dependent signaling. Compounds were serially diluted in DMSO and incubated with Set-2 cells (German Collection of Microorganisms and Cell Cultures (DSMZ); Braunschweig, Germany), which express the JAK2V617F mutant protein, in 96-well microtiter plates for 1 hour at 37° C. in RPMI medium at a final cell density of $10^5$ cells per well and a final DMSO concentration of 0.57%. Compound-mediated effects on STAT5 phosphorylation were then measured in the lysates of incubated cells using the Meso Scale Discovery (MSD) technology (Gaithersburg, Md.) according to the manufacturer's protocol and $EC_{50}$ values were determined Alternatively, serially diluted compounds were added to NK92 cells (American Type Culture Collection (ATCC); Manassas, Va.) in 96-well microtiter plates in RPMI medium at a final cell density of $10^5$ cells per well and a final DMSO concentration of 0.57%. Human recombinant IL-12 (R&D systems; Minneapolis, Minn.) was then added at a final concentration of 10 ng/ml to the microtiter plates containing the NK92 cells and compound and the plates were incubated for 1 hour at 37° C. Compound-mediated effects on STAT4 phosphorylation were then measured in the lysates of incubated cells using the Meso Scale Discovery (MSD) technology (Gaithersburg, Md.) according to the manufacturer's protocol and $EC_{50}$ values were determined.

The compounds of Examples 1-11, 14-20, 22, 24, 26-54, 56, 58-65, 68-70, 72, 74-80, 82-165, 168, 173-185, 188-196 and 198-618 were tested in the above assays and found to have $K_i$ values for TYK2 inhibition of less than about 3.5 μM. In particular, the following Examples were tested in the above assays and found to have about the corresponding $K_i$ values for TYK2 inhibition given in parentheses (μM): Example 2 (0.85), Example 3 (0.72), Example 4 (0.38), Example 6 (0.85), Example 11 (0.65), Example 17 (0.36), Example 76 (0.22), Example 84 (0.005) (100% inhibition of TYK2 activity measured at 10 μM concentration of compound), Example 115 (0.57), Example 156 (0.99), Example 178 (0.005), Example 238 (0.45), Example 243 (0.019), Example 256 (0.002), Example 260 (0.027), Example 263 (0.024), Example 264 (0.010), Example 271 (0.81), Example 272 (0.19), Example 281 (0.093), Example 315 (0.008), Example 320 (0.052), Example 350 (0.062), Example 380 (0.0035), Example 406 (0.0036), Example 415 (0.0005), Example 416 (0.0006), Example 495 (0.0015), Example 534 (0.0018), Example 551 (0.0033), Example 572 (0.080), Example 579 (0.0006) and Example 608 (0.14). The following compound was tested in the above assays and found to have a $K_i$ for TYK2 inhibition greater than 3.5 µM: 2,6-dichloro-N-(6-(cyclopropanecarboxamido)-pyridin-3-yl)benzamide (about 5.7% inhibition of TYK2 activity measured at 10 µM concentration of compound).

PREPARATIVE EXAMPLES

Abbreviations

AIBN Azobisisobutyronitrile
CDI 1,1'-Carbonyldiimidazole
CD$_3$OD Deuterated Methanol
DCM Dichloromethane
DEA Diethylamine
DIPAD Diisopropyl aza-1,2-dicarboxylate
DIPEA Diisopropylethylamine
DME Dimethoxyethane
DMSO Dimethylsulfoxide
DMF Dimethylformamide
EtOAc Ethyl Acetate
EtOH Ethanol
HCl Hydrochloric acid
HM-N Isolute® HM-N is a modified form of diatomaceous earth
IMS industrial methylated spirits
MeOH Methanol
POCl$_3$ Phosphorus oxychloride
NaH Sodium Hydride
Na$_2$SO$_4$ Sodium Sulfate
NaHCO$_3$ Sodium bicarbonate
NaOH Sodium hydroxide
NOE Nuclear Overhauser Effect
Pd(PPh$_3$)$_4$ Tetrakis(triphenylphosphine)palladium(0)
NEt$_3$ Triethylamine
Pd$_2$dba$_3$ Tris-(dibenzylideneacetone)dipalladium(0)
rpHPLC Reverse phase high-pressure liquid chromatography
SFC Supercritical Fluid Chromatography
Si—SPE Pre-packed Isolute® silica flash chromatography cartridge
Si-ISCO Pre-packed ISCO® silica flash chromatography cartridge
THF Tetrahydrofuran
TLC Thin layer chromatography
General Experimental Conditions Compounds of this invention may be prepared from commercially available starting materials using the general methods illustrated herein. Specifically, 2,6-dichlorobenzoic acid, 2,6-dichlorobenzoyl chloride, 2,4,6-trichlorobenzoyl chloride, 2-choro-6-fluorobenzoic acid, 2,6-bis(trifluoromethyl) benzoic acid, 2,6-dimethylbenzoic acid, 2-chloro-4-(methylsulfonyl)benzoic acid, 2-bromo-5-fluorobenzoic acid, 2-bromo-4-fluorobenzoic acid, 3,5-dichloropyridine-4-carboxylic acid, 2-bromobenzoic acid, 2-chlorobenzoic acid, 2-chloro-5-fluorobenzoic acid, 2-(trifluoromethyl)benzoic acid, 2-(trifluoromethoxy)benzoic acid, 2,6-difluorobenzoic acid, o-toluic acid, 3,5-dichloroisonicotinic acid, 4-amino 2-bromopyridine, 4-aminopyridine, 4-amino-6-chloropyrimidine, 4-amino-2-chloropyrimidine, cyclopropanecarboxylic acid, cyclopropanecarboxylic chloride, 2-methylcyclopropanecarboxylic acid, 3-oxabicyclo[3.1.0]hexane-2,4-dione, trans-1,2-cyclopropyldicarboxylic acid, 2,2-dimethyl cyclopropyl carboxylic acid, 2,2-difluorocyclopropane carboxylic acid, 1-methylcyclopropane-1-carboxylic acid, 1-aminocyclopropane-1-carboxylic acid were purchased from Aldrich (St. Louis, Mo.). Cis- and trans-2-fluoro-cyclopropanecarboxylic acid were purchased from Oakwood Products (West Columbis, S.C.). 3,5-difluoroisonicotinic acid was purchased from Frontier Scientific (Logan, Utah). All commercial chemicals, including reagents and solvents, were used as received.

$^1$H NMR spectra were recorded at ambient temperature using a Varian Unity Inova (400 MHz or 500 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP1100 LC system with diode array detector. This system uses a Higgins Clipeus 5 micron C18 100×3.0 mm column and a 1 ml/minute flow rate.

The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Microwave experiments were carried out using a Biotage Initiator 60™ which uses a single-mode resonator and dynamic field tuning Temperature from 40-250° C. can be achieved, and pressures of up to 30 bar can be reached.

Supercritical fluid chromatography (SFC) was used to analyze various compounds of the invention, under one of the following conditions, with UV detector monitoring at 220 nm and 254 nm, and mass spectrometry scanning 110-800 amu in ESI+ ionization mode. Method A: column: Chiralpak AD-H, 4.6×100 mm, 5.0 mm; mobile phase: A 20% methanol+0.1% triethylamine, B CO$_2$; pressure 120 Bars; flow rate: 3 mL/min; oven temperature 40° C. Method B: column: Chiralpak IC, 4.6×100 mm, 5.0 um; mobile phase: A 30% isopropanol+0.1% triethylamine, B CO$_2$; pressure 120 Bars; flow rate 3 mL/min; oven temperature 40° C.

Example 1

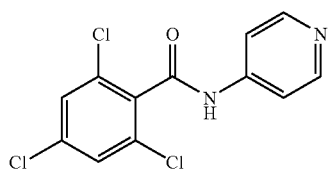 [SMILES: O=C(Nc1ccncc1)c1c(Cl)cc(Cl)cc1Cl]

2,4,6-trichloro-N-(pyridin-4-yl)benzamide

A mixture of 2,4,6-trichlorobenzoic acid (224 mg, 10 mmol), 4-aminopyridine (141 mg, 1.5 mmol), HATU (1140 mg, 3 mmol), and DIPEA (646 mg, 5 mmol) in 5 mL anhydrous DMF was stirred under nitrogen at room temperature overnight. The reaction mixture was poured into ice-water (20 mL) and extracted EtOAc (2×50 mL). The combined organics were evaporated to dryness in vacuum and the residue was purified by silica gel column chromatography (EtOAc) to afford the desired product (72 mg, yield: 24%). $^1$HNMR: (CD$_3$OD-d$_4$, 400 MHz): δ 8.38 (d, J=6.0 Hz, 2H), 7.65 (d, J=6.0 Hz, 2H), 7.52 (s, 2H). LCMS (ESI) m/z: 301.1 [M+H$^+$].

Example 2

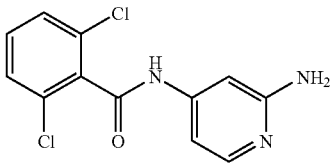 [SMILES: Nc1cc(NC(=O)c2c(Cl)cccc2Cl)ccn1]

N-(2-aminopyridin-4-yl)-2,6-dichlorobenzamide

Step 1

A solution of 2-bromopyridin-4-amine (0.74 g, 4.3 mmol) in DMF (5 mL) was added to a cooled (0° C.) mixture of NaH (0.31 g, 7.82 mmol, 60% in mineral oil) in DMF (15 mL). The resulting mixture was stirred for 20 minutes at 0° C. and then a solution of 2,6-dichlorobenzoyl chloride (0.82 g, 3.91 mmol) in DMF (5 mL) was added dropwise. The reaction was stirred at 0° C. for 4 hours and then poured onto ice-water (20 mL). The precipitate was collected and filtrate was extracted by EtOAc (2×50 mL). The combined organic extracts were dried over Na$_2$SO$_4$ and concentrated under reduced pressure. The resulting solid was combined with the precipitate to afford N-(2-bromopyridin-4-yl)-2,6-dichlorobenzamide (1.0 g, Yield: 74%). $^1$HNMR (DMSO-d$_6$, 400 MHz): δ 11.41 (s, 1H), 8.33 (d, J=5.6 Hz, 1H), 7.99 (d, J=1.6 Hz, 1H), 7.64-7.54 (m, 4H). LCMS (ESI) m/z: 345.0 [M+H$^+$].

Step 2

Procedure A

A stainless steel tube was charged with N-(2-bromopyridin-4-yl)-2,6-dichlorobenzamide (1.5 g, 4.34 mmol) and concentrated ammonia in water (w/w 38%, 20 mL). The tube was sealed and the mixture was heated to 200° C. in an autoclave for 5 hours. The mixture was concentrated under reduced pressure and the residue was purified by silica gel column chromatography (EtOAc/MeOH=20:1) to afford the desired product (0.53 g, yield: 43%). $^1$HNMR (DMSO-d$_6$, 400 MHz): δ 10.71 (s, 1H), 7.79 (d, J=5.6 Hz, 1H), 7.59-7.45 (m, 3H), 6.95 (s, 1H), 6.61 (d, J=5.6 Hz, 1H), 5.91 (s, 2H). LCMS ESI-MS m/z: 282.1 [M+H$^+$]

Alternative Procedure B

A 20 mL microwave tube was charged with N-(2-bromopyridin-4-yl)-2,6-dichlorobenzamide (346 mg, 1.00 mmol), Pd$_2$(dba)$_3$ (91.6 mg, 100 μmol) and 2-dicyclohexylphosphino-2'-(N,N-dimethylamino)biphenyl (DavePhos, 78.7 mg, 200 μmol). The tube was evacuated and back-filled with N$_2$ (3×). 1,4-Dioxane (6 mL) and lithium bis(trimethylsilyl)amide (4.0 mL of 1.0 M solution in THF, 4.0 mmol) were then added under N$_2$. The tube was sealed, and heated at 100° C. for 5 hours. The reaction was cooled to room temperature and diluted with 1 N HCl (5 mL). After stirring for 10 min, 1 N NaOH solution was added until the mixutre was pH=12. The mixture was extracted with dichloromethane (3×30 mL). The combined organic extracts were dried over Na$_2$SO$_4$, and concentrated under reduced pressure. The residue was purified by silica gel column chromatography (0-10% MeOH) to afford the desired product (282 mg, 64.5% yield).

Example 3

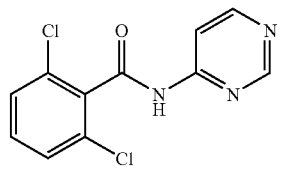 [SMILES: O=C(Nc1ccncn1)c1c(Cl)cccc1Cl]

2,6-dichloro-N-(pyrimidin-4-yl)benzamide 4-aminopyrimidine (0.16 g, 1.72 mmol) was added to a cooled (0° C.) mixture of NaH (0.17 g, 4.25 mmol, 60% in mineral oil) in DMF (5 mL). The resulting mixture was stirred for 20 minutes under N$_2$ at 0° C. and then 2,6-dichlorobenzoyl chloride (0.3 g, 1.43 mmol) was added dropwise. After one hour the reaction was poured into the ice-water (20 mL). The mixture was extracted with EtOAc (2×50 mL) and the combined organic extracts were concentrated under reduced pressue. The residue was purified by silica gel column chromatography (EtOAc/hexanes=1:1) to afford the desired product (38 mg, yield 10%). $^1$HNMR: (DMSO-d$_6$, 400 MHz): 611.73 (s, 1H), 8.91 (s, 1H), 8.74 (d, J=5.6 Hz, 1H), 8.17 (d, J=5.6 Hz, 1H), 7.55-7.47 (m, 3H). LCMS (ESI) m/z: 267.8 [M+H$^+$]

Example 4

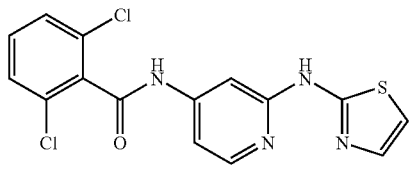 [SMILES: O=C(Nc1ccnc(Nc2nccs2)c1)c1c(Cl)cccc1Cl]

2,6-dichloro-N-(2-(thiazol-2-ylamino)pyridin-4-yl)benzamide

A 25 mL microwave tube containing N-(2-bromopyridin-4-yl)-2,6-dichlorobenzamide (0.21 g, 0.61 mmol), 2-aminothiazole (92 mg, 0.92 mmol), Pd$_2$(dba)$_3$ (56 mg, 0.061 mmol), Cs$_2$CO$_3$ (0.4 g, 1.22 mmol), 4,5-bis(diphenylphosphino)-9,9-dimethylxanthene (Xantphos, 71 mg, 0.122 mmol), and dioxane (8 mL) was degassed and then charged with N$_2$ (3×). The resulting mixture was heated at 80° C. overnight. After cooling, the mixture was diluted with dioxane (20 mL) and filtered through celite. The filtrate was concentrated under reduced pressure and the residue was purified by reverse-phase HPLC (Gemini, 200 mm×25 mm, gradient: CH$_3$CN/0.05% NH$_3$.H$_2$O, 50-80, 10 min) to afford the desired product (56.4 mg, yield: 25%). $^1$HNMR: (DMSO-d$_6$, 400 MHz): 611.26 (s, 1H), 11.13 (s, 1H), 8.21 (d, J=6.0 Hz, 1H), 7.61-7.50 (m, 4H), 7.36 (d, J=3.6 Hz, 1H), 7.11 (q, J=1.6, 6.0 Hz, 1H), 6.98 (d, J=3.6 Hz, 1H). LCMS (ESI) m/z: 364.8 [M+H$^+$]

Example 5

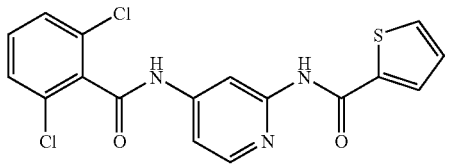 [SMILES: O=C(Nc1cc(NC(=O)c2c(Cl)cccc2Cl)ccn1)c1cccs1]

N-(4-(2,6-dichlorobenzamido)pyridin-2-yl)thiophene-2-carboxamide

N-(2-aminopyridin-4-yl)-2,6-dichlorobenzamide (240 mg, 0.86 mmol) was dissolved in pyridine (10 mL). The mixture was stirred at 0° C. for 20 min. and then thiophene-2-carbonyl chloride (113 mg, 0.77 mmol) was added dropwise. The mixture was warmed to 23° C. and stirred under nitrogen overnight. The next day, water (1 mL) was added and the mixture was stirred for 5 min. The reaction was concentrated under reduced pressure and the residue was purified by reverse-phase HPLC (Gemini, 200 mm×25 mm, gradient: CH$_3$CN/0.05% NH$_3$.H$_2$O, 50-80, 10 min) to afford the desired product (72.6 mg, yield: 22%). $^1$HNMR: (DMSO-d$_6$, 400 MHz): δ 11.38 (s, 1H), 10.92 (s, 1H), 8.47 (s, 1H), 8.33 (d, J=5.6 Hz, 1H), 8.26 (d, J=2.8 Hz, 1H), 7.90 (d, J=5.2 Hz, 1H), 7.62-7.51 (m, 4H), 7.22 (t, J=4.4 Hz, 1H). LCMS (ESI) (m/z): 414.3 [M+Na$^+$].

Example 6

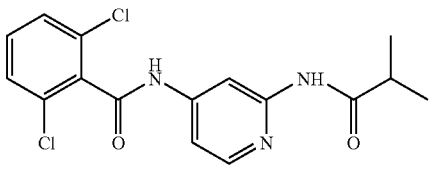 [SMILES: CC(C)C(=O)Nc1cc(NC(=O)c2c(Cl)cccc2Cl)ccn1]

2,6-dichloro-N-(2-isobutyramidopyridin-4-yl)benzamide

To a 10 ml microwave tube was added N-(2-aminopyridin-4-yl)-2,6-dichlorobenzamide (60 mg, 0.21 mmol), followed by 2-methylpropanamide (43 mg, 0.5 mmol), cesium carbonate (162 mg, 0.5 mmol), Pd$_2$(dba)$_3$ (15 mg, 0.016 mmol), 4,5-bis(diphenylphosphino)-9,9-dimethylxanthene (Xantphos, 11 mg, 0.02 mmol). The tube was degassed and filled with N$_2$ three times. The resulting mixture was then heated 100° C. overnight. The next day, the mixture was cooled to room temperature, filtered through celite. The filtrate was concentrated to dryness and the resulting thick oil was dissolved in EtOAc (10 mL), and washed with H$_2$O (10 mL). The aqueous layer was further extracted with EtOAc (10 mL). Combined organics were dried over Na$_2$SO$_4$, concentrated and purified by reverse-phase HPLC (Gemini, 3×10 cm, gradient: 5-85% CH$_3$CN/H$_2$O with 0.1% NH$_4$OH over 10 min) to afford the desired product (30 mg, 49% yield). $^1$HNMR: (DMSO-d$_6$, 400 MHz): δ 11.2 (s, 1H), 10.4 (s, 1H), 8.4 (s, 1H), 8.2 (d, J=5.2 Hz, 1H), 7.60-7.46 (m, 4H), 2.74 (m, 1H), 1.1 (d, J=6.8 Hz, 6H). LCMS (ESI) (m/z): 352.0 [M+H$^+$].

Example 7

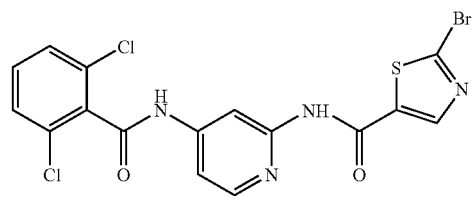 [SMILES: O=C(Nc1cc(NC(=O)c2c(Cl)cccc2Cl)ccn1)c1cnc(Br)s1]

2-Bromo-N-(4-(2,6-dichlorobenzamido)pyridin-2-yl)thiazole-5-carboxamide

To a solution of N-(2-aminopyridin-4-yl)-2,6-dichlorobenzamide (282 mg, 1.00 mmol), 5-bromothiophene-2-carboxylic acid (624 mg, 3.0 mmol) in N,N-dimethylformamide (5 mL) was added diisopropylethylamine (700 µL, 4.00 mmol), followed by O-(7-azabenzotriazol-1-yl)-N,N,N',N'-tetramethyluronium hexafluorophosphate (1.14 g, 3.0 mmol). The mixture was heated at 60° C. for 24 hours. The mixture was then concentrated under reduced pressure and the residue was partitioned between EtOAc (30 mL) and 1 N NaOH (20 mL). The aqueous layer was extracted with EtOAc (2×30 mL). The combined organic extracts were dried over Na$_2$SO$_4$, and concentrated under reduced pressure. The residue was purified by silica gel column chromatography (0-40% EtOAc/hexane) to afford the desired product as an off-white solid (141 mg, 30% yield). $^1$H NMR (400 MHz, DMSO) δ 11.24 (s, 1H), 8.65 (s, 1H), 8.44 (d, J=1.6 Hz, 1H), 8.33 (d, J=5.7 Hz, 1H), 7.66-7.47 (m, 5H). LCMS (ESI) m/z: 472.7 [M+H$^+$].

Example 8

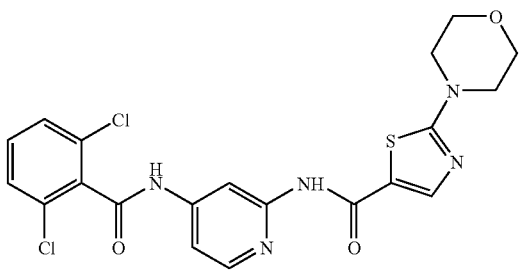 [SMILES: O=C(Nc1cc(NC(=O)c2c(Cl)cccc2Cl)ccn1)c1cnc(N2CCOCC2)s1]

N-(4-(2,6-dichlorobenzamido)pyridin-2-yl)-2-morpholinothiazole-5-carboxamide

To a suspension of 2-bromo-N-(4-(2,6-dichlorobenzamido)pyridin-2-yl)thiazole-5-carboxamide (Example 7) (24.0 mg, 0.051 mmol) in 1-butanol (1 mL) was added morpholine (44.4 mg, 0.51 mmol). The mixture was heated at 50° C. for 6 hours. The mixture was then concentrated under reduced pressure, and the residue was purified by reverse-phase HPLC (Gemini, 3×10 cm, gradient: 5-85% $CH_3CN/H_2O$ with 0.1% $NH_4OH$ over 10 min) to afford the desired product (17 mg, 69.4% yield). $^1H$ NMR (400 MHz, DMSO) δ 11.18 (s, 1H), 10.68 (s, 1H), 8.38 (s, 1H), 8.32 (s, 1H), 8.27 (d, J=5.5, 1H), 7.63-7.57 (m, 2H), 7.56-7.51 (m, 2H), 3.73-3.68 (m, 4H), 3.52-3.46 (m, 4H). LCMS (ESI) m/z: 478.2 [M+H$^+$]

Example 9

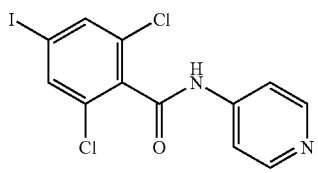 [SMILES: O=C(Nc1ccncc1)c1c(Cl)cc(I)cc1Cl]

2,6-dichloro-4-iodo-N-(pyridine-4-yl)benzamide

Step 1

4-amino-2,6-dichlorophenol (100 g, 0.56 mol) and di-tert-butyl dicarbonate (146 g, 0.73 mol) were dissolved in dioxane (1.5 L), and the mixture was stirred at 110° C. overnight. The solvent was evaporated to afford crude tert-butyl 3,5-dichloro-4-hydroxyphenylcarbamate (220 g) which was used without further purification.

Tert-butyl 3,5-dichloro-4-hydroxyphenylcarbamate (220 g, crude) and 2,6-dimethylpyridine (78 g, 0.73 mol) were dissolved in dichloromethane (2.0 L). Trifluoromethanesulfonic anhydride (174 g, 0.62 mol) was added dropwise at −78° C., and the mixture was stirred at room temperature for 1 hour. The reaction was concentrated under reduced pressure and the residue was purified by column chromatography on silica gel (petroleum ether/EtOAc 40:1) to give 4-(tert-butoxycarbonylamino)-2,6-dichlorophenyl trifluoromethanesulfonate (196 g, yield: 84%). $^1H$ NMR (CDCl$_3$, 400 MHz) δ7.51 (s, 2H), 6.60 (brs, 1H), 1.52 (s, 9H).

Step 2

A mixture of 4-(tert-butoxycarbonylamino)-2,6-dichlorophenyl trifluoromethanesulfonate (14 g, 34 mmol), dppp (1.4 g, 3.4 mmol), Pd(OAc)$_2$ (0.84 g, 3.4 mol) and Et$_3$N (19.6 mL) in MeOH (112 mL) and DMF (224 mL) was refluxed under an atmosphere of carbon monoxide (10 atm) overnight. The reaction was concentrated under reduced pressure and the residue was purified by column chromatography on silica gel (petroleum ether/EtOAc 80:1) to give methyl 4-(tert-butoxy carbonylamino)-2,6-dichlorobenzoate (6.5 g, yield: 60%). $^1H$ NMR (CDCl$_3$, 400 MHz) δ 7.40 (s, 2H), 6.56 (brs, 1H), 3.94 (s, 3H), 1.51 (s, 9H).

Step 3

A solution of methyl 4-(tert-butoxy carbonylamino)-2,6-dichlorobenzoate (65 g, 0.49 mol) in H$_2$SO$_4$/EtOAc (3 N, 20 mL) was stirred at room temperature for 2 hours. The reaction mixture was filtered, and the solid was collected to afford methyl 4-amino-2,6-dichlorobenzoate (60 g, yield: 92%). $^1H$ NMR (DMSO-d$_6$, 400 MHz) δ 8.40 (brs, 3H), 6.61 (s, 2H), 3.80 (s, 3H).

Step 4

Methyl 4-amino-2,6-dichlorobenzoate (104 g, 0.14 mol) was added to concentrated hydrochloric acid (884 mL) and the mixture was cooled (−5° C.). A solution of sodium nitrite (55.2 g, 0.8 mol) in water (312 mL) was added dropwise with vigorous stirring, maintaining the reaction temperature in a range of −5° C. and 0° C. After 30 min, the mixture was filtered and the filtrate was added to a cooled (0° C.) and mechanically stirred solution of potassium iodide (352.3 g, 2.12 mol) in water (200 mL). The mixture was warmed to room temperature and stirred overnight. The reaction was diluted with ethyl acetate (1 L) and the organic phase was separated. The aqueous phase was extracted with ethyl acetate (1 L). The combined organic extracts were washed with saturated solution of NaHSO$_3$, dried over Na$_2$SO$_4$ and concentrated under reduced pressure. The residue was purified by column chromatography on silica gel (petroleum ether/EtOAc 50/1) to give methyl 2,6-dichloro-4-iodobenzoate (140 g, yield 90%) as a yellow oil. $^1H$ NMR (CDCl$_3$ 400 MHz) δ 7.70 (s, 2H), 3.97 (s, 3H).

Step 5

Methyl 2,6-dichloro-4-iodobenzoate (46 g, 0.14 mol) was dissolved in pyridine (1380 mL) and water (230 mL). Lithium iodide (37.2 g, 0.28 mol) was added in one portion. The resulting mixture was heated at 130° C. for 30 hours. The reaction was concentrated under reduced pressure. The residue was dissolved in 2N HCl (500 mL) and extracted with ethyl acetate (3×1 L). The combined organic extracts were dried over Na$_2$SO$_4$ and concentrated under reduced pressure. The residue was dissolved in N-methyl morpholine (5 mL) and concentrated again. The residue was diluted with 2N HCl (100 mL) and extracted with dichloromethane (3×100 mL). The combined organic extracts were dried over Na$_2$SO$_4$ and concentrated under reduced pressure to give 2,6-dichloro-4-iodobenzoic acid (39 g, yield: 88%). $^1H$ NMR (DMSO-d$_{6, 400}$ MHz) δ 14.26 (brs, 1H), 7.99 (s, 2H).

Step 6

Thionyl chloride (20 mL) was added to 2,6-dichloro-4-iodobenzoic acid (1.5 g, 4.73 mmol) and the mixture was heated to reflux for 5 h under nitrogen. After cooling the mixture was concentrated under reduced pressue. Toluene (10 mL) was added and the mixture was concentrated under reduced pressure again to remove residual thionyl chloride. The residue was dissolved in anhydrous THF (20 mL) and this was added dropwise to a cooled (0° C.) solution of 4-aminopyridine (0.53 g, 5.68 mmol) and triethylamine (1.32 mL, 9.46 mmol) in anhydrous THF (20 mL). After addition was complete, the mixture was stirred at room temperature under nitrogen overnight. The reaction was poured onto the ice water (50 mL) and extracted with EtOAc (2×50 mL). The combined organic extracts were dried over sodium sulfate and concentrated under reduced pressure. The residue was purified by silica gel column chromatography (Hexanes/EtOAc=3:1) to afford the desired product (1.8 g, yield: 97%.) $^1$HNMR (DMSO-d$_6$, 400 MHz): δ11.14 (s, 1H), 8.47 (dd, J=1.6, 4.8 Hz, 2H), 8.03 (d, J=2.0 Hz, 2H), 7.59 (dd, J=1.6, 4.8 Hz, 2H). LCMS (ESI) m/z: 393.0 [M+H$^+$].

Example 10

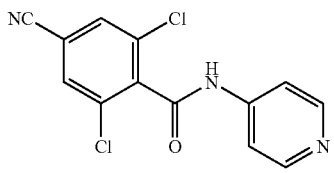

2,6-dichloro-4-cyano-N-(pyridine-4-yl)benzamide

To the solution of 2,6-dichloro-4-iodo-N-(pyridin-4-yl)benzamide (0.15 g, 0.38 mmol) in DMF (2 mL) was added CuCN (0.17 g, 1.9 mmol). The mixture was heated at 150° C. under the irradiation of microwave for 1 hour. After the completion of the reaction, the mixture was filtered through Celite and purified by acid HPLC(YMC, 150 mm×30 mm, gradient: CH$_3$CN/0.5% TFA, 10-50, 17 min) to afford the desired product (25.4 mg, yield: 23%). $^1$HNMR (DMSO-d$_6$, 400 MHz): δ11.95 (s, 1H), 8.74 (br, 2H), 8.33 (s, 2H), 7.97 (2H). LCMS (ESI) m/z: 292.1 [M+H$^+$]

Example 11

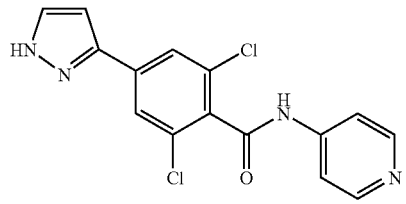 [SMILES: O=C(Nc1ccncc1)c1c(Cl)cc(-c2cc[nH]n2)cc1Cl]

2,6-dichloro-4-(1H-pyrazol-3-yl)-N-(pyridin-4-yl)benzamide

To the solution of 2,6-dichloro-4-iodo-N-(pyridin-4-yl)benzamide (0.17 g, 0.43 mmol), 4-(4,4,5,5-tetramethyl-1,3,2-dioxaborolan-2-yl)-1H-pyrazole (0.125 g, 0.65 mmol), Cs$_2$CO$_3$ (0.28 g, 0.86 mmol) in CH$_3$CN/H$_2$O (1 mL/1 mL) was added PdCl$_2$(dppf) (31 mg, 0.043 mmol) under N$_2$ atmosphere. The mixture was heated at 160° C. under the irradiation of microwave for 30 minutes. After the completion of the reaction, the mixture was filtered through Celite and purified by preparative basic HPLC (Gemini, 200 mm×25 mm, gradient: CH$_3$CN/0.05% NH$_3$.H$_2$O, 50-80, 10 min) to afford the desired product (23.8 mg, 17% yield). $^1$HNMR (DMSO-d$_6$, 400 MHz): δ11.19 (s, 1H), 8.49 (s, 2H), 8.29 (s, 2H), 7.88 (s, 2H), 7.65 (s, 2H), 7.07 (s, 1H). LCMS (ESI) m/z: 333.1 [M+H$^+$]

Additional exemplary compounds of Formulas I-VII, Examples 12-223 shown in Table 1 below, were prepared according to the above-described methods, characterized, and tested for inhibition of the Janus kinases according to the above methods, and have the following structures and corresponding names (ChemDraw Ultra, Version 9.0.1, CambridgeSoft Corp., Cambridge Mass.).

TABLE 1

| Ex | Structure | Name | LCMS (ESI) m/z |
|---|---|---|---|
| 12 | 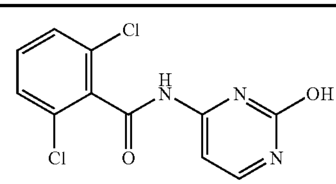 | 2,6-dichloro-N-(2-hydroxypyrimidin-4-yl)benzamide | 283.9 |
| 13 | 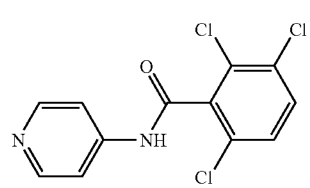 [SMILES: O=C(Nc1ccncc1)c1c(Cl)ccc(Cl)c1Cl] | 2,3,6-trichloro-N-(pyridin-4-yl)benzamide | 301.1 |
| 14 | 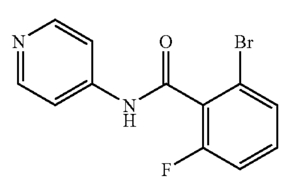 [SMILES: O=C(Nc1ccncc1)c1c(F)cccc1Br] | 2-bromo-6-fluoro-N-(pyridin-4-yl)benzamide | 295.1 |

TABLE 1-continued

| Ex | Structure | Name | LCMS (ESI) m/z |
|---|---|---|---|
| 15 | 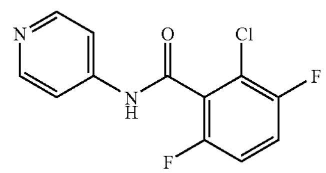 [SMILES: O=C(Nc1ccncc1)c1c(F)ccc(F)c1Cl] | 2-chloro-3,6-difluoro-N-(pyridin-4-yl)benzamide | 269.1 |
| 16 | 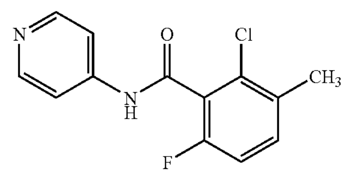 [SMILES: Cc1ccc(F)c(C(=O)Nc2ccncc2)c1Cl] | 2-chloro-6-fluoro-3-methyl-N-(pyridin-4-yl)benzamide | 265.0 |
| 17 | 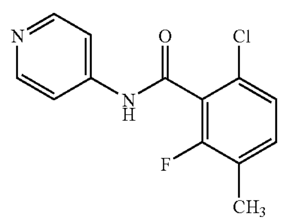 [SMILES: Cc1ccc(Cl)c(C(=O)Nc2ccncc2)c1F] | 6-chloro-2-fluoro-3-methyl-N-(pyridin-4-yl)benzamide | 265.0 |
| 18 | 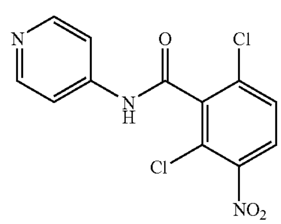 | 2,6-dichloro-3-nitro-N-(pyridin-4-yl)benzamide | 312.1 |
| 19 | 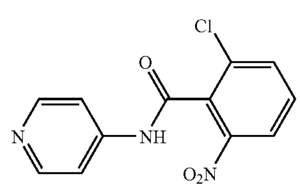 [SMILES: O=C(Nc1ccncc1)c1c(Cl)cccc1[N+](=O)[O-]] | 2-chloro-6-nitro-N-(pyridin-4-yl)benzamide | 278.1 |
| 20 | 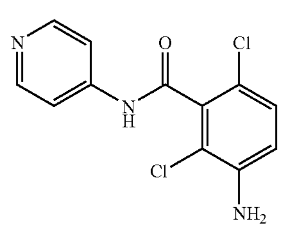 [SMILES: Nc1ccc(Cl)c(C(=O)Nc2ccncc2)c1Cl] | 3-amino-2,6-dichloro-N-(pyridin-4-yl)benzamide | 282.1 |
| 21 | 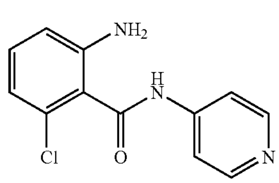 [SMILES: Nc1cccc(Cl)c1C(=O)Nc1ccncc1] | 2-amino-6-chloro-N-(pyridin-4-yl)benzamide | 247.7 |

TABLE 1-continued

| Ex | Structure | Name | LCMS (ESI) m/z |
|---|---|---|---|
| 22 | 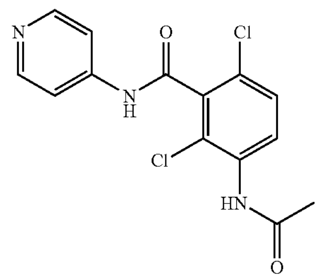 [SMILES: CC(=O)Nc1ccc(Cl)c(C(=O)Nc2ccncc2)c1Cl] | 3-acetamido-2,6-dichloro-N-(pyridin-4-yl)benzamide | 324.1 |
| 23 | 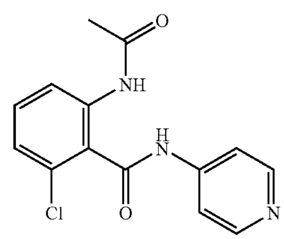 [SMILES: CC(=O)Nc1cccc(Cl)c1C(=O)Nc1ccncc1] | 2-acetamido-6-chloro-N-(pyridin-4-yl)benzamide | 290.1 |
| 24 | 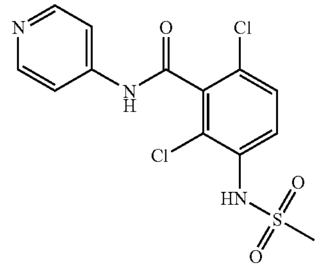 [SMILES: CS(=O)(=O)Nc1ccc(Cl)c(C(=O)Nc2ccncc2)c1Cl] | 2,6-dichloro-3-(methylsulfonamido)-N-(pyridin-4-yl)benzamide | 360.1 |
| 25 | 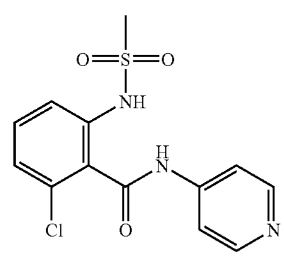 [SMILES: CS(=O)(=O)Nc1cccc(Cl)c1C(=O)Nc1ccncc1] | 2-chloro-6-(methylsulfonamido)-N-(pyridin-4-yl)benzamide | 326.2 |
| 26 | 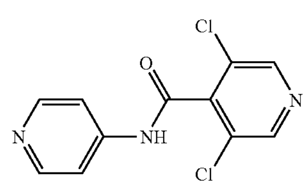 [SMILES: O=C(Nc1ccncc1)c1c(Cl)cncc1Cl] | 3,5-dichloro-N-(pyridin-4-yl)isonicotinamide | 268.1 |
| 27 | 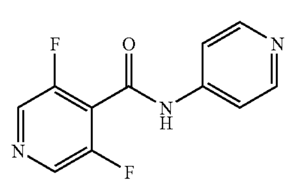 [SMILES: O=C(Nc1ccncc1)c1c(F)cncc1F] | 3,5-difluoro-N-(pyridin-4-yl)isonicotinamide | 236.2 |

TABLE 1-continued

| Ex | Structure | Name | LCMS (ESI) m/z |
|---|---|---|---|
| 28 | 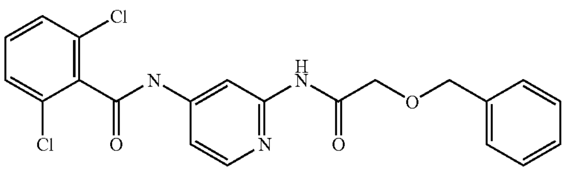 [SMILES: O=C(COCc1ccccc1)Nc1cc(NC(=O)c2c(Cl)cccc2Cl)ccn1] | N-(2-(2-(benzyloxy)acetamido)pyridin-4-yl)-2,6-dichlorobenzamide | 429.9 |
| 29 | 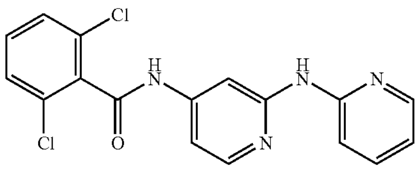 [SMILES: O=C(Nc1ccnc(Nc2ccccn2)c1)c1c(Cl)cccc1Cl] | 2,6-dichloro-N-(2-(pyridin-2-ylamino)pyridin-4-yl)benzamide | 359.2 |
| 30 | 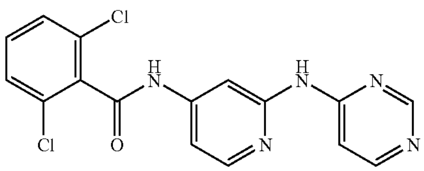 [SMILES: O=C(Nc1ccnc(Nc2ccncn2)c1)c1c(Cl)cccc1Cl] | 2,6-dichloro-N-(2-(pyrimidin-4-ylamino)pyridin-4-yl)benzamide | 359.9 |
| 31 | 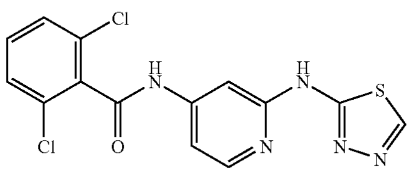 [SMILES: O=C(Nc1ccnc(Nc2nncs2)c1)c1c(Cl)cccc1Cl] | N-(2-(1,3,4-thiadiazol-2-ylamino)pyridin-4-yl)-2,6-dichlorobenzamide | 365.9 |
| 32 | 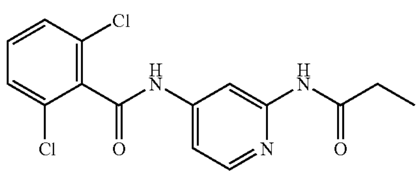 [SMILES: CCC(=O)Nc1cc(NC(=O)c2c(Cl)cccc2Cl)ccn1] | 2,6-dichloro-N-(2-propionamidopyridin-4-yl)benzamide | 338.2 |
| 33 | 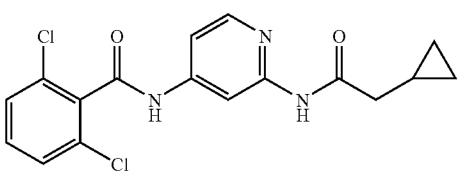 [SMILES: O=C(CC1CC1)Nc1cc(NC(=O)c2c(Cl)cccc2Cl)ccn1] | 2,6-dichloro-N-(2-(2-cyclopropylacetamido)-pyridin-4-yl)benzamide | 364.2 |
| 34 | 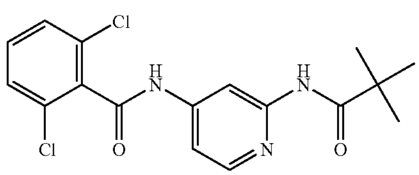 [SMILES: CC(C)(C)C(=O)Nc1cc(NC(=O)c2c(Cl)cccc2Cl)ccn1] | 2,6-dichloro-N-(2-pivalamidopyridin-4-yl)benzamide | 366.3 |
| 35 | 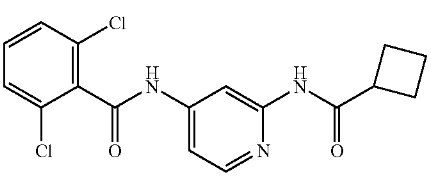 [SMILES: O=C(Nc1ccnc(NC(=O)C2CCC2)c1)c1c(Cl)cccc1Cl] | 2,6-dichloro-N-(2-(cyclobutanecarboxamido)-pyridin-4-yl)benzamide | 364.2 |

TABLE 1-continued

| Ex | Structure | Name | LCMS (ESI) m/z |
|---|---|---|---|
| 36 | 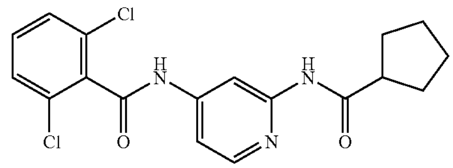 | 2,6-dichloro-N-(2-(cyclopentanecarboxamido)-pyridin-4-yl)benzamide | 378.3 |
| 37 | 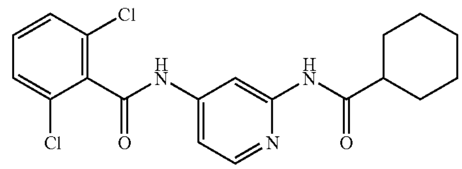 [SMILES: O=C(Nc1ccnc(NC(=O)C2CCCCC2)c1)c1c(Cl)cccc1Cl] | 2,6-dichloro-N-(2-(cyclohexanecarboxamido)-pyridin-4-yl)benzamide | 394.2 |
| 38 | 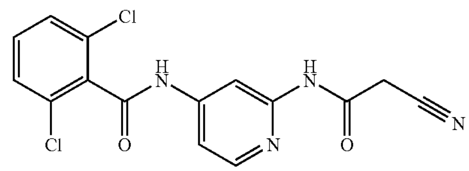 [SMILES: N#CCC(=O)Nc1cc(NC(=O)c2c(Cl)cccc2Cl)ccn1] | 2,6-dichloro-N-(2-(2-cyanoacetamido)pyridin-4-yl)benzamide | 348.9 |
| 39 | 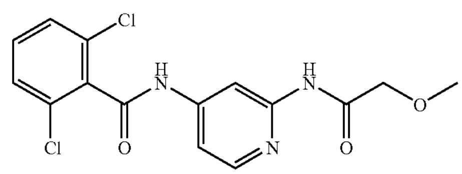 [SMILES: COCC(=O)Nc1cc(NC(=O)c2c(Cl)cccc2Cl)ccn1] | 2,6-dichloro-N-(2-(2-methoxyacetamido)pyridin-4-yl)benzamide | 354.2 |
| 40 | 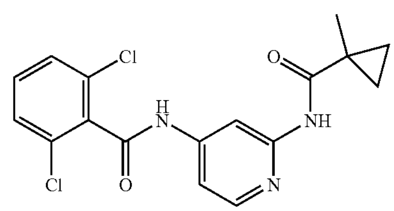 [SMILES: CC1(C(=O)Nc2cc(NC(=O)c3c(Cl)cccc3Cl)ccn2)CC1] | 2,6-dichloro-N-(2-(1-methylcyclopropanecarboxamido)pyridin-4-yl)benzamide | 364.3 |
| 41 | 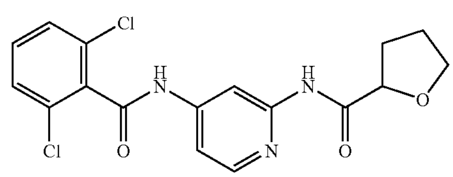 [SMILES: O=C(Nc1ccnc(NC(=O)C2CCCO2)c1)c1c(Cl)cccc1Cl] | N-(4-(2,6-dichlorobenzamido)pyridin-2-yl)tetrahydrofuran-2-carboxamide | 379.9 |
| 42 | 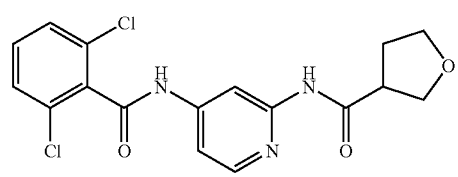 [SMILES: O=C(Nc1ccnc(NC(=O)C2CCOC2)c1)c1c(Cl)cccc1Cl] | N-(4-(2,6-dichlorobenzamido)-pyridin-2-yl)tetrahydrofuran-3-carboxamide | 380.2 |
| 43 | 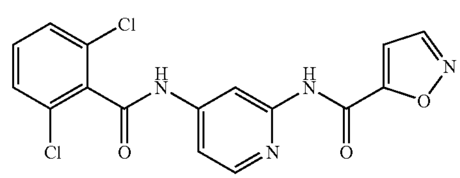 [SMILES: O=C(Nc1cc(NC(=O)c2c(Cl)cccc2Cl)ccn1)c1ccno1] | N-(4-(2,6-dichlorobenzamido)-pyridin-2-yl)isoxazole-5-carboxamide | 376.7 |

TABLE 1-continued

| Ex | Structure | Name | LCMS (ESI) m/z |
|---|---|---|---|
| 44 | 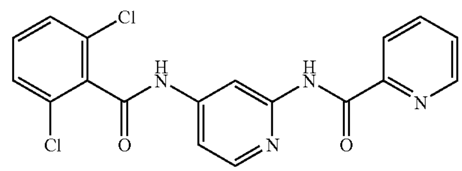 [SMILES: O=C(Nc1cc(NC(=O)c2c(Cl)cccc2Cl)ccn1)c1ccccn1] | N-(4-(2,6-dichlorobenzamido)-pyridin-2-yl)picolinamide | 387.2 |
| 45 | 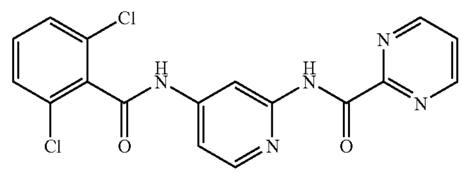 [SMILES: O=C(Nc1cc(NC(=O)c2c(Cl)cccc2Cl)ccn1)c1ncccn1] | N-(4-(2,6-dichlorobenzamido)-pyridin-2-yl)pyrimidine-2-carboxamide | 387.7 |
| 46 | 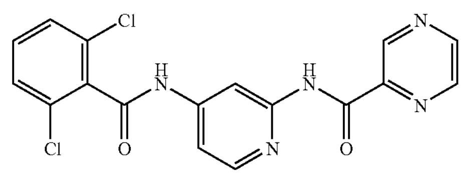 [SMILES: O=C(Nc1cc(NC(=O)c2c(Cl)cccc2Cl)ccn1)c1cnccn1] | N-(4-(2,6-dichlorobenzamido)-pyridin-2-yl)pyrazine-2-carboxamide | 388.3 |
| 47 | 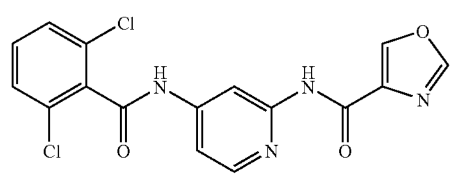 [SMILES: O=C(Nc1cc(NC(=O)c2c(Cl)cccc2Cl)ccn1)c1cocn1] | N-(4-(2,6-dichlorobenzamido)-pyridin-2-yl)oxazole-4-carboxamide | 377.0 |
| 48 | 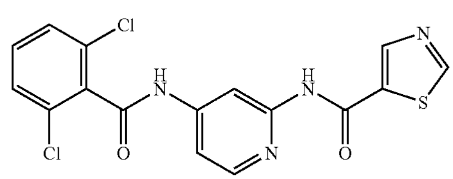 [SMILES: O=C(Nc1cc(NC(=O)c2c(Cl)cccc2Cl)ccn1)c1cncs1] | N-(4-(2,6-dichlorobenzamido)-pyridin-2-yl)thiazole-5-carboxamide | 393.1 |
| 49 | 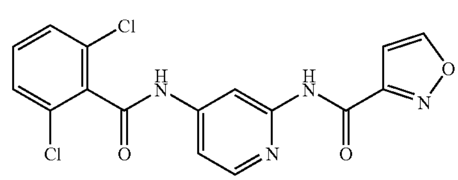 [SMILES: O=C(Nc1cc(NC(=O)c2c(Cl)cccc2Cl)ccn1)c1ccon1] | N-(4-(2,6-dichlorobenzamido)-pyridin-2-yl) isoxazole-3-carboxamide | 377.2 |
| 50 | 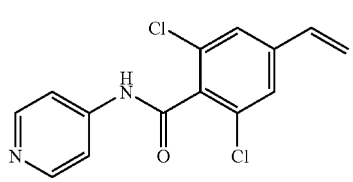 [SMILES: C=Cc1cc(Cl)c(C(=O)Nc2ccncc2)c(Cl)c1] | 2,6-dichloro-4-(3-hydroxyprop-1-ynyl)-N-(pyridin-4-yl)benzamide | 321.0 |
| 51 | 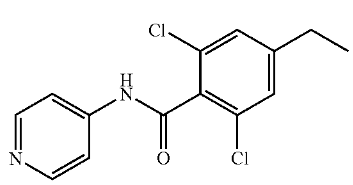 [SMILES: CCc1cc(Cl)c(C(=O)Nc2ccncc2)c(Cl)c1] | 2,6-dichloro-4-ethyl-N-(pyridin-4-yl)benzamide | 295.2 |

TABLE 1-continued

| Ex | Structure | Name | LCMS (ESI) m/z |
|---|---|---|---|
| 52 | 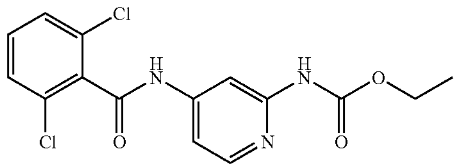 [SMILES: CCOC(=O)Nc1cc(NC(=O)c2c(Cl)cccc2Cl)ccn1] | ethyl 4-(2,6-dichlorobenzamido)pyridin-2-ylcarbamate | 354.2 |
| 53 | 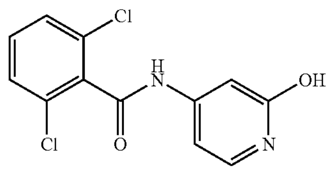 [SMILES: O=C(Nc1ccnc(O)c1)c1c(Cl)cccc1Cl] | 2,6-dichloro-N-(2-hydroxypyridin-4-yl)benzamide | 282.9 |
| 54 | 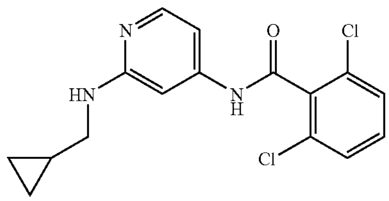 [SMILES: O=C(Nc1ccnc(NCC2CC2)c1)c1c(Cl)cccc1Cl] | 2,6-dichloro-N-(2-(cyclopropylmethylamino)-pyridin-4-yl)benzamide | 336.1 |
| 55 | 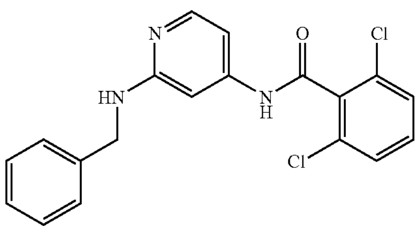 [SMILES: O=C(Nc1ccnc(NCc2ccccc2)c1)c1c(Cl)cccc1Cl] | N-(2-(benzylamino)pyridin-4-yl)-2,6-dichlorobenzamide | 372.1 |
| 56 | 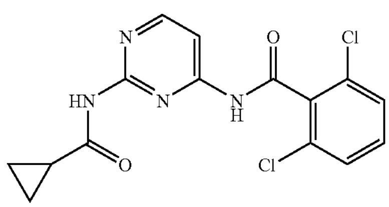 [SMILES: O=C(Nc1ccnc(NC(=O)C2CC2)n1)c1c(Cl)cccc1Cl] | 2,6-dichloro-N-(2-(cyclopropanecarboxamido)-pyrimidin-4-yl)benzamide | 352.2 |
| 57 | 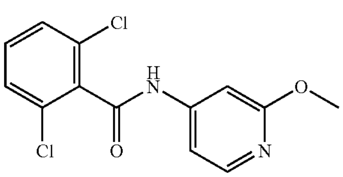 [SMILES: COc1cc(NC(=O)c2c(Cl)cccc2Cl)ccn1] | 2,6-dichloro-N-(2-methoxypyridin-4-yl)benzamide | 296.7 |
| 58 | 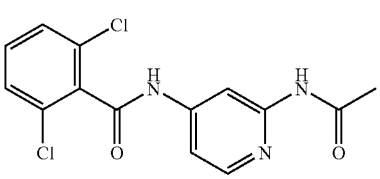 [SMILES: CC(=O)Nc1cc(NC(=O)c2c(Cl)cccc2Cl)ccn1] | N-(2-acetamidopyridin-4-yl)-2,6-dichlorobenzamide | 323.9 |
| 59 | 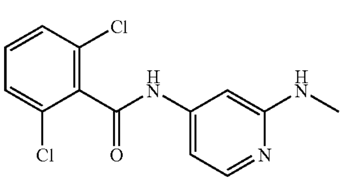 [SMILES: CNc1cc(NC(=O)c2c(Cl)cccc2Cl)ccn1] | 2,6-dichloro-N-(2-(methylamino)pyridin-4-yl)benzamide | 296.1 |

TABLE 1-continued

| Ex | Structure | Name | LCMS (ESI) m/z |
|---|---|---|---|
| 60 | 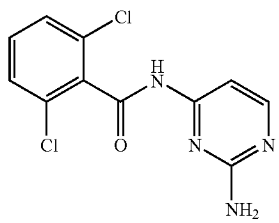 [SMILES: Nc1nccc(NC(=O)c2c(Cl)cccc2Cl)n1] | N-(2-aminopyrimidin-4-yl)-2,6-dichlorobenzamide | 282.9 |
| 61 | 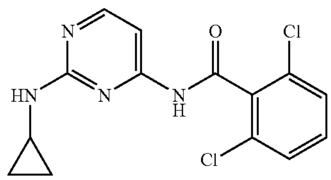 [SMILES: O=C(Nc1ccnc(NC2CC2)n1)c1c(Cl)cccc1Cl] | 2,6-dichloro-N-(2-(cyclopropylamino)-pyrimidin-4-yl)benzamide | 323.0 |
| 62 | 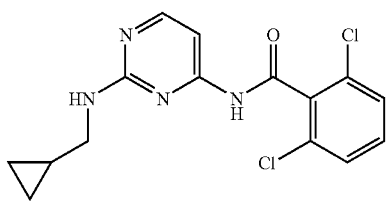 [SMILES: O=C(Nc1ccnc(NCC2CC2)n1)c1c(Cl)cccc1Cl] | 2,6-dichloro-N-(2-(cyclopropylmethylamino)-pyrimidin-4-yl)benzamide337.2 | 337.2 |
| 63 | 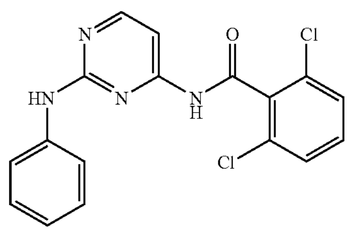 [SMILES: O=C(Nc1ccnc(Nc2ccccc2)n1)c1c(Cl)cccc1Cl] | 2,6-dichloro-N-(2-(phenylamino)pyrimidin-4-yl)benzamide | 359.0 |
| 64 | 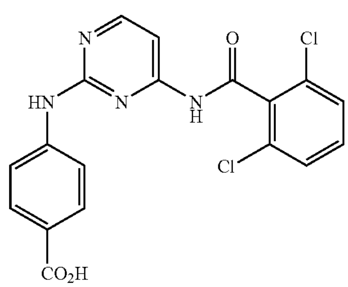 [SMILES: O=C(O)c1ccc(Nc2nccc(NC(=O)c3c(Cl)cccc3Cl)n2)cc1] | 4-(4-(2,6-dichlorobenzamido)pyrimidin-2-ylamino)benzoic acid | 403.0 |
| 65 | 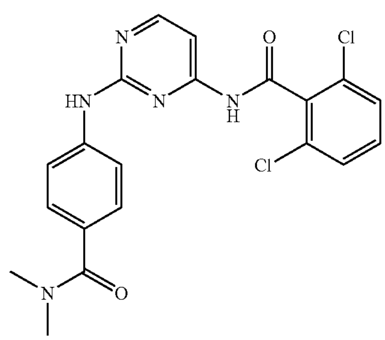 [SMILES: CN(C)C(=O)c1ccc(Nc2nccc(NC(=O)c3c(Cl)cccc3Cl)n2)cc1] | 2,6-dichloro-N-(2-(4-(dimethylcarbamoyl)phenylamino)pyrimidin-4-yl)benzamide | 430.1 |

| Ex | Structure | Name | LCMS (ESI) m/z |
|---|---|---|---|
| 66 | 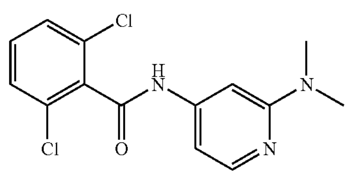 [SMILES: CN(C)c1cc(NC(=O)c2c(Cl)cccc2Cl)ccn1] | 2,6-dichloro-N-(2-(dimethylamino)pyridin-4-yl)benzamide | 310.1 |
| 67 | 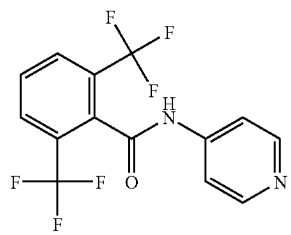 [SMILES: O=C(Nc1ccncc1)c1c(C(F)(F)F)cccc1C(F)(F)F] | N-(pyridin-4-yl)-2,6-bis(trifluoromethyl)benzamide | 335.1 |
| 68 | 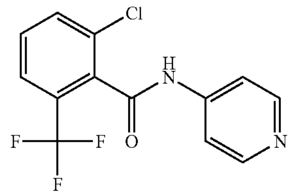 [SMILES: O=C(Nc1ccncc1)c1c(Cl)cccc1C(F)(F)F] | 2-chloro-N-(pyridin-4-yl)-6-(trifluoromethyl)benzamide | 300.9 |
| 69 | 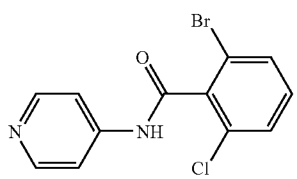 [SMILES: O=C(Nc1ccncc1)c1c(Cl)cccc1Br] | 2-bromo-6-chloro-N-(pyridin-4-yl)benzamide | 311.0 |
| 70 | 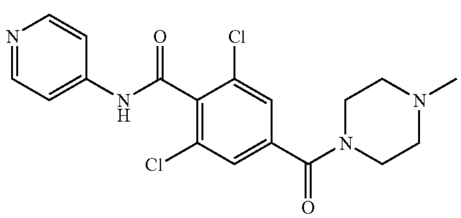 [SMILES: CN1CCN(C(=O)c2cc(Cl)c(C(=O)Nc3ccncc3)c(Cl)c2)CC1] | 2,6-dichloro-4-(4-methylpiperazine-1-carbonyl)-N-(pyridin-4-yl)benzamide | 393.0 |
| 71 | 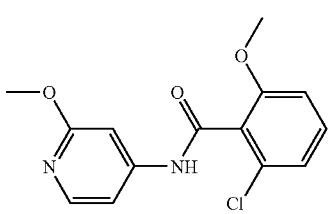 [SMILES: COc1cc(NC(=O)c2c(Cl)cccc2OC)ccn1] | 2-chloro-6-methoxy-N-(2-methoxypyridin-4-yl)benzamide | 292.9 |
| 72 | 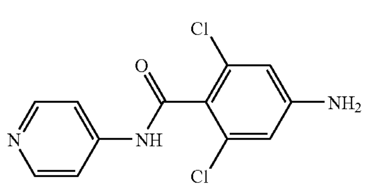 [SMILES: Nc1cc(Cl)c(C(=O)Nc2ccncc2)c(Cl)c1] | 4-amino-2,6-dichloro-N-(pyridin-4-yl)benzamide | 282.0 |

US 8,486,950 B2

TABLE 1-continued

| Ex | Structure | Name | LCMS (ESI) m/z |
|---|---|---|---|
| 73 | 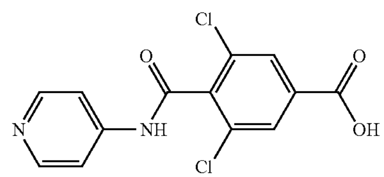 [SMILES: O=C(O)c1cc(Cl)c(C(=O)Nc2ccncc2)c(Cl)c1] | 3,5-dichloro-4-(pyridin-4-ylcarbamoyl)benzoic acid | 311.1 |
| 74 | 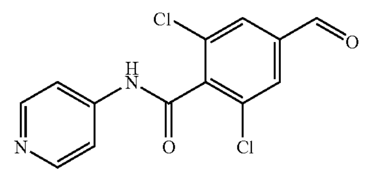 [SMILES: O=Cc1cc(Cl)c(C(=O)Nc2ccncc2)c(Cl)c1] | 2,6-dichloro-4-formyl-N-(pyridin-4-yl)benzamide | 295.3 |
| 75 | 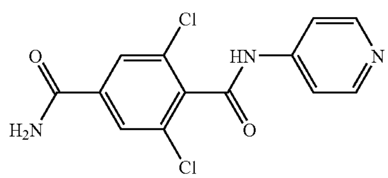 [SMILES: NC(=O)c1cc(Cl)c(C(=O)Nc2ccncc2)c(Cl)c1] | 2,6-dichloro-N1-(pyridin-4-yl)terephthalamide | 309.9 |
| 76 | 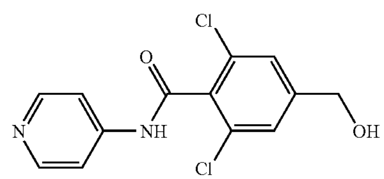 [SMILES: O=C(Nc1ccncc1)c1c(Cl)cc(CO)cc1Cl] | 2,6-dichloro-4-(hydroxymethyl)-N-(pyridin-4-yl)benzamide | 297.1 |
| 77 | 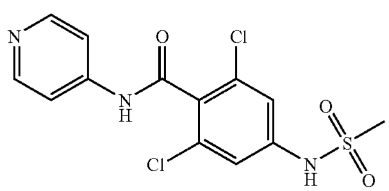 [SMILES: CS(=O)(=O)Nc1cc(Cl)c(C(=O)Nc2ccncc2)c(Cl)c1] | 2,6-dichloro-4-(methylsulfonamido)-N-(pyridin-4-yl)benzamide | 360.0 |
| 78 | 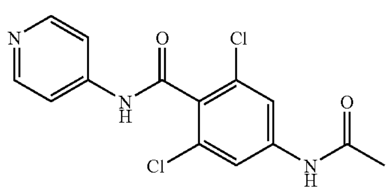 [SMILES: CC(=O)Nc1cc(Cl)c(C(=O)Nc2ccncc2)c(Cl)c1] | 4-acetamido-2,6-dichloro-N-(pyridin-4-yl)benzamide | 323.9 |
| 79 | 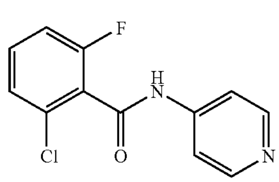 [SMILES: O=C(Nc1ccncc1)c1c(F)cccc1Cl] | 2-chloro-6-fluoro-N-(pyridin-4-yl)benzamide | 251.1 |
| 80 | 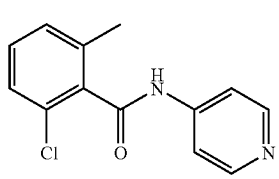 [SMILES: Cc1cccc(Cl)c1C(=O)Nc1ccncc1] | 2-chloro-6-methyl-N-(pyridin-4-yl)benzamide | 247.1 |

TABLE 1-continued

| Ex | Structure | Name | LCMS (ESI) m/z |
|---|---|---|---|
| 81 | 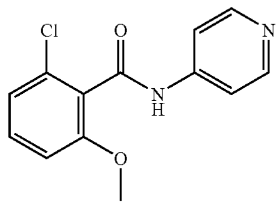 [SMILES: COc1cccc(Cl)c1C(=O)Nc1ccncc1] | 2-chloro-6-methoxy-N-(pyridin-4-yl)benzamide | 262.9 |
| 82 | 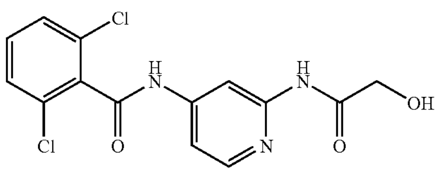 [SMILES: O=C(CO)Nc1cc(NC(=O)c2c(Cl)cccc2Cl)ccn1] | 2,6-dichloro-N-(2-(2-hydroxyacetamido)-pyridin-4-yl)benzamide | 339.9 |
| 83 | 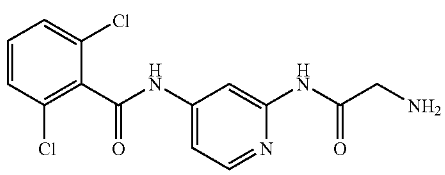 [SMILES: NCC(=O)Nc1cc(NC(=O)c2c(Cl)cccc2Cl)ccn1] | N-(2-(2-aminoacetamido)-pyridin-4-yl)-2,6-dichlorobenzamide | 338.8 |
| 84 | 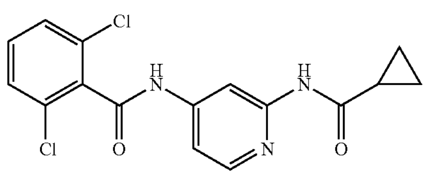 [SMILES: O=C(Nc1ccnc(NC(=O)C2CC2)c1)c1c(Cl)cccc1Cl] | 2,6-dichloro-N-(2-(cyclopropanecarboxamido)-pyridin-4-yl)benzamide | 349.8 |
| 85 | 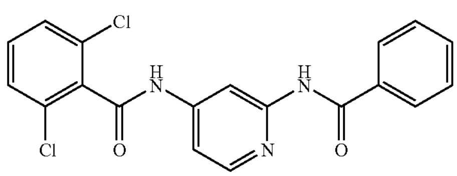 [SMILES: O=C(Nc1cc(NC(=O)c2c(Cl)cccc2Cl)ccn1)c1ccccc1] | N-(2-benzamidopyridin-4-yl)-2,6-dichlorobenzamide | 385.8 |
| 86 | 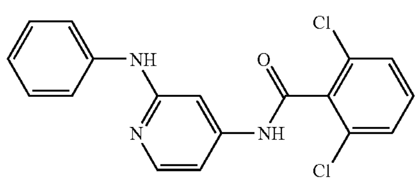 [SMILES: O=C(Nc1ccnc(Nc2ccccc2)c1)c1c(Cl)cccc1Cl] | 2,6-dichloro-N-(2-(phenylamino)pyridin-4-yl)benzamide | 358.0 |
| 87 | 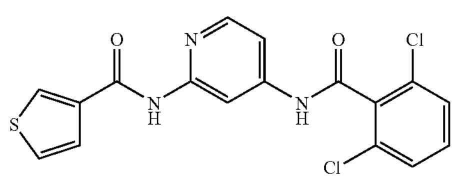 [SMILES: O=C(Nc1cc(NC(=O)c2c(Cl)cccc2Cl)ccn1)c1ccsc1] | N-(4-(2,6-dichloro-benzamido)pyridin-2-yl)thiophene-3-carboxamide | 392.0 |
| 88 | 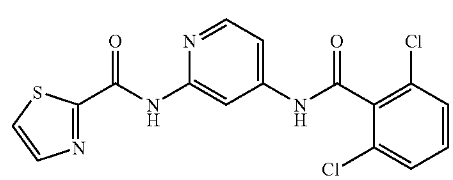 [SMILES: O=C(Nc1cc(NC(=O)c2c(Cl)cccc2Cl)ccn1)c1nccs1] | N-(4-(2,6-dichloro-benzamido)pyridin-2-yl)thiazole-2-carboxamide | 393.0 |

TABLE 1-continued

| Ex | Structure | Name | LCMS (ESI) m/z |
|---|---|---|---|
| 89 | 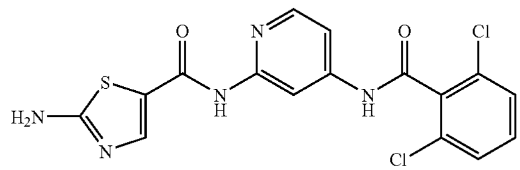 [SMILES: Nc1ncc(C(=O)Nc2cc(NC(=O)c3c(Cl)cccc3Cl)ccn2)s1] | 2-amino-N-(4-(2,6-dichlorobenzamido)-pyridin-2-yl)thiazole-5-carboxamide | 408.0 |
| 90 | 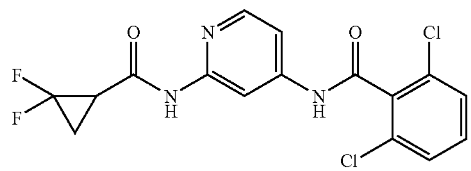 [SMILES: O=C(Nc1ccnc(NC(=O)C2CC2(F)F)c1)c1c(Cl)cccc1Cl] | 2,6-dichloro-N-(2-(2,2-difluorocyclopropanecarboxamido)pyridin-4-yl)benzamide | 386.0 |
| 91 | 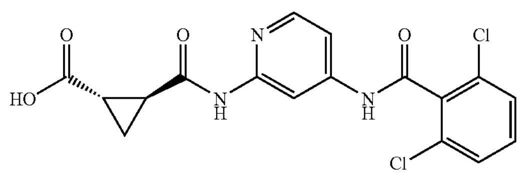 [SMILES: O=C(Nc1ccnc(NC(=O)[C@H]2C[C@@H]2C(=O)O)c1)c1c(Cl)cccc1Cl] | (1S,2S)-2-(4-(2,6-dichlorobenzamido)-pyridin-2-ylcarbamoyl)cyclopropanecarboxylic acid | 394.2 |
| 92 | 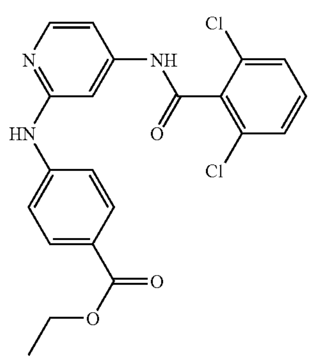 [SMILES: CCOC(=O)c1ccc(Nc2cc(NC(=O)c3c(Cl)cccc3Cl)ccn2)cc1] | ethyl 4-(4-(2,6-dichlorobenzamido)-pyridin-2-ylamino)benzoate | 430.3 |
| 93 | 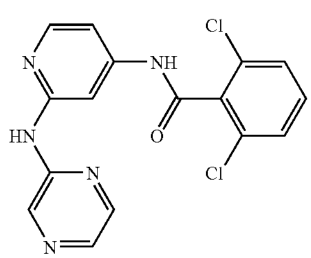 [SMILES: O=C(Nc1ccnc(Nc2cnccn2)c1)c1c(Cl)cccc1Cl] | 2,6-dichloro-N-(2-(pyrazin-2-ylamino)-pyridin-4-yl)benzamide | 360.2 |
| 94 | 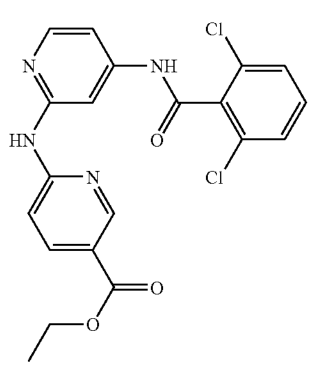 [SMILES: CCOC(=O)c1ccc(Nc2cc(NC(=O)c3c(Cl)cccc3Cl)ccn2)nc1] | ethyl 6-(4-(2,6-dichloro-benzamido)-pyridin-2-ylamino)nicotinate | 431.2 |

TABLE 1-continued

| Ex | Name | LCMS (ESI) m/z |
|---|---|---|
| 95 | 6-(4-(2,6-dichlorobenzamido)-pyridin-2-ylamino)-nicotinic acid | 403.2 |
| 96 | 2,6-dichloro-N-(2-(5-(4-methylpiperazine-1-carbonyl)pyridin-2-ylamino)pyridin-4-yl)-benzamide | 485.3 |
| 97 | 2,6-dichloro-N-(2-(5-(morpholine-4-carbonyl)-pyridin-2-ylamino)-pyridin-4-yl)benzamide | 472.3 |
| 98 | 2,6-dichloro-N-(2-(4-(4-methylpiperazine-1-carbonyl)phenylamino)-pyridin-4-yl)benzamide | 484.3 |

TABLE 1-continued

| Ex | Structure | Name | LCMS (ESI) m/z |
|---|---|---|---|
| 99 | 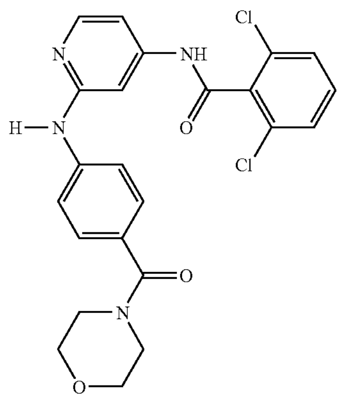 [SMILES: O=C(Nc1ccnc(Nc2ccc(C(=O)N3CCOCC3)cc2)c1)c1c(Cl)cccc1Cl] | 2,6-dichloro-N-(2-(4-(morpholine-4-carbonyl)-phenylamino)pyridin-4-yl)-benzamide | 471.3 |
| 100 | 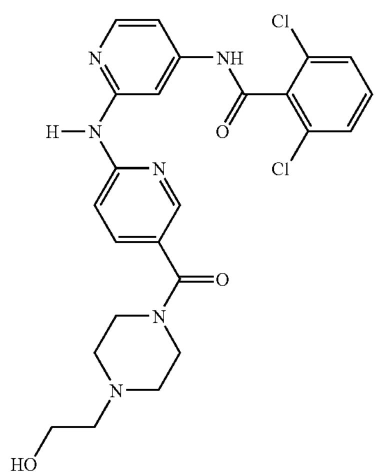 [SMILES: O=C(Nc1ccnc(Nc2ccc(C(=O)N3CCN(CCO)CC3)cn2)c1)c1c(Cl)cccc1Cl] | 2,6-dichloro-N-(2-(5-(4-(2-hydroxyethyl)piperazine-1-carbonyl)pyridin-2-ylamino)-pyridin-4-yl)benzamide | 515.3 |
| 101 | 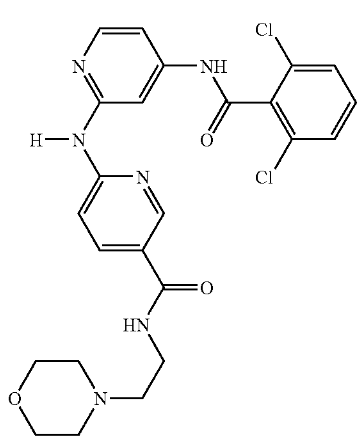 [SMILES: O=C(NCCN1CCOCC1)c1ccc(Nc2cc(NC(=O)c3c(Cl)cccc3Cl)ccn2)nc1] | 6-(4-(2,6-dichloro-benzamido)pyridin-2-ylamino)-N-(2-morpholino-ethyl)nicotin amide | 515.3 |

TABLE 1-continued

| Ex | Structure | Name | LCMS (ESI) m/z |
|---|---|---|---|
| 102 | 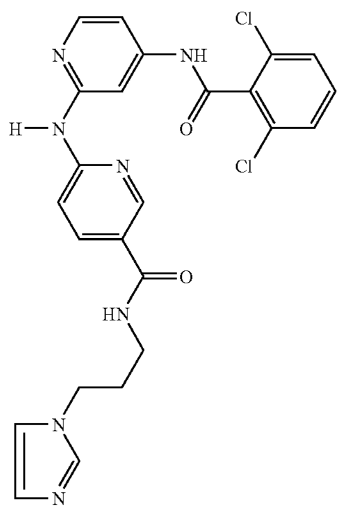 [SMILES: O=C(NCCCn1ccnc1)c1ccc(Nc2cc(NC(=O)c3c(Cl)cccc3Cl)ccn2)nc1] | N-(3-(1H-imidazol-1-yl)-propyl)-6-(4-(2,6-dichlorobenzamido)-pyridin-2-ylamino)-nicotinamide | 510.4 |
| 103 | 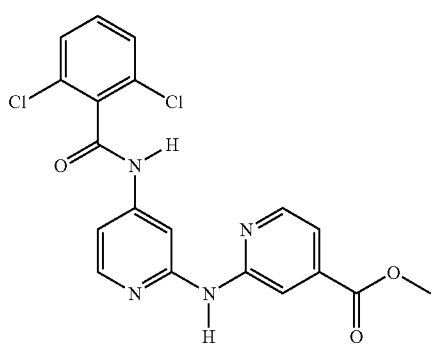 [SMILES: COC(=O)c1ccnc(Nc2cc(NC(=O)c3c(Cl)cccc3Cl)ccn2)c1] | methyl 2-(4-(2,6-dichlorobenzamido)-pyridin-2-ylamino)-isonicotinate | 417.2 |
| 104 | 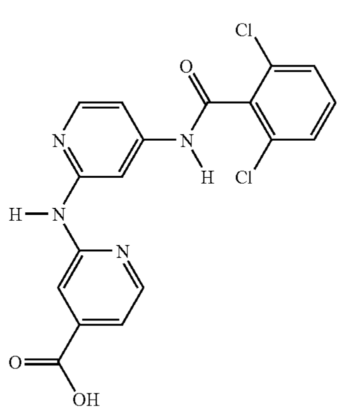 [SMILES: O=C(O)c1ccnc(Nc2cc(NC(=O)c3c(Cl)cccc3Cl)ccn2)c1] | 2-(4-(2,6-dichloro-benzamido)pyridin-2-ylamino)isonicotinic acid | 403.2 |

TABLE 1-continued

| Ex | Structure | Name | LCMS (ESI) m/z |
|---|---|---|---|
| 105 | 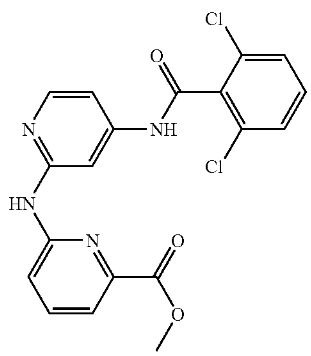 [SMILES: COC(=O)c1cccc(Nc2cc(NC(=O)c3c(Cl)cccc3Cl)ccn2)n1] | methyl 6-(4-(2,6-dichlorobenzamido)-pyridin-2-ylamino)picolinate | 417.3 |
| 106 | 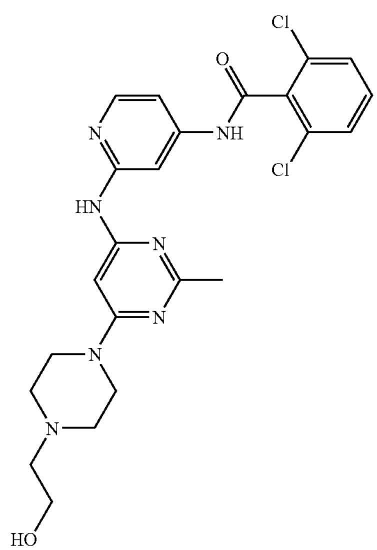 [SMILES: Cc1nc(Nc2cc(NC(=O)c3c(Cl)cccc3Cl)ccn2)cc(N2CCN(CCO)CC2)n1] | 2,6-dichloro-N-(2-(6-(4-(2-hydroxyethyl)piperazin-1-yl)-2-methylpyrimidin-4-ylamino)pyridin-4-yl)benzamide | 502.4 |
| 107 | 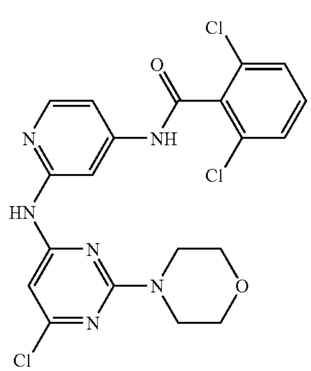 [SMILES: O=C(Nc1ccnc(Nc2cc(Cl)nc(N3CCOCC3)n2)c1)c1c(Cl)cccc1Cl] | 2,6-dichloro-N-(2-(6-chloro-2-morpholinopyrimidin-4-ylamino)pyridin-4-yl)benzamide | 479.8 |

TABLE 1-continued

| Ex | Structure | Name | LCMS (ESI) m/z |
|---|---|---|---|
| 108 | 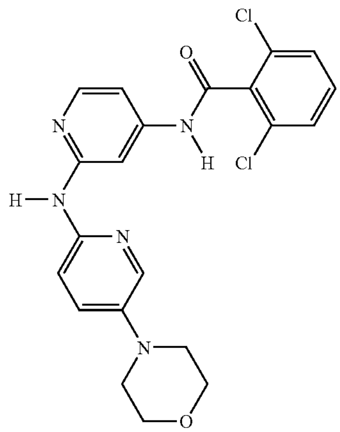 [SMILES: O=C(Nc1ccnc(Nc2ccc(N3CCOCC3)cn2)c1)c1c(Cl)cccc1Cl] | 2,6-dichloro-N-(2-(5-morpholinopyridin-2-ylamino)pyridin-4-yl)-benzamide | 444.3 |
| 109 | 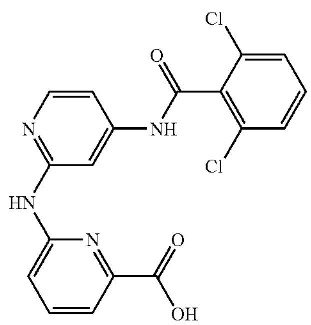 [SMILES: O=C(O)c1cccc(Nc2cc(NC(=O)c3c(Cl)cccc3Cl)ccn2)n1] | 6-(4-(2,6-dichloro-benzamido)pyridin-2-ylamino)picolinic acid | 403.2 |
| 110 | 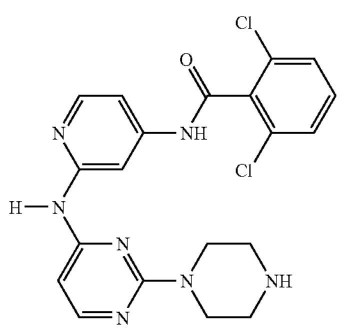 [SMILES: O=C(Nc1ccnc(Nc2ccnc(N3CCNCC3)n2)c1)c1c(Cl)cccc1Cl] | 2,6-dichloro-N-(2-(2-(piperazin-1-yl)-pyrimidin-4-ylamino)-pyridin-4-yl)benzamide | 444.3 |
| 111 | 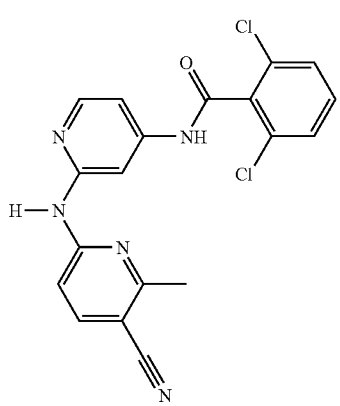 [SMILES: Cc1nc(Nc2cc(NC(=O)c3c(Cl)cccc3Cl)ccn2)ccc1C#N] | 2,6-dichloro-N-(2-(5-cyano-6-methylpyridin-2-ylamino)pyridin-4-yl)benzamide | 398.3 |

TABLE 1-continued
| Ex | Structure | Name | LCMS (ESI) m/z |
|---|---|---|---|
| 112 | 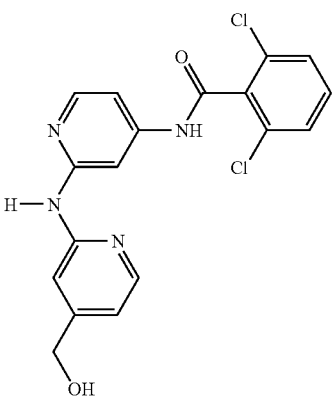 [SMILES: O=C(Nc1ccnc(Nc2cc(CO)ccn2)c1)c1c(Cl)cccc1Cl] | 2,6-dichloro-N-(2-(4-(hydroxymethyl)pyridin-2-ylamino)pyridin-4-yl)benzamide | 389.2 |
| 113 | 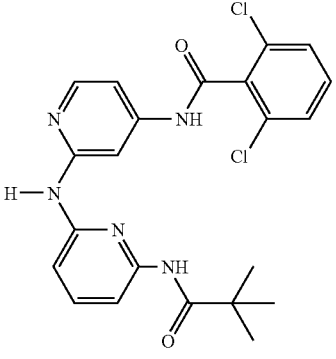 [SMILES: CC(C)(C)C(=O)Nc1cccc(Nc2cc(NC(=O)c3c(Cl)cccc3Cl)ccn2)n1] | 2,6-dichloro-N-(2-(6-pivalamidopyridin-2-ylamino)pyridin-4-yl)benzamide | 458.3 |
| 114 | 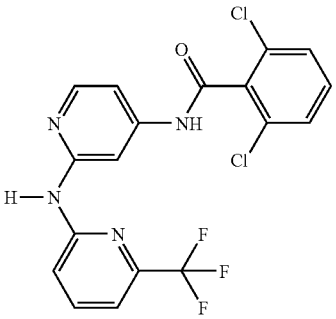 [SMILES: O=C(Nc1ccnc(Nc2cccc(C(F)(F)F)n2)c1)c1c(Cl)cccc1Cl] | 2,6-dichloro-N-(2-(6-(trifluoromethyl)pyridin-2-ylamino)pyridin-4-yl)benzamide | 427.3 |

TABLE 1-continued
| Ex | Structure | Name | LCMS (ESI) m/z |
|---|---|---|---|
| 115 | 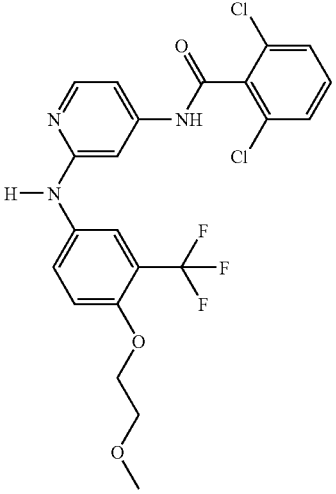 [SMILES: COCCOc1ccc(Nc2cc(NC(=O)c3c(Cl)cccc3Cl)ccn2)cc1C(F)(F)F] | 2,6-dichloro-N-(2-(4-(2-methoxyethoxy)-3-(trifluoromethyl)phenyl-amino)pyridin-4-yl)benzamide | 500.3 |
| 116 | 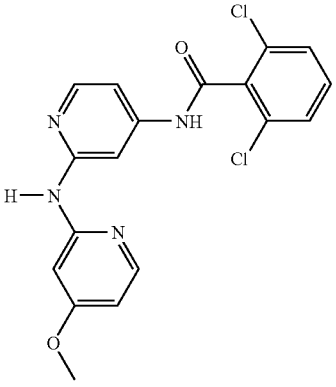 [SMILES: COc1ccnc(Nc2cc(NC(=O)c3c(Cl)cccc3Cl)ccn2)c1] | o-N-(2-(4-methoxypyridin-2-ylamino)pyridin-4-yl)benzamide | 389.2 |
| 117 | 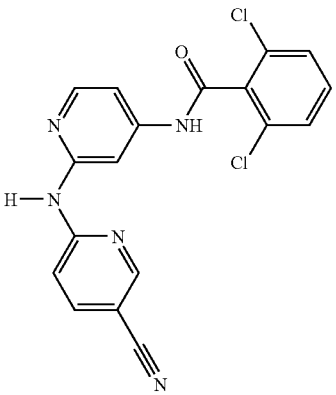 [SMILES: N#Cc1ccc(Nc2cc(NC(=O)c3c(Cl)cccc3Cl)ccn2)nc1] | 2,6-dichloro-N-(2-(5-cyanopyridin-2-ylamino)pyridin-4-yl)benzamide | 384.2 |

TABLE 1-continued

| Ex | Structure | Name | LCMS (ESI) m/z |
|---|---|---|---|
| 118 | 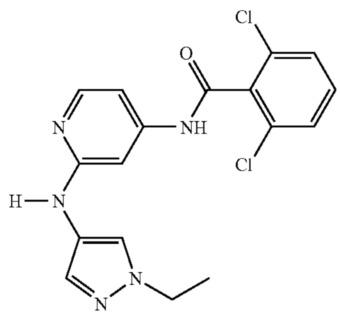 [SMILES: CCn1cc(Nc2cc(NC(=O)c3c(Cl)cccc3Cl)ccn2)cn1] | 2,6-dichloro-N-(2-(1-ethyl-1H-pyrazol-4-ylamino)pyridin-4-yl)benzamide | 376.2 |
| 119 | 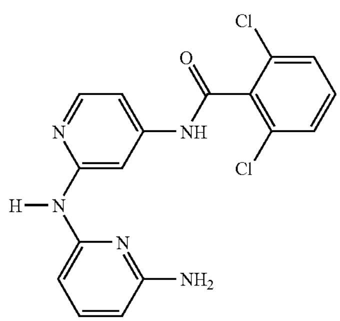 [SMILES: Nc1cccc(Nc2cc(NC(=O)c3c(Cl)cccc3Cl)ccn2)n1] | N-(2-(6-aminopyridin-2-ylamino)pyridin-4-yl)-2,6-dichlorobenzamide | 374.2 |
| 120 | 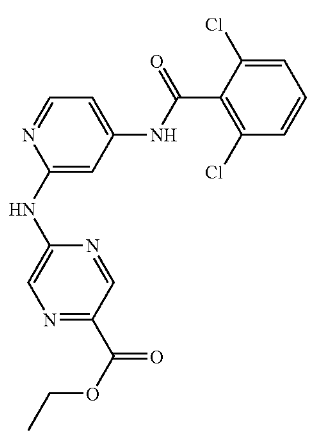 [SMILES: CCOC(=O)c1cnc(Nc2cc(NC(=O)c3c(Cl)cccc3Cl)ccn2)cn1] | ethyl 5-(4-(2,6-dichlorobenzamido)-pyridin-2-ylamino)pyrazine-2-carboxylate | 432.3 |
| 121 | 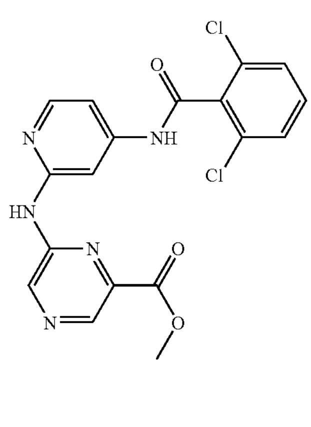 [SMILES: COC(=O)c1cncc(Nc2cc(NC(=O)c3c(Cl)cccc3Cl)ccn2)n1] | methyl 6-(4-(2,6-dichlorobenzamido)-pyridin-2-ylamino)-pyrazine-2-carboxylate | 418.2 |

TABLE 1-continued

| Ex | Structure | Name | LCMS (ESI) m/z |
|---|---|---|---|
| 122 | 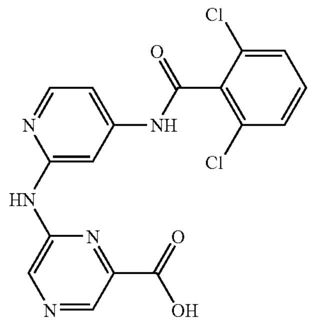 [SMILES: O=C(O)c1cncc(Nc2cc(NC(=O)c3c(Cl)cccc3Cl)ccn2)n1] | 6-(4-(2,6-dichlorobenzamido)-pyridin-2-ylamino)-pyrazine-2-carboxylic acid | 404.2 |
| 123 | 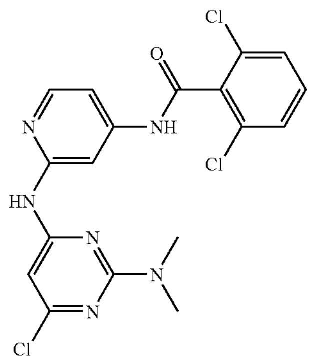 [SMILES: CN(C)c1nc(Cl)cc(Nc2cc(NC(=O)c3c(Cl)cccc3Cl)ccn2)n1] | 2,6-dichloro-N-(2-(6-chloro-2-(dimethylamino)-pyrimidin-4-ylamino)-pyridin-4-yl)benzamide | 437.7 |
| 124 | 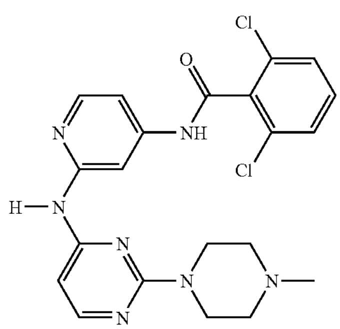 [SMILES: CN1CCN(c2nccc(Nc3cc(NC(=O)c4c(Cl)cccc4Cl)ccn3)n2)CC1] | 2,6-dichloro-N-(2-(2-(4-methylpiperazin-1-yl)-pyrimidin-4-ylamino)-pyridin-4-yl)benzamide | 458.3 |
| 125 | 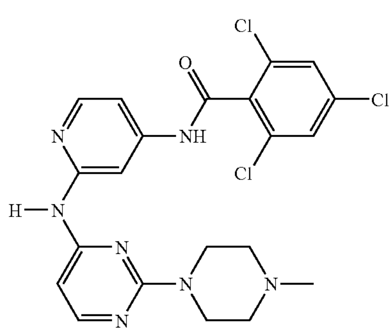 [SMILES: CN1CCN(c2nccc(Nc3cc(NC(=O)c4c(Cl)cc(Cl)cc4Cl)ccn3)n2)CC1] | 2,4,6-trichloro-N-(2-(2-(4-methylpiperazin-1-yl)-pyrimidin-4-ylamino)-pyridin-4-yl)benzamide | 492.8 |

TABLE 1-continued
| Ex | Structure | Name | LCMS (ESI) m/z |
|---|---|---|---|
| 126 | 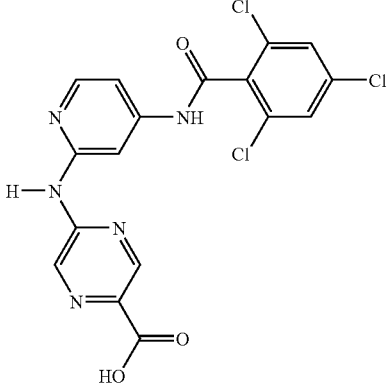 [SMILES: O=C(O)c1cnc(Nc2cc(NC(=O)c3c(Cl)cc(Cl)cc3Cl)ccn2)cn1] | 5-(4-(2,6-dichlorobenzamido)-pyridin-2-ylamino)-pyrazine-2-carboxylic acid | 404.2 |
| 127 | 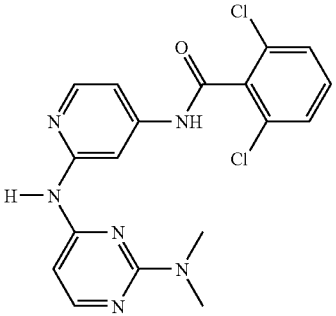 [SMILES: CN(C)c1nccc(Nc2cc(NC(=O)c3c(Cl)cccc3Cl)ccn2)n1] | 2,6-dichloro-N-(2-(2-(dimethylamino)pyrimidin-4-ylamino)pyridin-4-yl)benzamide | 403.3 |
| 128 | 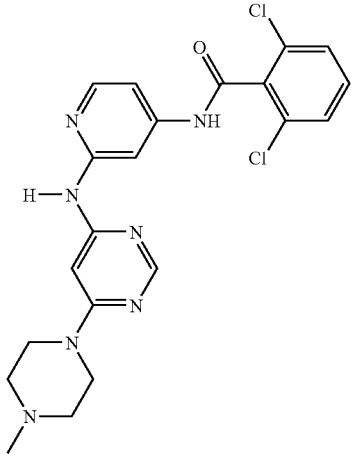 [SMILES: CN1CCN(c2cc(Nc3cc(NC(=O)c4c(Cl)cccc4Cl)ccn3)ncn2)CC1] | 2,6-dichloro-N-(2-(6-(4-methylpiperazin-1-yl)-pyrimidin-4-ylamino)-pyridin-4-yl)benzamide | 458.3 |

TABLE 1-continued
| Ex | Structure | Name | LCMS (ESI) m/z |
|---|---|---|---|
| 129 | 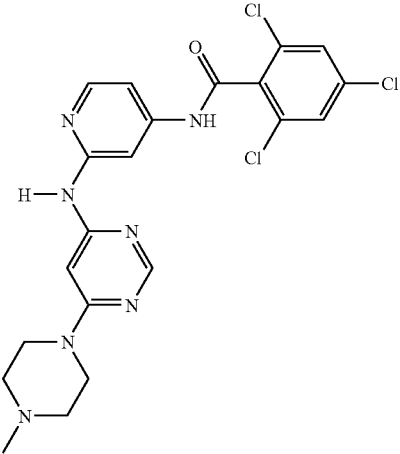 [SMILES: CN1CCN(c2cc(Nc3cc(NC(=O)c4c(Cl)cc(Cl)cc4Cl)ccn3)ncn2)CC1] | 2,4,6-trichloro-N-(2-(6-(4-methylpiperazin-1-yl)-pyrimidin-4-ylamino)-pyridin-4-yl)benzamide | 492.8 |
| 130 | 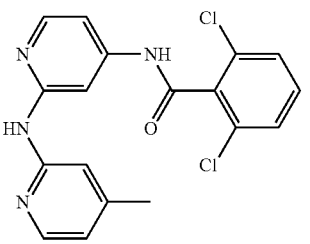 [SMILES: Cc1ccnc(Nc2cc(NC(=O)c3c(Cl)cccc3Cl)ccn2)c1] | 2,6-dichloro-N-(2-(4-methylpyridin-2-ylamino)-pyridin-4-yl)benzamide | 373.2 |
| 131 | 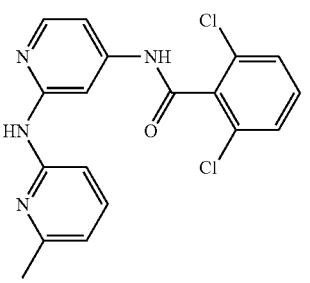 [SMILES: Cc1cccc(Nc2cc(NC(=O)c3c(Cl)cccc3Cl)ccn2)n1] | 2,6-dichloro-N-(2-(6-methylpyridin-2-ylamino)pyridin-4-yl)benzamide | 373.2 |
| 132 | 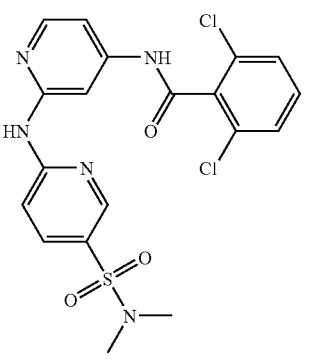 [SMILES: CN(C)S(=O)(=O)c1ccc(Nc2cc(NC(=O)c3c(Cl)cccc3Cl)ccn2)nc1] | 2,6-dichloro-N-(2-(5-(N,N-dimethylsulfamoyl)-pyridin-2-ylamino)-pyridin-4-yl)benzamide | 466.3 |

TABLE 1-continued
| Ex | Structure | Name | LCMS (ESI) m/z |
|---|---|---|---|
| 133 | 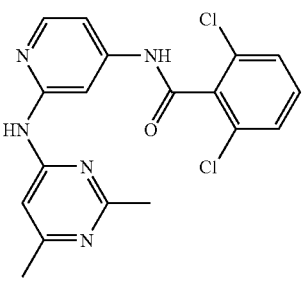 [SMILES: Cc1cc(Nc2cc(NC(=O)c3c(Cl)cccc3Cl)ccn2)nc(C)n1] | 2,6-dichloro-N-(2-(2,6-dimethylpyrimidin-4-ylamino)pyridin-4-yl)-benzamide | 388.3 |
| 134 | 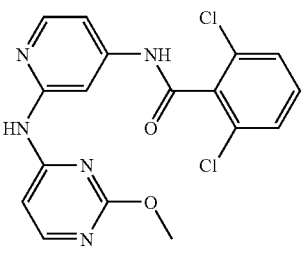 [SMILES: COc1nccc(Nc2cc(NC(=O)c3c(Cl)cccc3Cl)ccn2)n1] | 2,6-dichloro-N-(2-(2-methoxypyrimidin-4-ylamino)pyridin-4-yl)benzamide | 390.2 |
| 135 | 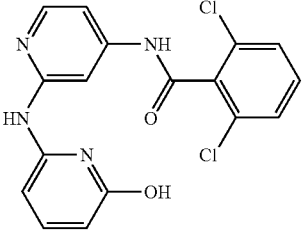 [SMILES: O=C(Nc1ccnc(Nc2cccc(O)n2)c1)c1c(Cl)cccc1Cl] | 2,6-dichloro-N-(2-(6-hydroxypyridin-2-ylamino)pyridin-4-yl)benzamide | 375.2 |
| 136 | 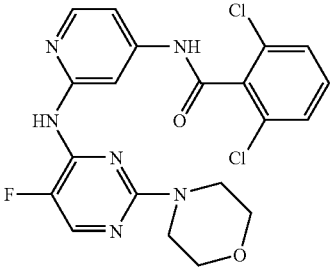 [SMILES: O=C(Nc1ccnc(Nc2nc(N3CCOCC3)ncc2F)c1)c1c(Cl)cccc1Cl] | 2,6-dichloro-N-(2-(5-fluoro-2-morpholino-pyrimidin-4-ylamino)-pyridin-4-yl)benzamide | 463.3 |
| 137 | 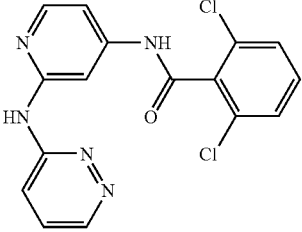 [SMILES: O=C(Nc1ccnc(Nc2cccnn2)c1)c1c(Cl)cccc1Cl] | 2,6-dichloro-N-(2-(pyridazin-3-ylamino)-pyridin-4-yl)benzamide | 360.2 |

TABLE 1-continued

| Ex | Structure | Name | LCMS (ESI) m/z |
|---|---|---|---|
| 138 | 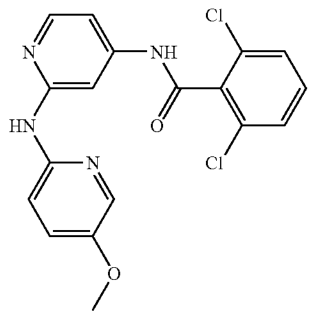 [SMILES: COc1ccc(Nc2cc(NC(=O)c3c(Cl)cccc3Cl)ccn2)nc1] | 2,6-dichloro-N-(2-(5-methoxypyridin-2-ylamino)-pyridin-4-yl)benzamide | 389.2 |
| 139 | 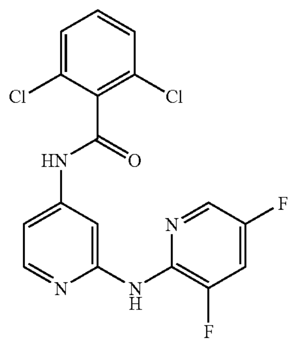 [SMILES: O=C(Nc1ccnc(Nc2ncc(F)cc2F)c1)c1c(Cl)cccc1Cl] | 2,6-dichloro-N-(2-(3,5-difluoropyridin-2-ylamino)pyridin-4-yl)benzamide | 395.1 |
| 140 | 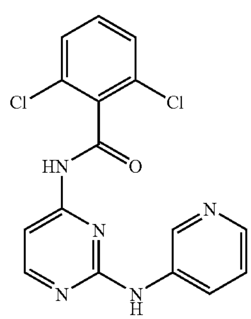 [SMILES: O=C(Nc1ccnc(Nc2cccnc2)n1)c1c(Cl)cccc1Cl] | 2,6-dichloro-N-(2-(pyridin-3-ylamino)-pyrimidin-4-yl)benzamide | 360.2 |
| 141 | 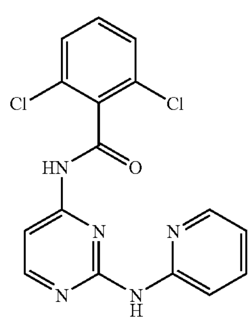 [SMILES: O=C(Nc1ccnc(Nc2ccccn2)n1)c1c(Cl)cccc1Cl] | 2,6-dichloro-N-(2-(pyridin-2-ylamino)-pyrimidin-4-yl)benzamide | 360.2 |

TABLE 1-continued

| Ex | Structure | Name | LCMS (ESI) m/z |
|---|---|---|---|
| 142 | 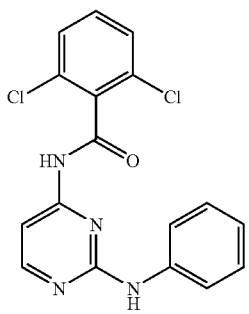 | 2,6-dichloro-N-(2-(phenylamino)pyrimidin-4-yl)benzamide | 359.2 |
| 143 | 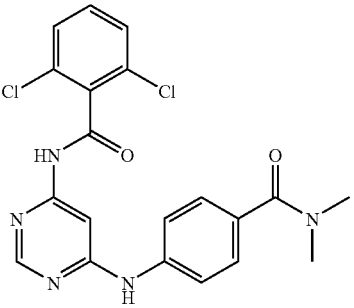 | 2,6-dichloro-N-(6-(4-(dimethylcarbamoyl)-phenylamino)pyrimidin-4-yl)benzamide | 430.3 |
| 144 | 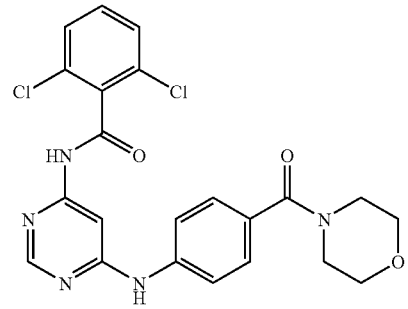 [SMILES: O=C(Nc1cc(Nc2ccc(C(=O)N3CCOCC3)cc2)ncn1)c1c(Cl)cccc1Cl] | 2,6-dichloro-N-(6-(4-(morpholine-4-carbonyl)-phenylamino)pyrimidin-4-yl)benzamide | 472.3 |
| 145 | 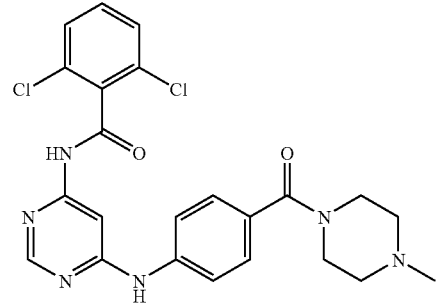 | 2,6-dichloro-N-(6-(4-(4-methylpiperazine-1-carbonyl)phenylamino)-pyrimidin-4-yl)benzamide | 485.4 |
| 146 | 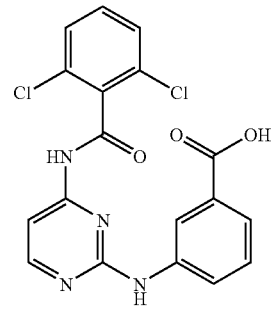 [SMILES: O=C(O)c1cccc(Nc2nccc(NC(=O)c3c(Cl)cccc3Cl)n2)c1] | 3-(4-(2,6-dichlorobenzamido)-pyrimidin-2-ylamino)-benzoic acid | 403.2 |

TABLE 1-continued

| Ex | Structure | Name | LCMS (ESI) m/z |
|---|---|---|---|
| 147 | 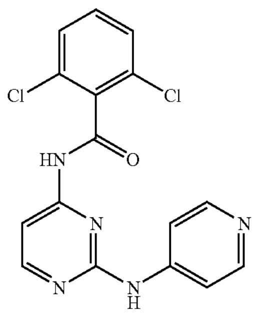 [SMILES: O=C(Nc1ccnc(Nc2ccncc2)n1)c1c(Cl)cccc1Cl] | 2,6-dichloro-N-(2-(pyridin-4-ylamino)-pyrimidin-4-yl)benzamide | 360.2 |
| 148 | 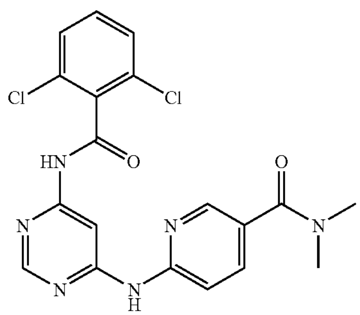 [SMILES: CN(C)C(=O)c1ccc(Nc2cc(NC(=O)c3c(Cl)cccc3Cl)ncn2)nc1] | 6-(6-(2,6-dichlorobenzamido)-pyrimidin-4-ylamino)-N,N-dimethylnicotinamide | 431.3 |
| 149 | 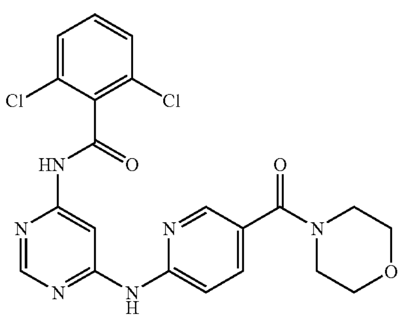 [SMILES: O=C(Nc1cc(Nc2ccc(C(=O)N3CCOCC3)cn2)ncn1)c1c(Cl)cccc1Cl] | 2,6-dichloro-N-(6-(5-(morpholine-4-carbonyl)-pyridin-2-ylamino)-pyrimidin-4-yl)benzamide | 473.3 |
| 150 | 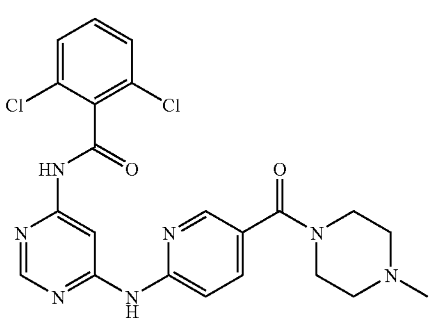 [SMILES: CN1CCN(C(=O)c2ccc(Nc3cc(NC(=O)c4c(Cl)cccc4Cl)ncn3)nc2)CC1] | 2,6-dichloro-N-(6-(5-(4-methylpiperazine-1-carbonyl)-pyridin-2-ylamino)-pyrimidin-4-yl)benzamide | 486.3 |

TABLE 1-continued

| Ex | Structure | Name | LCMS (ESI) m/z |
|---|---|---|---|
| 151 | 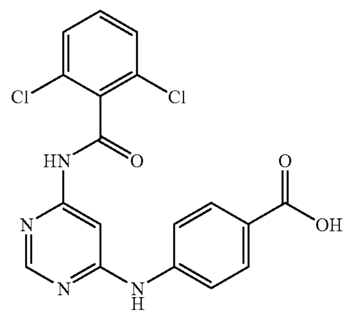 | 4-(6-(2,6-dichlorobenzamido)-pyrimidin-4-ylamino)benzoic acid | 403.2 |
| 152 | 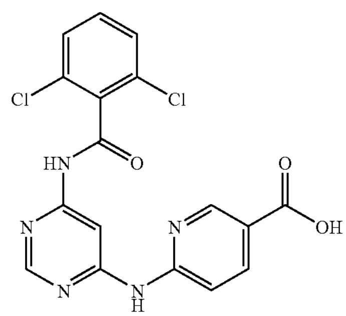 [SMILES: O=C(O)c1ccc(Nc2cc(NC(=O)c3c(Cl)cccc3Cl)ncn2)nc1] | 6-(6-(2,6-dichlorobenzamido)-pyrimidin-4-ylamino)nicotinic acid | 404.2 |
| 153 | 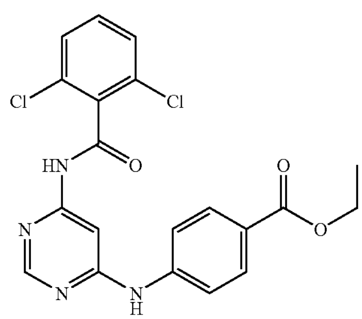 [SMILES: CCOC(=O)c1ccc(Nc2cc(NC(=O)c3c(Cl)cccc3Cl)ncn2)cc1] | ethyl 4-(6-(2,6-dichlorobenzamido)-pyrimidin-4-ylamino)benzoate | 431.3 |
| 154 | 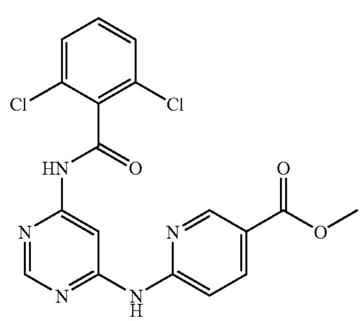 [SMILES: COC(=O)c1ccc(Nc2cc(NC(=O)c3c(Cl)cccc3Cl)ncn2)nc1] | methyl 6-(6-(2,6-dichlorobenzamido)-pyrimidin-4-ylamino)nicotinate | 418.2 |

TABLE 1-continued

| Ex | Structure | Name | LCMS (ESI) m/z |
|----|-----------|------|----------------|
| 155 | 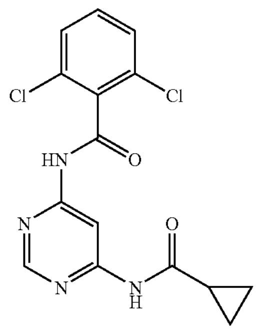 [SMILES: O=C(Nc1cc(NC(=O)C2CC2)ncn1)c1c(Cl)cccc1Cl] | 2,6-dichloro-N-(6-(cyclopropanecarboxamido)-pyrimidin-4-yl)benzamide | 351.2 |
| 156 | 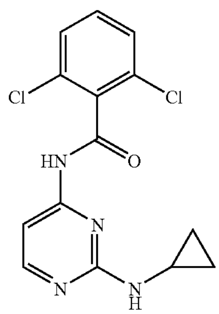 [SMILES: O=C(Nc1ccnc(NC2CC2)n1)c1c(Cl)cccc1Cl] | 2,6-dichloro-N-(2-(cyclopropylamino)-pyrimidin-4-yl)benzamide | 323.2 |
| 157 | 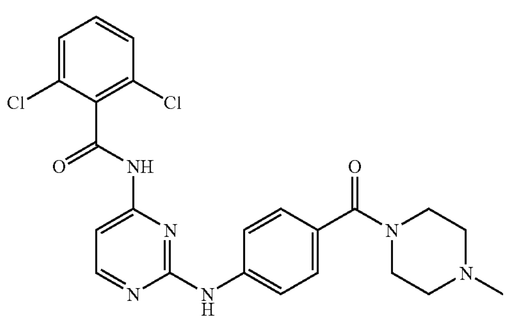 [SMILES: CN1CCN(C(=O)c2ccc(Nc3nccc(NC(=O)c4c(Cl)cccc4Cl)n3)cc2)CC1] | 2,6-dichloro-N-(2-(4-(4-methylpiperazine-1-carbonyl)phenylamino)-pyrimidin-4-yl)benzamide | 485.4 |
| 158 | 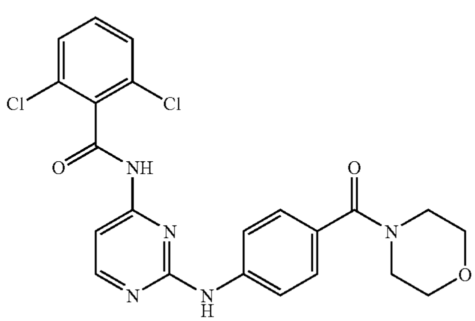 [SMILES: O=C(Nc1ccnc(Nc2ccc(C(=O)N3CCOCC3)cc2)n1)c1c(Cl)cccc1Cl] | 2,6-dichloro-N-(2-(4-(morpholine-4-carbonyl)-phenylamino)pyrimidin-4-yl)benzamide | 472.3 |

TABLE 1-continued

| Ex | Structure | Name | LCMS (ESI) m/z |
|---|---|---|---|
| 159 | 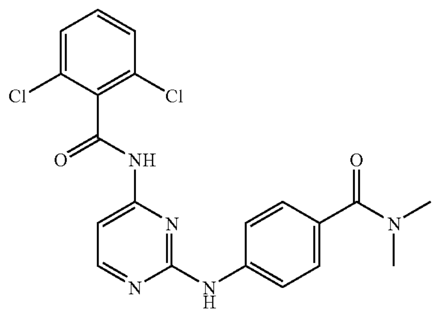 [SMILES: CN(C)C(=O)c1ccc(Nc2nccc(NC(=O)c3c(Cl)cccc3Cl)n2)cc1] | 2,6-dichloro-N-(2-(4-(dimethylcarbamoyl)-phenylamino)pyrimidin-4-yl)benzamide | 430.3 |
| 160 | 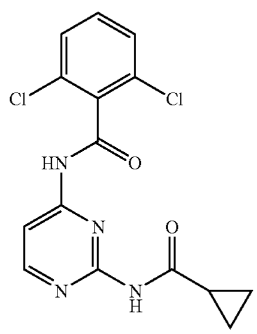 [SMILES: O=C(Nc1ccnc(NC(=O)C2CC2)n1)c1c(Cl)cccc1Cl] | 2,6-dichloro-N-(2-(cyclopropanecarboxamido)-pyrimidin-4-yl)benzamide | 351.2 |
| 161 | 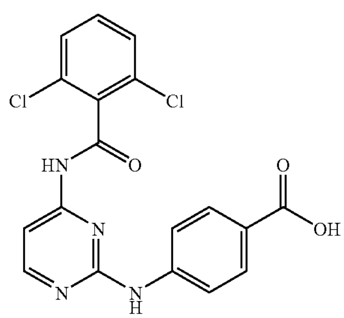 [SMILES: O=C(O)c1ccc(Nc2nccc(NC(=O)c3c(Cl)cccc3Cl)n2)cc1] | 4-(4-(2,6-dichlorobenzamido)-pyrimidin-2-ylamino)benzoic acid | 403.2 |
| 162 | 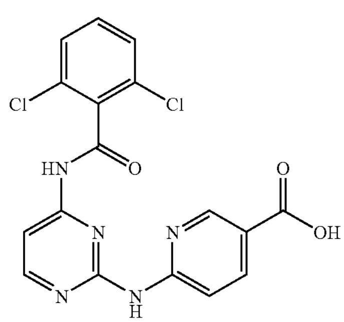 | 6-(4-(2,6-dichlorobenzamido)-pyrimidin-2-ylamino)nicotinic acid | 404.2 |

TABLE 1-continued

| Ex | Structure | Name | LCMS (ESI) m/z |
|---|---|---|---|
| 163 | 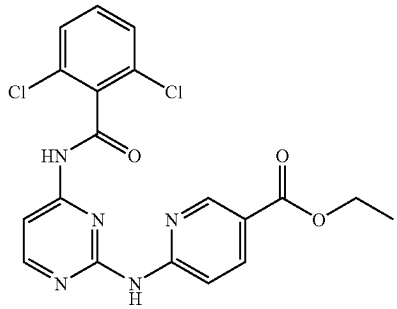 | ethyl 6-(4-(2,6-dichlorobenzamido)-pyrimidin-2-ylamino)-nicotinate | 432.3 |
| 164 | 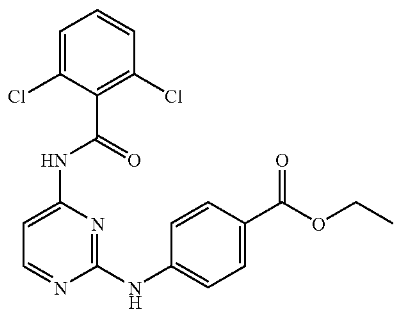 [SMILES: CCOC(=O)c1ccc(Nc2nccc(NC(=O)c3c(Cl)cccc3Cl)n2)cc1] | ethyl 4-(4-(2,6-dichlorobenzamido)-pyrimidin-2-ylamino)-benzoate | 431.3 |
| 165 | 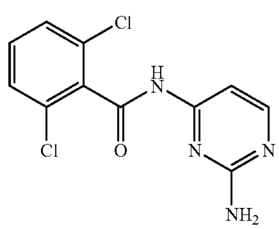 [SMILES: Nc1nccc(NC(=O)c2c(Cl)cccc2Cl)n1] | N-(2-aminopyrimidin-4-yl)-2,6-dichlorobenzamide | 283.1 |
| 166 | 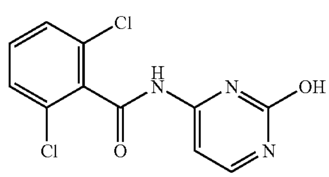 [SMILES: O=C(Nc1ccnc(O)n1)c1c(Cl)cccc1Cl] | 2,6-dichloro-N-(2-hydroxypyrimidin-4-yl)benzamide | 284.1 |
| 167 | 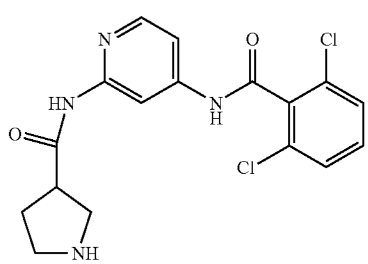 [SMILES: O=C(Nc1ccnc(NC(=O)C2CCNC2)c1)c1c(Cl)cccc1Cl] | N-(4-(2,6-dichlorobenzamido)-pyridin-2-yl)pyrrolidine-3-carboxamide | 379.2 |
| 168 | 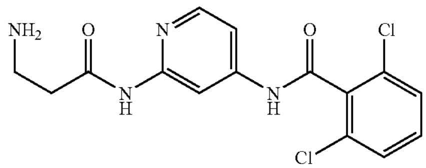 [SMILES: NCCC(=O)Nc1cc(NC(=O)c2c(Cl)cccc2Cl)ccn1] | N-(2-(3-aminopropanamido)-pyridin-4-yl)-2,6-dichlorobenzamide | 353.2 |

TABLE 1-continued

| Ex | Structure | Name | LCMS (ESI) m/z |
|---|---|---|---|
| 169 | 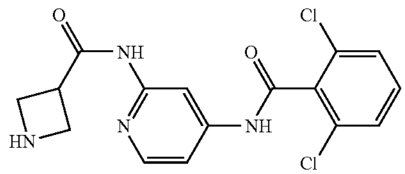 [SMILES: O=C(Nc1ccnc(NC(=O)C2CNC2)c1)c1c(Cl)cccc1Cl] | N-(4-(2,6-dichlorobenzamido)-pyridin-2-yl)azetidine-3-carboxamide | 365.2 |
| 170 | 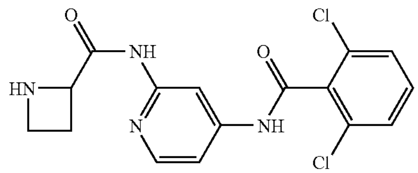 [SMILES: O=C(Nc1ccnc(NC(=O)C2CCN2)c1)c1c(Cl)cccc1Cl] | N-(4-(2,6-dichlorobenzamido)-pyridin-2-yl)azetidine-2-carboxamide | 365.2 |
| 171 | 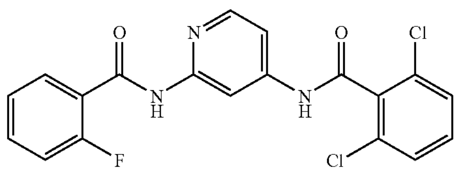 [SMILES: O=C(Nc1cc(NC(=O)c2c(Cl)cccc2Cl)ccn1)c1ccccc1F] | 2,6-dichloro-N-(2-(2-fluorobenzamido)pyridin-4-yl)benzamide | 404.2 |
| 172 | 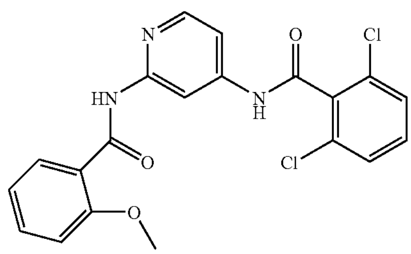 [SMILES: COc1ccccc1C(=O)Nc1cc(NC(=O)c2c(Cl)cccc2Cl)ccn1] | 2,6-dichloro-N-(2-(2-methoxybenzamido)-pyridin-4-yl)benzamide | 416.3 |
| 173 | 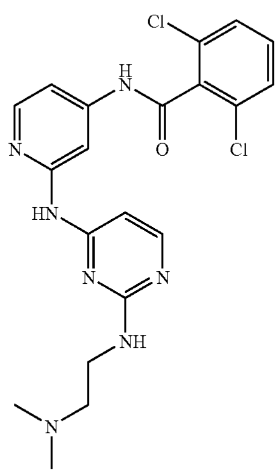 [SMILES: CN(C)CCNc1nccc(Nc2cc(NC(=O)c3c(Cl)cccc3Cl)ccn2)n1] | 2,6-dichloro-N-(2-(2-(2-(dimethylamino)-ethylamino)pyrimidin-4-ylamino)pyridin-4-yl)benzamide | 446.3 |
| 174 | 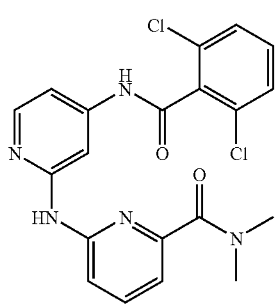 [SMILES: CN(C)C(=O)c1cccc(Nc2cc(NC(=O)c3c(Cl)cccc3Cl)ccn2)n1] | 6-(4-(2,6-dichlorobenzamido)-pyridin-2-ylamino)-N,N-dimethylpicolinamide | 430.3 |

TABLE 1-continued

| Ex | Structure | Name | LCMS (ESI) m/z |
|---|---|---|---|
| 175 | 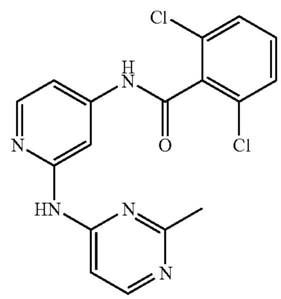 [SMILES: Cc1nccc(Nc2cc(NC(=O)c3c(Cl)cccc3Cl)ccn2)n1] | 2,6-dichloro-N-(2-(2-methylpyrimidin-4-ylamino)pyridin-4-yl)-benzamide | 374.2 |
| 176 | 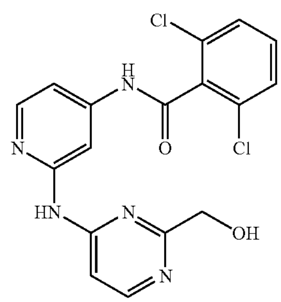 [SMILES: O=C(Nc1ccnc(Nc2ccnc(CO)n2)c1)c1c(Cl)cccc1Cl] | 2,6-dichloro-N-(2-(2-(hydroxymethyl)pyrimidin-4-ylamino)pyridin-4-yl)benzamide | 390.2 |
| 177 | 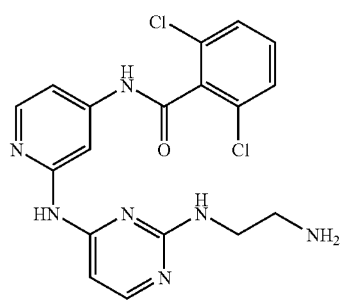 [SMILES: NCCNc1nccc(Nc2cc(NC(=O)c3c(Cl)cccc3Cl)ccn2)n1] | N-(2-(2-(2-aminoethylamino)-pyrimidin-4-ylamino)-pyridin-4-yl)-2,6-dichlorobenzamide | 418.3 |
| 178 | 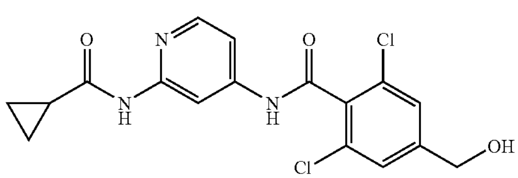 [SMILES: O=C(Nc1ccnc(NC(=O)C2CC2)c1)c1c(Cl)cc(CO)cc1Cl] | 2,6-dichloro-N-(2-(cyclopropanecarboxamido)-pyridin-4-yl)-4-(hydroxymethyl)benzamide | 380.2 |
| 179 | 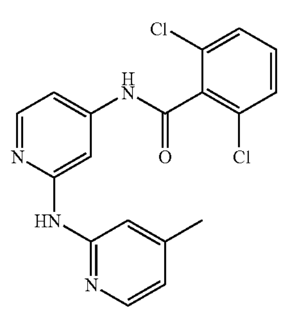 [SMILES: Cc1ccnc(Nc2cc(NC(=O)c3c(Cl)cccc3Cl)ccn2)c1] | 2,6-dichloro-N-(2-(4-methylpyridin-2-ylamino)pyridin-4-yl)benzamide | 373.2 |

TABLE 1-continued

| Ex | Structure | Name | LCMS (ESI) m/z |
|---|---|---|---|
| 180 | 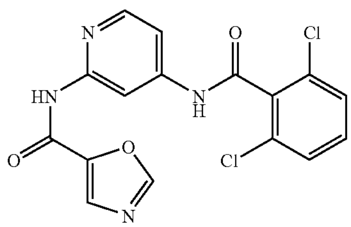 [SMILES: O=C(Nc1cc(NC(=O)c2c(Cl)cccc2Cl)ccn1)c1cnco1] | N-(4-(2,6-dichloro-benzamido)pyridin-2-yl)-oxazole-5-carboxamide | 377.2 |
| 181 | 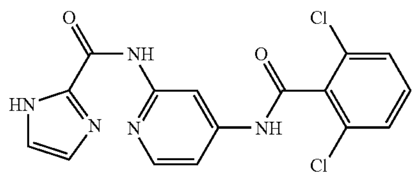 [SMILES: O=C(Nc1cc(NC(=O)c2c(Cl)cccc2Cl)ccn1)c1ncc[nH]1] | N-(4-(2,6-dichloro-benzamido)pyridin-2-yl)-1H-imidazole-2-carboxamide | 376.2 |
| 182 | 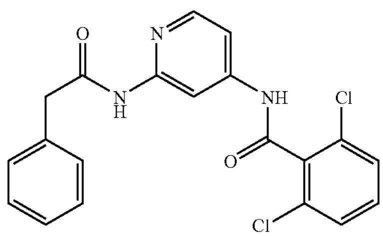 [SMILES: O=C(Cc1ccccc1)Nc1cc(NC(=O)c2c(Cl)cccc2Cl)ccn1] | 2,6-dichloro-N-(2-(2-phenylacetamido)-pyridin-4-yl)benzamide | 400.3 |
| 183 | 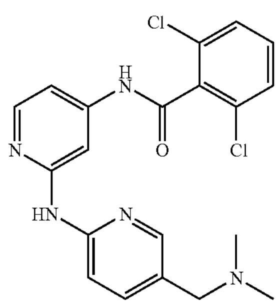 [SMILES: CN(C)Cc1ccc(Nc2cc(NC(=O)c3c(Cl)cccc3Cl)ccn2)nc1] | 2,6-dichloro-N-(2-(5-((dimethylamino)methyl)-pyridin-2-ylamino)-pyridin-4-yl)benzamide | 416.3 |
| 184 | 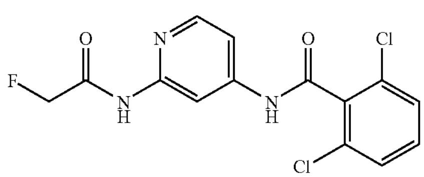 [SMILES: O=C(CF)Nc1cc(NC(=O)c2c(Cl)cccc2Cl)ccn1] | 2,6-dichloro-N-(2-(2-fluoroacetamido)-pyridin-4-yl)benzamide | 342.2 |
| 185 | 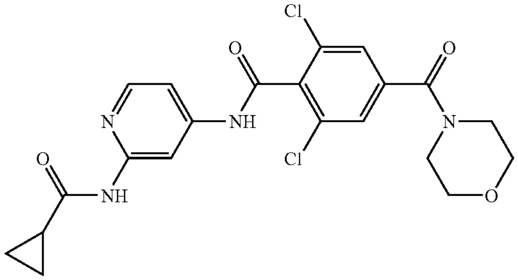 [SMILES: O=C(Nc1ccnc(NC(=O)C2CC2)c1)c1c(Cl)cc(C(=O)N2CCOCC2)cc1Cl] | 2,6-dichloro-N-(2-(cyclopropanecarboxamido)-pyridin-4-yl)-4-(morpholine-4-carbonyl)benzamide | 463.3 |

TABLE 1-continued

| Ex | Structure | Name | LCMS (ESI) m/z |
|---|---|---|---|
| 186 | 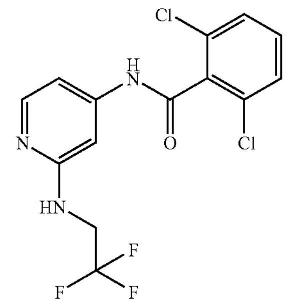 [SMILES: O=C(Nc1ccnc(NCC(F)(F)F)c1)c1c(Cl)cccc1Cl] | 2,6-dichloro-N-(2-(2,2,2-trifluoroethylamino)-pyridin-4-yl)benzamide | 364.2 |
| 187 | 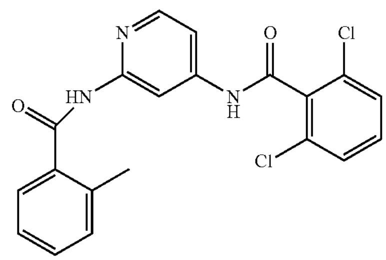 [SMILES: Cc1ccccc1C(=O)Nc1cc(NC(=O)c2c(Cl)cccc2Cl)ccn1] | 2,6-dichloro-N-(2-(2-methylbenzamido)-pyridin-4-yl)benzamide | 400.3 |
| 188 | 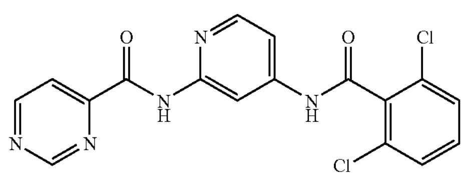 [SMILES: O=C(Nc1cc(NC(=O)c2c(Cl)cccc2Cl)ccn1)c1ccncn1] | N-(4-(2,6-dichloro-benzamido)pyridin-2-yl)-pyrimidine-4-carboxamide | 388.2 |
| 189 | 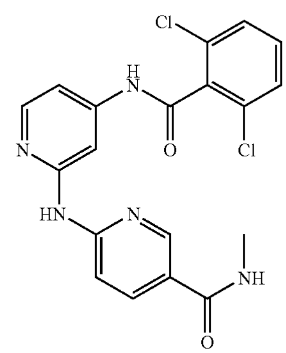 [SMILES: CNC(=O)c1ccc(Nc2cc(NC(=O)c3c(Cl)cccc3Cl)ccn2)nc1] | 6-(4-(2,6-dichloro-benzamido)pyridin-2-ylamino)-N-methyl-nicotinamide | 416.3 |
| 190 | 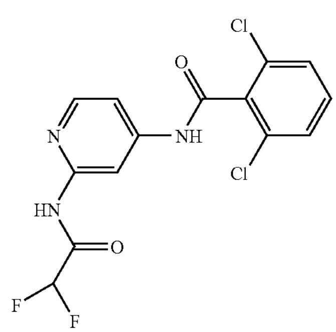 [SMILES: O=C(Nc1ccnc(NC(=O)C(F)F)c1)c1c(Cl)cccc1Cl] | 2,6-dichloro-N-(2-(2,2-difluoroacetamido)-pyridin-4-yl)benzamide | 360.1 |

TABLE 1-continued
| Ex | Structure | Name | LCMS (ESI) m/z |
|---|---|---|---|
| 191 | 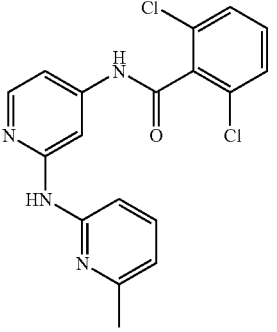 [SMILES: Cc1cccc(Nc2cc(NC(=O)c3c(Cl)cccc3Cl)ccn2)n1] | 2,6-dichloro-N-(2-(6-methylpyridin-2-ylamino)pyridin-4-yl)benzamide | 373.2 |
| 192 | 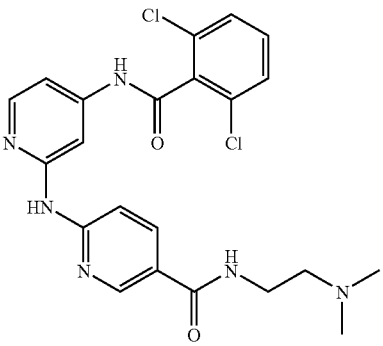 [SMILES: CN(C)CCNC(=O)c1ccc(Nc2cc(NC(=O)c3c(Cl)cccc3Cl)ccn2)nc1] | 6-(4-(2,6-dichlorobenzamido)-pyridin-2-ylamino)-N-(2-(dimethylamino)-ethyl)nicotinamide | 473.4 |
| 193 | 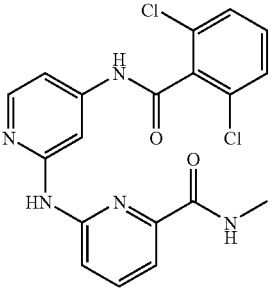 [SMILES: CNC(=O)c1cccc(Nc2cc(NC(=O)c3c(Cl)cccc3Cl)ccn2)n1] | 6-(4-(2,6-dichlorobenzamido)-pyridin-2-ylamino)-N-methylpicolinamide | 416.3 |
| 194 | 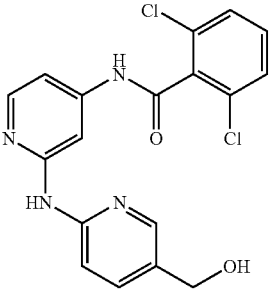 [SMILES: O=C(Nc1ccnc(Nc2ccc(CO)cn2)c1)c1c(Cl)cccc1Cl] | 2,6-dichloro-N-(2-(5-(hydroxymethyl)pyridin-2-ylamino)pyridin-4-yl)benzamide | 389.2 |
| 195 | 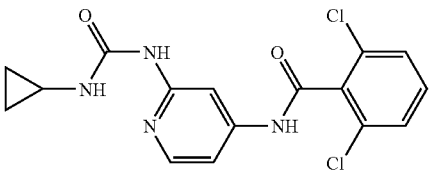 [SMILES: O=C(Nc1cc(NC(=O)c2c(Cl)cccc2Cl)ccn1)NC1CC1] | 2,6-dichloro-N-(2-(3-cyclopropylureido)pyridin-4-yl)benzamide | 365.2 |

TABLE 1-continued

| Ex | Structure | Name | LCMS (ESI) m/z |
|---|---|---|---|
| 196 | 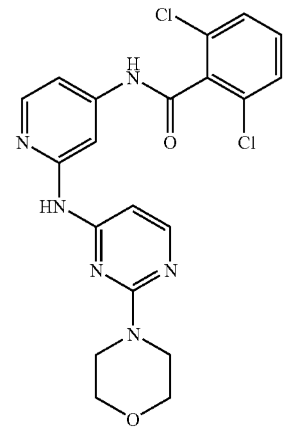 [SMILES: O=C(Nc1ccnc(Nc2ccnc(N3CCOCC3)n2)c1)c1c(Cl)cccc1Cl] | 2,6-dichloro-N-(2-(2-morpholinopyrimidin-4-ylamino)pyridin-4-yl)benzamide | 445.3 |
| 197 | 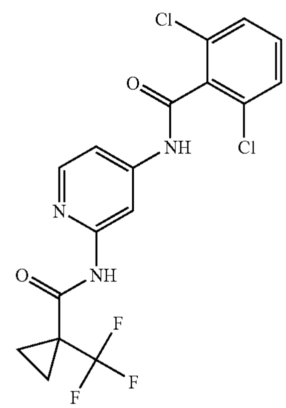 [SMILES: O=C(Nc1ccnc(NC(=O)C2(C(F)(F)F)CC2)c1)c1c(Cl)cccc1Cl] | 2,6-dichloro-N-(2-(1-(trifluoromethyl)cyclopropanecarboxamido)-pyridin-4-yl)benzamide | 418.2 |
| 198 | 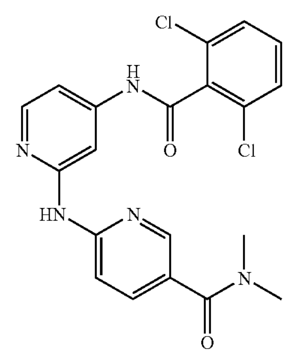 [SMILES: CN(C)C(=O)c1ccc(Nc2cc(NC(=O)c3c(Cl)cccc3Cl)ccn2)nc1] | 6-(4-(2,6-dichlorobenzamido)-pyridin-2-ylamino)-N,N-dimethylnicotinamide | 430.3 |
| 199 | 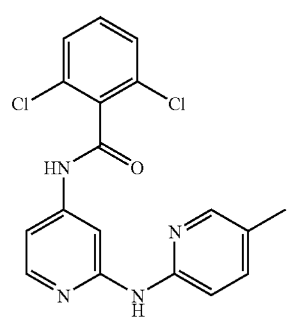 [SMILES: Cc1ccc(Nc2cc(NC(=O)c3c(Cl)cccc3Cl)ccn2)nc1] | 2,6-dichloro-N-(2-(5-methylpyridin-2-ylamino)-pyridin-4-yl)benzamide | 373.2 |

TABLE 1-continued

| Ex | Structure | Name | LCMS (ESI) m/z |
|---|---|---|---|
| 200 | 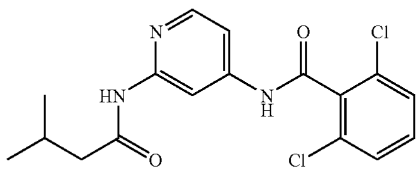 | 2,6-dichloro-N-(2-(3-methylbutanamido)-pyridin-4-yl)benzamide | 366.2 |
| 201 | 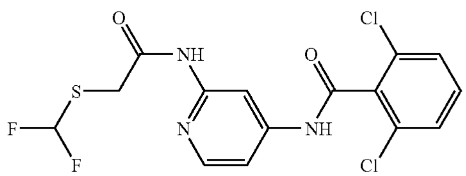 [SMILES: O=C(CSC(F)F)Nc1cc(NC(=O)c2c(Cl)cccc2Cl)ccn1] | 2,6-dichloro-N-(2-(2-(difluoromethylthio)-acetamido)pyridin-4-yl)benzamide | 406.2 |
| 202 | 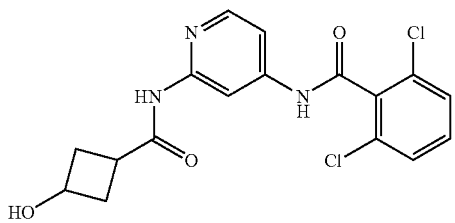 [SMILES: O=C(Nc1ccnc(NC(=O)C2CC(O)C2)c1)c1c(Cl)cccc1Cl] | 2,6-dichloro-N-(2-(3-hydroxycyclobutanecar-boxamido)pyridin-4-yl)benzamide | 380.2 |
| 203 | 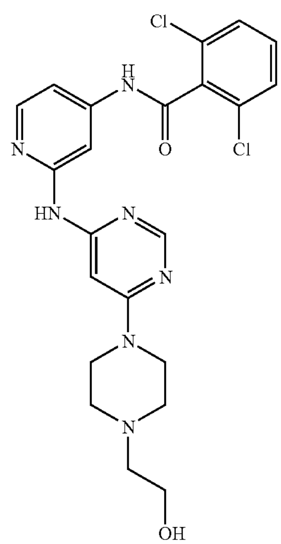 [SMILES: O=C(Nc1ccnc(Nc2cc(N3CCN(CCO)CC3)ncn2)c1)c1c(Cl)cccc1Cl] | 2,6-dichloro-N-(2-(6-(4-(2-hydroxyethyl)piperazin-1-yl)pyrimidin-4-ylamino)-pyridin-4-yl)benzamide | 488.4 |
| 204 | 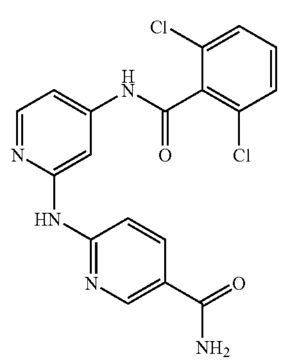 [SMILES: NC(=O)c1ccc(Nc2cc(NC(=O)c3c(Cl)cccc3Cl)ccn2)nc1] | 6-(4-(2,6-dichloro-benzamido)pyridin-2-ylamino)nicotinamide | 402.2 |

TABLE 1-continued

| Ex | Structure | Name | LCMS (ESI) m/z |
|---|---|---|---|
| 205 | 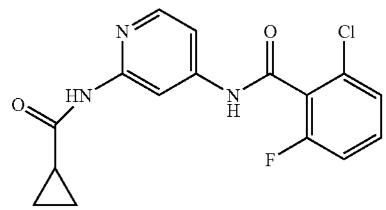 [SMILES: O=C(Nc1ccnc(NC(=O)C2CC2)c1)c1c(F)cccc1Cl] | 2-chloro-N-(2-(cyclopropanecarboxamido)-pyridin-4-yl)-6-fluorobenzamide | 333.7 |
| 206 | 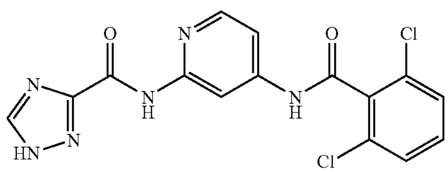 [SMILES: O=C(Nc1cc(NC(=O)c2c(Cl)cccc2Cl)ccn1)c1nc[nH]n1] | N-(4-(2,6-dichloro-benzamido)pyridin-2-yl)-1H-1,2,4-triazole-3-carboxamide | 377.2 |
| 207 | 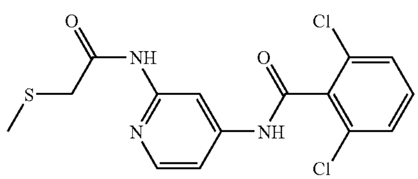 [SMILES: CSCC(=O)Nc1cc(NC(=O)c2c(Cl)cccc2Cl)ccn1] | 2,6-dichloro-N-(2-(2-(methylthio)acetamido)-pyridin-4-yl)benzamide | 370.2 |
| 208 | 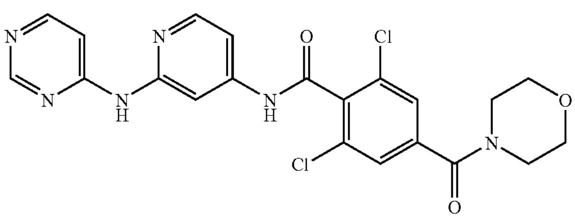 [SMILES: O=C(Nc1ccnc(Nc2ccncn2)c1)c1c(Cl)cc(C(=O)N2CCOCC2)cc1Cl] | 2,6-dichloro-4-(morpholine-4-carbonyl)-N-(2-pyridin-4-ylamino)pyridin-4-yl)benzamide | 473.3 |
| 209 | 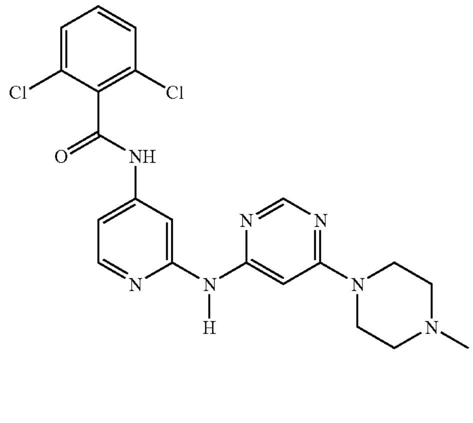 [SMILES: CN1CCN(c2cc(Nc3cc(NC(=O)c4c(Cl)cccc4Cl)ccn3)ncn2)CC1] | 2,6-dichloro-N-(2-(6-(4-methylpiperazin-1-yl)-pyrimidin-4-ylamino)-pyridin-4-yl)benzamide | 458.3 |

TABLE 1-continued
| Ex | Structure | Name | LCMS (ESI) m/z |
|---|---|---|---|
| 210 | 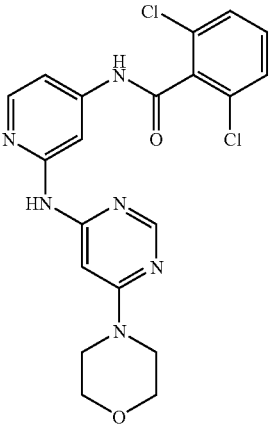 [SMILES: O=C(Nc1ccnc(Nc2cc(N3CCOCC3)ncn2)c1)c1c(Cl)cccc1Cl] | 2,6-dichloro-N-(2-(6-morpholinopyrimidin-4-ylamino)pyridin-4-yl)benzamide | 445.3 |
| 211 | 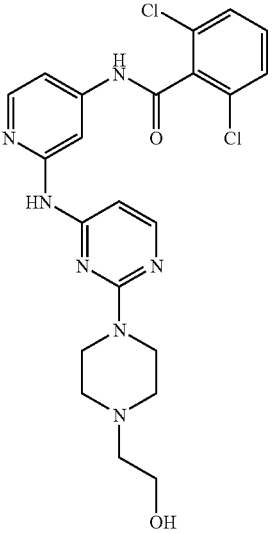 [SMILES: O=C(Nc1ccnc(Nc2ccnc(N3CCN(CCO)CC3)n2)c1)c1c(Cl)cccc1Cl] | 2,6-dichloro-N-(2-(2-(4-(2-hydroxyethyl)piperazin-1-yl)pyrimidin-4-ylamino)-pyridin-4-yl)benzamide | 488.4 |
| 212 | 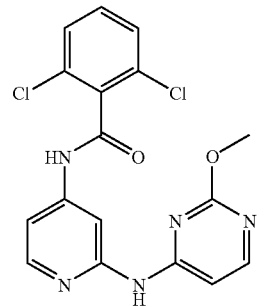 [SMILES: COc1nccc(Nc2cc(NC(=O)c3c(Cl)cccc3Cl)ccn2)n1] | 2,6-dichloro-N-(2-(2-methoxypyrimidin-4-ylamino)pyridin-4-yl)benzamide | 390.2 |

TABLE 1-continued

| Ex | Structure | Name | LCMS (ESI) m/z |
|---|---|---|---|
| 213 | 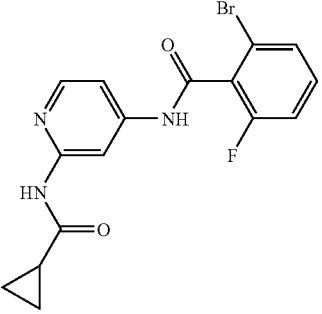 [SMILES: O=C(Nc1ccnc(NC(=O)C2CC2)c1)c1c(F)cccc1Br] | 2-bromo-N-(2-(cyclopropanecarboxamido)-pyridin-4-yl)-6-fluorobenzamide | 378.2 |
| 214 | 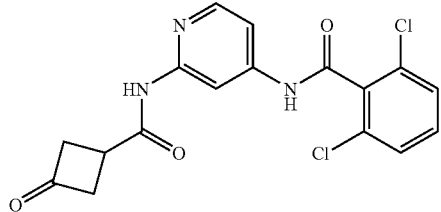 [SMILES: O=C1CC(C(=O)Nc2cc(NC(=O)c3c(Cl)cccc3Cl)ccn2)C1] | 2,6-dichloro-N-(2-(3-oxocyclobutanecarboxamido)-pyridin-4-yl)benzamide | 378.2 |
| 215 | 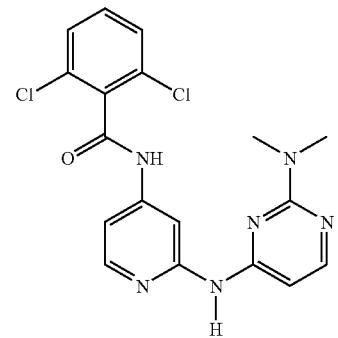 [SMILES: CN(C)c1nccc(Nc2cc(NC(=O)c3c(Cl)cccc3Cl)ccn2)n1] | 2,6-dichloro-N-(2-(2-(dimethylamino)pyrimidin-4-ylamino)pyridin-4-yl)benzamide | 403.3 |
| 216 | 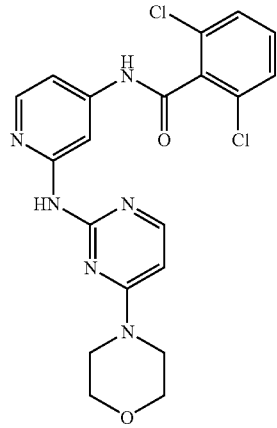 | 2,6-dichloro-N-(2-(4-morpholinopyrimidin-2-ylamino)pyridin-4-yl)benzamide | 445.3 |
| 217 | 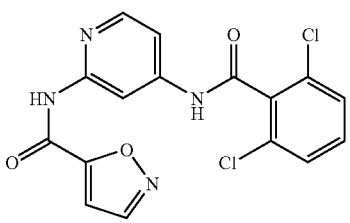 [SMILES: O=C(Nc1cc(NC(=O)c2c(Cl)cccc2Cl)ccn1)c1ccno1] | N-(4-(2,6-dichlorobenzamido)-pyridin-2-yl)isoxazole-5-carboxamide | 377.2 |

TABLE 1-continued

| Ex | Structure | Name | LCMS (ESI) m/z |
|---|---|---|---|
| 218 | 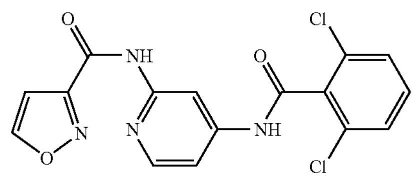 [SMILES: O=C(Nc1cc(NC(=O)c2c(Cl)cccc2Cl)ccn1)c1ccon1] | N-(4-(2,6-dichlorobenzamido)-pyridin-2-yl)isoxazole-3-carboxamide | 377.2 |
| 219 | 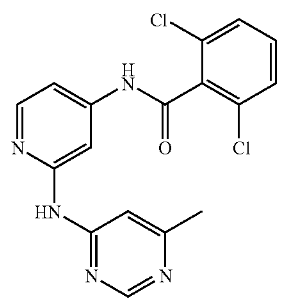 | 2,6-dichloro-N-(2-(6-methylpyrimidin-4-ylamino)pyridin-4-yl)benzamide | 374.2 |
| 220 | 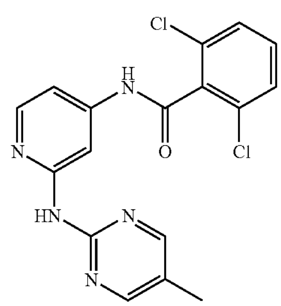 [SMILES: Cc1cnc(Nc2cc(NC(=O)c3c(Cl)cccc3Cl)ccn2)nc1] | 2,6-dichloro-N-(2-(5-methyl pyrimidin-2-ylamino)pyridin-4-yl)benzamide | 374.2 |
| 221 | 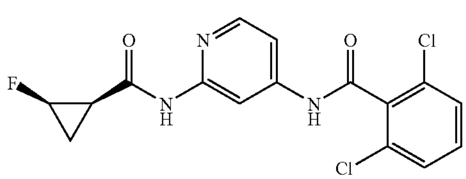 [SMILES: O=C(Nc1ccnc(NC(=O)[C@H]2C[C@H]2F)c1)c1c(Cl)cccc1Cl] | 2,6-dichloro-N-(2-((1R,2R)-2-fluorocyclo-propanecarboxamido)pyridin-4-yl)benzamide | 368.2 |
| 222 | 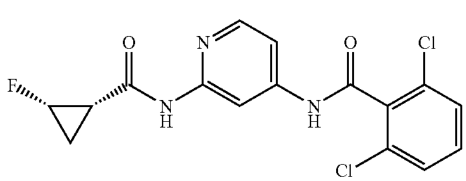 [SMILES: O=C(Nc1ccnc(NC(=O)[C@@H]2C[C@@H]2F)c1)c1c(Cl)cccc1Cl] | 2,6-dichloro-N-(2-((1S,2S)-2-fluorocyclo-propanecarboxamido)pyridin-4-yl)benzamide | 368.2 |
| 223 | 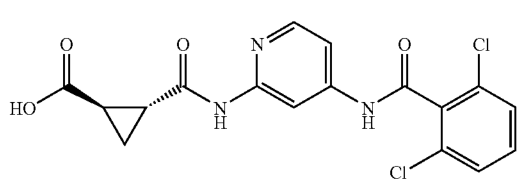 [SMILES: O=C(Nc1ccnc(NC(=O)[C@@H]2C[C@H]2C(=O)O)c1)c1c(Cl)cccc1Cl] | (1R,2R)-2-(4-(2,6-dichlorobenzamido)-pyridin-2-ylcarbamoyl)-cyclopropanecarboxylic acid | 394.2 |

Example 224

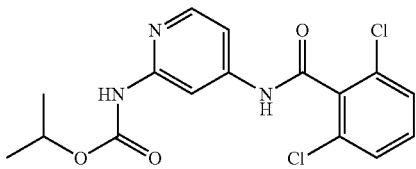

Isopropyl 4-(2,6-dichlorobenzamido)pyridin-2-ylcarbamate

To a stirred solution of isopropyl chloroformate (0.066 g, 0.53 mmol) in 3 ml of pyridine was added N-(2-aminopyridin-4-yl)-2,6-dichlorobenzamide (0.1 g, 0.36 mmol). The resulting mixture was stirred for another 30 min and then concentrated under reduced pressure. The residue was purified via prep-HPLC (Gilson GX 281, Shim-pack PRC-ODS 250 mm×20 mm×2, gradient: CH$_3$CN/10 mm/L NH$_4$HCO$_3$, 17 min) to give the desired product as a white solid (0.025 g, yield: 19%). $^1$H NMR (DMSO-d$_6$, 500 MHz): δ 11.17 (s, 1H), 9.97 (s, 1H), 8.21-8.17 (m, 2H), 7.61-7.53 (m, 3H), 7.40 (m, 1H), 4.90 (m, 1H), 1.25 (t, J=5.5 Hz, 6H). LCMS (ESI) m/z: 368.0 [M+H$^+$].

Example 225

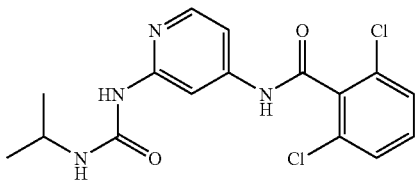 [SMILES: CC(C)NC(=O)Nc1cc(NC(=O)c2c(Cl)cccc2Cl)ccn1]

2,6-dichloro-N-(2-(3-isopropylureido)pyridin-4-yl)benzamide

A mixture of 2-isocyanatopropane (0.050 g, 0.59 mmol), N-(2-aminopyridin-4-yl)-2,6-dichlorobenzamide (0.047 g, 0.17 mmol) and diisopropylethylamine (50 mg, 0.39 mmol) in 1,2-dichloroethane (3.0 mL) was stirred at 60° C. for 3 hours. The mixture was concentrated under reduced pressure, and the residue was purified via prep-HPLC (Gilson GX 281, Shim-pack PRC-ODS 250 mm×20 mm×2, gradient: CH$_3$CN/10 mm/L NH$_4$HCO$_3$, 17 min) to give the desired product as a white solid (0.025 g, yield: 41%). $^1$H NMR (DMSO-d$_6$, 500 MHz): δ 8.02 (d, J=5.5 Hz, 1H). 7.51 (s, 1H), 7.40-7.34 (m, 3H), 7.05 (m, 1H), 3.87 (m, 1H), 1.14 (t, J=6.5 Hz, 6H). LCMS (ESI) m/z: 367.1 [M+H$^+$].

Example 226

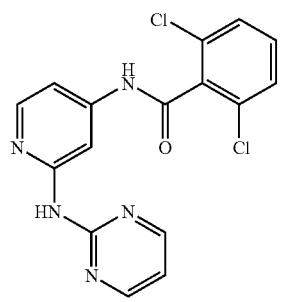 [SMILES: O=C(Nc1ccnc(Nc2ncccn2)c1)c1c(Cl)cccc1Cl]

2,6-dichloro-N-(2-(pyrimidin-2-ylamino)pyridin-4-yl)benzamide

To a microwave tube were added N-(2-bromopyridin-4-yl)-2,6-dichlorobenzamide (0.120 g, 0.347 mmol), 2-aminopyrimidine (0.040 g, 0.42 mmol), Pd$_2$(dba)$_3$ (0.030 g, 0.035 mmol), XantPhos (0.040 g, 0.070 mmol), Cs$_2$CO$_3$ (0.23 g, 0.70 mmol) and dioxane (2 mL). The mixture was degassed with N$_2$ for 5 min. The resulting mixture was irradiated in a microwave reactor at 140° C. for 50 min and then cooled to room temperature. The mixture was filtered through Celite and concentrated under reduced pressure. The residue was dissolved in DMF and purified by prep-HPLC (Gilson GX 281, Shim-pack PRC-ODS 250 mm×20 mm×2, gradient: CH$_3$CN/10 mm/L NH$_4$HCO$_3$, 17 min) to give the desired product as a white solid (15 mg, 12% yield). $^1$H NMR (500 MHz, MeOH-d$_4$): δ 8.72 (s, 1H), 8.56 (d, J=4.5 Hz, 2H), 8.21 (d, J=5.5 Hz, 2H), 7.53-7.45 (m, 4H), 6.95 (t, J=5.0 Hz, 1H). LCMS (ESI) m/z: 360.0 [M+H$^+$].

Example 227

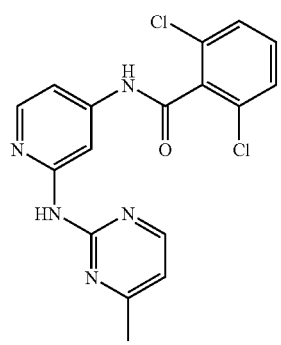

2,6-dichloro-N-(2-(4-methylpyrimidin-2-ylamino)pyridin-4-yl)benzamide

To a microwave tube were added N-(2-bromopyridin-4-yl)-2,6-dichlorobenzamide (0.15 g, 0.43 mmol), 2-amino-4-methylpyrimidine (0.056 g, 0.52 mmol), Pd$_2$(dba)$_3$ (0.040 g, 0.043 mmol), XantPhos (0.050 g, 0.087 mmol), Cs$_2$CO$_3$ (0.28 g, 0.87 mmol) and dioxane (2 mL). The mixture was degassed with $N_2$ for 10 min. The resulting mixture was irradiated in a microwave reactor at 140° C. for 3 hours and then cooled to room temperature. The mixture was filtered through Celite and concentrated under reduced pressure. The residue was dissolved in DMF and purified by prep-HPLC (Gilson GX 281, Shim-pack PRC-ODS 250 mm×20 mm×2, gradient: $CH_3CN$/10 mm/L $NH_4HCO_3$, 17 min) to give the desired product as a white solid (19 mg, yield: 12%). $^1H$ NMR (500 MHz, MeOH-$d_4$): δ 8.88 (s, 1H), 8.36 (d, J=5.5 Hz, 1H), 8.16 (d, J=6.0 Hz, 1H), 7.64 (s, 1H), 7.45-7.38 (m, 4H), 6.85 (d, J=5.5 Hz, 1H), 2.50 (s, 3H). LCMS (ESI) m/z: 374.0 [M+H$^+$].

Example 228

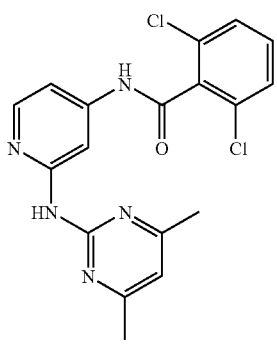 [SMILES: Cc1cc(C)nc(Nc2cc(NC(=O)c3c(Cl)cccc3Cl)ccn2)n1]

2,6-dichloro-N-(2-(4,6-dimethylpyrimidin-2-ylamino)pyridin-4-yl)benzamide

To a microwave tube was added N-(2-aminopyridin-4-yl)-2,6-dichlorobenzamide (0.25 g, 0.89 mmol), 2-chloro-4,6-dimethylpyrimidine (0.19 g, 1.34 mmol), $Pd_2(dba)_3$ (0.81 g, 0.089 mmol), XantPhos (0.104 g, 0.179 mmol), $Cs_2CO_3$ (0.85 g, 2.6 mmol) and dioxane (4 mL). The mixture was degassed with $N_2$ for 10 min. The resulting mixture was irradiated in a microwave reactor at 140° C. for 3 hours and then cooled to room temperature. The mixture was filtered through Celite and concentrated under reduced pressure. The residue was purified by column chromatography to afford the desired product as a white solid (22 mg, yield: 8%). $^1H$ NMR (500 MHz, MeOH-$d_4$): δ 8.96 (d, J=1.5 Hz, 1H), 8.17 (d, J=5.5 Hz, 1H), 7.41-7.54 (m, 4H), 6.77 (s, 1H), 2.44 (s, 6H). LCMS (ESI) m/z: 388.0 [M+H$^+$].

Example 229

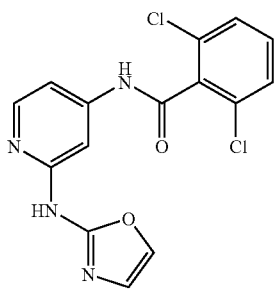 [SMILES: O=C(Nc1ccnc(Nc2ncco2)c1)c1c(Cl)cccc1Cl]

2,6-dichloro-N-(2-(oxazol-2-ylamino)pyridin-4-yl)benzamide

To a microwave tube was added N-(2-bromopyridin-4-yl)-2,6-dichlorobenzamide (0.30 g, 0.87 mmol), 2-aminooxazole (0.11 g, 1.0 mmol), $Pd_2(dba)_3$ (0.078 g, 0.087 mmol), XantPhos (0.096 g, 0.17 mmol), $Cs_2CO_3$ (0.57 g, 1.7 mmol) and dioxane (5 mL). The mixture was degassed with $N_2$ for 10 min. The resulting mixture was irradiated in a microwave reactor at 140° C. for 3 hours and then cooled to room temperature. The mixture was filtered through Celite and concentrated under reduced pressure. The residue was dissolved in DMF and purified by prep-HPLC (Gilson GX 281, Shim-pack PRC-ODS 250 mm×20 mm×2, gradient: $CH_3CN$/10 mm/L $NH_4HCO_3$, 17 min) to give the desired product as a yellow solid (26 mg, yield: 9%). $^1H$ NMR (500 MHz, DMSO-$d_6$): δ 11.2 (s, 1H), 8.28 (s, 1H), 8.17 (d, J=5.5 Hz, 1H), 7.71 (s, 1H), 7.59 (d, J=7.5 Hz, 2H), 7.52 (t, J=3.5 Hz, 1H), 7.41 (m, 1H), 7.03 (s, 1H). LC-MS (ESI) m/z: 349.0 [M+H$^+$].

Example 230

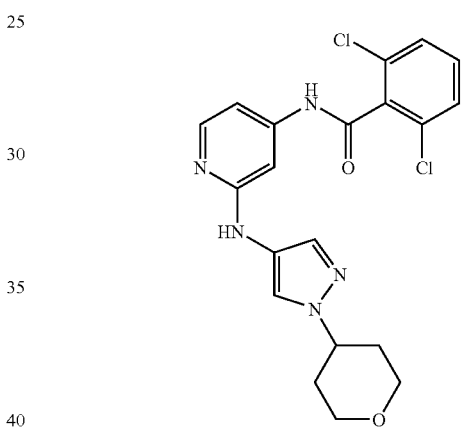

2,6-dichloro-N-(2-(1-(tetrahydro-2H-pyran-4-yl)-1H-pyrazol-4-ylamino)pyridin-4-yl)benzamide Step 1

4-nitro-1H-pyrazole (0.15 g, 1.3 mmol), tetrahydro-2H-pyran-4-ol (0.14 g, 1.3 mmol), DIPAD (0.35 g, 1.7 mmol), $PPh_3$ (0.42 g, 1.6 mmol) were dissolved in THF (5 mL) and the resulting mixture was stirred at 25° C. for 3 hours. The mixture was concentrated under reduced pressure and the residue was purified by column chromatography (EtOAc/petroleum ether=6/1) to give 4-nitro-1-(tetrahydro-2H-pyran-4-yl)-1H-pyrazole (0.45 g). $^1H$ NMR (500 MHz, $CDCl_3$): δ 8.19 (s, 1H), 8.10 (s, 1H), 4.38 (m, 1H), 4.16-4.12 (m, 2H), 3.57-3.53 (m, 2H), 2.17-2.05 (m, 4H).

Step 2

To the above 4-nitro-1-(tetrahydro-2H-pyran-4-yl)-1H-pyrazole (0.45 g) in MeOH (5 mL) was added 5% Pd/C (0.045 g). The reaction vessel was evacuated and filled with $H_2$ (3×). The reaction was stirred under $H_2$ (1.1 KPa) at room temperature overnight. The mixture was filtered through Celite and concentrated under reduced pressure. The residue was purified by column chromatography ($CH_2Cl_2$/MeOH=6/1 then 1/1) to give 1-(tetrahydro-2H-pyran-4-yl)-1H-pyrazol-4-amine (0.17 g, 78% yield for 2 steps). $^1H$ NMR (500 MHz, CDCl$_3$): δ 7.17 (s, 1H), 7.06 (s, 1H), 4.22 (m, 1H), 4.10-4.06 (m, 2H), 3.53-3.49 (m, 2H), 2.06-1.99 (m, 4H). LCMS (ESI) m/z: 168.1 [M+H$^+$].

Step 3

To a microwave tube was added N-(2-bromopyridin-4-yl)-2,6-dichlorobenzamide (0.083 g, 0.24 mmol), 1-(tetrahydro-2H-pyran-4-yl)-1H-pyrazol-4-amine (0.048 g, 0.29 mmol), Pd$_2$(dba)$_3$ (0.022 g, 0.024 mmol), XantPhos (0.028 g, 0.048 mmol), Cs$_2$CO$_3$ (0.16 g, 0.48 mmol) and dioxane (2 mL). The mixture was degassed with N$_2$ for 10 min. The resulting mixture was irradiated in a microwave reactor at 140° C. for 3 hours and then cooled to room temperature. The mixture was filtered through Celite and concentrated under reduced pressure. The residue was dissolved in DMF and purified by prep-HPLC (Gilson GX 281, Shim-pack PRC-ODS 250 mm×20 mm×2, gradient: CH$_3$CN/10 mm/L NH$_4$HCO$_3$, 17 min) to give the desired product as a white solid (26 mg, yield: 25%). $^1$H NMR (500 MHz, d$_6$-DMSO): δ 10.87 (s, 1H), 8.83 (s, 1H), 8.02 (d, J=5.5 Hz, 1H), 7.97 (s, 1H), 7.60 (d, J=3.0 Hz, 2H), 7.53 (t, J=3 Hz, 1H), 7.43 (s, 1H), 7.24 (s, 1H), 6.77 (d, J=5.0 Hz, 1H), 4.34 (m, 1H), 3.98-3.94 (m, 2H), 3.49-3.45 (m, 2H), 1.95-1.91 (m, 4H). LCMS (ESI) m/z: 432.0 [M+H$^+$].

Example 231

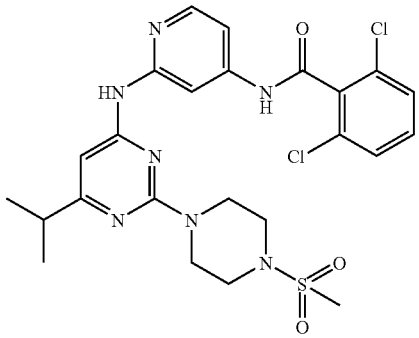 [SMILES: CC(C)c1cc(Nc2cc(NC(=O)c3c(Cl)cccc3Cl)ccn2)nc(N2CCN(S(C)(=O)=O)CC2)n1]

2,6-dichloro-N-(2-(6-isopropyl-2-(4-(methylsulfonyl)piperazin-1-yl)pyrimidin-4-ylamino)pyridin-4-yl)benzamide Step 1

Thiourea (1.0 g, 13 mmol) was dissolved in 1.6 mL of water at 70° C. Methyl 4-methyl-3-oxopentanoate (2.8 g, 20 mmol) was added and followed by K$_2$CO$_3$ (2.7 g, 19 mmol). The reaction was heated at 105° C. open to air for 1 hour to boil off any remaining methanol. After being cooled to room temperature, water (6.6 mL) was added and followed by 6 mL of concentrated HCl. The white precipitate was collected by filtration and washed with water and 1 N HCl to afford 6-isopropyl-2-mercaptopyrimidin-4-ol as a white solid (1.5 g, yield: 46%). $^1$H NMR (400 MHz, DMSO-d$_6$): δ 12.34 (s, 1H), 12.19 (s, 1H), 5.67 (s, 1H), 2.66 (m, 1H), 1.13 (d, J=6.8 Hz, 6H). LCMS (ESI) m/z: 171.0 [M+H$^+$].

Step 2

Chloroacetic acid (22 g, 0.23 mol) and 6-isopropyl-2-mercaptopyrimidin-4-ol (10 g, 59 mmol) were suspended in water (150 mL). The reaction mixture was refluxed for 6 hours. Concentrated HCl (0.36 mL) was added carefully, and the reaction was returned to reflux for 12 hours. After cooling to room temperature, the mixture was concentrated under reduced pressure to give 6-isopropylpyrimidine-2,4-diol (9.0 g, yield: 100%), which was used in the next step without further purification. LCMS (ESI) m/z: 155.0 [M+H$^+$].

Step 3

A mixture of phosphorous oxychloride (40 mL), N,N-dimethyl aniline (4 mL) and 6-isopropylpyrimidine-2,4-diol (10 g, 67 mmol) was heated to reflux for 6 hours. The mixutre was concentrated under reduced pressure and the residue was diluted with ice-water (200 mL). The mixture was extracted with dichloromethane (3×200 mL) and the combined organic extracts were dried over Na$_2$SO$_4$ and concentrated under reduced pressure to give 2,4-dichloro-6-isopropylpyrimidine as an oil (9.0 g, yield: 89%). This crude material was used in the next step without further purification. LCMS (ESI) m/z: 191.0 [M+H$^+$].

Step 4

A solution of 2,4-dichloro-6-isopropylpyrimidine (9.2 g, 48 mmol) in NH$_3$H$_2$O (250 mL) was stirred at room temperature for 2 days. The resulting mixture was extracted with dichloromethane (3×100 mL). The combined organic extracts were dried with Na$_2$SO$_4$ and concentrated under reduced pressure. The residue was purified by rpHPLC(H$_2$O/CH$_3$CN/5% NH$_3$H$_2$O=80/20/1) to give 2-chloro-6-isopropylpyrimidin-4-amine (1.1 g, 13% yield). $^1$H NMR (500 MHz, DMSO-d$_6$): δ 7.24 (s, 2H), 6.22 (s, 1H), 2.68 (m, 1H), 1.13 (d, J=6.5 Hz, 6H). LC-MS (ESI) m/z: 172.0 [M+H$^+$].

Step 5

To a microwave tube was added N-(2-bromopyridin-4-yl)-2,6-dichlorobenzamide (0.25 g, 0.72 mmol), 2-chloro-6-isopropylpyrimidin-4-amine (0.16 g, 0.94 mmol), Pd$_2$(dba)$_3$ (0.020 g, 0.022 mmol), XantPhos (0.008 g, 0.014 mmol), Cs$_2$CO$_3$ (0.47 g, 1.4 mmol) dioxane (20 mL) and DME (5 mL). The mixture was degassed with N$_2$ for 10 min. The resulting mixture was irradiated in a microwave reactor at 130° C. for 2 hours and then cooled to room temperature. The mixture was filtered through Celite and concentrated under reduced pressure. The residue was purified by column chromatography (EtOAc/Petrolum ether=20/80 to 30/70) to give 2,6-dichloro-N-(2-(2-chloro-6-isopropylpyrimidin-4-ylamino)pyridin-4-yl)benzamide (370 mg, yield: 90%). LCMS (ESI) m/z: 436.0 [M+H$^+$].

Step 6

To a microwave tube with a solution of 2,6-dichloro-N-(2-(2-chloro-6-isopropylpyrimidin-4-ylamino)pyridin-4-yl) benzamide (0.050 g, 0.11 mmol) in ethanol (2 mL) was added diisopropylethylamine (1.5 mL) and 1-(methylsulfonyl)piperazine (0.18 g, 1.1 mmol). The resulting mixture was heated to 140° C. under microwave irradiation for 2 hours. The mixture was cooled to room temperature and concentrated under reduced pressure. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to give the desired product (30 mg, 46% yield). $^1$H NMR ((500 MHz, DMSO-d$_6$): δ 11.05 (s, 1H), 9.77 (s, 1H), 8.77 (s, 1H), 8.16 (d, J=5.5 Hz, 1H), 7.63 (s, 1H), 7.61 (s, 1H), 7.54 (m, 1H), 6.87 (m, 1H), 6.48 (s, 1H), 3.95-3.91 (m, 4H), 3.17-3.14

(m, 4H), 2.85 (s, 3H), 2.67 (m, 1H), 1.17 (d, J=7.0 Hz, 6H). LCMS (ESI) m/z: 564.0 [M+H⁺].

Example 232

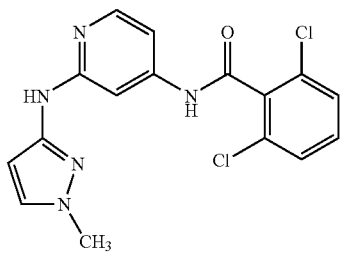 [SMILES: Cn1ccc(Nc2cc(NC(=O)c3c(Cl)cccc3Cl)ccn2)n1]

2,6-dichloro-N-(2-(1-methyl-1H-pyrazol-3-ylamino)pyridin-4-yl)benzamide

To a microwave tube were added N-(2-bromopyridin-4-yl)-2,6-dichlorobenzamide (0.12 g, 0.36 mmol), 1-methyl-1H-pyrazol-3-amine (0.045 g, 0.46 mmol), $Pd_2(dba)_3$ (0.031 g, 0.033 mmol), XantPhos (0.031 g, 0.052 mmol), $Cs_2CO_3$ (0.31 g, 0.94 mmol) and dioxane (3 mL). The mixture was degassed with $N_2$ for 10 min. The resulting mixture was irradiated in a microwave reactor at 140° C. for 1 hour and then cooled to room temperature. The mixture was filtered through Celite and concentrated under reduced pressure. The residue was in DMF and purified by prep-HPLC (Gilson GX 281, Shim-pack PRC-ODS 250 mm×20 mm×2, gradient: $CH_3CN/10$ mm/L $NH_4HCO_3$, 17 min) to give the desired product (30 mg, yield: 24%). ¹H NMR (500 MHz, DMSO-$d_6$): δ 10.92 (s, 1H). 9.16 (s, 1H), 8.01 (m, 1H), 7.60-7.50 (m, 5H), 7.04 (d, J=4.0 Hz, 1H), 6.27 (d, J=1.5 Hz, 1H), 3.72 (s, 3H). LCMS (ESI) m/z: 362.0 [M+H+].

Example 233

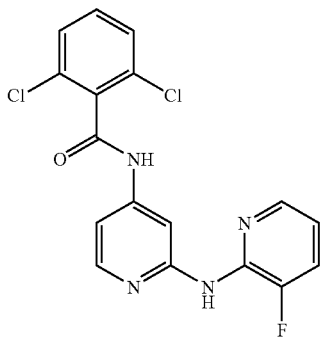 [SMILES: O=C(Nc1ccnc(Nc2ncccc2F)c1)c1c(Cl)cccc1Cl]

2,6-dichloro-N-(2-(3-fluoropyridin-2-ylamino)pyridin-4-yl)benzamide

A 25 mL microwave tube containing N-(2-bromopyridin-4-yl)-2,6-dichlorobenzamide (100 mg, 0.29 mmol), 3-fluoropyridin-2-amine (42 mg, 0.38 mmol), $Pd_2(dba)_3$ (8 mg, 0.008 mmol), $Cs_2CO_3$ (190 mg, 0.58 mmol), 4,5-bis(diphenylphosphino)-9,9-dimethylxanthene (Xantphos, 4 mg, 0.003 mmol), and dioxane (15 mL) was degassed and then charged by $N_2$ (3×). The resulting mixture was then irradiated in a microwave reactor at 130° C. for 30 min. The mixture was diluted with dioxane (20 mL) and filtered through Celite. The filtrate was concentrated under reduced pressure and the residue was purified by reverse-phase HPLC (Gemini, 200 mm×25 mm, gradient: $CH_3CN/0.05\% NH_3.H_2O$, 50-80%, 10 min) to afford the desired product (377 mg, yield: 45%). ¹H NMR (400 MHz, DMSO) δ 11.07 (s, 1H), 8.98 (s, 1H), 8.28-8.01 (m, 3H), 7.70-7.48 (m, 4H), 7.37 (s, 1H), 7.01 (s, 1H). LCMS (ESI) m/z: 378.5 [M+H⁺].

Example 234

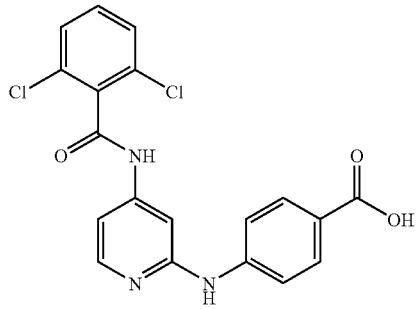 [SMILES: O=C(O)c1ccc(Nc2cc(NC(=O)c3c(Cl)cccc3Cl)ccn2)cc1]

4-(4-(2,6-dichlorobenzamido)pyridin-2-ylamino)benzoic acid

Step 1

A 25 mL microwave tube containing N-(2-bromopyridin-4-yl)-2,6-dichlorobenzamide (0.50 g, 1.40 mmol), ethyl 4-aminobenzoate (0.31 g, 1.92 mmol), $Pd_2(dba)_3$ (40 mg, 0.043 mmol), $Cs_2CO_3$ (0.94 g, 2.91 mmol), 4,5-bis(diphenylphosphino)-9,9-dimethylxanthene (Xantphos, 17 mg, 0.029 mmol), and dioxane (20 mL) was degassed and then charged by $N_2$ (3×). The mixture was then heated at 120° C. for 30 min and then diluted with dioxane (20 mL). The reaction was filtered through Celite and concentrated under reduced pressure. The residue was purified by reverse-phase HPLC (Gemini, 200 mm×25 mm, gradient: $CH_3CN/0.05\% NH_3.H_2O$, 50-80%, 10 min) to afford ethyl 4-(4-(2,6-dichlorobenzamido)pyridin-2-ylamino)benzoate (500 mg, yield: 80%). ¹H NMR (400 MHz, DMSO) δ 11.02 (s, 1H), 9.60 (s, 1H), 8.15 (d, J=5.6, 1H), 7.96-7.76 (m, 4H), 7.57 (ddd, J=16.0, 9.0, 4.2, 4H), 6.92 (dd, J=5.6, 1.6, 1H), 4.27 (q, J=7.1, 2H), 1.31 (t, J=7.1, 3H). LCMS (ESI) m/z: 431.4 [M+H⁺].

Step 2

To a solution of ethyl 4-(4-(2,6-dichlorobenzamido)pyridin-2-ylamino)benzoate (500 mg, 1.2 mmol) in THF (30 mL) was added 2 N LiOH solution (2 mL, 1.5 mmol) dropwise. The reaction mixture was then stirred at 60° C. overnight. After cooling to room temperature, the reaction mixture was adjusted to pH=3-4 using HCl (2N, 2 mL). The mixture was extracted with EtOAc (3×50 mL). The combined organic extracts were washed with brine, dried over $MgSO_4$ and concenrated under reduced pressure. The residue was purified by silica gel column chromatography ($MeOH/CH_2Cl_2$: 1/10) to afford desired product (440 mg, yield: 94%). ¹H NMR (400 MHz, DMSO) δ 12.36 (s, 1H), 11.01 (s, 1H), 9.55 (s, 1H), 8.14 (d, J=5.7, 1H), 7.90-7.73 (m, 5H), 7.67-7.43 (m, 5H), 6.91 (dd, J=5.7, 1.6, 1H). LCMS (ESI) m/z: 403.4 [M+H⁺].

Example 235

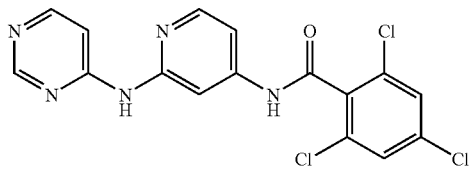 [SMILES: O=C(Nc1ccnc(Nc2ccncn2)c1)c1c(Cl)cc(Cl)cc1Cl]

2,4,6-trichloro-N-(2-(pyrimidin-4-ylamino)pyridin-4-yl)benzamide

Step 1

A solution of 2,4,6-trichlorobenzoic acid (337 mg, 1.5 mmol) in $SOCl_2$ (10 ml) was heated at reflux overnight and then cooled to room temperature. The reaction was concentrated under reduced pressure and to afford the desired acid chloride intermediate in quantitative yield. This material was used in the following step without purification.

Step 2

To a cooled (0° C.) solution of 2-bromo-4-aminopyridine (296 mg, 1.5 mmol) in dry DMF (5 mL) was added NaH (120 mg, 3.0 mmol, 60% dispersion in mineral oil) carefully. The mixture was stirred at room temperature for 30 min and then cooled to 0° C. again. A solution of the acid chloride from the preceeding step in dry DMF (5 mL) was added to the mixture slowly. The resulting mixture was stirred for further an additional hour at room temperature and then quenched with ice-water (20 mL). The mixture was extracted with ethyl acetate (3×50 ml). The combined organic extracts were washed with brine (20 mL), dried over $MgSO_4$ and concentrated under reduced pressure. The residue was purified by flash column chromatography on silica gel (EA/PE=1:10) to give N-(2-bromopyridin-4-yl)-2,4,6-trichlorobenzamide (390 mg, yield: 69%). LCMS (ESI) m/z: 378.9 [M+H⁺].

Step 3

A mixture of N-(2-bromopyridin-4-yl)-2,4,6-trichlorobenzamide (76 mg, 0.20 mmol), pyrimidin-4-amine (38 mg, 0.40 mmol), $Pd_2(dba)_3$ (18.3 mg, 0.020 mmol), Xantphos (23.3 mg, 0.040 mmol), $Cs_2CO_3$ (131 mg, 0.40 mmol), and dioxane (1.2 mL) was heated at 140° C. for 1 hour in a microwave reactor under nitrogen atmosphere. The mixture was filtered through Celite and concentrated under reduced pressure. The residue was purified by prep-HPLC (Gilson GX 281, Shim-pack PRC-ODS 250 mm×20 mm×2, gradient: $CH_3CN$/10 mm/L $NH_4HCO_3$, 17 min) to afford the desired product (46.5 mg, yield: 59%). ¹H NMR (500 MHz, MeOH-d₄): δ 8.68 (s, 1H), 8.36 (d, J=6.0 Hz, 1H), 8.26 (d, J=6.0 Hz, 1H), 8.19 (s, 1H), 7.71 (d, J=6.0 Hz, 1H), 7.65 (s, 2H), 7.35 (m, 1H). LCMS (ESI) m/z: 394.0 [M+H⁺].

Example 236

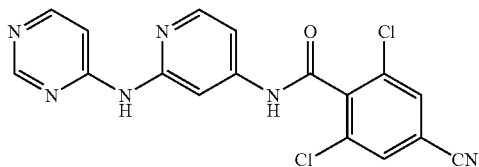 [SMILES: N#Cc1cc(Cl)c(C(=O)Nc2ccnc(Nc3ccncn3)c2)c(Cl)c1]

2,6-dichloro-4-cyano-N-(2-(pyrimidin-4-ylamino)pyridin-4-yl)benzamide

Step 1

To a solution of dimethyl 2-aminoterephthalate (500 g, 2.39 mol) in $CCl_4$ (4 L) at 60° C. was slowly added NCS (957 g, 7.17 mol). The reaction mixture was heated at 80° C. for 16 hours, cooled to room temperature and filtered. The solid was washed with dichloromethane (2×500 mL) and the combined organic solution was washed with 1 N NaOH (2×3 L), water (3 L) and brine (1 L). The mixture was dried over $Na_2SO_4$, and concentrated under reduced pressure to afford dimethyl 2-amino-3,5-dichloroterephthalate (645 g, yield: 97%) as a red oil. ¹H NMR (400 MHz, DMSO-d₆) δ 3.81 (s, 3H), 3.87 (s, 3H), 7.04 (s, 2H), 7.77 (s, 1H). LCMS (ESI) m/z: 210.0 [M+H⁺].

Step 2

To a solution of dimethyl 2-amino-3,5-dichloroterephthalate (200 g, 0.72 mol) in THF (1 L) at room temperature was slowly added isoamylnitrite (240 mL). The mixture was heated under reflux for 3 hours, cooled to room temperature and concentrated under reduced pressure. The residue was purified by column chromatography on silica gel, eluting with petroleum-diethyl:ether (50:1) to give dimethyl 2,6-dichloroterephthalate (187 g, yield: 98%) as a light yellow solid.

¹H NMR (400 MHz, DMSO-d₆) δ 3.86 (s, 3H), 3.92 (s, 3H), 8.00 (s, 2H). LCMS (ESI) m/z: 263.0 [M+H⁺].

Step 3

To a solution of dimethyl 2,6-dichloroterephthalate (186 g, 707 mmol) in THF (600 mL) at room temperature was added a solution of sodium hydroxide (29.7 g, 742 mmol) in water (600 mL). The reaction mixture was stirred at room temperature for 48 hours and concentrated under reduce pressure to a volume of 600 mL. The residue was diluted with water (400 mL), cooled to 0° C. and acidified with 1 N HCl (800 mL). The resulting precipitate was collected by filtration and dried in vacuo to give 3,5-dichloro-4-(methoxycarbonyl)benzoic acid (72 g, yield: 41%) as a white solid: ¹H NMR (400 MHz, DMSO-d₆) δ 3.90 (s, 3H), 7.92 (s, 2H). LCMS (ESI) m/z: 249.0 [M+H⁺].

Step 4

To a solution of 3,5-dichloro-4-(methoxycarbonyl)benzoic acid (72 g, 289 mmol) and triethylamine (40 mL) in THF (240 mL) at room temperature was added ethyl chloroformate (40 mL). The reaction mixture was stirred for 20 min at room temperature and filtered. To the filtrate was added $(NH_4)_2CO_3$ (28 g, 292 mmol) and the mixture was stirred at room temperature for 18 hours. The mixture was diluted with water (300 mL) and extracted with ethyl acetate (3×300 mL). The combined organic extracts were washed with brine (200 mL), dried over $Na_2SO_4$, and concentrated under reduced pressure.

The residue was purified by column chromatography on silica gel, eluting with petroleum-diethyl ether (5:1) to give methyl 4-carbamoyl-2,6-dichlorobenzoate (57 g, yield: 80%) as a pale yellow solid. $^1$H NMR (400 MHz, DMSO-d$_6$) δ 3.90 (s, 3H), 7.76 (s, 1H), 7.99 (s, 2H), 8.28 (s, 1H). LCMS (ESI) m/z: 248.0 [M+H$^+$].

Step 5

A mixture of methyl 4-carbamoyl-2,6-dichlorobenzoate (57 g, 230 mmol), trifluoroacetic anhydride (46 mL) and pyridine (46 mL) in dixoane (400 mL) was stirred at room temperature for 24 hours, diluted with water (300 mL) and extracted with ethyl acetate (3×300 mL). The combined organic extracts were washed with brine (200 mL), dried over Na$_2$SO$_4$, and concentrated under reduced pressure. The residue was purified by column chromatography on silica gel, eluting with petroleum-diethyl ether (10:1) to give methyl 2,6-dichloro-4-cyanobenzoate (32 g, yield: 61%) as a pale yellow solid. $^1$H NMR (400 MHz, DMSO-d$_6$) δ 3.91 (s, 3H), 7.95 (s, 2H). LCMS (ESI) m/z: 230.1 [M+H$^+$].

Step 6

To a solution of methyl 2,6-dichloro-4-cyanobenzoate (160 g, 694 mmol) in pyridine (1.5 L) at room temperature was added LiI (186 g, 1.39 mol). The mixture was heated under reflux for 2 hours, cooled to room temperature and concentrated under reduced pressure. The residue was treated with 2 N HCl (1 L) and the resulting precipitate was collected by filtration. The solid was recrystallized from DMF and water to give 2,6-dichloro-4-cyanobenzoic acid (110 g, yield: 73%) as a white solid. $^1$H NMR (400 MHz, DMSO-d$_6$) δ 8.18 (s, 2H). LCMS (ESI) m/z: 216.0 [M+H$^+$].

Step 7

A solution of 2,6-dichloro-4-cyanobenzoic acid (324 mg, 1.5 mmol) in SOCl$_2$ (10 mL) was heated at reflux overnight and then cooled to room temperature. The mixture was concentrated under reduced pressure to afford the acid chloride intermediate in quantitative yield. This material was used in the next step without purification.

Step 8

To a cooled (0° C.) solution of 2-bromo-4-aminopyridine (295 mg, 1.5 mmol) in dry DMF (5 ml) was added NaH (120 mg, 3.0 mmol, 60% dispersion in mineral oil) carefully. The mixture was stirred at room temperature for 30 min and then cooled to 0° C. again. A solution of the acid chloride from the preceeding step in dry DMF (5 ml) was added into the mixture slowly. The resulting mixture was stirred for an additional hour at room temperature and then quenched with ice-water (20 ml). The mixture was extracted with ethyl acetate (3×50 ml). The combined organic extracts were washed with brine (20 mL), dried over MgSO$_4$ and concentrated under reduced pressure. The residue was purified by flash chromatography (ethyl acetate/petroleum ether=1:10) to give N-(2-bromopyridin-4-yl)-2,6-dichloro-4-cyanobenzamide (389 mg, 70% yield). LCMS (ESI) m/z: 369.9 [M+H$^+$].

Step 9

A mixture of N-(2-bromopyridin-4-yl)-2,6-dichloro-4-cyanobenzamide (74 mg, 0.20 mmol), pyrimidin-4-amine (38 mg, 0.40 mmol), Pd$_2$(dba)$_3$ (18 mg, 0.020 mmol), Xantphos (23 mg, 0.040 mmol), Cs$_2$CO$_3$ (131 mg, 0.40 mmol), dioxane (1.2 mL) was heated to 140° C. for 1 hour in a microwave reactor under nitrogen atmosphere. The mixture was filtered through Celite and concentrated under reduced pressure. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford the desired product (50 mg, yield: 65%). $^1$H NMR (500 MHz, MeOH-d$_4$): δ 8.68 (s, 1H), 8.36 (d, J=5.5 Hz, 1H), 8.27 (d, J=5.5 Hz, 1H), 8.19 (s, 1H), 8.00 (s, 2H), 7.71 (d, J=5.5 Hz, 1H), 7.36 (m, 1H). LC-MS (ESI) m/z: 385.0 [M+H$^+$].

Example 237

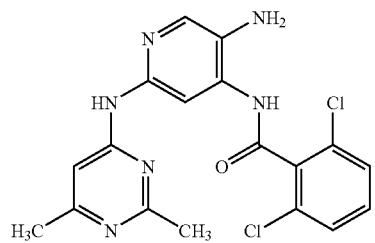 [SMILES: Cc1cc(Nc2cc(NC(=O)c3c(Cl)cccc3Cl)c(N)cn2)nc(C)n1]

N-(5-amino-2-(2,6-dimethylpyrimidin-4-ylamino) pyridine-4-yl)-2,6-dichlorobenzamide Step 1

To a 200 ml flask was added 4-amino-2-chloro-5-nitropyridine (1.00 g, 5.76 mmol), 4-amino-2,6-dimethylpyrimidine (1.42 g, 11.5 mmol), Pd$_2$(dba)$_3$ (0.528 g, 0.576 mmol), Xant-Phos (0.400 g, 0.691 mmol), Cs$_2$CO$_3$ (4.13 g, 12.7 mmol) and dioxane (45 mL). The mixture was degassed with N$_2$ for 2 min and then heated at 110° C. for 16 hrs. After cooling to room temperature the reaction was filtered and concentrated under reduced pressure. The residue was purified by column chromatography on silica gel (0-10% methanol/dichloromethane) to give N-(2,6-dimethylpyrimidin-4-yl)-5-nitropyridine-2,4-diamine (0.348 g, yield: 23%). LCMS (ESI) m/z: 261.2 [M+H$^+$].

Step 2

To a cooled (0° C.) solution of N-(2,6-dimethylpyrimidin-4-yl)-5-nitropyridine-2,4-diamine (0.348 g, 1.337 mmol) in anhydrous N,N-dimethylformamide (10 mL) under nitrogen was added sodium hydride (0.064 g, 2.67 mmol, 60% dispersion in mineral oil) in one portion. The reaction mixture was stirred at 0° C. for 15 mins and then a solution of 2,6-dichlorobenzoyl chloride (220 uL, 1.5 mmol) in DMF (1.5 mL) was added dropwise. The mixture was stirred at room temperature for 3.5 hours and then quenched with water (60 mL). The mixture was extracted with ethyl acetate (200 mL). The organic layer was dried over Na$_2$SO$_4$, and concentrated under reduced pressure. The residue was purified by column chromatography on silica gel (20-80% ethyl acetate/heptane) to give 2,6-dichloro-N-(2-(2,6-dimethylpyrimidin-4-ylamino)-5-nitropyridin-4-yl)benzoamide (0.57 g, yield: 100%). LCMS (ESI) m/z: 433.1 [M+H$^+$].

Step 3

To a solution of 2,6-dichloro-N-(2-(2,6-dimethylpyrimidin-4-ylamino)-5-nitropyridine-4-yl)benzoamide (0.057 g, 0.13 mmol) in dry ethanol (8 mL) was added palladium (0.015 g, 0.14 mmol) (10% on activated carbon powder, 50% water wet) in one portion at room temperature under N$_2$. The resulting mixture was stirred under H$_2$ balloon for 60 mins The mixture was filtered with Celite and the filtrate was concentrated by vacuum. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to give the desired product (9.8 mg, yield: 18%). $^1$H NMR (DMSO-d$_6$, 400 MHz): δ 10.2 (d, J=24.6 Hz, 1H), 9.58 (s, 1H), 8.17 (d, J=28.7 Hz, 1H), 7.85 (s, 1H), 7.59 (s, 3H), 7.08 (s, 1H), 4.81 (s, 2H), 2.38 (s, 3H), 2.25 (s, 3H). LCMS (ESI) m/z: 403.0 [M+H$^+$].

Example 238

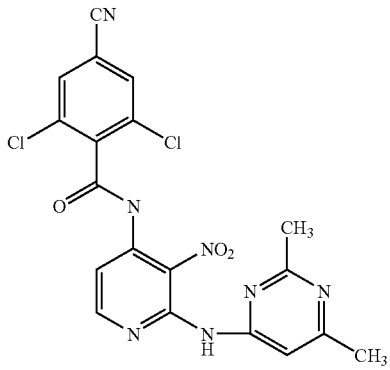 [SMILES: Cc1cc(Nc2nccc(NC(=O)c3c(Cl)cc(C#N)cc3Cl)c2[N+](=O)[O-])nc(C)n1]

2,6-dichloro-4-cyano-N-(2-(2,6-dimethylpyrimidin-4-ylamino)-3-nitropyridin-4-yl)benzamide Step 1

NaH (0.46 g, 11.6 mmol, 60% dispersion in mineral oil) was added in one portion to a cooled (0° C.) solution of 2-chloro-3-nitropyridin-4-amine (1.00 g, 5.8 mmol) in DMF (15 mL). The mixture was stirred for 20 mins and then a solution of 2,6-dichloro-4-cyanobenzoyl chloride (0.68 g, 2.9 mmol) in DMF (5 mL) was added dropwise. The reaction mixture was stirred at 0° C. for 4 hours and then poured onto ice-water (20 mL). The resulting precipitate was collected by filtration and then the filtrate was extracted by EtOAc (2×50 mL). The combined organic extracts were dried over Na$_2$SO$_4$ and concentrated under reduced pressure. The residue was combined with previously collected precipirate and the material was purified by silica gel column chromatography (MeOH:CH$_2$Cl$_2$ 1:10) to afford N-(2-chloro-3-nitropyridin-4-yl)-2,6-dichloro-4-cyanobenzamide (0.5 g, yield: 23%). LCMS (ESI) m/z: 372.6 [M+H$^+$]

Step 2

A 25 mL microwave tube containing N-(2-chloro-3-nitropyridin-4-yl)-2,6-dichloro-4-cyanobenzamide (100 mg, 0.27 mmol), 2,6-dimethylpyrimidin-4-amine (43 mg, 0.35 mmol), Pd$_2$(dba)$_3$ (8 mg, 0.009 mmol), Cs$_2$CO$_3$ (180 mg, 0.54 mmol), 4,5-bis(diphenylphosphino)-9,9-dimethylxanthene (Xantphos, 4 mg, 0.005 mmol), dioxane (8 mL) and DME (3 mL) was degassed and then charged by N$_2$ (3×). The mixture was then irradiated in a microwave reactor at 160° C. for 2 hours and then diluted with dioxane (20 mL). The reaction was filtered through Celite and concentrated under reduced pressure. The residue was purified by reverse-phase HPLC (Gemini, 200 mm×25 mm, gradient: CH$_3$CN/0.05% NH$_3$.H$_2$O, 50-80, 10 min) to afford the desired product (4 mg, yield: 5%). LCMS (ESI) m/z: 458.3 [M+H$^+$].

Examples 239, 240, 241 and 242

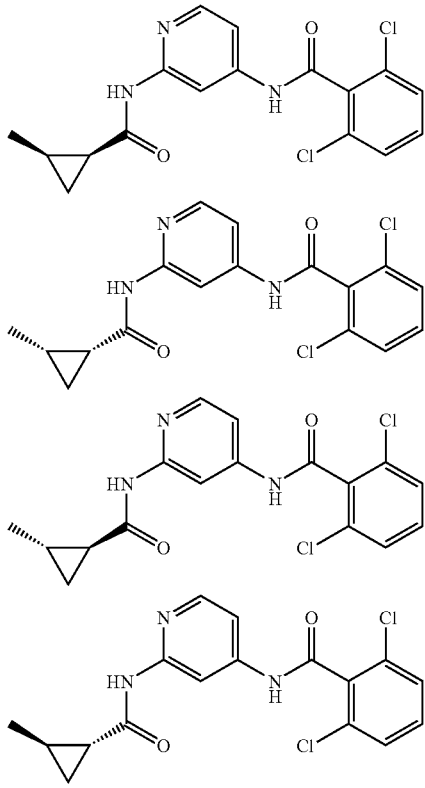

2,6-dichloro-N-(2-(((1S,2R)-2-methylcyclopropanecarboxamido)pyridin-4-yl)benzamide 2,6-dichloro-N-(2-(((1R,2S)-2-methylcyclopropanecarboxamido)pyridin-4-yl)benzamide 2,6-dichloro-N-(2-(((1S,2S)-2-methylcyclopropanecarboxamido)pyridin-4-yl)benzamide 2,6-dichloro-N-(2-(((1R,2R)-2-methylcyclopropanecarboxamido)pyridin-4-yl)benzamide Step 1

To a cooled (0° C.) solution of 2-methylcyclopropanecarboxylic acid (500 mg, 5.0 mmol) and triethylamine (1.5 g, 15 mmol) in acetone (2 mL) was added ethyl chloroformate (810 mg, 15 mmol) dropwise. Stirring was continued at 0° C. for 1.5 hours and then a 1N solution of ammonium hydroxide (25 mL, 25 mmol) was added dropwise. The reaction was stirred at room temperature for 3 hours and then concentrated under reduced pressure. The residue was purified by silica gel chromatography (EtOAc/hexane=3:7) to afford 2-methylcyclopropanecarboxamide (410 mg, yield: 84%).

Step 2

To a microwave tube was added N-(2-bromopyridin-4-yl)-2,6-dichlorobenzamide (50 mg, 0.15 mmol), 2-methylcyclopropanecarboxamide (15 mg, 0.15 mmol), Pd$_2$(dba)$_3$ (21 mg, 0.020 mmol), XantPhos (12 mg, 0.020 mmol), Cs$_2$CO$_3$ (147 mg, 0.45 mmol) and dioxane (3 mL).

The mixture was degassed with N$_2$ for 10 min. The resulting mixture was irradiated in a microwave reactor at 160° C. for 2 hours and then cooled to room temperature. The mixture was filtered through Celite and concentrated under reduced pressure. The residue was dissolved in DMF and purified by preparative HPLC (Gilson GX 281, Shim-pack PRC-ODS 250 mm×20 mm×2, gradient: CH$_3$CN/10 mm/L NH$_4$HCO$_3$, 17 min) to give the desired product (20 mg, 38% yield) as a mixture of 4 stereoisomers. These enantiomers could be separated as described below.

A mixture of four enantiomers (~220 mg) was separated via chiral prep-HPLC (AD-H column, mobile phase: n-hexane/ethanol (0.1% DEA)=90:10) to give the first eluting peak (50 mg), which was assigned as trans-configuration via NOE. >99% ee (12.78 min, AS-H column, n-hexane/ethanol (0.1% DEA)=90:10, 25 min) $^1$H-NMR (500 MHz, MeOH-d$_4$): δ 8.30 (s, 1H), 8.24 (d, J=6.0 Hz, 1H), 7.60 (d, J=6.05 Hz, 1H), 7.49-7.43 (m, 4H), 1.62 (m, 1H), 1.41 (m, 1H), 1.16 (d, J=6.5 Hz, 3H), 1.15 (m, 1H), 0.72 (m, 1H). LCMS (ESI) m/z: 364.1 [M+H$^+$].

The remaining steroisomers was separated via chiral prep-HPLC (AS-H column, mobile phase: n-hexane/ethanol (0.1% DEA)=90:10) to give the three remaining enantiomers.

First eluting peak, 25 mg, which was assigned as trans-configuration via NOE. >99% ee (10.13 min, AS-H column, n-hexane/ethanol (0.1% DEA)=90:10, 25 min) $^1$H-NMR (500 MHz, MeOHd$_4$): δ 8.32 (s, 1H), 8.24 (d, J=5.5 Hz, 1H), 7.60 (d, J=5.5 Hz, 1H,), 7.50-7.45 (m, 4H), 1.93 (m, 1H), 1.36 (m, 1H), 1.20 (d, J=6.5 Hz, 3H), 1.03 (m, 1H), 0.95 (m, 1H). LCMS (ESI) m/z: 364.1 [M+H$^+$].

Second eluting peak, 30 mg, which was assigned as cis-configuration via NOE. >99% ee (13.17 min, AS-H column, n-hexane/ethanol (0.1% DEA)=90:10, 25 min) $^1$H-NMR (500 MHz, MeOH-d$_4$): δ 8.32 (s, 1H), 8.24 (d, J=5.5 Hz, 1H), 7.60 (d, J=5.5 Hz, 1H,), 7.50-7.45 (m, 4H), 1.93 (m, 1H), 1.36 (m, 1H), 1.20 (d, J=6.5 Hz, 3H), 1.03 (m, 1H), 0.95 (m, 1H). LCMS (ESI) m/z: 364.1 [M+H$^+$].

Third eluting peak, 35 mg, which was assigned as cis-configuration via NOE. >99% ee (18.61 min, AS-H column, n-hexane/ethanol (0.1% DEA)=90:10, 25 min) $^1$H-NMR (500 MHz, MeOH-d$_4$): δ 8.30 (s, 1H), 8.24 (d, J=6.0 Hz, 1H), 7.60 (d, J=6.05 Hz, 1H), 7.49-7.43 (m, 4H), 1.62 (m, 1H), 1.41 (m, 1H), 1.16 (d, J=6.5 Hz, 3H), 1.15 (m, 1H), 0.72 (m, 1H). LCMS (ESI) m/z: 364.1 [M+H$^+$].

Example 243 and 244

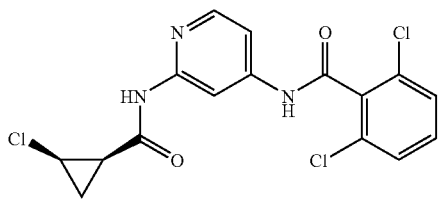

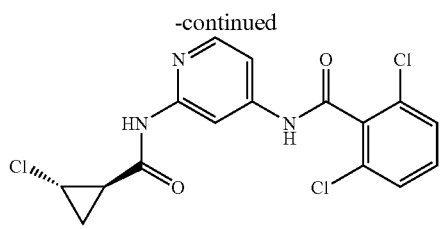

2,6-dichloro-N-(2-((1R,2R)-2-chlorocyclopropan-ecarboxamido)pyridin-4-yl)benzamide 2,6-dichloro-N-(2-((1R,2S)-2-chlorocyclopropan-ecarboxamido)pyridin-4-yl)benzamide Step 1

Tert-butyl acrylate (32 g, 0.25 mol), CHCl$_3$ (318 g, 3 mol), tetramethyl ammonium chloride (0.75 g, 0.0050 mol) and 50% aqueous NaOH (300 mL) were stirred at 45-50° C. for 8 hours. The mixture was diluted with water (400 mL) and the organic layer was separated. The aqueous layer was extracted with CHCl$_3$ (75 mL). The combined organic extracts were washed with 1N HCl (200 mL) and water (250 mL), dried over Na$_2$SO$_4$, and concentrated under reduced pressure. The crude product was distilled to give tert-butyl 2,2-dichlorocyclopropanecarboxylate as colorless oil (16 g, yield: 30%). $^1$H-NMR (500 MHz, CDCl$_3$,): δ 2.48 (m, 1H), 2.00 (m, 1H), 1.81 (m, 1H), 1.52 (s, 9H).

Step 2

A mixture of tert-butyl 2,2-dichlorocyclopropanecarboxylate (1.0 g, 4.7 mmol), tributyltin hydride (1.68 g, 5.7 mmol) and AIBN (50 mg) were heated to 90° C. for 1 h. The mixture was cooled to room temperature and distillation afforded a mixture of cis and trans t-butyl 2-chloro-1-cyclopropane carboxylate (220 mg, yield: 26%).

Step 3

To a solution of tert-butyl 2-chlorocyclopropanecarboxylate (100 mg, 0.57 mmol) in toluene (1 mL) was added 4-methylbenzenesulfonic acid hydrate (5.4 mg, 0.028 mmol). The mixture was heated to reflux for 1.5 hours and then cooled to room temperature. 2.5 N NaOH solution (2 mL) was added and the organic layer was separated. The aqueous layer was adjusted to pH 1 using 1 N HCl solution and then extracted with ethyl acetate (3×5 mL). The combined organic extracts were dried over Na$_2$SO$_4$ and concentrated under reduced pressure to give 2-chlorocyclopropanecarboxylic acid (60 mg crude) as a mixture of cis- and trans-isomers. This material was used in the next step without further purification.

Step 4

To a solution of N-(2-aminopyridin-4-yl)-2,6-dichlorobenzamide (150 mg, 0.54 mmol), 2-chlorocyclopropanecarboxylic acid (66 mg, 0.54 mmol) and HATU (381 mg, 1.08 mmol) in dry DMF (4.5 mL) was added DIPEA (144 mg, 1.08 mmol). The mixture was stirred at 110° C. in a microwave reactor for 1 hour. The mixture was cooled to room temperature and diluted with EtOAc (30 mL). The organic solution was washed with water (10 mL) and brine (10 mL), dried over Na$_2$SO$_4$ and concentrated under reduced pressure. The residue was purified by prep-HPLC (Gilson GX 281, Shim-pack PRC-ODS 250 mm×20 mm×2, gradient: CH$_3$CN/ 10 mm/L NH$_4$HCO$_3$, 17 min) to give the desired compounds.

First eluting peak, 25 mg, 12% yield, which was assigned via NOE as cis-configuration (Example 243). $^1$H-NMR (500 MHz, MeOH-d$_4$): δ 8.33 (s, 1H), 8.26 (d, J=5.0 Hz, 1H), 7.56

(d, J=5.0 Hz, 1H), 7.50-7.44 (m, 3H), 3.50 (m, 1H), 2.30 (m, 1H), 1.57 (m, 1H), 1.44 (m, 1H). LCMS (ESI) m/z: 384.0 [M+H$^+$].

Second eluting peak, 62 mg, 30% yield, which was assigned via NOE as trans-configuration (Example 244). $^1$H-NMR (500 MHz, MeOH-d$_4$): δ 8.33 (s, 1H), 8.25 (d, J=5.5 Hz, 1H), 7.60 (d, J=5.5 Hz, 1H), 7.49-7.43 (m, 3H), 3.46 (m, 1H), 2.23 (m, 1H), 1.61 (m, 1H), 1.39 (m, 1H). LCMS (ESI) m/z: 384.0 [M+H$^+$].

Examples 245 and 246

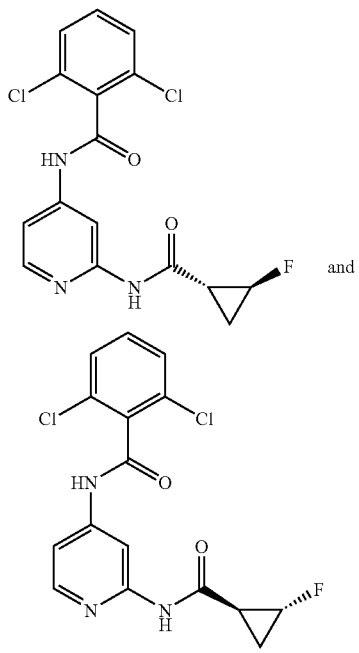

2,6-dichloro-N-(2-((1R,2S)-2-fluorocyclopropanecarboxamido)pyridin-4-yl)benzamide and 2,6-dichloro-N-(2-((1S,2R)-2-fluorocyclopropanecarboxamido)pyridin-4-yl)benzamide To a solution of N-(2-aminopyridin-4-yl)-2,6-dichlorobenzamide (28 mg, 0.10 mmol), trans-2-fluorocyclopropanecarboxylic acid (31 mg, 0.30 mmol) and disiopropylethylamine (52 mg, 0.40 mmol) in dry DMF (1 mL) was added HATU (114 mg, 0.30 mmol). The reaction mixture was stirred at room temperature for 18 hours and then quenched with sat. NH$_4$Cl (20 mL). The mixture was extracted with EtOAc (2×20 mL). The combined organic extracts were dried with Na$_2$SO$_4$, and concentrated under reduced pressure. The residue was purified by chiral SFC (Chiralpak IC, 20% Methanol+0.1% TEA, 5 min) to give two desired products:

First eluted peak, 3.4 mg, 9.2% yield. >99% ee (0.65 min, Chiralpak IC, 20% Methanol+0.1% TEA, 5 min) $^1$H NMR (400 MHz, DMSO-d$_6$) δ 11.14 (s, 1H), 10.88 (s, 1H), 8.38 (d, J=1.6 Hz, 1H), 8.24 (d, J=5.6 Hz, 1H), 7.62-7.55 (m, 2H), 7.51 (dd, J=9.2, 6.8 Hz, 1H), 7.46 (dd, J=5.6, 1.9 Hz, 1H), 4.99-4.75 (m, 1H), 2.62-2.54 (m, 1H), 1.58-1.43 (m, 1H), 1.23 (m, 1H). LCMS (ESI) m/z: 368.0 [M+H$^+$].

Second eluted peak, 3.3 mg, 9% yield. >99% ee (0.74 min, Chiralpak IC, 20% Methanol+0.1% TEA, 5 min) $^1$H NMR (400 MHz, DMSO-d$_6$) δ 11.14 (s, 1H), 10.88 (s, 1H), 8.38 (d, J=1.6 Hz, 1H), 8.24 (d, J=5.6 Hz, 1H), 7.61-7.55 (m, 2H), 7.51 (dd, J=9.2, 6.8 Hz, 1H), 7.46 (dd, J=5.6, 1.9 Hz, 1H), 4.99-4.75 (m, 1H), 2.58 (dd, J=11.0, 6.2 Hz, 1H), 1.58-1.43 (m, 1H), 1.23 (dq, J=12.7, 6.4 Hz, 1H). LCMS (ESI) m/z: 368.0 [M+H$^+$].

Examples 247 and 248

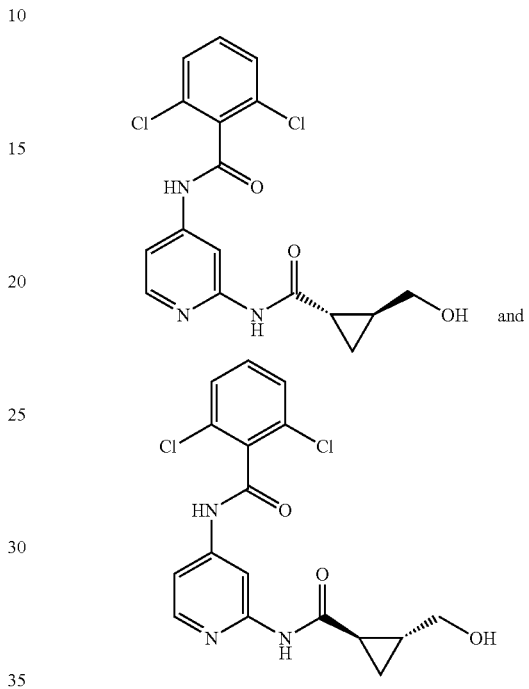

2,6-dichloro-N-(2-((1S,2S)-2-(hydroxymethyl)cyclopropanecarboxamido)pyridin-4-yl)benzamide and 2,6-dichloro-N-(2-((1R,2R)-2-(hydroxymethyl)cyclopropanecarboxamido)pyridin-4-yl)benzamide Step 1

To a solution of N-(2-aminopyridin-4-yl)-2,6-dichlorobenzamide (141 mg, 0.50 mmol), trans-cyclopropane-1,2-dicarboxylic acid (325 mg, 2.5 mmol), and disiopropylethylamine (339 mg, 2.63 mmol) in dry DMF (5 mL) was added HATU (1951 mg, 2.5 mmol). The reaction mixture was heated at 70° C. for 6 hours and then quenched with sat. NH$_4$Cl (100 mL). The mixture was extracted with EtOAc (3×100 mL). The combined organic extracts were dried with Na$_2$SO$_4$ and concentrated under reduced pressure. The residue was purified by prep HPLC (10-50% CH$_3$CN/H$_2$O with 0.1% formic acid) to give trans-2-(4-(2,6-dichlorobenzamido)pyridin-2-ylcarbamoyl)cyclopropanecarboxylic acid (132 mg, 67% yield). $^1$H NMR (400 MHz, DMSO-d$_6$) δ 11.14 (s, 1H), 10.86 (s, 1H), 8.38 (s, 1H), 8.23 (d, J=5.6 Hz, 1H), 7.62-7.55 (m, 2H), 7.54-7.45 (m, 2H), 1.90-1.82 (m, 1H), 1.25 (dt, J=8.0, 5.4 Hz, 3H). LCMS (ESI) m/z: 394.0 [M+H$^+$].

Step 2

To a cooled (0° C.) suspension of trans-2-(4-(2,6-dichlorobenzamido)pyridin-2-ylcarbamoyl)cyclopropanecarboxylic acid (50 mg, 0.127 mmol) and triethylamine (17 mg, 0.165 mmol) in dry THF (2 mL) was added ethyl chloroformate (18 mg, 0.165 mmol). The reaction mixture was stirred at 0° C. for 1.5 hours. A solution of NaBH$_4$ (17 mg, 0.444 mmol) in water (0.1 mL) was then added at 0° C. and stirring was continued for 30 min. The reaction was diluted with water (20 mL) and extracted with EtOAc (3×15 mL). The combined organic extracts were dried over Na$_2$SO$_4$ and concentrated under reduced pressure. The residue was purified by chiral SFC (Chiralpak AD-H, 25% Methanol+0.1% TEA, 25 min) to give two desired products:

First eluting peak, 6.9 mg, 14% yield. >98% ee (2.70 min, Chiralpak AD-H, 25% Methanol+0.1% TEA, 5 min) $^1$H NMR (400 MHz, DMSO-d$_6$) δ 11.12 (s, 1H), 10.62 (s, 1H), 8.37 (d, J=1.7 Hz, 1H), 8.22 (d, J=5.6 Hz, 1H), 7.61-7.55 (m, 2H), 7.51 (dd, J=9.2, 6.8 Hz, 1H), 7.47 (dd, J=5.6, 1.9 Hz, 1H), 4.62 (t, J=5.5 Hz, 1H), 3.43 (dt, J=11.3, 5.6 Hz, 1H), 3.27 (m, 2H), 1.92 (dt, J=8.4, 4.3 Hz, 1H), 1.51-1.41 (m, 1H), 1.01-0.92 (m, 1H), 0.82-0.75 (m, 1H). LCMS (ESI) m/z: 380.0 [M+H$^+$].

Second eluting peak, 6.7 mg, 14% yield. >99% ee (3.20 min, Chiralpak AD-H, 25% Methanol+0.1% TEA, 5 min) $^1$H NMR (400 MHz, DMSO-d$_6$) δ 11.12 (s, 1H), 10.62 (s, 1H), 8.37 (d, J=1.7 Hz, 1H), 8.22 (d, J=5.6 Hz, 1H), 7.61-7.56 (m, 2H), 7.51 (dd, J=9.2, 6.8 Hz, 1H), 7.47 (dd, J=5.6, 1.9 Hz, 1H), 4.62 (t, J=5.5 Hz, 1H), 3.44 (dt, J=11.2, 5.6 Hz, 1H), 3.26 (m, 2H), 1.92 (dt, J=8.4, 4.3 Hz, 1H), 1.47 (tt, J=12.4, 6.1 Hz, 1H), 1.01-0.94 (m, 1H), 0.83-0.74 (m, 1H). LCMS (ESI) m/z: 380.0 [M+H$^+$].

Examples 249 and 250

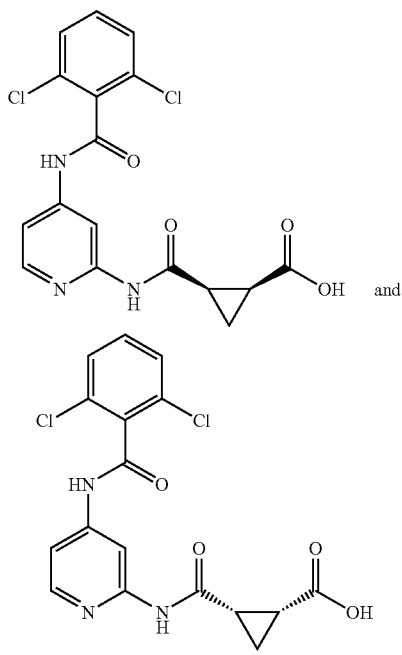

(1S,2R)-2-(4-(2,6-dichlorobenzamido)pyridin-2-ylcarbamoyl)cyclopropanecarboxylic acid and (1R, 2S)-2-(4-(2,6-dichlorobenzamido)pyridin-2-ylcarbamoyl)cyclopropanecarboxylic acid Step 1

A solution of N-(2-aminopyridin-4-yl)-2,6-dichlorobenzamide (1.41 g, 5 mmol) and 3-oxabicyclo[3.1.0]hexane-2,4-dione (2.24 g, 20 mmol) in 1,4-dioxane (25 mL) was heated at 90° C. for 4 hours. The reaction was cooled to room temperature and the precipitated white solid was collected by filtration to give 2,6-dichloro-N-(2-(-2,4-dioxo-3-azabicyclo [3.1.0]hexan-3-yl)pyridin-4-yl)benzamide (1.28 g, yield: 68%). $^1$H NMR (400 MHz, DMSO-d$_6$) δ 11.42 (s, 1H), 8.47 (d, J=5.6 Hz, 1H), 7.69 (d, J=1.8 Hz, 1H), 7.67-7.59 (m, 3H), 7.55 (dd, J=9.2, 6.8 Hz, 1H), 2.74 (dd, J=8.0, 3.6 Hz, 2H), 1.69 (ddt, J=20.6, 8.1, 4.2 Hz, 2H). LCMS (ESI) m/z: 376.0 [M+H$^+$].

Step 2

To a suspension of 2,6-dichloro-N-(2-(-2,4-dioxo-3-azabicyclo[3.1.0]hexan-3-yl)pyridin-4-yl)benzamide (136 mg, 0.36 mmol) in dry THF (4 mL) was added a solution of LiOH (1 M, 2 mL, 2 mmol). The reaction mixture was stirred at room temperature for 2 hours and diluted with water (10 mL). The mixture was extracted with EtOAc (10 mL). The aqueous layer was acidified to pH 2 with 1 N HCl and the resulting precipitate was collected by filtration. The precipitate was purified by chiral SFC (Chiralpak AD-H, 35% ethanol+0.1% TEA, 6 min) to give two desired products:

First eluting peak, 43 mg, 30% yield. >99% ee (0.56 min, Chiralpak AD-H, 35% ethanol+0.1% TEA, 3 min) $^1$H NMR (400 MHz, DMSO-d$_6$) δ 12.11 (s, 1H), 11.13 (s, 1H), 10.82 (s, 1H), 8.36 (d, J=1.6 Hz, 1H), 8.22 (d, J=5.6 Hz, 1H), 7.61-7.55 (m, 2H), 7.54-7.50 (m, 1H), 7.48 (dd, J=5.4, 1.7 Hz, 1H), 2.28 (dd, J=14.2, 7.6 Hz, 1H), 2.02 (dd, J=15.9, 8.4 Hz, 1H), 1.40 (dt, J=10.8, 5.5 Hz, 1H), 1.16 (td, J=8.3, 4.2 Hz, 1H). LCMS (ESI) m/z: 394.0 [M+H$^+$].

Second eluting peak, 641 mg, 29% yield. >99% ee (0.66 min, Chiralpak AD-H, 35% ethanol+0.1% TEA, 3 min) $^1$H NMR (400 MHz, DMSO-d$_6$) δ 12.10 (s, 1H), 11.13 (s, 1H), 10.85 (s, 1H), 8.36 (d, J=1.5 Hz, 1H), 8.22 (d, J=5.6 Hz, 1H), 7.61-7.55 (m, 2H), 7.54-7.50 (m, 1H), 7.48 (dd, J=5.5, 1.8 Hz, 1H), 2.27 (dd, J=14.6, 7.5 Hz, 1H), 2.01 (dd, J=15.9, 8.5 Hz, 1H), 1.39 (td, J=6.6, 4.2 Hz, 1H), 1.16 (td, J=8.3, 4.1 Hz, 1H). LCMS (ESI) m/z: 394.0 [M+H$^+$].

Examples 251 and 252

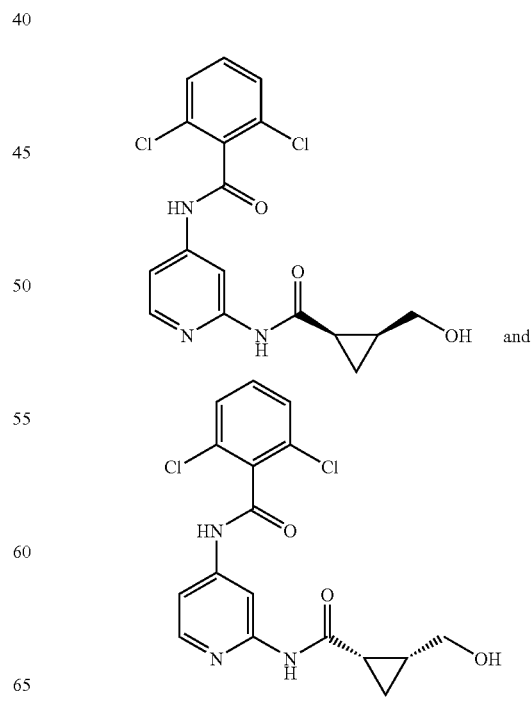

2,6-dichloro-N-(2-((1R,2S)-2-(hydroxymethyl)cyclopropanecarboxamido)pyridin-4-yl)benzamide and 2,6-dichloro-N-(2-((1S,2R)-2-(hydroxymethyl)cyclopropanecarboxamido)pyridin-4-yl)benzamide To a suspension of 2,6-dichloro-N-(2-(−2,4-dioxo-3-azabicyclo[3.1.0]hexan-3-yl)pyridin-4-yl)benzamide (34 mg, 0.09 mmol) in isopropanol (0.77 mL) and water (0.13 mL) was added NaBH$_4$ (17 mg, 0.45 mmol). The reaction mixture was stirred at room temperature for 1 hour and then concentrated under reduced pressure. The residue was diluted with water (20 mL) and extracted with EtOAc (3×10 mL). The combined organic extracts were dried over Na$_2$SO$_4$ and concentrated under reduced pressure. The residue was purified by chiral SFC (Chiralpak IC, 30% IPA+0.1% TEA, 10 min) to give two desired products:

First eluting peak, 10 mg, 30% yield. >99% ee (2.19 min, Chiralpak IC, 30% IPA+0.1% TEA, 5 min) $^1$H NMR (400 MHz, DMSO-d$_6$) δ 11.13 (s, 1H), 10.62 (s, 1H), 8.38 (s, 1H), 8.21 (d, J=5.5 Hz, 1H), 7.61-7.55 (m, 2H), 7.55-7.46 (m, 2H), 4.44 (t, J=5.0 Hz, 1H), 3.64 (dt, J=10.7, 5.2 Hz, 1H), 3.49 (dd, J=15.2, 9.7 Hz, 1H), 2.08 (dd, J=13.9, 7.9 Hz, 1H), 1.49-1.37 (m, 1H), 0.98 (td, J=7.9, 3.9 Hz, 1H), 0.90 (dd, J=10.7, 5.7 Hz, 1H). LCMS (ESI) m/z: 380.0 [M+H$^+$].

Second eluting peak, 11 mg, 31% yield. >99% ee (2.88 min, Chiralpak IC, 30% IPA+0.1% TEA, 5 min) $^1$H NMR (400 MHz, DMSO-d$_6$) δ 11.13 (s, 1H), 10.62 (s, 1H), 8.38 (d, J=1.4 Hz, 1H), 8.21 (d, J=5.6 Hz, 1H), 7.61-7.55 (m, 2H), 7.54-7.46 (m, 2H), 4.44 (t, J=5.0 Hz, 1H), 3.69-3.57 (m, 1H), 3.55-3.41 (m, 1H), 2.08 (dd, J=14.0, 8.0 Hz, 1H), 1.51-1.36 (m, 1H), 0.98 (td, J=7.9, 4.0 Hz, 1H), 0.90 (dd, J=10.8, 5.4 Hz, 1H). LCMS (ESI) m/z: 380.0 [M+H$^+$].

Examples 253 and 254

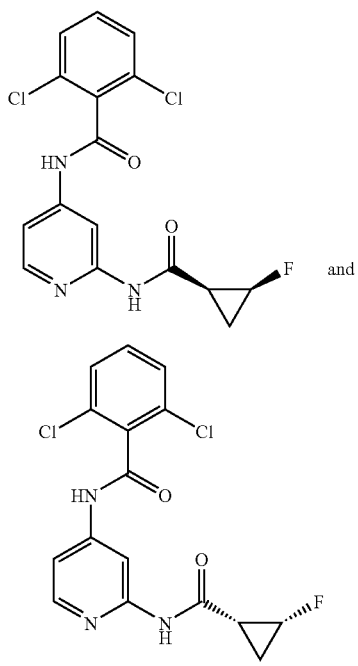

2,6-dichloro-N-(2-((1S,2S)-2-fluorocyclopropanecarboxamido)pyridin-4-yl)benzamide and 2,6-dichloro-N-(2-((1R,2R)-2-fluorocyclopropanecarboxamido)pyridin-4-yl)benzamide To a solution of N-(2-aminopyridin-4-yl)-2,6-dichlorobenzamide (60 mg, 0.213 mmol), cis-2-fluorocyclopropanecarboxylic acid (111 mg, 1.06 mmol), and disiopropylethylamine (137 mg, 1.06 mmol) in dry DMF (2 mL) was added HATU (404 mg, 1.06 mmol). The mixture was heated at 60° C. for 12 hours and then quenched with sat. NH$_4$Cl (20 mL). The reaction was extracted with EtOAc (3×20 mL). The combined organic extracts were dried over Na$_2$SO$_4$ and concentrated under reduced pressure. The residue was purified by chiral SFC (Chiralpak IC, 35% IPA+0.1% TEA, 5 min) to give two desired products:

First eluted peak, 22 mg, 28% yield. >99% ee (0.61 min, Chiralpak IC, 35% IPA+0.1% TEA, 5 min) $^1$H NMR (400 MHz, DMSO-d$_6$) δ 11.15 (s, 1H), 10.77 (s, 1H), 8.39 (s, 1H), 8.24 (d, J=5.6 Hz, 1H), 7.62-7.56 (m, 2H), 7.55-7.45 (m, 2H), 4.91 (m, 1H), 2.26-2.16 (m, 1H), 1.70-1.55 (m, 1H), 1.21-1.13 (m, 1H). LCMS (ESI) m/z: 368.0 [M+H$^+$].

Second eluted peak, 21 mg, 27% yield. >99% ee (0.87 min, Chiralpak IC, 35% IPA+0.1% TEA, 5 min) $^1$H NMR (400 MHz, DMSO-d$_6$) δ 11.15 (s, 1H), 10.77 (s, 1H), 8.39 (s, 1H), 8.24 (d, J=5.6 Hz, 1H), 7.62-7.55 (m, 2H), 7.55-7.43 (m, 2H), 5.04-4.77 (m, 1H), 2.21 (dt, J=14.0, 7.0 Hz, 1H), 1.71-1.55 (m, 1H), 1.16 (dd, J=8.2, 5.6 Hz, 1H). LCMS (ESI) m/z: 368.0 [M+H$^+$].

Example 255

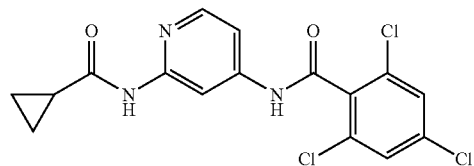 [SMILES: O=C(Nc1ccnc(NC(=O)C2CC2)c1)c1c(Cl)cc(Cl)cc1Cl]

2,4,6-trichloro-N-(2-(cyclopropanecarboxamido)pyridin-4-yl)benzamide

Step 1

To a solution of 2-chloropyridin-4-amine (2.0 g, 15.6 mmol) in DMF (20 mL) under nitrogen was added NaN$_3$ (2.0 g, 31.2 mmol) and NH$_4$Cl (1.7 g, 31.2 mmol). The mixture was heated to 110° C. for 10 hours and then quenched with saturated Na$_2$CO$_3$. The reaction was filtered and then the filtrate was extracted with ethyl acetate (3×20 mL). The combined organic extracts were washed with water (50 mL), dried over Na$_2$SO$_4$, and concentrated under reduced pressure to afford 2-azidopyridin-4-amine (1.5 g, yield: 83%). LCMS (ESI) m/z: 136.2 [M+H$^+$].

Step 2

A solution of 2,4,6-trichlorobenzoic acid (1.0 g, 4.0 mmol) in SOCl$_2$ (5 mL) was heated to reflux for 30 min under nitrogen atmosphere. The reaction was concentrated under reduced pressure to give 2,4,6-trichlorobenzoyl chloride (900 mg, 93% yield), which was used in the next step without further purification.

Step 3

To a cooled (0° C.) solution of 2-azidopyridin-4-amine (500 mg, 3.7 mmol) in dry DMF (10 ml) was added NaH (178 mg, 7.4 mmol). After stirring for 10 min, a solution 2,4,6-trichlorobenzoyl chloride (1.8 g, 7.4 mmol) in DMF (5 mL) was added dropwise. The reaction was warmed to 25° C. and stirring was continued for 30 min. The reaction was diluted with water (50 mL) and extracted with ethyl acetate (3×10 mL). The combined organic extracts were washed with water (20 mL), dried over $Na_2SO_4$, and concentrated under reduced pressure. The residue was purified by silica-gel chromatography (petroleum ether/ethyl acetate=1:1) to afford N-(2-azidopyridin-4-yl)-2,4,6-trichlorobenzamide (180 mg, yield: 14%). LCMS (ESI) m/z: 342.0 [M+H$^+$].

Step 4

To a solution of N-(2-azidopyridin-4-yl)-2,4,6-trichlorobenzamide (90 mg, 0.26 mmol) in ethanol (5 mL) was added $SnCl_2 \cdot 2H_2O$ (300 mg, 1.31 mmol). The mixture was heated at reflux for 1 hour and then cooled to room temperature. The reaction was concentrated under reduced pressure and the residue was diluted with water (10 mL). The mixture was extracted with ethyl acetate (3×5 mL). The combined organic extracts were dried over $MgSO_4$ and concentrated under reduced pressure to give N-(2-aminopyridin-4-yl)-2,4,6-trichlorobenzamide (82 mg, yield: 100%). LCMS (ESI) m/z: 316.0 [M+H$^+$].

Step 5

To a cooled (0° C.) solution of N-(2-aminopyridin-4-yl)-2,4,6-trichlorobenzamide (82 mg, 0.26 mmol) in pyridine (5 mL) under nitrogen atmosphere was added cyclopropanecarbonyl chloride (41 mg, 0.39 mmol) dropwise. The mixture was allowed to warm to room temperature, stirred overnight, and then quenched with water (15 mL). The reaction was extracted with ethyl acetate (3×10 ml). The combined organic extracts were washed with water (20 mL), dried over $Na_2SO_4$ and concentrated under reduced pressure. The residue was purified by prep-HPLC (Gilson GX 281, Shim-pack PRC-ODS 250 mm×20 mm×2, gradient: $CH_3CN$/10 mm/L $NH_4HCO_3$, 17 min) to afford the desired product (10 mg, 17% yield). $^1H$ NMR (500 MHz, CDCl$_3$): δ 8.19 (d, J=1.5 Hz, 1H), 8.13 (d, J=6.0 Hz, 1H), 7.52 (s, 2H), 7.49-7.47 (m, 2H) 1.78 (s, 1H), 0.88-0.86 (m, 2H), 0.81-0.78 (m, J=9.5 Hz, 2H). LCMS (ESI) m/z: 367.1 [M+H$^+$].

Example 256

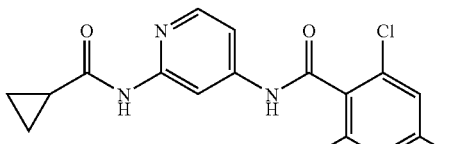

2,6-dichloro-4-cyano-N-(2-(cyclopropanecarboxamido)pyridin-4-yl)benzamide

Step 1

A solution of 2,6-dichloro-4-cyanobenzoic acid (1.15 g, 5.32 mmol) in $SOCl_2$ (5 ml) was refluxed overnight and then cooled to room temperature. The reaction was concentrated under reduced pressure to afford a quantitative yield of the desired acid chloride intermediate. This material was used without further purification.

To a cooled (0° C.) solution of 2-bromo-4-aminopyridine (0.912 g, 5.32 mmol) in dry DMF (5 mL) was added NaH (0.424 g, 10.6 mmol, 60% dispersion in mineral oil) in one portion. The mixture was stirred at room temperature for 30 min and then cooled to 0° C. again. A solution of the acid chloride described above in dry DMF (4 mL) was added slowly and then the reaction was stirred at room temperature for 1 hour. The mixture was quenched with ice-water (20 mL), and extracted with ethyl acetate (3×50 ml). The combined organic extracts were dried over $Na_2SO_4$ and concentrated under reduced pressure. The residue was purified by column chromatography on silica gel (EA/PE=1:10), to afford N-(2-bromopyridin-4-yl)-2,6-dichloro-4-cyanobenzamide (1.18 g, 59% yield). LCMS (ESI) m/z: 369.9 [M+H$^+$].

Step 2

A mixture of N-(2-bromopyridin-4-yl)-2,6-dichloro-4-cyanobenzamide (74 mg, 0.20 mmol), cyclopropanecarboxamide (34 mg, 0.40 mmol), Pd$_2$(dba)$_3$ (18 mg, 0.020 mmol), Xantphos (23 mg, 0.040 mmol), Cs$_2$CO$_3$ (131 mg, 0.40 mmol), dioxane (1.2 mL) was heated to 140° C. for 1 hour in a microwave reactor under nitrogen atmosphere. The mixture was filtered through Celite and then conentrated under reduced pressure. The residue was purified by prep-HPLC (Gilson GX 281, Shim-pack PRC-ODS 250 mm×20 mm×2, gradient: $CH_3CN$/10 mm/L $NH_4HCO_3$, 17 min) to afford the desired product (30 mg, yield: 40%). $^1H$ NMR (500 MHz, DMSO-d$_6$): δ 11.28 (s, 1H), 10.79 (s, 1H), 8.36-8.24 (m, 4H), 7.47 (m, 1H), 2.00 (m, 1H), 0.81-0.79 (m, 4H). LCMS (ESI) m/z: 375 [M+H$^+$].

Example 257

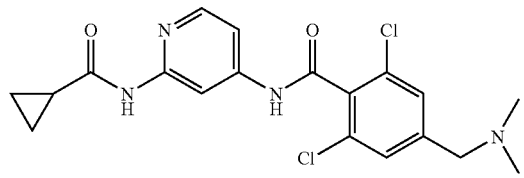 [SMILES: CN(C)Cc1cc(Cl)c(C(=O)Nc2ccnc(NC(=O)C3CC3)c2)c(Cl)c1]

2,6-dichloro-N-(2-(cyclopropanecarboxamido)pyridin-4-yl)-4-((dimethylamino)methyl)benzamide Step 1

A solution of 2,6-dichloro-4-iodobenzoic acid (65 mg, 0.21 mmol) in SOCl$_2$ (3 mL) was heated to reflux under nitrogen atmosphere overnight and then cooled to room temperature. The reaction was conentrated under reduced pressure to afford 2,6-dichloro-4-iodobenzoyl chloride (70 mg, 100% yield).

Step 2

To a cooled (0° C.) solution of 2,6-dichloro-4-iodobenzoyl chloride (70 mg, 0.21 mmol) in DMF (2 mL) was added NaH (17 mg, 0.42 mmol). The mixture was stirred for 10 minutes and then 2-bromopyridin-4-amine (40 mg, 0.23 mmol) was added. The resulting mixture was slowly warmed to 25° C., diluted with ethyl acetate (10 mL), quenched with water (1 mL), washed with saturated Na$_2$CO$_3$ and water, dried over Na$_2$SO$_4$, and concentrated under reduced pressure. The residue was purified by silica-gel chromatography (Pet Ether/EtOAc=20:1 to 3:1) to afford N-(2-bromopyridin-4-yl)-2,6-dichloro-4-iodobenzamide (40 mg, 40% yield). LCMS (ESI) m/z: 470.9 [M+H$^+$].

Step 3

To a solution of N-(2-bromopyridin-4-yl)-2,6-dichloro-4-iodobenzamide (3.0 g, 6.4 mmol) in THF (40 mL) was added 4,4,5,5-tetramethyl-2-vinyl-1,3,2-dioxaborolane (2.0 g, 12.8 mmol), 2M Na$_2$CO$_3$ (12 ml) and Pd$_2$(PPh$_3$)$_4$ (222 mg, 0.19 mmol). The solution was degrassed with N$_2$, and heated at 80° C. overnight. Then the reaction mixture was cooled to room temperature, poured into water (200 mL), and extracted with EtOAc (3×100 mL). The combined organic extracts were washed with brine (2×20 mL), dried over MgSO$_4$, and concentrated under reduced pressure. The residue was purified by silica-gel chromatography (Pet Ether/EtOAc=10:1 to 3:1) to give N-(2-bromopyridin-4-yl)-2,6-dichloro-4-vinylbenzamide (2.2 g, yield: 92%). $^1$H NMR (500 MHz, CDCl$_3$): δ 8.27 (d, J=5.0 Hz, 1H), 8.11 (s, 1H), 7.88 (s, 1H), 7.51 (d, J=3.5 Hz, 1H), 7.35 (s, 2H), 6.61 (m, 1H), 5.86 (d, J=17.5 Hz, 1H), 5.48 (d, J=11.0 Hz, 1H). LCMS (ESI) m/z: 371.0 [M+H$^+$].

Step 4

A solution of N-(2-bromopyridin-4-yl)-2,6-dichloro-4-vinylbenzamide (23 mg, 0.062 mmol), cyclopropanecarboxamide (16 mg, 0.19 mmol), Pd$_2$(dba)$_3$ (6.0 mg, 0.0062 mmol), Xantphos (7.0 mg, 0.012 mmol) and Cs$_2$CO$_3$ (40 mg, 0.12 mmol) in dioxane (2 mL) was heated to 140° C. for 1 hour in a microwave reactor under nitrogen atmosphere. The mixture was filtered through Celite and concentrated under reduced pressure. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford 2,6-dichloro-N-(2-(cyclopropanecarboxamido)pyridin-4-yl)-4-vinylbenzamide (10 mg, yield: 43%). $^1$H NMR (500 MHz, CDCl$_3$): δ 8.26 (s, 1H), 7.99-7.97 (m, 2H), 7.74 (s, 1H), 7.37 (s, 2H), 6.64 (m, 1H), 5.86 (m, 1H), 5.47 (m, 1H), 1.52 (m, 1H), 1.09-1.05 (m, 2H), 0.92-0.88 (m, 2H). LCMS (ESI) m/z: 376.1 [M+H$^+$].

Step 5

2,6-dichloro-N-(2-(cyclopropanecarboxamido)pyridin-4-yl)-4-vinylbenzamide (750 mg, 1.99 mmol) was dissolved in a solution of MeOH (14 mL) and DCM (28 mL). The resulting mixture was cooled to −78° C., O$_3$ was bubbled into the solution for 7 min, N$_2$ was bubbled for 10 min, and then Me$_2$S (14 mL) was added. The reaction mixture was slowly warmed to room temperature and stirred for 20 min. The mixture was concentrated under reduced pressure to provide 2,6-dichloro-N-(2-(cyclopropanecarboxamido)pyridin-4-yl)-4-formylbenzamide (0.70 g, yield: 86%). LCMS (ESI) m/z: 378.1 [M+H$^+$].

Step 6

To a solution of Et$_3$N (121 mg, 1.2 mmol) in absolute methanol (1 mL) was added Me$_2$NH HCl (103 mg, 1.2 mmol), Ti(O-iPr)$_4$ (114 mg, 0.40 mmol), and 2,6-dichloro-N-(2-(cyclopropanecarboxamido)pyridin-4-yl)-4-formylbenzamide (80 mg, 0.20 mmol). The reaction was stirred at room temperature for 9 hours and then NaBH$_4$ (12 mg, 0.30 mmol) was added. The resulting mixture was stirred for 10 hours and then diluted with EtOAc (20 mL). The organic solution was washed with water (3×10 ml) and then concentrated under reduced pressure. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford the desired product (30 mg, 31% yield). $^1$H NMR (500 MHz, MeOH-d$_4$): δ 8.31 (s, 1H), 8.24 (s, 1H), 7.60 (m, 1H), 7.48 (s, 2H), 3.52 (s, 2H), 2.28 (s, 6H), 1.91 (m, 1H), 1.02-0.98 (m, 2H), 0.94-0.90 (m, 2H). LCMS (ESI) m/z: 407.1 [M+H$^+$].

Example 258 and 259

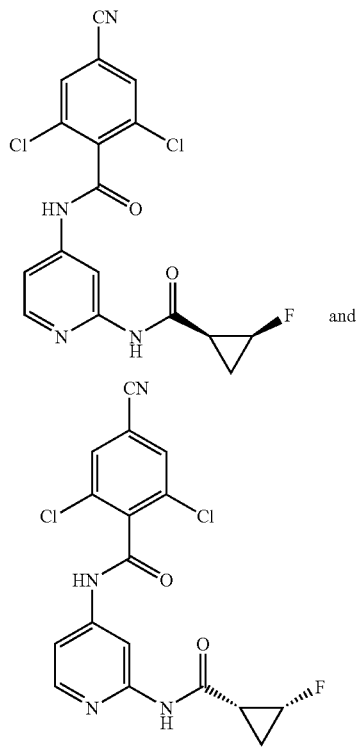

2,6-dichloro-4-cyano-N-(2-((1S,2S)-2-fluorocyclopropanecarboxamido)pyridin-4-yl)benzamide and
2,6-dichloro-4-cyano-N-(2-((1R,2R)-2-fluorocyclopropanecarboxamido)pyridin-4-yl)benzamide To a microwave tube was added cis-2-fluorocyclopropanecarboxamide (0.045 g, 0.44 mmol), N-(2-bromopyridin-4-yl)-2,6-dichloro-4-cyanobenzamide (0.16 g, 0.40 mmol), Pd$_2$(dba)$_3$ (0.045 g, 0.049 mmol), XantPhos (0.035 g, 0.061 mmol), Cs$_2$CO$_3$ (0.51 g, 1.6 mmol) and dioxane (6 mL). The mixture was degassed with N$_2$ for 10 min. The resulting mixture was irradiated in a microwave reactor at 140° C. for 1 hour and then cooled to room temperature. The mixture was filtered through Celite and concentrated under reduced pressure. The residue was dissolved in DMF and purified by preparative HPLC (Gilson GX 281, Shim-pack PRC-ODS 250 mm×20 mm×2, gradient: CH$_3$CN/10 mm/L NH$_4$HCO$_3$, 17 min) to give the cis-fluoro mixture as a white solid (40 mg, 24% yield). The cis-fluoro mixture was then purified by chiral SFC (Chiralpak IC, 15% Methanol, 5 min) to give two pure enantiomers as following.

First eluting peak, >99% ee (retention time 1.12 min) $^1$H NMR (400 MHz, DMSO) δ 11.32 (s, 1H), 10.86 (s, 1H), 8.37 (d, J=1.7 Hz, 1H), 8.32-8.24 (m, 3H), 7.49 (dd, J=5.6, 1.9 Hz, 1H), 4.93 (dtd, J=10.2, 6.2, 3.8 Hz, 1H), 2.21 (dt, J=14.0, 7.1 Hz, 1H), 1.63 (dtd, J=23.2, 6.7, 3.7 Hz, 1H), 1.16 (ddt, J=12.4, 9.0, 6.2 Hz, 1H). LCMS (ESI) m/z: 393.0 [M+H$^+$].

Second eluting peak, >99% ee (retention time 1.31 min). $^1$H NMR (400 MHz, DMSO) δ 11.33 (s, 1H), 10.86 (s, 1H), 8.37 (d, J=1.6 Hz, 1H), 8.31-8.23 (m, 3H), 7.49 (dd, J=5.6, 1.9 Hz, 1H), 4.93 (dtd, J=10.2, 6.2, 3.8 Hz, 1H), 2.27-2.15 (m, 1H), 1.70-1.56 (m, 1H), 1.16 (ddt, J=12.4, 9.1, 6.3 Hz, 1H). LCMS (ESI) m/z: 377.1 [M+H$^+$].

Example 260

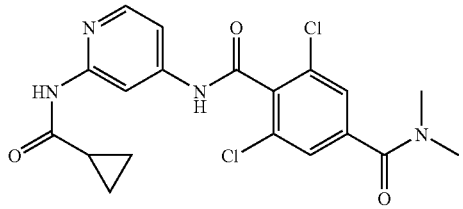 [SMILES: CN(C)C(=O)c1cc(Cl)c(C(=O)Nc2ccnc(NC(=O)C3CC3)c2)c(Cl)c1]

2,6-dichloro-N$^1$-(2-(cyclopropanecarboxamido)pyridin-4-yl)-N$^4$,N$^4$-dimethylterephthalamide Step 1

To a solution of 2,6-dichloroterephthalic acid (100 mg, 0.46 mmol) in dichloromenthane was added CDI (62 mg, 0.46 mmol) in one portion. The reaction mixture was stirred at room temperature for 1.5 hours and then dimethyl amine (1.0 M in THF, 2 mL, 2.0 mmol) was added. The reaction was concentrated under reduced pressure to give the crude 2,6-dichloro-4-(dimethylcarbamoyl)benzoic acid, which was used in the next step without further purification. $^1$H NMR (500 MHz, DMSO-d$_6$): δ 14.35 (s, 1H), 7.56 (s, 2H), 2.97 (s, 3H), 2.89 (s, 3H).

Step 2

A solution of 2,6-dichloro-4-(dimethylcarbamoyl)benzoic acid (65 mg, 0.21 mmol) in SOCl$_2$ (3 mL) was heated to reflux for overnight and then cooled to room temperature. The mixture was concentrated under reduced pressure to give crude 2,6-dichloro-4-(dimethylcarbamoyl)benzoyl chloride (70 mg, yield: 100%), which was used in the next step without further purification.

Step 3

To a cooled (0° C.) solution of 2-bromo-4-aminopyridine (40 mg, 0.23 mmol) in dry DMF (2 mL), was added NaH (17 mg, 0.42 mmol, 60% dispersion in mineral oil) in one portion. The mixture was warmed to room temperature for 30 min and then cooled to 0° C. again. A solution of the acid chloride from the preceeding step (70 mg, 0.21 mmol) in dry DMF (1 mL) was added slowly and stirred for another 30 min at room temperature. The mixture was diluted with ethyl acetate (10 mL) and quenched with water (1 mL). The organic layer was washed with saturated Na$_2$CO$_3$ and water, dried over Na$_2$SO$_4$ and concentrated under reduced pressure. The residue was purified by a silica-gel chromatography (Pet Ether/EtOAc=20/1 to 3/1) to get N$^1$-(2-bromopyridin-4-yl)-2,6-dichloro-N$^4$,N$^4$-dimethylterephthalamide (40 mg, 40% yield). LCMS (ESI) m/z: 415.9 [M+H$^+$].

Step 4

To a microwave tube was added N$^1$-(2-bromopyridin-4-yl)-2,6-dichloro-N$^4$,N$^4$-dimethylterephthalamide (84 mg, 0.20 mmol), pyrimidin-4-amine (38 mg, 0.40 mmol), Pd$_2$(dba)$_3$ (18 mg, 0.020 mmol), Xantphos (23 mg, 0.040 mmol), Cs$_2$CO$_3$ (131 mg, 0.40 mmol) and dioxane (1.2 mL). The mixture was degassed with N$_2$ for 5 min and then irradiated in a microwave reactor at 140° C. for 60 min. After cooling, the reaction was filtered through Celite and concentrated under reduced pressure. The residue was dissolved in DMF and purified by prep-HPLC (Gilson GX 281, Shim-pack PRC-ODS 250 mm×20 mm×2, gradient: CH$_3$CN/10 mm/L NH$_4$HCO$_3$, 17 min) to afford the desired product (50 mg, 58% yield). $^1$H NMR (500 MHz, DMSO-d$_6$): δ 8.30-8.22 (m, 2H), 7.60-7.56 (m, 3H), 3.10 (s, 3H), 3.00 (s, 3H), 1.86 (m, 1H), 0.99-0.88 (m, 4H). LCMS (ESI) m/z: 421.1 [M+H$^+$].

Examples 261 and 262

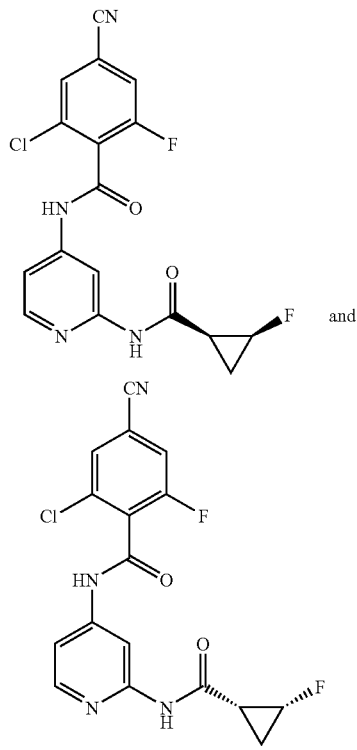

2-chloro-4-cyano-6-fluoro-N-(2-((1S,2S)-2-fluorocyclopropanecarboxamido)pyridin-4-yl)benzamide and
2-chloro-4-cyano-6-fluoro-N-(2-((1R,2R)-2-fluorocyclopropanecarboxamido)pyridin-4-yl)benzamide Step 1

An autoclave equipped with a stir bar was charged with 2,5-dibromo-1-chloro-3-fluorobenzene (3.0 g, 10.4 mmoles), triethylamine (52 mmoles, 7.251 mL, 5.264 g), bis(diphenylphosphino)ferrocene)palladium(II) Chloride (520 μmoles, 425 mg) and methanol (100 mL) was degassed with nitrogen for 10 min. Then the container was sealed and filled with CO to 400 psi. The reaction mixture was heated at 110° C. with stirring for 10 hours. The reaction mixture was filtered through Celite, washed with MeOH, and concentrated under reduced pressure. The residue was purified by silica gel chromatography (0-10% EtOAc/hexane) to afford dimethyl 2-chloro-6-fluoroterephthalate as a colorless oil which solidified in high vacuum (1.77 g, yield: 69%). $^1$H NMR (400 MHz, CDCl$_3$) δ 7.90 (s, 1H), 7.69 (dd, J=9.0, 1.2 Hz, 1H), 3.99 (s, 3H), 3.95 (s, 3H). LCMS (APCI+) [M+H]$^+$247.0

Step 2

To a solution of dimethyl 2-chloro-6-fluoroterephthalate (2.784 g, 11.3 mmoles) in tetrahydrofuran (20 mL) was added a solution of 1 N NaOH (12.4 mmol, 12.4 mL). The reaction mixture was stirred at room temperature for 30 min. The reaction was concentrated under reduced pressure and the residue was suspended in water (10 mL). The aqueous solution was acidified to pH 3 with 1 N HCl. The resulting white precipitate was collected by filtration, washed with water and ether, dried in high vacuum to afford 3-chloro-5-fluoro-4-(methoxycarbonyl)benzoic acid as a white solid (2.52 g, yield: 96%). $^1$H NMR (400 MHz, CDCl$_3$) δ 7.96 (s, 1H), 7.76 (dd, J=8.8, 1.3 Hz, 1H), 4.01 (s, 3H). LCMS (APCI+) [M+H]$^+$ 233.0.

Step 3

To a suspension of 3-chloro-5-fluoro-4-(methoxycarbonyl)benzoic acid (2.537 g, 10.9 mmoles) in toluene (25 mL) was added thionyl chloride (130.9 mmoles, 9.536 mL, 15.572 g). The mixture was heated at 90° C. for 4 hrs and then cooled to room temperature. The reaction was concentrated under reduced pressure and the residue was dissolved in THF (20 mL). NH$_3$ gas was then bubbled in the solution for 10 min and then the mixutre was concentrated under reduced pressure to give methyl 4-carbamoyl-2-chloro-6-fluorobenzoate as an off-white solid (2.9 g) which was used in the next step without purification. $^1$H NMR (400 MHz, DMSO) δ 8.22 (s, 1H), 7.91 (s, 1H), 7.80 (dd, J=10.0, 1.0 Hz, 1H), 7.77 (s, 1H), 3.94 (s, 3H). MS (APCI+) [M+H]$^+$232.0.

Step 4

To a suspension of methyl 4-carbamoyl-2-chloro-6-fluorobenzoate (2.527 g, 10.9 mmoles) in 1,4-dioxane (25 mL) at room temperature was added pyridine (38.2 mmoles, 3.02 g), followed by trifluoroacetic anhydride (5.04 g, 24.0 mmoles). The reaction mixture was stirred at room temperature for 2 hours. The reaction was quenched with water (100 mL), extracted with EtOAc (3×100 mL). The combined organics were dried over Na$_2$SO$_4$ and concentrated under reduced pressure. The residue was purified by silica gel chromatography (0-15% EtOAc/hexane) to afford methyl 2-chloro-4-cyano-6-fluorobenzoate as a white solid (1.953 g, yield: 84%). $^1$H NMR (400 MHz, CDCl$_3$) δ 7.55 (d, J=1.1 Hz 1H), 7.37 (dd, J=8.0, 1.2 Hz, 1H), 4.00 (s, 3H). LCMS (APCI+) 214.0 [M+H]$^+$.

Step 5

To a solution of methyl 2-chloro-4-cyano-6-fluorobenzoate (1.953 g, 9.143 mmoles) in pyridine (50 mL) was added lithium iodide (2.45 g, 18.3 mmoles). The reaction mixture was heated at 115° C. for 3 hours. The reaction was concentrated under reduced pressure and the resulting solid was triturated with EtOAc. The solid was dissolved in water and acidified to pH 4 with 1 N HCl. The aqueous solution was extracted with EtOAc (3×30 mL). The combined organic extracts were dried with Na$_2$SO$_4$, and concentrated under reduced pressure. The residue was purified by silica gel chromatography [0-20% (10% formic acid in MeOH)/DCM] to afford 2-chloro-4-cyano-6-fluorobenzoic acid as a white solid (1.616 g, yield: 89%). $^1$H NMR (400 MHz, CDCl$_3$) δ 7.58 (s, 1H), 7.40 (dd, J=8.1, 1.0 Hz, 1H). LCMS (APCI+) [M+H]$^+$ 200.0.

Step 6

A suspension of 2-chloro-4-cyano-6-fluorobenzoic acid (443 mg, 2.22 mmol) in thionyl chloride (2 mL) was heated at reflux for 3 hours and cooled to room temperature. The mixture was concentrated under reduced pressure to crude 2-chloro-4-cyano-6-fluorobenzoyl chloride as a white solid, which was used in the next step without purification.

Step 7

To a cooled (0° C.) solution of 4-amino-2-bromopyridine (346 mg, 2.0 mmol) and diisopropylethylamine (461 mg, 4.0 mmol) in dichloromethane (5 mL) and CH$_3$CN (0.5 mL) was added a solution of 2-chloro-4-cyano-6-fluorobenzoyl chloride (484 mg, 2.2 mmol) in dichlormethane (5 mL) drop wise. The reaction mixture was warmed up to room temperature and stirred for 16 hours. The reaction was quenched with saturated NH$_4$Cl (40 mL) and extracted with EtOAc (3×50 mL). The combined organic extractss were dried with Na$_2$SO$_4$ and concentrated under reduced pressure. The residue wars purified by silica gel column chromatography (0-50% EtOAc/hexane) to give N-(2-bromopyridin-4-yl)-2-chloro-4-cyano-6-fluorobenzamide as an off-white solid (379 mg, yield: 53%).

Step 8

To a microwave tube was added N-(2-bromopyridin-4-yl)-2-chloro-4-cyano-6-fluorobenzamide (681 mg, 1.92 mmol), cis-2-fluorocyclopropanecarboxamide (218 mg, 2.11 mmol), Pd$_2$(dba)$_3$ (88 mg, 0.096 mmol), XantPhos (0.111 g, 192 mmol), Cs$_2$CO$_3$ (1.25 g, 3.84 mmol), dioxane (10 mL) and 1,2-methoxyethane (3 mL). The mixture was degassed with N$_2$ for 1 minute and then irradiated in a microwave reactor at 130° C. for 0.5 hours. The mixture was cooled to room temperature, filtered through Celite, and concentrated under reduced pressure. The residue was purified by chiral SFC (Chiralpak AS-H, 15% Methanol, 12 min) to give two desired products:

First eluting peak, 290 mg, 40% yield. >99% ee (1.03 min, Chiralpak AS-H, 15% Methanol, 2.5 min) $^1$H NMR (400 MHz, DMSO) δ 11.33 (s, 1H), 10.82 (s, 1H), 8.35 (d, J=1.6 Hz, 1H), 8.26 (d, J=5.6 Hz, 1H), 8.18-8.08 (m, 2H), 7.49 (dd, J=5.6, 1.8 Hz, 1H), 5.03-4.79 (m, 1H), 2.26-2.16 (m, 1H), 1.71-1.56 (m, 1H), 1.16 (ddt, J=12.6, 9.3, 6.3 Hz, 1H). LCMS (ESI) m/z: 377.1 [M+H$^+$].

Second eluting peak, 288 mg, 40% yield. >99% ee (1.23 min, Chiralpak AS-H, 15% Methanol, 2.5 min) $^1$H NMR (400 MHz, DMSO) δ 11.33 (s, 1H), 10.82 (s, 1H), 8.35 (d, J=1.6 Hz, 1H), 8.26 (d, J=5.6 Hz, 1H), 8.17-8.08 (m, 2H), 7.49 (dd, J=5.6, 1.9 Hz, 1H), 5.04-4.78 (m, 1H), 2.21 (dt, J=13.9, 6.9 Hz, 1H), 1.64 (dtd, J=23.3, 6.8, 3.7 Hz, 1H), 1.16 (ddt, J=12.4, 9.0, 6.3 Hz, 1H). LCMS (ESI) m/z: 377.1 [M+H$^+$].

Example 263 and 264

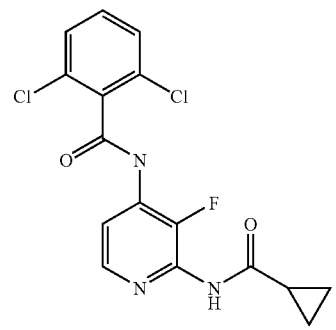

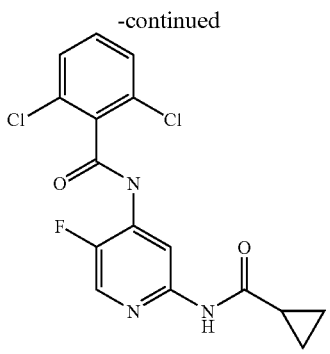

2,6-dichloro-N-(3-fluoro-2-cyclopropanecarboxamidopyridin-4-yl)benzamide and 2,6-dichloro-N-(5-fluoro-2-cyclopropanecarboxamidopyridin-4-yl)benzamide Step 1

To a cooled (0° C.) mixture of 3-fluoropyridin-4-amine (1.0 g, 8.9 mmol) and DIPEA (2.7 mL, 18 mmol) in dichloromethane (20 mL) and MeCN (10 mL) was added a solution of 2,6-dichlorobenzoyl chloride (2.1 g, 9.8 mmol) in dichloromethane (20 mL). The reaction mixture was stirred at room temperature overnight and concentrated under reduced pressure. The residue was partitioned between EtOAc (30 mL) and sat. NaHCO$_3$ (30 mL). The aqueous layer was extracted with EtOAc (2×15 mL) and then the combined organic extracts were concentrated under reduced pressure. The residue was purified by silica gel column chromatography (EtOAc) to afford N-(3-fluoropyridin-4-yl)-2,6-dichlorobenzamide (1.2 g, yield: 47%). $^1$H NMR (400 MHz, DMSO) δ 11.21 (s, 1H), 8.59 (d, J=2.8, 1H), 8.41 (d, J=5.4, 1H), 8.21 (dd, J=6.7, 5.4, 1H), 7.77-7.33 (m, 3H). LCMS (ESI) m/z: 285.2 [M+H$^+$]

Step 2

To a solution of N-(3-fluoropyridin-4-yl)-2,6-dichlorobenzamide (1.3 g, 4.6 mmol) in CHCl$_3$ (15 mL), CH$_2$Cl$_2$ (15 mL), and MeOH (3 mL), was added m-chloroperoxybenzoic acid (1.4 g, 8.1 mmol). The reaction mixture was refluxed at 70° C. for 30 min, 0.25 g of Na$_2$CO$_3$ was added, and then heating at reflux was continued for 1 hour. The mixture was cooled to room temperature. The solid was collected by filtration, washed with CH$_2$Cl$_2$ and ether, and then dried in an oven under vacuum to afford N-(3-fluoropyridin-N-oxide-4-yl)-2,6-dichlorobenzamide (1.3 g, yield: 95%). $^1$H NMR (400 MHz, DMSO) δ 11.20 (s, 1H), 8.59 (s, 1H), 8.26-7.97 (m, 2H), 7.70-7.29 (m, 3H). LCMS (ESI) m/z: 302.3 [M+H$^+$]

Step 3

To a solution of N-(3-fluoropyridin-N-oxide-4-yl)-2,6-dichlorobenzamide (1.3 g, 4.3 mmol) in propyl nitrile (40 mL), was added POBr$_3$ (2.5 g, 8.6 mmol). The reaction mixture was refluxed at 100° C. overnight. The mixture was cooled to room temperature and poured into saturated K$_2$CO$_3$ solution (100 mL). The aqueous layer was extracted with EtOAc (3×50 mL). The combined organic extracts were washed with brine, dried over MgSO$_4$ and concentrated under reduced pressure. The residue was purified by silica gel column chromatography (MeOH/CH$_2$Cl$_2$:1/10) to afford two desired products N-(2-bromo-3-fluoropyridin-4-yl)-2,6-dichlorobenzamide and N-(2-bromo-5-fluoropyridin-4-yl)-2,6-dichlorobenzamide as a mixture (3:1 ratio, 1.15 g, yield: 73%). LCMS (ESI) m/z: 365.2 [M+H$^+$] and 365.0 [M+H$^+$].

Step 4

A 25 mL microwave tube containing a mixture of N-(2-bromo-3-fluoropyridin-4-yl)-2,6-dichlorobenzamide and N-(2-bromo-5-fluoropyridin-4-yl)-2,6-dichlorobenzamide (200 mg, 0.55 mmol), cyclopropyl amide (61 mg, 0.71 mmol), Pd$_2$(dba)$_3$ (15 mg, 0.016 mmol), Cs$_2$CO$_3$ (360 mg, 1.1 mmol), 4,5-bis(diphenylphosphino)-9,9-dimethylxanthene (Xantphos, 6 mg, 0.011 mmol), and dioxane (8 mL) and DME (3 mL) was degassed and charged by N$_2$ (3×). The resulting mixture was irradiated at 140° C. for 20 min, cooled to room temperature, and diluted with dioxane (20 mL). The reaction was filtered through Celite and concentrated under reduced pressure. The residue was purified by reverse-phase HPLC (Gemini, 200 mm×25 mm, gradient: CH$_3$CN/0.05% NH$_3$.H$_2$O, 50-80%, 10 min) to give two desired products:

First eluting peak, 2,6-dichloro-N-(5-fluoro-2-cyclopropanecarboxamidopyridin-4-yl)benzamide (Example 264), 56 mg, 23% yield. $^1$H NMR (400 MHz, DMSO) δ 11.26 (s, 1H), 10.53 (s, 1H), 8.14 (d, J=39.5, 2H), 7.55 (s, 3H), 1.88 (s, 1H), 1.00-0.65 (m, 5H). LCMS (ESI) m/z: 369.4 [M+H$^+$].

Second eluting peak, 2,6-dichloro-N-(3-fluoro-2-cyclopropanecarboxamidopyridin-4-yl)benzamide (Example 263), 23 mg, 11% yield. $^1$H NMR (400 MHz, DMSO) δ 11.12 (s, 1H), 10.83 (d, J=22.7, 1H), 8.99 (d, J=6.1, 1H), 8.33 (d, J=2.3, 1H), 7.69-7.45 (m, 3H), 2.05-1.86 (m, 1H), 0.94-0.70 (m, 5H). LCMS (ESI) m/z: 369.0 [M+H$^+$].

Example 265

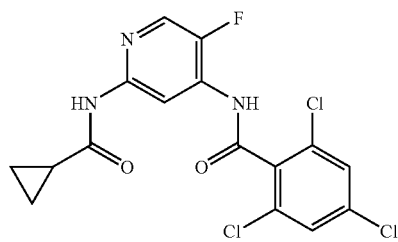 [SMILES: O=C(Nc1cc(NC(=O)C2CC2)ncc1F)c1c(Cl)cc(Cl)cc1Cl]

2,4,6-trichloro-N-(2-(cyclopropanecarboxamido)-5-fluoropyridin-4-yl)benzamide

Step 1

To a solution of 2-chloro-5-fluoropyridin-4-amine (200 mg, 1.36 mmol) in dry N,N-dimethylformamide (10 mL) was added sodium hydride (65.5 mg, 2.73 mmol) in one portion at room temperature under N$_2$. The reaction mixture was then stirred for 15 min and then a solution of 2,4,6-trichlorobenzoyl chloride (320 uL, 2.0 mmol) in N,N-dimethylforamide (400 uL) was added dropwise. The mixture was stirred at room temperature for 10 mins, and then poured into water (30 mL). The mixture was extracted with ethyl acetate (2×50 mL), and combined organic extracts were dried over Na$_2$SO$_4$ and concentrated under reduced pressure. The residue was purified by column chromatography on silica gel (0-5% methanol/dichloromethane) to give 2,4,6-trichloro-N-(2-chloro-5-fluoropyridin-4-yl)benzamide (260 mg, yield: 54%). $^1$H NMR (DMSO-d$_6$, 400 MHz): δ 11.52 (s, 1H), 8.49 (s, 1H), 8.33 (d, J=5.5 Hz, 1H), 7.84 (s, 2H). LCMS (ESI) m/z: 354.9 [M+H$^+$].

Step 2

To a microwave tube was added 2,4,6-trichloro-N-(2-chloro-5-fluoropyridin-4-yl)benzamide (71 mg, 0.20 mmol), cyclopropanecarboxamide (42.8 mg, 0.50 mmol), Pd$_2$(dba)$_3$ (18 mg, 0.020 mmol), XantPhos (14 mg, 0.025 mmol), Cs₂CO₃ (197 mg, 0.60 mmol) and dioxane (1.5 mL). The mixture was degassed with N₂ for 2 min. The resulting mixture was irradiated in a microwave reactor at 140° C. for 35 min and then cooled to room temperature. The mixture was filtered through Celite and concentrated under reduced pressure. The residue was purified by prep-HPLC (Gilson GX 281, Shim-pack PRC-ODS 250 mm×20 mm×2, gradient: CH₃CN/10 mm/L NH₄HCO₃, 17 min) to give the desired product (7.5 mg, yield: 9.2%). ¹H NMR (DMSO-d₆, 400 MHz): δ 11.08 (s, 1H), 10.83 (d, 1H), 9.00 (s, 1H), 8.32 (s, 1H), 7.82 (s, 2H), 1.98 (d, J=4.6 Hz, 1H), 0.82 (t, J=6.1 Hz, 4H). LCMS (ESI) m/z: 402.0 [M+H⁺].

Example 266

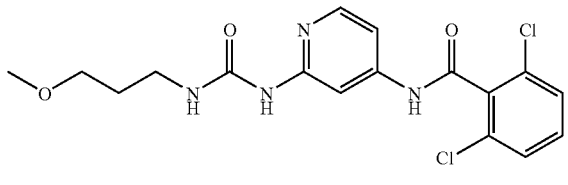 [SMILES: COCCCNC(=O)Nc1cc(NC(=O)c2c(Cl)cccc2Cl)ccn1]

2,6-Dichloro-N-{2-[3-(3-methoxypropyl)ureido]-pyridin-4-yl}benzamide

To a solution of N-(2-amino-pyridin-4-yl)-2,6-dichloro-benzamide (281 mg, 1.0 mmol) in anhydrous THF (5 mL) were added pyridine (97 μL, 1.2 mmol) and phenyl chloroformate (138 μL, 1.1 mmol). The reaction mixture was stirred at room temperature for 1 hr and then 3-methoxy propylamine (123 μL, 1.2 mmol) was added. The reaction mixture was stirred for 1 hr then partitioned between EtOAc (10 mL) and water (10 mL). The organic layer was washed with 1 N HCl, water and brine, dried over sodium sulfate, and concentraged under reduced pressure. The residue was purified by silica gel column chromatography (EtOAC/cyclohexane: gradient 0% to 100%) to give the desired compound (105 mg, yield: 26%). NMR (400 MHz, DMSO-d₆): δ 11.09 (br s, 1H), 9.18 (br s, 1H), 8.20 (br s, 1H), 8.09 (d, J=5.7 Hz, 1H), 7.69 (d, J=1.8 Hz, 1H), 7.57-7.58 (m, 2H), 7.51 (dd, J=9.2, 6.8 Hz, 1H), 7.24 (dd, J=5.7, 1.9 Hz, 1H), 3.37 (t, J=6.2 Hz, 2H), 3.24 (s, 3H), 3.21-3.19 (m, 2H), 1.69 (m, 2H). LCMS (ESI) m/z: 397, 399 [M+H]⁺.

Example 267

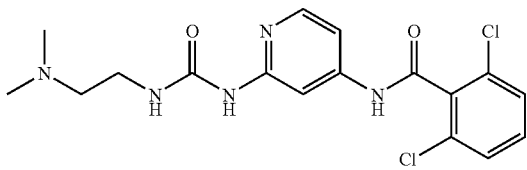 [SMILES: CN(C)CCNC(=O)Nc1cc(NC(=O)c2c(Cl)cccc2Cl)ccn1]

2,6-Dichloro-N-{2-[3-(2-dimethylaminoethyl)ureido]pyridin-4-yl}benzamide

Step 1
To a solution of N-(2-amino-pyridin-4-yl)-2,6-dichloro-benzamide (281 mg, 1.0 mmol) in pyridine (5 mL) was added phenyl chloroformate (138 μL, 1.1 mmol). The reaction mixture was stirred at room temperature for 1 hr and then concentrated under reduced pressure. The residue was partitioned between EtOAc (20 mL) and water (20 mL). The organic layer was washed with 1 N HCl, water, 1N NaOH and brine, dried over sodium sulphate, and concentrated under reduced pressure to give a white solid (421 mg) that was used into the next step without purification.

Step 2
To a solution of the solid isolated from step 1 (125 mg) in THF (2.5 mL) was added N,N-dimethylethane-1,2-diamine (68 μL, 0.62 mmol). The mixture was stirred for 1 hr and then DMF (1 mL) and pyridine (100 μL, 1.24 mmol) were added. Stirring was continued for 18 hrs and then the reaction mixture was partitioned between EtOAc (10 mL) and water (10 mL). The organic layer was washed with water and brine, dried over sodium sulfate, and concentrated under reduced pressure. The residue was purified by basic silica gel column chromatography (MeOH/EtOAC: gradient 0% to 100%) to give the desired compound as a white solid (70 mg, yield: 60%). ¹H NMR (400 MHz, DMSO-d₆): δ 11.10 (br s, 1H), 9.23 (br, s, 1H), 8.10 (d, J=5.7 Hz, 1H), 8.05 (br s, 1H), 7.76 (s, 1H), 7.61-7.59 (m, 2H), 7.53 (dd, J=9.2, 6.8 Hz, 1H), 7.27 (dd, J=5.7, 1.9 Hz, 1H), 3.26-3.24 (m, 2H), 2.36 (t, J=6.4 Hz, 2H), 2.19 (s, 6H). LCMS (ESI) m/z: 418 [M+Na]⁺.

Examples 268 and 269

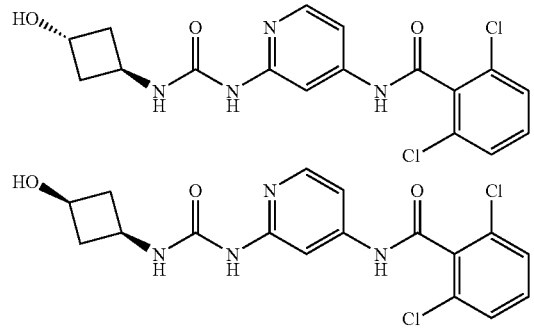

Trans- and cis-2,6-Dichloro-N-{2-[3-(3-hydroxycyclobutyl)ureido]pyridin-4-yl}benzamide Step 1
To a solution of (3-hydroxycyclobutyl)carbamic acid tent-butyl ester (180 mg, 0.96 mmol) in pyridine (4 mL) was added benzoyl chloride (116 μL, 1.0 mmol). The reaction mixture was stirred at room temperature for 2 hrs and then concentrated under reduced pressure. The residue was dissolved in EtOAc (20 mL), washed with 1 N HCl, water and brine, dried over sodium sulfate, and concentrated under reduced pressure. The residue was purified by silica gel column chromatography (Et₂O/pentane: gradient 0% to 50%) to give benzoic acid 3-tert-butoxycarbonylaminocyclobutyl ester as a white solid (262 mg, yield: 94%). LCMS (ESI) m/z: 192 [M+H-BOC]⁺

Step 2
To a solution of benzoic acid 3-tert-butoxycarbonylaminocyclobutyl ester (100 mg, 0.34 mmol) in DCM (2 mL) was added TFA (2 mL). The reaction mixture was stirred at room temperature for 2 hrs and then concentrated under reduced pressure. The residue was partitioned between EtOAc (20 mL) and saturated aqueous sodium hydrogenocarbonate solution (20 mL). The organic layer was washed with brine, dried over sodium sulfate, and concentrated under reduced pressure to give benzoic acid 3-aminocyclobutyl ester as a colorless oil (62 mg, yield: 94%).

Major diastereoisomer (80%): $^1$H NMR (400 MHz, DMSO-d$_6$): δ 8.06-8.01 (m, 2H), 7.58-7.53 (m, 1H), 7.46-7.41 (m, 2H), 4.93-4.85 (m, 1H), 3.25-3.15 (m, 1H), 2.95-2.86 (m, 2H), 1.98-1.87 (m, 2H)

Minor diastereoisomer (20%): $^1$H NMR (400 MHz, DMSO-d$_6$): δ 8.06-8.01 (m, 2H), 7.58-7.53 (m, 1H), 7.46-7.41 (m, 2H), 5.41-5.35 (m, 1H), 3.86-3.79 (m, 1H), 2.56-2.48 (m, 2H), 2.30-2.22 (m, 2H)

Step 3

To a solution of N-(2-amino-pyridin-4-yl)-2,6-dichlorobenzamide (281 mg, 1.0 mmol) in pyridine (5 mL) was added phenyl chloroformate (138 μL, 1.1 mmol). The reaction mixture was stirred at room temperature for 1 hr then concentrated under reduced pressure. The residue was partitioned between EtOAc (30 mL) and water (30 mL). The organic layer was washed with 1 N HCl, water, 1 N NaOH, and brine, dried over sodium sulfate, and concentrated under reduced pressure to give a white solid (421 mg) used into the next step without purification.

Step 4

To a solution of the solid isolated in step 1 (125 mg) in THF (2 mL) was added benzoic acid 3-aminocyclobutyl ester (60 mg, 0.31 mmol) and the mixture was stirred for 1 hr. DMF (1 mL) and pyridine (100 μL, 1.24 mmol) were added and stirring was continued for 18 hrs. The reaction mixture was partitioned between EtOAc (20 mL) and water (20 mL). The organic layer was washed with 1 N HCl, water and brine, dried over sodium sulfate, and concentrated under reduced pressure. The residue was purified by silica gel column chromatography (EtOAC/cyclohexane gradient 0% to 100%) to give benzoic acid 3-{3-[4-(2,6-dichlorobenzoylamino)pyridin-2-yl]ureido}cyclobutyl ester as a white solid (34 mg, yield: 23%). LCMS (ESI) m/z: 499 [M+H]$^+$ Step 5

To a solution of benzoic acid 3-{3-[4-(2,6-dichlorobenzoylamino)pyridin-2-yl]ureido}cyclobutyl ester (34 mg, 0.068 mmol) in THF (2 mL) was added 1 N NaOH (0.10 mL, 0.10 mmol). The reaction mixture was stirred at 50° C. for 18 hrs and then concentrated under reduced pressure. The residue was partitioned between EtOAc (10 mL) and water (10 mL). The organic layer was washed with saturated aqueous sodium hydrogenocarbonate solution, water and brine, dried over sodium sulfate, and concentrated under reduced pressure. The residue was purified by silica gel column chromatography (EtOAC) to give the title compound as a white solid (18 mg, yield: 67%).

Major diastereoisomer (85%): $^1$H NMR (400 MHz, CH$_3$OH-d$_4$): δ 8.14 (dd, J=5.8, 0.6 Hz, 1H), 7.62 (d, J=1.9 Hz, 1H), 7.49-7.48 (m, 3H), 7.17 (dd, J=5.8, 1.9 Hz, 1H), 4.03-3.95 (m, 1H), 3.88-3.80 (m, 1H), 2.77-2.76 (m, 2H), 1.88-1.87 (m, 2H). LCMS (ESI) m/z: 395 [M+H]$^+$ Minor diastereoisomer (15%): $^1$H NMR (400 MHz, CH$_3$OH-d$_4$): 8.14 (dd, J=5.8, 0.6 Hz, 1H), 7.62 (d, J=1.90 Hz, 1H), 7.49-7.48 (m, 3H), 7.18 (dd, J=5.8, 1.9 Hz, 1H), 4.47-4.40 (m, 1H), 4.39-4.31 (m, 1H), 2.35-2.30 (m, 4H). LCMS (ESI) m/z: 395 [M+H]$^+$.

Example 270

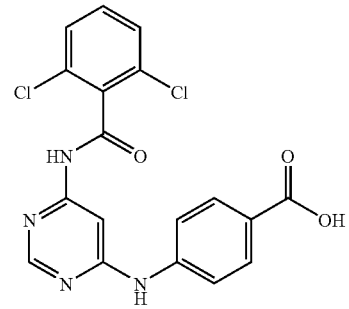 [SMILES: O=C(O)c1ccc(Nc2cc(NC(=O)c3c(Cl)cccc3Cl)ncn2)cc1]

4-(6-(2,6-dichlorobenzamido)pyrimidin-4-ylamino)benzoic acid

Step 1

To a cooled (0° C.) solution of 6-chloropyrimidin-4-amine (1.295 g, 10 mmol) in DMF (25 mL) was added sodium hydride (1.2 g, 30 mmol, 60% dispersion in mineral oil) in one portion. The mixture was stirred at 0° C. for 10 min and then 2,6-dichlorobenzoyl chloride (2.304 g, 11 mmol) was added dropwise. The mixture was warmed to room temperature and stirred under nitrogen overnight. The mixture was quenched with ice water and the resulting precipitate was collected by filtration. The solid was washed with water, then 1:1 ether/hexane (10 mL,) to give N-(6-chloropyrimidin-4-yl)-2,6-dichlorobenzamide (1.95 g, yield: 64%). $^1$H NMR (500 MHz, DMSO) δ 12.09 (s, 1H), 8.84 (s, 1H), 8.24 (s, 1H), 7.61-7.56 (m, 2H), 7.53 (dd, J=9.2, 6.8 Hz, 1H). LCMS (ESI) m/z: 302.1 [M+H$^+$].

Step 2

A mixture of N-(6-chloropyrimidin-4-yl)-2,6-dichlorobenzamide (302 mg, 1.0 mmol), ethyl 4-aminobenzoate (0.33 g, 2.0 mmol), Pd$_2$(dba)$_3$ (0.1 mmole, 92 mg), 4,5-Bis(diphenylphosphino)-9,9-dimethylxanthene (0.15 mmol, 87 mg) and cesium carbonate (2.0 mmoles; 652 mg) in a microwave tube was evacuated, back-filled with N$_2$ (2×). 1,4-Dioxane (10 mL) was then added. The tube was sealed, and heated at 130° C. in microwave for 15 min. The mixture was filtered through Celite using EtOAc to rinse. The combined filtrates were concentrated under reduced pressure. The residue was purified by column chromatography on silica gel (0-50% EtOAc/hexane) to afford ethyl 4-(6-(2,6-dichlorobenzamido)pyrimidin-4-ylamino)benzoate as an off-white solid (0.279 g, yield: 65%). LCMS (ESI) m/z: 431.0 [M+H$^+$].

Step 3

To a solution of ethyl 4-(6-(2,6-dichlorobenzamido)pyrimidin-4-ylamino)benzoate (0.279 g, 0.647 mmol) in THF (5 mL) was added a solution of 3 N LiOH (2 mL). The mixture was heated at 60° C. for 12 hrs. THF was removed under reduced pressure. The residue was diluted with water, acidified with 1 N HCl to pH 3.0. The precipitated white solid was collected by filtration, washed with water, dried in high vacuum to give 4-(6-(2,6-dichlorobenzamido)pyrimidin-4-ylamino)benzoic acid (0.24 g, yield: 92%). $^1$H NMR (500 MHz, DMSO) δ 12.52 (s, 1H), 11.41 (s, 1H), 10.07 (s, 1H), 8.53 (s, 1H), 7.90 (d, J=8.9 Hz, 2H), 7.85 (d, J=8.9 Hz, 2H), 7.78 (d, J=0.8 Hz, 1H), 7.58-7.53 (m, 2H), 7.49 (dd, J=9.1, 6.9 Hz, 1H). LCMS (ESI) m/z: 403.0 [M+H⁺].

Additional exemplary compounds of Formulas I-VII, Examples 271-618 shown in Tables 2 and 3 below, were prepared according to the above-described methods, characterized, and tested for inhibition of the Janus kinases according to the above methods, and have the following structures and corresponding names (ChemDraw Ultra, Version 9.0.1, CambridgeSoft Corp., Cambridge Mass.).

TABLE 2

| Ex | Structure | Name | LCMS (ESI) (m/z) |
|---|---|---|---|
| 271 | 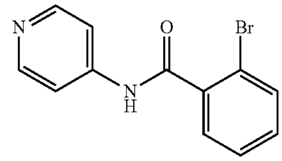 [SMILES: O=C(Nc1ccncc1)c1ccccc1Br] | 2-bromo-N-(pyridine-4-yl)benzamide | 277.1 |
| 272 | 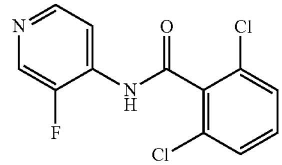 [SMILES: O=C(Nc1ccncc1F)c1c(Cl)cccc1Cl] | 2,6-dichloro-N-(3-fluoropyridin-4-yl)benzamide | 285.2 |
| 273 | 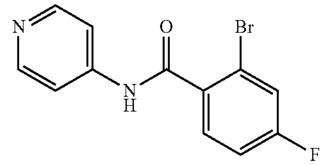 [SMILES: O=C(Nc1ccncc1)c1ccc(F)cc1Br] | 2-bromo-4-fluoro-N-(pyridine-4-yl)benzamide | 295.2 |
| 274 | 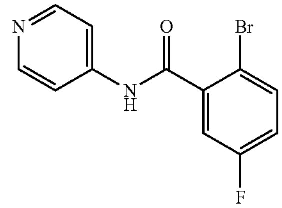 [SMILES: O=C(Nc1ccncc1)c1cc(F)ccc1Br] | 2-bromo-5-fluoro-N-(pyridine-4-yl)benzamide | 295.1 |
| 275 | 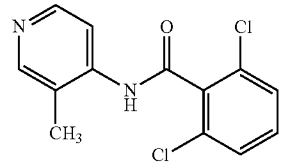 [SMILES: Cc1cnccc1NC(=O)c1c(Cl)cccc1Cl] | 2,6-dichloro-N-(3-methylpyridin-4-yl)benzamide | 281.0 |
| 276 | 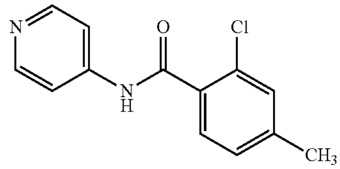 [SMILES: Cc1ccc(C(=O)Nc2ccncc2)c(Cl)c1] | 2-chloro-4-methyl-N-(pyridine-4-yl)benzamide | 247.0 |
| 277 | 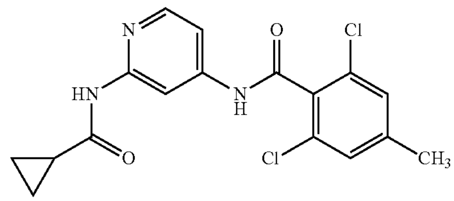 [SMILES: Cc1cc(Cl)c(C(=O)Nc2ccnc(NC(=O)C3CC3)c2)c(Cl)c1] | 2,6-dichloro-N-(2-(cyclopropanecarboxamido)pyridine-4-yl)-4-methylbenzamide | 364.1 |

TABLE 2-continued

| Ex | Structure | Name | LCMS (ESI) (m/z) |
|---|---|---|---|
| 278 | 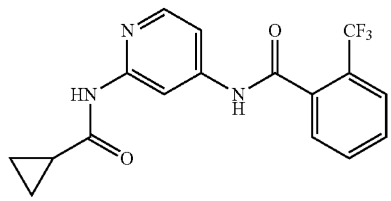 [SMILES: O=C(Nc1ccnc(NC(=O)C2CC2)c1)c1ccccc1C(F)(F)F] | N-(2-(cyclopropanecarboxamido)pyridine-4-yl)-2-(trifluoromethyl)benzamide | 350.1 |
| 279 | 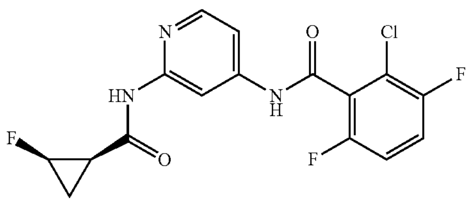 [SMILES: O=C(Nc1ccnc(NC(=O)[C@H]2C[C@H]2F)c1)c1c(F)ccc(F)c1Cl] | 2-chloro-3,6-difluoro-N-(2-((1R,2R)-2-fluorocyclopropanecarboxamido)pyridine-4-yl)benzamide | 370.1 |
| 280 | 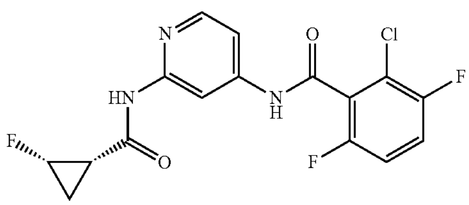 [SMILES: O=C(Nc1ccnc(NC(=O)[C@@H]2C[C@@H]2F)c1)c1c(F)ccc(F)c1Cl] | 2-chloro-3,6-difluoro-N-(2-((1S,2S)-2-fluorocyclopropanecarboxamido)pyridine-4-yl)benzamide | 370.1 |
| 281 | 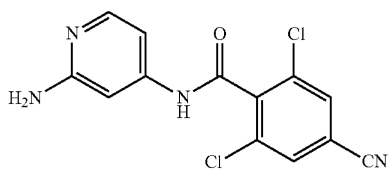 [SMILES: N#Cc1cc(Cl)c(C(=O)Nc2ccnc(N)c2)c(Cl)c1] | N-(2-aminopyridin-4-yl)-2,6-dichloro-4-cyanobenzamide | 307.1 |
| 282 | 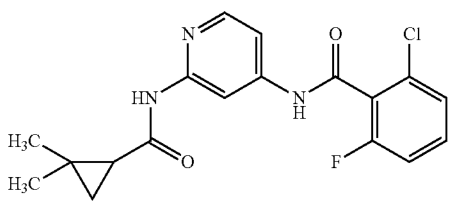 [SMILES: CC1(C)CC1C(=O)Nc1cc(NC(=O)c2c(F)cccc2Cl)ccn1] | 2-chloro-N-(2-(2,2-dimethylcyclopropanecarboxamido)pyridine-4-yl)6-fluorobenzamide | 362.0 |
| 283 | 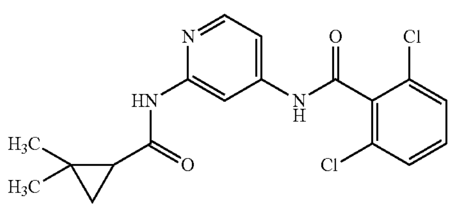 [SMILES: CC1(C)CC1C(=O)Nc1cc(NC(=O)c2c(Cl)cccc2Cl)ccn1] | 2,6-dichloro-N-(2-(2,2-dimethylcyclopropanecarboxamido)pyridine-4-yl)benzamide | 378.1 |
| 284 | 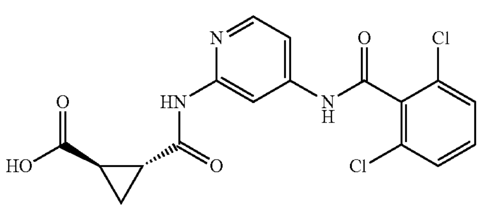 [SMILES: O=C(Nc1ccnc(NC(=O)[C@@H]2C[C@H]2C(=O)O)c1)c1c(Cl)cccc1Cl] | (1R,2R)-2-(4-(2,6-dichlorobenamido)-pyridine-2-ylcarbamoyl)cyclopropanecarboxylic acid | 394.0 |

TABLE 2-continued

| Ex | Structure | Name | LCMS (ESI) (m/z) |
|---|---|---|---|
| 285 | 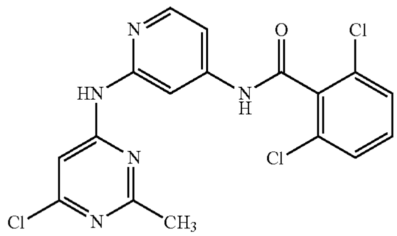 [SMILES: Cc1nc(Cl)cc(Nc2cc(NC(=O)c3c(Cl)cccc3Cl)ccn2)n1] | 2,6-dichloro-2-methylpyrimidin-4-ylamino)pyridine-4-yl)benzamide | 408.1 |
| 286 | 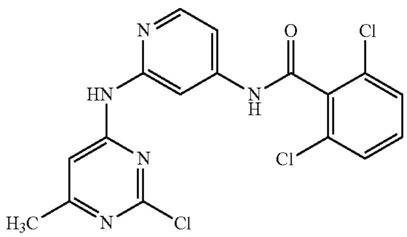 [SMILES: Cc1cc(Nc2cc(NC(=O)c3c(Cl)cccc3Cl)ccn2)nc(Cl)n1] | 2,6-dichloro-N-(2-(2-chloro-6-methylpyrimidin-4-ylamino)pyridine-4-yl)benzamide | 408.0 |
| 287 | 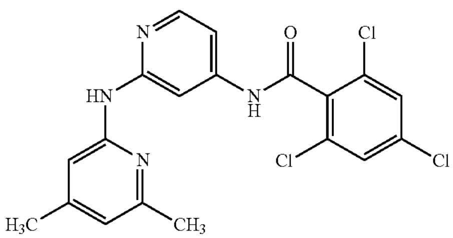 [SMILES: Cc1cc(C)nc(Nc2cc(NC(=O)c3c(Cl)cc(Cl)cc3Cl)ccn2)c1] | 2,4,6-trichloro-N-(2-4,6-dimethylpyridin-2-ylamino)pyridin-4-yl)benzamide | 421.0 |
| 288 | 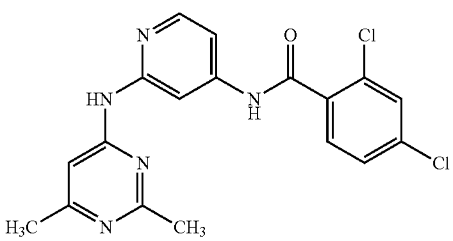 [SMILES: Cc1cc(Nc2cc(NC(=O)c3ccc(Cl)cc3Cl)ccn2)nc(C)n1] | 2,4-dichloro-N-(2-(2,6-dimethylpyrimidin-4-ylamino)pyridine-4-yl)benzamide | 388.1 |
| 289 | 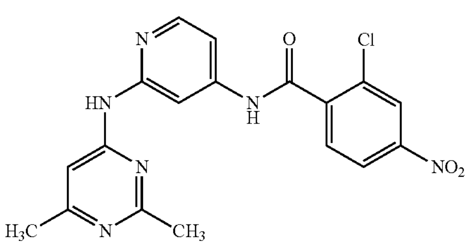 [SMILES: Cc1cc(Nc2cc(NC(=O)c3ccc([N+](=O)[O-])cc3Cl)ccn2)nc(C)n1] | 2-chloro-N-(2-(2,6-dimethylpyrimidin-4-ylamino)pyridine-4-yl)-4-nitrobenzamide | 389.1 |
| 290 | 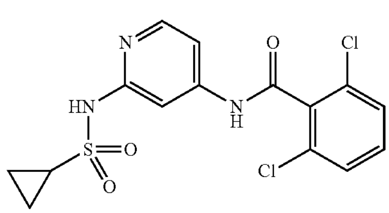 [SMILES: O=C(Nc1ccnc(NS(=O)(=O)C2CC2)c1)c1c(Cl)cccc1Cl] | 2,6-dichloro-N-(2-(cyclopropanesulfonamido)pyridine-4-yl)benzamide | 386.0 |

TABLE 2-continued

| Ex | Structure | Name | LCMS (ESI) (m/z) |
|---|---|---|---|
| 291 | 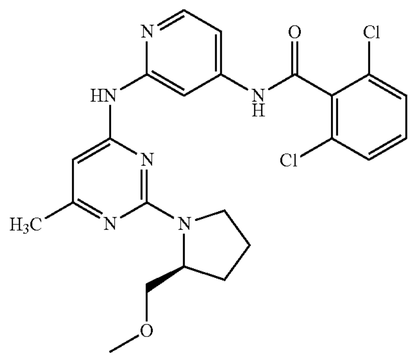 [SMILES: COC[C@@H]1CCCN1c1nc(C)cc(Nc2cc(NC(=O)c3c(Cl)cccc3Cl)ccn2)n1] | (S)-2,6-dichloro-N-(2-(2-(2-(methoxymethyl)-pyrrolidin-1-yl)-6-methylpyrimidin-4-ylamino)pyridine-4-yl)benzamide | 487.1 |
| 292 | 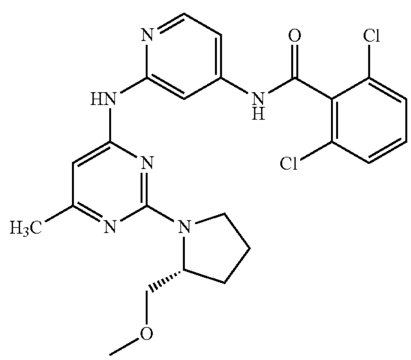 [SMILES: COC[C@H]1CCCN1c1nc(C)cc(Nc2cc(NC(=O)c3c(Cl)cccc3Cl)ccn2)n1] | (R)-2,6-dichloro-N-(2-(2-(2-(methoxymethyl)-pyrrolidin-1-yl)-6-methylpyrimidin-4-ylamino)pyridine-4-yl)benzamide | 487.1 |
| 293 | 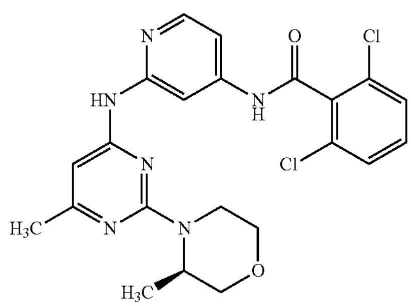 [SMILES: Cc1cc(Nc2cc(NC(=O)c3c(Cl)cccc3Cl)ccn2)nc(N2CCOC[C@H]2C)n1] | (R)-2,6-dichloro-N-(2-(6-methyl-2-(3-methylmorpholino)-pyrimidin-4-ylamino)pyridine-4-yl)benzamide | 473.1 |
| 294 | 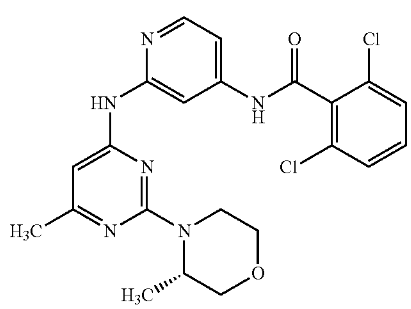 [SMILES: Cc1cc(Nc2cc(NC(=O)c3c(Cl)cccc3Cl)ccn2)nc(N2CCOC[C@@H]2C)n1] | (S)-2,6-dichloro-N-(2-(6-methyl-2-(3-methylmorpholino)-pyrimidin-4-ylamino)pyridine-4-yl)benzamide | 473.1 |
| 295 | 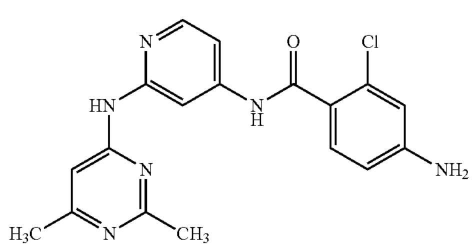 | 4-amino-2-chloro-N-(2-(2-(2,6-dimethylpyrimidin-4-ylamino)pyridine-4-yl)benzamide | 369.1 |

TABLE 2-continued

| Ex | Structure | Name | LCMS (ESI) (m/z) |
|---|---|---|---|
| 296 | 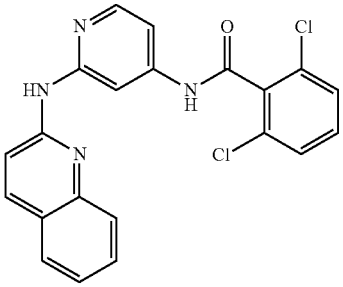 [SMILES: O=C(Nc1ccnc(Nc2ccc3ccccc3n2)c1)c1c(Cl)cccc1Cl] | 2,6-dichloro-N-(2-(quinolin-2-ylamino)pyridine-4-yl)benzamide | 409.1 |
| 297 | 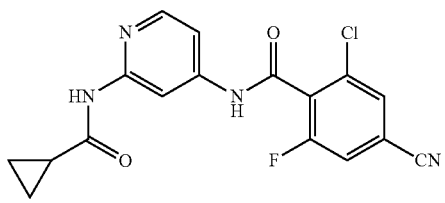 [SMILES: N#Cc1cc(F)c(C(=O)Nc2ccnc(NC(=O)C3CC3)c2)c(Cl)c1] | 2-chloro-4-cyano-N-(2-(cyclopropanecarbox-amido)pyridine-4-yl)-6-fluorobenzamide | 359.1 |
| 298 | 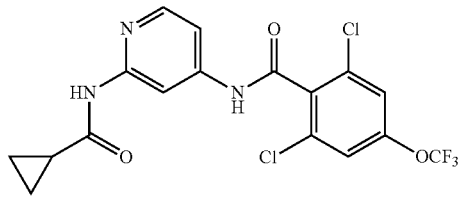 [SMILES: O=C(Nc1ccnc(NC(=O)C2CC2)c1)c1c(Cl)cc(OC(F)(F)F)cc1Cl] | 2,6-dichloro-N-(2-(cyclopropanecarbox-amido)pyridine-4-yl)-4-trifluoromethoxy)benzamide | 434.0 |
| 299 | 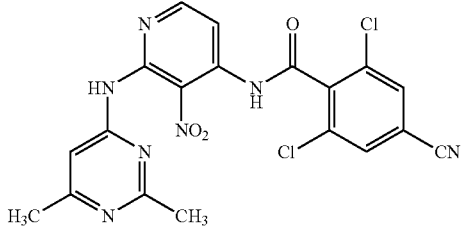 [SMILES: Cc1cc(Nc2nccc(NC(=O)c3c(Cl)cc(C#N)cc3Cl)c2[N+](=O)[O-])nc(C)n1] | 2,6-dichloro-4-cyano-N-(2-(2,6-dimethylpyrimidin-4-ylamino)3-nitropyridine-4-yl)benzamide | 458.1 |
| 300 | 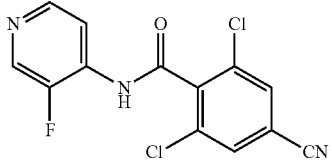 [SMILES: N#Cc1cc(Cl)c(C(=O)Nc2ccncc2F)c(Cl)c1] | 2,6-dichloro-4-cyano-N-(2-fluoropyridin-4-yl)benzamide | 310.1 |
| 301 | 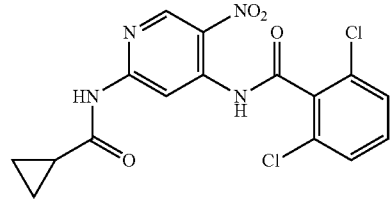 [SMILES: O=C(Nc1cc(NC(=O)C2CC2)ncc1[N+](=O)[O-])c1c(Cl)cccc1Cl] | 2,6-dichloro-N-(2-cyclopropanecarbox-amido)-5-nitropyridin-4-yl)benzamide | 395.0 |
| 302 | 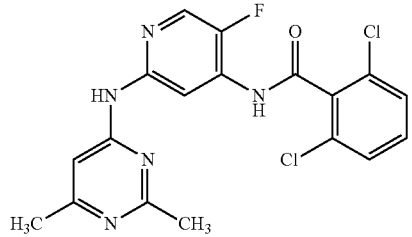 [SMILES: Cc1cc(Nc2cc(NC(=O)c3c(Cl)cccc3Cl)c(F)cn2)nc(C)n1] | 2,6-dichloro-N-(2-(2,6-dimethylpyrimidin-4-ylamino)-5-fluoropyridin-4-yl)benzamide | 406.1 |

TABLE 2-continued

| Ex | Structure | Name | LCMS (ESI) (m/z) |
|---|---|---|---|
| 303 | 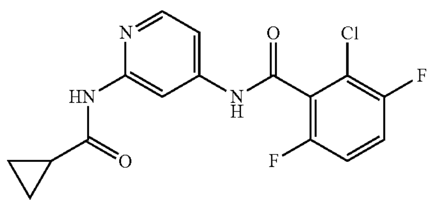 [SMILES: O=C(Nc1ccnc(NC(=O)C2CC2)c1)c1c(F)ccc(F)c1Cl] | 2-chloro-N-(2-(cyclopropanecabox-amido)pyridine-4-yl)-3,6-difluorobenzamide | 352.0 |
| 304 | 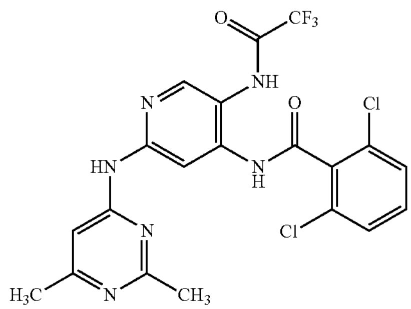 [SMILES: Cc1cc(Nc2cc(NC(=O)c3c(Cl)cccc3Cl)c(NC(=O)C(F)(F)F)cn2)nc(C)n1] | 2,6-dichloro-N-(2-(2,6-dimethylpyrimidin-4-ylamino)-5-(2,2,2-trifluoroacetamido)pyridin-4-yl)benzamide | 499.1 |

TABLE 3

| Ex | Structure | Name | LCMS (ESI) (m/z) |
|---|---|---|---|
| 305 | 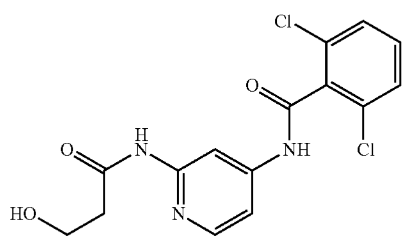 [SMILES: O=C(CCO)Nc1cc(NC(=O)c2c(Cl)cccc2Cl)ccn1] | 2,6-dichloro-N-(2-(3-hydroxypropanamido)-pyridin-4-yl)benzamide | 354.0 |
| 306 | 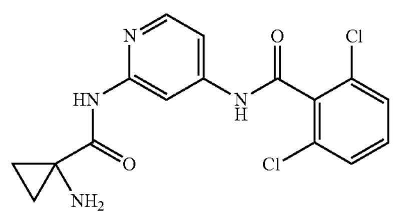 [SMILES: NC1(C(=O)Nc2cc(NC(=O)c3c(Cl)cccc3Cl)ccn2)CC1] | N-(2-(1-aminocyclopropanecar-boxamido)pyridin-4-yl)-2,6-dichlorobenzamide | 365.1 |
| 307 | 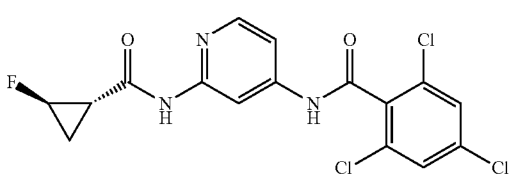 [SMILES: O=C(Nc1ccnc(NC(=O)[C@@H]2C[C@H]2F)c1)c1c(Cl)cc(Cl)cc1Cl] | 2,4,6-trichloro-N-(2-(trans-2-fluorocyclopropanecar-boxamido)pyridin-4-yl)benzamide | 402.0 |
| 308 | 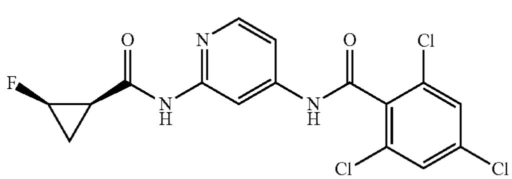 [SMILES: O=C(Nc1ccnc(NC(=O)[C@H]2C[C@H]2F)c1)c1c(Cl)cc(Cl)cc1Cl] | 2,4,6-trichloro-N-(2-(cis-2-fluorocyclopropanecar-boxamido)pyridin-4-yl)benzamide | 402.0 |

TABLE 3-continued

| # | Structure | Name | Mass |
|---|---|---|---|
| 309 | 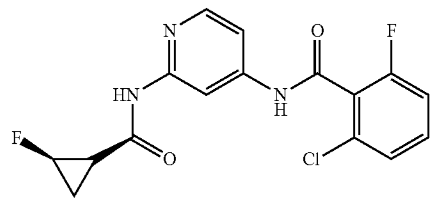 | 2-chloro-6-fluoro-N-(2-(cis-2-fluorocyclopropanecarboxamido)pyridin-4-yl)benzamide | 352.1 |
| 310 | 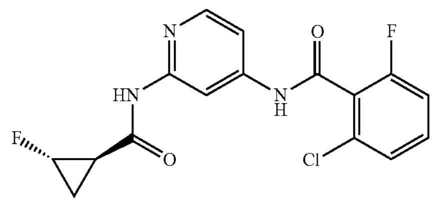 [SMILES: O=C(Nc1ccnc(NC(=O)[C@H]2C[C@@H]2F)c1)c1c(F)cccc1Cl] | 2-chloro-6-fluoro-N-(2-(trans-2-fluorocyclopropanecarboxamido)pyridin-4-yl)benzamide | 352.1 |
| 311 | 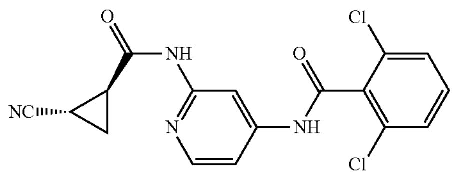 [SMILES: N#C[C@H]1C[C@@H]1C(=O)Nc1cc(NC(=O)c2c(Cl)cccc2Cl)ccn1] | 2,6-dichloro-N-(2-(trans-2-cyanocyclopropanecarboxamido)pyridin-4-yl)benzamide | 375.0 |
| 312 | 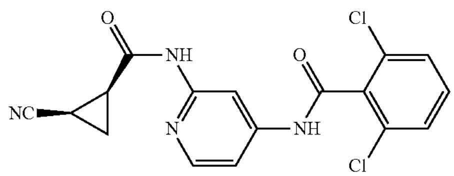 [SMILES: N#C[C@@H]1C[C@@H]1C(=O)Nc1cc(NC(=O)c2c(Cl)cccc2Cl)ccn1] | 2,6-dichloro-N-(2-(cis-2-cyanocyclopropanecarboxamido)pyridin-4-yl)benzamide | 375.0 |
| 313 | 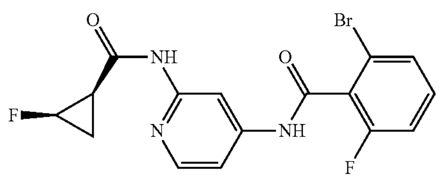 [SMILES: O=C(Nc1ccnc(NC(=O)[C@H]2C[C@H]2F)c1)c1c(F)cccc1Br] | 2-bromo-6-fluoro-N-(2-(cis-2-fluorocyclopropanecarboxamido)pyridin-4-yl)benzamide | 398.0 |
| 314 | 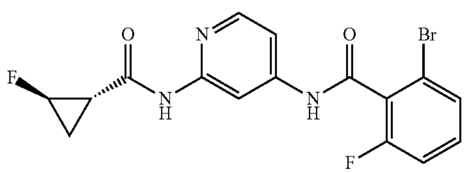 [SMILES: O=C(Nc1ccnc(NC(=O)[C@@H]2C[C@H]2F)c1)c1c(F)cccc1Br] | 2-bromo-6-fluoro-N-(2-(trans-2-fluorocyclopropanecarboxamido)pyridin-4-yl)benzamide | 398.0 |
| 315 | 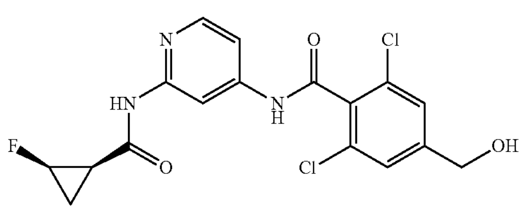 [SMILES: O=C(Nc1ccnc(NC(=O)[C@H]2C[C@H]2F)c1)c1c(Cl)cc(CO)cc1Cl] | 2,6-dichloro-N-(2-(cis-2-fluorocyclopropanecarboxamido)pyridin-4-yl)-4-(hydroxymethyl)benzamide | 398.0 |
| 316 | 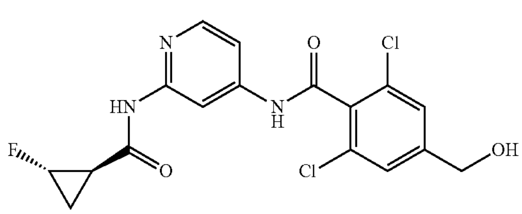 [SMILES: O=C(Nc1ccnc(NC(=O)[C@H]2C[C@@H]2F)c1)c1c(Cl)cc(CO)cc1Cl] | 2,6-dichloro-N-(2-(trans-2-fluorocyclopropanecarboxamido)pyridin-4-yl)-4-(hydroxymethyl)benzamide | 398.0 |

TABLE 3-continued

| | | | |
|---|---|---|---|
| 317 | 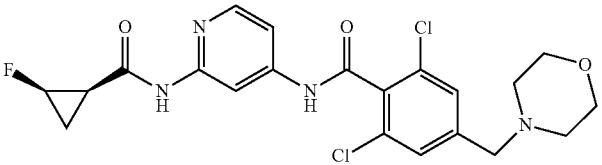 [SMILES: O=C(Nc1ccnc(NC(=O)[C@H]2C[C@H]2F)c1)c1c(Cl)cc(CN2CCOCC2)cc1Cl] | 2,6-dichloro-N-(2-(cis-2-fluorocyclopropanecarboxamido)pyridin-4-yl)-4-(morpholinomethyl)benzamide | 467.1 |
| 318 | 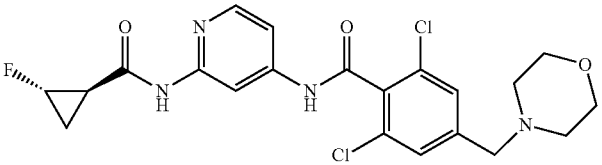 [SMILES: O=C(Nc1ccnc(NC(=O)[C@H]2C[C@@H]2F)c1)c1c(Cl)cc(CN2CCOCC2)cc1Cl] | 2,6-dichloro-N-(2-(trans-2-fluorocyclopropanecarboxamido)pyridin-4-yl)-4-(morpholinomethyl)benzamide | 467.0 |
| 319 | 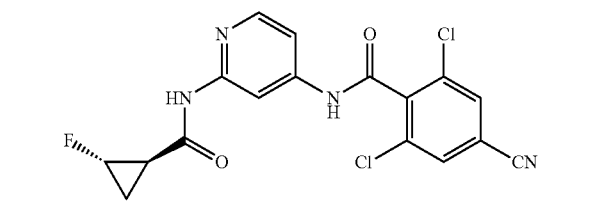 [SMILES: N#Cc1cc(Cl)c(C(=O)Nc2ccnc(NC(=O)[C@H]3C[C@@H]3F)c2)c(Cl)c1] | 2,6-dichloro-4-cyano-N-(2-(trans-2-fluorocyclopropanecarboxamido)pyridin-4-yl)benzamide | 393.0 |
| 320 | 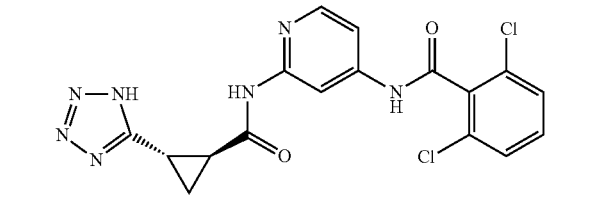 [SMILES: O=C(Nc1ccnc(NC(=O)[C@H]2C[C@@H]2c2nnn[nH]2)c1)c1c(Cl)cccc1Cl] | N-(2-(trans-2-(1H-tetrazol-5-yl)cyclopropanecarboxamido)pyridin-4-yl)-2,6-dichlorobenzamide | 418.1 |
| 321 | 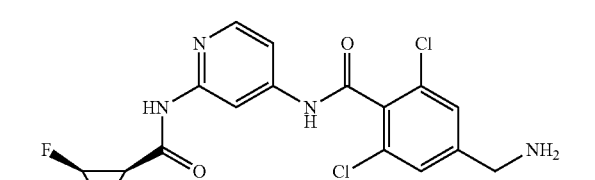 | 4-(aminomethyl)-2,6-dichloro-N-(2-(cis-2-fluorocyclopropanecarboxamido)pyridin-4-yl)benzamide | 397.1 |
| 322 | 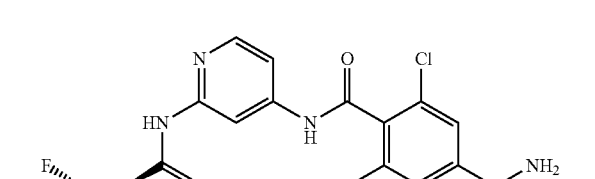 | 4-(aminomethyl)-2,6-dichloro-N-(2-(trans-2-fluorocyclopropanecarboxamido)pyridin-4-yl)benzamide | 397.1 |
| 323 | 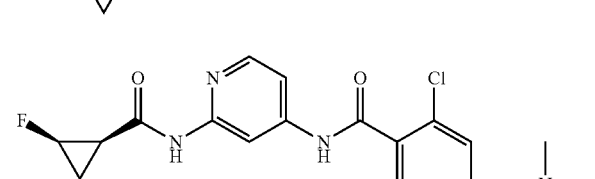 | 2,6-dichloro-4-((dimethylamino)methyl)-N-(2-(cis-2-fluorocyclopropanecarboxamido)pyridin-4-yl)benzamide | 425.1 |
| 324 | 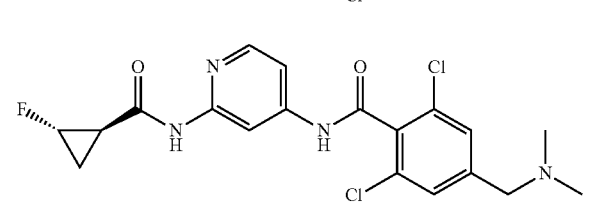 | 2,6-dichloro-4-((dimethylamino)methyl)-N-(2-(trans-2-fluorocyclopropanecarboxamido)pyridin-4-yl)benzamide | 425.1 |

TABLE 3-continued

| # | Structure | Name | Mass |
|---|---|---|---|
| 325 | 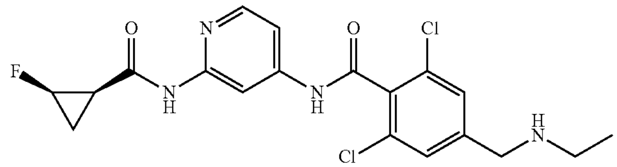 [SMILES: CCNCc1cc(Cl)c(C(=O)Nc2ccnc(NC(=O)[C@H]3C[C@H]3F)c2)c(Cl)c1] | 2,6-dichloro-4-((ethylamino)methyl)-N-(2-((1R,2R)-2-fluorocyclopropanecarboxamido)pyridin-4-yl)benzamide | 425.1 |
| 326 | 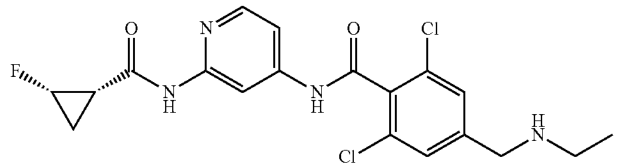 [SMILES: CCNCc1cc(Cl)c(C(=O)Nc2ccnc(NC(=O)[C@@H]3C[C@@H]3F)c2)c(Cl)c1] | 2,6-dichloro-4-((ethylamino)methyl)-N-(2-((1S,2S)-2-fluorocyclopropanecarboxamido)pyridin-4-yl)benzamide | 425.0 |
| 327 | 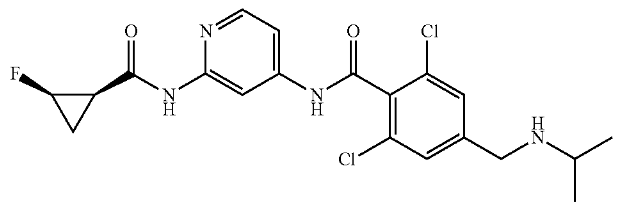 [SMILES: CC(C)NCc1cc(Cl)c(C(=O)Nc2ccnc(NC(=O)[C@H]3C[C@H]3F)c2)c(Cl)c1] | 2,6-dichloro-N-(2-((1R,2R)-2-fluorocyclopropanecarboxamido)pyridin-4-yl)-4-((isopropylamino)methyl)benzamide | 439.1 |
| 328 | 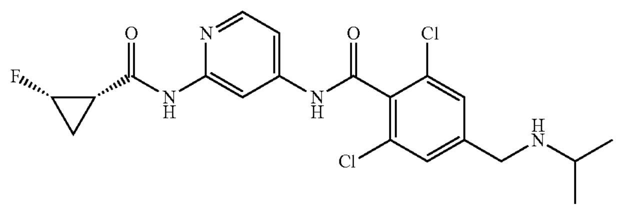 [SMILES: CC(C)NCc1cc(Cl)c(C(=O)Nc2ccnc(NC(=O)[C@@H]3C[C@@H]3F)c2)c(Cl)c1] | 2,6-dichloro-N-(2-((1S,2S)-2-fluorocyclopropanecarboxamido)pyridin-4-yl)-4-((isopropylamino)methyl)benzamide | 439.1 |
| 329 | 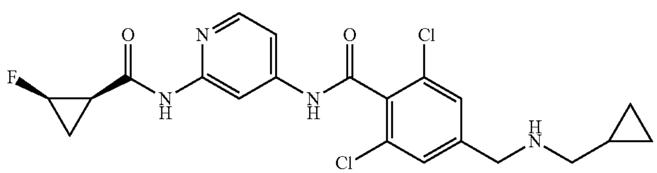 [SMILES: O=C(Nc1ccnc(NC(=O)[C@H]2C[C@H]2F)c1)c1c(Cl)cc(CNCC2CC2)cc1Cl] | 2,6-dichloro-4-((cyclopropylmethylamino)methyl)-N-(2-((1R,2R)-2-fluorocyclopropanecarboxamido)pyridin-4-yl)benzamide | 451.1 |
| 330 | 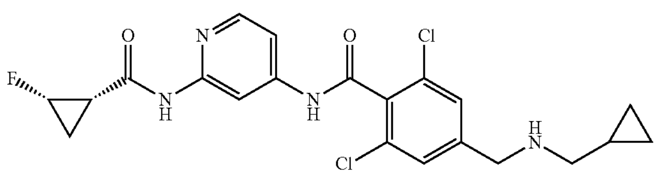 [SMILES: O=C(Nc1ccnc(NC(=O)[C@@H]2C[C@@H]2F)c1)c1c(Cl)cc(CNCC2CC2)cc1Cl] | 2,6-dichloro-4-((cyclopropylmethylamino)methyl)-N-(2-((1S,2S)-2-fluorocyclopropanecarboxamido)pyridin-4-yl)benzamide | 451.1 |
| 331 | 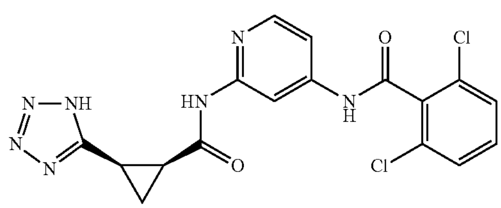 [SMILES: O=C(Nc1ccnc(NC(=O)[C@H]2C[C@H]2c2nnn[nH]2)c1)c1c(Cl)cccc1Cl] | N-(2-(cis-2-(1H-tetrazol-5-yl)cyclopropanecarboxamido)pyridin-4-yl)-2,6-dichlorobenzamide | 418.0 |
| 332 | 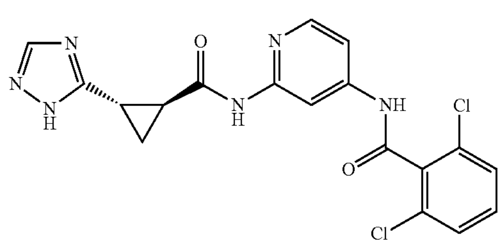 [SMILES: O=C(Nc1ccnc(NC(=O)[C@H]2C[C@@H]2c2ncn[nH]2)c1)c1c(Cl)cccc1Cl] | N-(2-(trans-2-(2H-1,2,4-triazol-3-yl)cyclopropanecarboxamido)pyridin-4-yl)-2,6-dichlorobenzamide | 417.0 |

TABLE 3-continued

| # | Structure | Name | Mass |
|---|---|---|---|
| 333 | 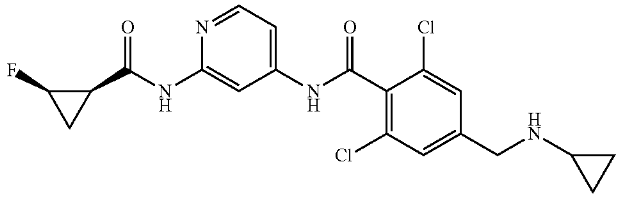 [SMILES: O=C(Nc1ccnc(NC(=O)[C@H]2C[C@H]2F)c1)c1c(Cl)cc(CNC2CC2)cc1Cl] | 2,6-dichloro-4-((cyclopropylamino)-methyl)-N-(2-((1R,2R)-2-fluorocyclopropanecarboxamido)pyridin-4-yl)benzamide | 437.1 |
| 334 | 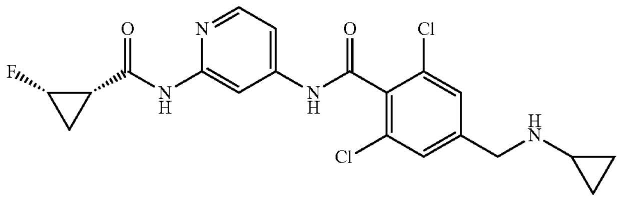 [SMILES: O=C(Nc1ccnc(NC(=O)[C@@H]2C[C@@H]2F)c1)c1c(Cl)cc(CNC2CC2)cc1Cl] | 2,6-dichloro-4-((cyclopropylamino)-methyl)-N-(2-((1S,2S)-2-fluorocyclopropanecarboxamido)pyridin-4-yl)benzamide | 437.1 |
| 335 | 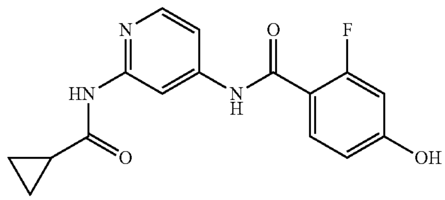 [SMILES: O=C(Nc1ccnc(NC(=O)C2CC2)c1)c1ccc(O)cc1F] | N-(2-(cyclopropanecarboxamido)pyridin-4-yl)-2-fluoro-4-hydroxybenzamide | 316.1 |
| 336 | 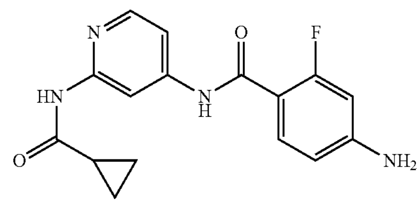 [SMILES: Nc1ccc(C(=O)Nc2ccnc(NC(=O)C3CC3)c2)c(F)c1] | 4-amino-N-(2-(cyclopropanecarboxamido)pyridin-4-yl)-2-fluorobenzamide | 315.1 |
| 337 | 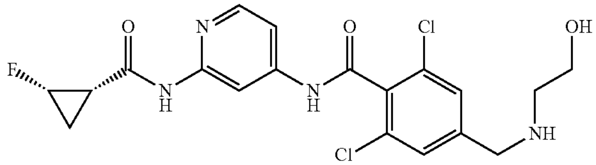 [SMILES: O=C(Nc1ccnc(NC(=O)[C@@H]2C[C@@H]2F)c1)c1c(Cl)cc(CNCCO)cc1Cl] | 2,6-dichloro-N-(2-((1S,2S)-2-fluorocyclopropanecarboxamido)pyridin-4-yl)-4-((2-hydroxyethylamino)-methyl)benzamide | 441.0 |
| 338 | 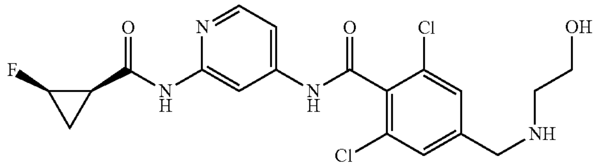 [SMILES: O=C(Nc1ccnc(NC(=O)[C@H]2C[C@H]2F)c1)c1c(Cl)cc(CNCCO)cc1Cl] | 2,6-dichloro-N-(2-((1R,2R)-2-fluorocyclopropanecarboxamido)pyridin-4-yl)-4-((2-hydroxyethylamino)-methyl)benzamide | 441.1 |
| 339 | 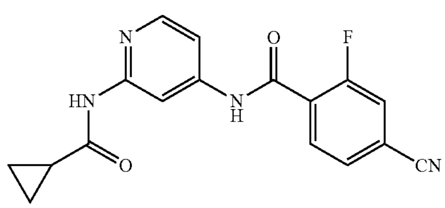 [SMILES: N#Cc1ccc(C(=O)Nc2ccnc(NC(=O)C3CC3)c2)c(F)c1] | 4-cyano-N-(2-(cyclopropanecarboxamido)pyridin-4-yl)-2-fluorobenzamide | 325.1 |
| 340 | 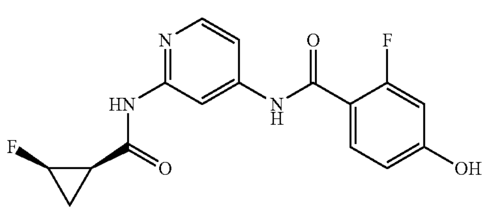 | 2-fluoro-N-(2-((1R,2R)-2-fluorocyclopropanecarboxamido)pyridin-4-yl)-4-hydroxybenzamide | 334.1 |

TABLE 3-continued

| # | Structure | Name | Mass |
|---|---|---|---|
| 341 | 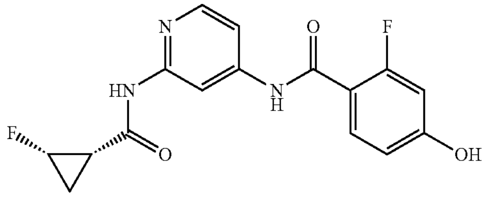 [SMILES: O=C(Nc1ccnc(NC(=O)[C@@H]2C[C@@H]2F)c1)c1ccc(O)cc1F] | 2-fluoro-N-(2-((1S,2S)-2-fluorocyclopropanecarboxamido)pyridin-4-yl)-4-hydroxybenzamide | 334.1 |
| 342 | 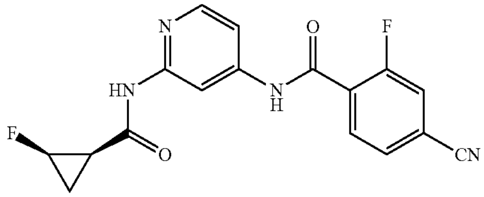 [SMILES: N#Cc1ccc(C(=O)Nc2ccnc(NC(=O)[C@H]3C[C@H]3F)c2)c(F)c1] | 4-cyano-2-fluoro-N-(2-((1R,2R)-2-fluorocyclopropanecarboxamido)pyridin-4-yl)benzamide | 343.1 |
| 343 | 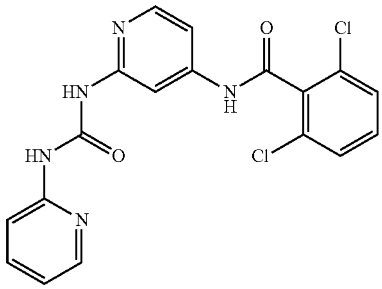 [SMILES: O=C(Nc1ccccn1)Nc1cc(NC(=O)c2c(Cl)cccc2Cl)ccn1] | 2,6-dichloro-N-(2-(3-pyridin-2-ylureido)pyridin-4-yl)benzamide | 402.0 |
| 344 | 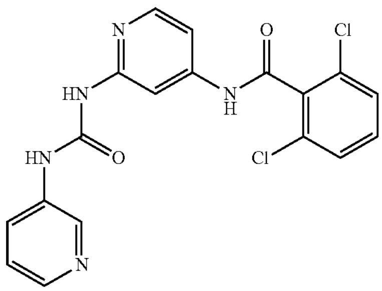 [SMILES: O=C(Nc1cccnc1)Nc1cc(NC(=O)c2c(Cl)cccc2Cl)ccn1] | 2,6-dichloro-N-(2-(3-pyridin-3-ylureido)pyridin-4-yl)benzamide | 402.0 |
| 345 | 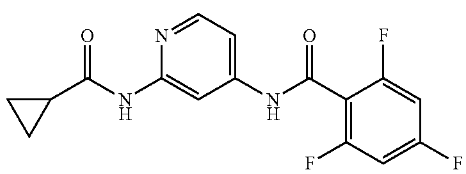 [SMILES: O=C(Nc1ccnc(NC(=O)C2CC2)c1)c1c(F)cc(F)cc1F] | N-(2-(cyclopropanecarboxamido)pyridin-4-yl)-2,4,6-trifluorobenzamide | 336.1 |
| 346 | 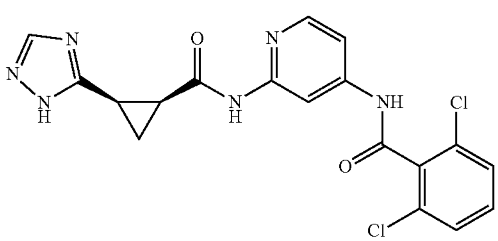 [SMILES: O=C(Nc1ccnc(NC(=O)[C@H]2C[C@H]2c2ncn[nH]2)c1)c1c(Cl)cccc1Cl] | N-(2-(cis-2-(2H-1,2,4-triazol-3-yl)cyclopropanecarboxamido)pyridin-4-yl)-2,6-dichlorobenzamide | 417.0 |
| 347 | 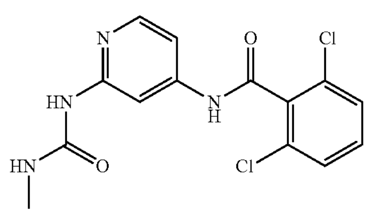 [SMILES: CNC(=O)Nc1cc(NC(=O)c2c(Cl)cccc2Cl)ccn1] | 2,6-dichloro-N-(2-(3-methylureido)pyridin-4-yl)benzamide | 339.0 |

TABLE 3-continued

| | | | |
|---|---|---|---|
| 348 | | 2,6-dichloro-N-(2-(3-cyclobutylureido)pyridin-4-yl)benzamide | 379.0 |
| 349 | | N-(2-(3-benzylureido)pyridin-4-yl)-2,6-dichlorobenzamide | 415.0 |
| 350 | | phenyl 4-(2,6-dichlorobenzamido)pyridin-2-ylcarbamate | 402.0 |
| 351 | | 2,6-dichloro-N-(2-(cyclopropanecarboxamido)pyridin-4-yl)-4-ethynylbenzamide | 374.0 |
| 352 | | 2,6-dichloro-N-(2-(cyclopropanecarboxamido)pyridin-4-yl)-4-morpholinobenzamide | 435.1 |
| 353 | | 2,6-dichloro-N-(2-(cyclopropanecarboxamido)pyridin-4-yl)-4-(2-oxopyrrolidin-2-yl)benzamide | 433.1 |
| 354 | | 2,6-dichloro-N-(2-(cyclopropanecarboxamido)pyridin-4-yl)-4-(2-oxooxazolidin-3-yl)benzamide | 435.0 |

TABLE 3-continued

| | | | |
|---|---|---|---|
| 355 | | 2,6-dichloro-N-(2-(3-hydroxy-2-(hydroxymethyl)propan-amido)pyridin-4-yl)benzamide | 384.1 |
| 356 | | 2,6-dichloro-N-(2-(3-(hydroxymethyl)-2-oxoazetidin-1-yl)pyridin-4-yl)benzamide | 366.0 |
| 357 | | 4-acetyl-2,6-dichloro-N-(2-(cyclopropanecarbox-amido)pyridin-4-yl)benzamide | 392.0 |
| 358 | | 2,6-dichloro-N-(2-(cyclopropanecarbox-amido)pyridin-4-yl)-4-(4H-1,2,4-triazol-3-yl)benzamide | 417.1 |
| 359 | | N-(4-(2,6-dichlorobenzamido)py-ridin-2-yl)oxetane-3-carboxamide | 366.0 |
| 360 | | 2,6-dichloro-4-(morpholine-4-carbonyl)-N-(2-(pyrimidin-4-ylamino)pyridin-4-yl)benzamide | 473.1 |
| 361 | | 2-chloro-6-fluoro-N-(2-(pyrimidin-4-ylamino)pyridin-4-yl)benzamide | 344.1 |

TABLE 3-continued

| | | | |
|---|---|---|---|
| 362 | | 2-bromo-6-fluoro-N-(2-(pyrimidin-4-ylamino)pyridin-4-yl)benzamide | 390.0 |
| 363 | | 2-chloro-N-(2-(cyclopropanecarbox-amido)pyridin-4-yl)benzamide | 316.1 |
| 364 | | N-(2-(cyclopropanecarbox-amido)pyridin-4-yl)-2,6-dimethylbenzamide | 310.2 |
| 365 | | N-(2-(cyclopropanecarbox-amido)pyridin-4-yl)-2-fluoro-6-methoxybenzamide | 330.1 |
| 366 | | 2-bromo-6-chloro-N-(2-(cyclopropanecarbox-amido)pyridin-4-yl)benzamide | 396.0 |
| 367 | | 2,6-dichloro-N-(2-(cyclopropanecarbox-amido)pyridin-4-yl)-4-(1H-pyrazol-4-yl)benzamide | 416.1 |
| 368 | | N-(2-(cyclopropanecarbox-amido)pyridin-4-yl)-2,6-difluorobenzamide | 318.1 |
| 369 | | 2-chloro-N-(2-(cyclopropanecarbox-amido)pyridin-4-yl)-6-methylbenzamide | 330.1 |

TABLE 3-continued

| # | Structure | Name | Mass |
|---|---|---|---|
| 370 | 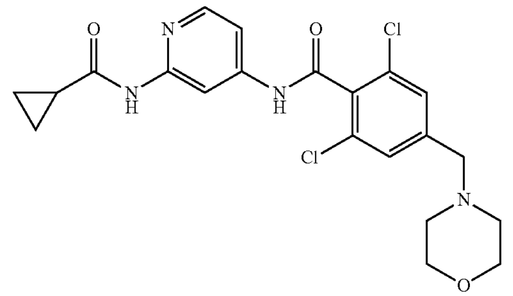 [SMILES: O=C(Nc1ccnc(NC(=O)C2CC2)c1)c1c(Cl)cc(CN2CCOCC2)cc1Cl] | 2,6-dichloro-N-(2-(cyclopropanecarboxamido)pyridin-4-yl)-4-(morpholinomethyl)benzamide | 449.1 |
| 371 | 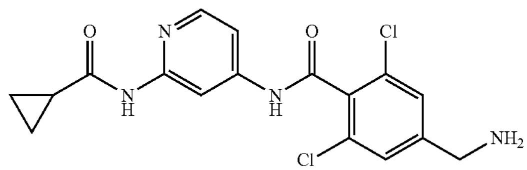 [SMILES: NCc1cc(Cl)c(C(=O)Nc2ccnc(NC(=O)C3CC3)c2)c(Cl)c1] | 4-(aminomethyl)-2,6-dichloro-N-(2-(cyclopropanecarboxamido)pyridin-4-yl)benzamide | 379.1 |
| 372 | 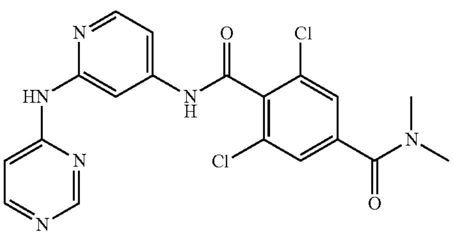 [SMILES: CN(C)C(=O)c1cc(Cl)c(C(=O)Nc2ccnc(Nc3ccncn3)c2)c(Cl)c1] | 2,6-dichloro-N4,N4-dimethyl-N1-(2-(pyrimidin-4-ylamino)pyridin-4-yl)terephthalamide | 431.1 |
| 373 | 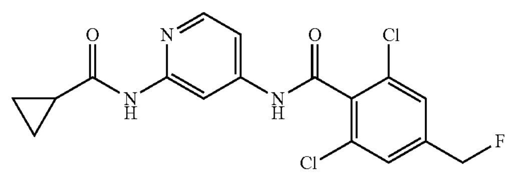 [SMILES: O=C(Nc1ccnc(NC(=O)C2CC2)c1)c1c(Cl)cc(CF)cc1Cl] | 2,6-dichloro-N-(2-(cyclopropanecarboxamido)pyridin-4-yl)-4-(fluoromethyl)benzamide | 382.0 |
| 374 | 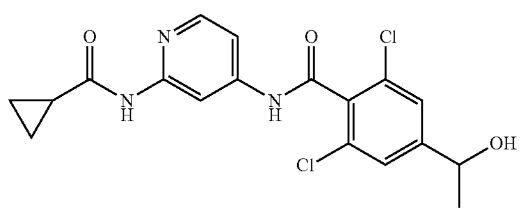 [SMILES: CC(O)c1cc(Cl)c(C(=O)Nc2ccnc(NC(=O)C3CC3)c2)c(Cl)c1] | 2,6-dichloro-N-(2-(cyclopropanecarboxamido)pyridin-4-yl)-4-(1-hydroxyethyl)benzamide | 394.1 |
| 375 | 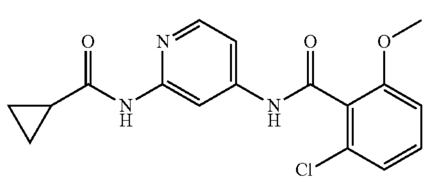 [SMILES: COc1cccc(Cl)c1C(=O)Nc1ccnc(NC(=O)C2CC2)c1] | 2-chloro-N-(2-(cyclopropanecarboxamido)pyridin-4-yl)-6-methoxybenzamide | 346.1 |
| 376 | 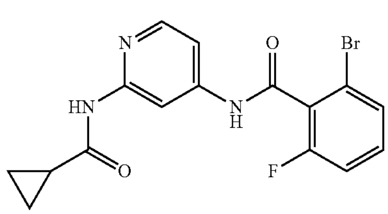 [SMILES: O=C(Nc1ccnc(NC(=O)C2CC2)c1)c1c(F)cccc1Br] | 2-bromo-N-(2-(cyclopropanecarboxamido)pyridin-4-yl)-6-fluorobenzamide | 380.0 |

TABLE 3-continued

| | | | |
|---|---|---|---|
| 377 | | 2,6-dichloro-N-(2-(2,6-dimethylpyrimidin-4-ylamino)pyridin-4-yl)-4-(hydroxymethyl)benzamide | 418.1 |
| 378 | | 2,6-dichloro-4-((dimethylamino)methyl)-N-(2-(2,6-dimethylpyrimidin-4-ylamino)pyridin-4-yl)benzamide | 445.1 |
| 379 | | 2,6-dichloro-N-(2-(2,6-dimethylpyrimidin-4-ylamino)pyridin-4-yl)-4-(morpholinomethyl)benzamide | 487.1 |
| 380 | | 2,4,6-trichloro-N-(2-(6-methyl-2-morpholinopyrimidin-4-ylamino)pyridin-4-yl)benzamide | 495.0 |
| 381 | | 2-chloro-6-fluoro-N-(2-(6-methyl-2-morpholinopyrimidin-4-ylamino)pyridin-4-yl)benzamid | 443.1 |
| 382 | | 2-chloro-N-(2-(6-methyl-2-morpholinopyrimidin-4-ylamino)pyridin-4-yl)benzamide | 425.2 |

TABLE 3-continued

| # | Structure | Name | Mass |
|---|---|---|---|
| 383 | 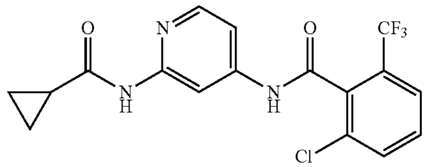 [SMILES: O=C(Nc1ccnc(NC(=O)C2CC2)c1)c1c(Cl)cccc1C(F)(F)F] | 2-chloro-N-(2-(cyclopropanecarbox-amido)pyridin-4-yl)-6-(trifluoromethyl)benz-amide | 384.1 |
| 384 | 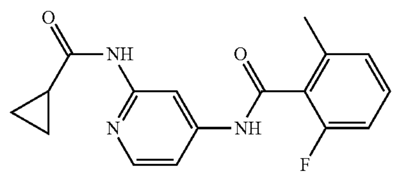 [SMILES: Cc1cccc(F)c1C(=O)Nc1ccnc(NC(=O)C2CC2)c1] | N-(2-(cyclopropanecarbox-amido)pyridin-4-yl)-2-fluoro-6-methylbenzamide | 314.1 |
| 385 | 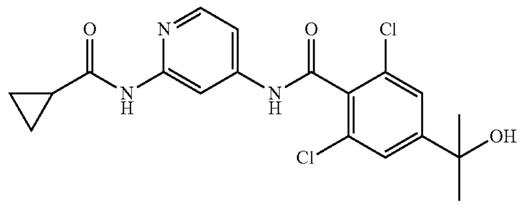 [SMILES: CC(C)(O)c1cc(Cl)c(C(=O)Nc2ccnc(NC(=O)C3CC3)c2)c(Cl)c1] | 2,6-dichloro-N-(2-(cyclopropanecarbox-amido)pyridin-4-yl)-4-(2-hydroxypropan-2-yl)benzamide | 408.0 |
| 386 | 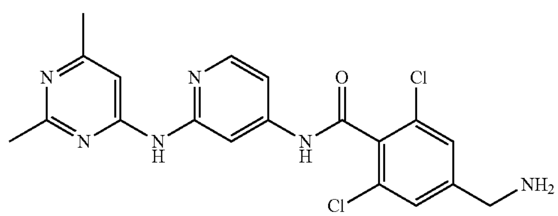 [SMILES: Cc1cc(Nc2cc(NC(=O)c3c(Cl)cc(CN)cc3Cl)ccn2)nc(C)n1] | 4-(aminomethyl)-2,6-dichloro-N-(2-(2,6-dimethylpyrimidin-4-ylamino)pyridin-4-yl)benzamide | 417.1 |
| 387 | 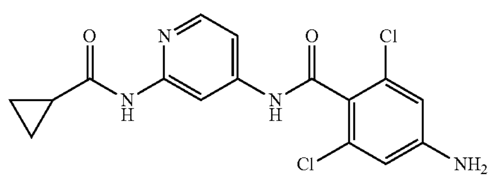 [SMILES: Nc1cc(Cl)c(C(=O)Nc2ccnc(NC(=O)C3CC3)c2)c(Cl)c1] | 4-amino-2,6-dichloro-N-(2-(cyclopropanecarbox-amido)pyridin-4-yl)benzamide | 365.0 |
| 388 | 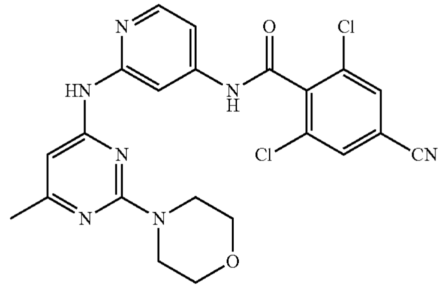 [SMILES: Cc1cc(Nc2cc(NC(=O)c3c(Cl)cc(C#N)cc3Cl)ccn2)nc(N2CCOCC2)n1] | 2,6-dichloro-4-cyano-N-(2-(6-methyl-2-morpholinopyrimidin-4-ylamino)pyridin-4-yl)benzamide | 484.1 |
| 389 | 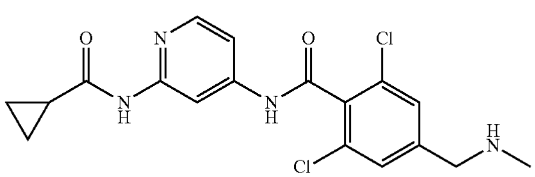 [SMILES: CNCc1cc(Cl)c(C(=O)Nc2ccnc(NC(=O)C3CC3)c2)c(Cl)c1] | 2,6-dichloro-N-(2-(cyclopropanecarbox-amido)pyridin-4-yl)-4-((methylamino)methyl)benzamide | 393.1 |
| 390 | 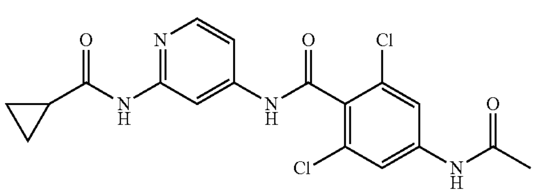 [SMILES: CC(=O)Nc1cc(Cl)c(C(=O)Nc2ccnc(NC(=O)C3CC3)c2)c(Cl)c1] | 4-acetamido-2,6-dichloro-N-(2-(cyclopropanecarbox--amido)pyridin-4-yl)benzamide | 407.0 |

| | | | |
|---|---|---|---|
| 391 | 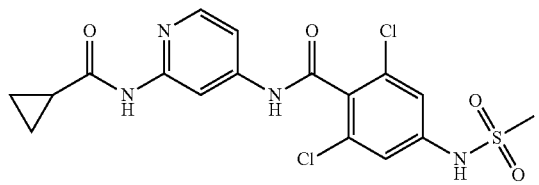 [SMILES: CS(=O)(=O)Nc1cc(Cl)c(C(=O)Nc2ccnc(NC(=O)C3CC3)c2)c(Cl)c1] | 2,6-dichloro-N-(2-(cyclopropanecarboxamido)pyridin-4-yl)-4-(methylsulfonamido)-benzamide | 443.0 |
| 392 | 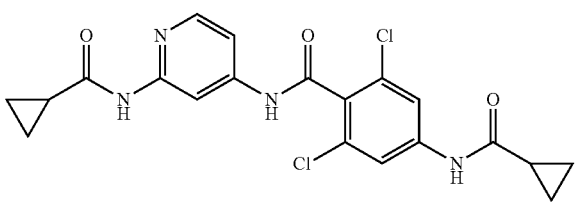 [SMILES: O=C(Nc1ccnc(NC(=O)C2CC2)c1)c1c(Cl)cc(NC(=O)C2CC2)cc1Cl] | 2,6-dichloro-4-(cyclopropanecarboxamido)pyridin-4-yl)benzamide | 433.1 |
| 393 | 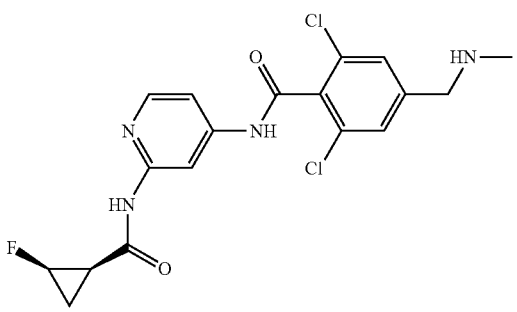 [SMILES: CNCc1cc(Cl)c(C(=O)Nc2ccnc(NC(=O)[C@H]3C[C@H]3F)c2)c(Cl)c1] | 2,6-dichloro-N-(2-(cis-2-fluorocyclopropanecarboxamido)pyridin-4-yl)-4-((methylamino)methyl)-benzamide | 411.0 |
| 394 | 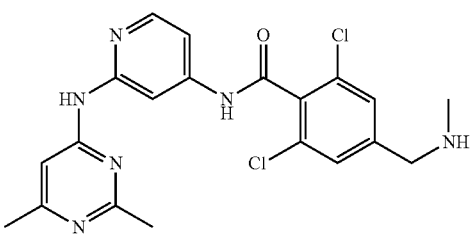 | 2,6-dichloro-N-(2-(2,6-dimethylpyrimidin-4-ylamino)pyridin-4-yl)-4-((methylamino)methyl)-benzamide | 431.1 |
| 395 | 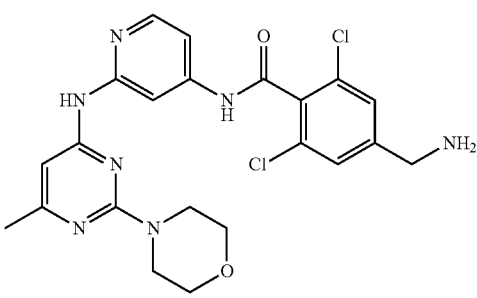 [SMILES: Cc1cc(Nc2cc(NC(=O)c3c(Cl)cc(CN)cc3Cl)ccn2)nc(N2CCOCC2)n1] | 4-(aminomethyl)-2,6-dichloro-N-(2-(6-methyl-2-morpholinopyrimidin-4-ylamino)pyridin-4-yl)benzamide | 488.1 |
| 396 | 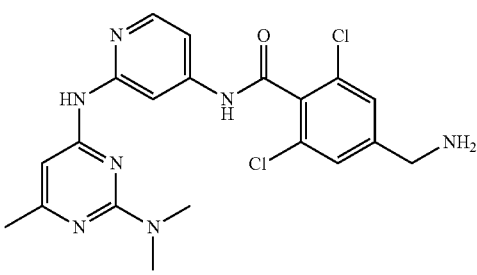 [SMILES: Cc1cc(Nc2cc(NC(=O)c3c(Cl)cc(CN)cc3Cl)ccn2)nc(N(C)C)n1] | 4-(aminomethyl)-2,6-dichloro-N-(2-(2-(dimethylamino)-6-methylpyrimidin-4-ylamino)pyridin-4-yl)benzamide | 446.1 |

TABLE 3-continued

| # | Structure | Name | MW |
|---|-----------|------|-----|
| 397 | 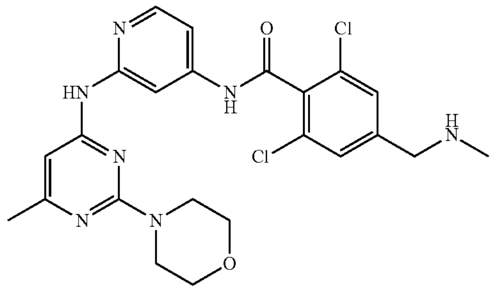 | 2,6-dichloro-N-(2-(6-methyl-2-morpholinopyrimidin-4-ylamino)pyridin-4-yl)-4-((methylamino)methyl)-benzamide | 502.1 |
| 398 | 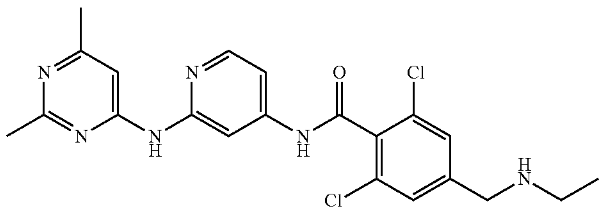 [SMILES: CCNCc1cc(Cl)c(C(=O)Nc2ccnc(Nc3cc(C)nc(C)n3)c2)c(Cl)c1] | 2,6-dichloro-N-(2-(2,6-dimethylpyrimidin-4-ylamino)pyridin-4-yl)-4-((ethylamino)methyl)-benzamide | 445.1 |
| 399 | 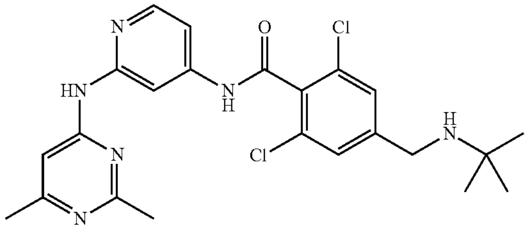 [SMILES: Cc1cc(Nc2cc(NC(=O)c3c(Cl)cc(CNC(C)(C)C)cc3Cl)ccn2)nc(C)n1] | 4-((tert-butylamino)methyl)-2,6-dichloro-N-(2-(2,6-dimethylpyrimidin-4-ylamino)pyridin-4-yl)benzamide | 473.1 |
| 400 | 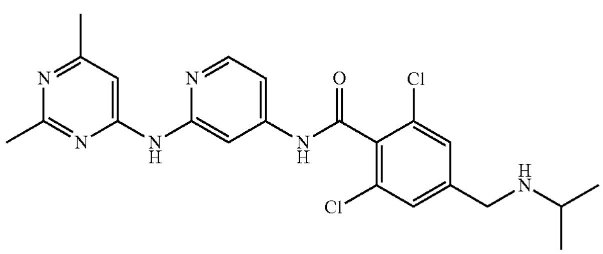 [SMILES: Cc1cc(Nc2cc(NC(=O)c3c(Cl)cc(CNC(C)C)cc3Cl)ccn2)nc(C)n1] | 2,6-dichloro-N-(2-(2,6-dimethylpyrimidin-4-ylamino)pyridin-4-yl)-4-((isopropylamino)methyl)-benzamide | 459.1 |
| 401 | 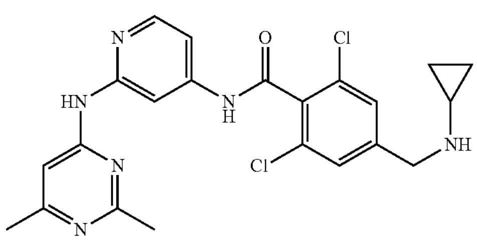 [SMILES: Cc1cc(Nc2cc(NC(=O)c3c(Cl)cc(CNC4CC4)cc3Cl)ccn2)nc(C)n1] | 2,6-dichloro-4-((cyclopropylamino)methyl)-N-(2-(2,6-dimethylpyrimidin-4-ylamino)pyridin-4-yl)benzamide | 457.1 |
| 402 | 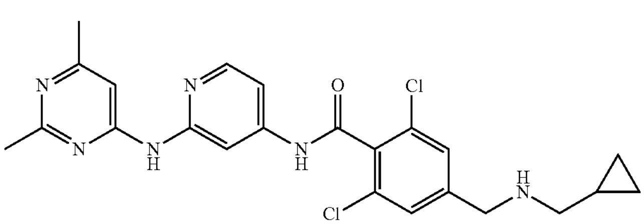 [SMILES: Cc1cc(Nc2cc(NC(=O)c3c(Cl)cc(CNCC4CC4)cc3Cl)ccn2)nc(C)n1] | 2,6-dichloro-4-((cyclopropanemethylamino)methyl)-N-(2-(2,6-dimethylpyrimidin-4-ylamino)pyridin-4-yl)benzamide | 471.1 |

TABLE 3-continued

| | | | |
|---|---|---|---|
| 403 | | 2,6-dichloro-4-((ethylamino)methyl)-N-(2-(6-methyl-2-morpholinopyrimidin-4-ylamino)pyridin-4-yl)benzamide | 516.2 |
| 404 | | 2,6-dichloro-4-((isopropylamino)methyl)-N-(2-(6-methyl-2-morpholinopyrimidin-4-ylamino)pyridin-4-yl)benzamide | 530.1 |
| 405 | | 2,6-dichloro-4-((cyclopropylamino)methyl)-N-(2-(6-methyl-2-morpholinopyrimidin-4-ylamino)pyridin-4-yl)benzamide | 528.2 |
| 406 | | 2,6-dichloro-4-((cyclopropylmethylamino)methyl)-N-(2-(6-methyl-2-morpholinopyrimidin-4-ylamino)pyridin-4-yl)benzamide | 542.2 |
| 407 | | 2,6-dichloro-N-(2-(cyclopropanecarboxamido)pyridin-4-yl)-4-methoxybenzamide | 380.0 |

| | | | |
|---|---|---|---|
| 408 | | 2,6-dichloro-N-(2-(2,6-dimethylpyrimidin-4-ylamino)pyridin-4-yl)-4-((2-hydroxyethylamino)-methyl)-benzamide | 461.1 |
| 409 | | 2,4-dichloro-N-(2-(cyclopropanecarbox-amido)pyridin-4-yl)-6-methoxybenzamide | 380.0 |
| 410 | | 2,6-dichloro-N-(2-(cyclopropanecarbox-amido)pyridin-4-yl)-4-hydroxybenzamide | 366.0 |
| 411 | | 2,4-dichloro-N-(2-(cyclopropanecarbox-amido)pyridin-4-yl)-6-hydroxybenzamide | 366.0 |
| 412 | | 2,4,6-trichloro-N-(2-(2-((2-hydroxyethyl)(methyl)-amino)-6-methylpyrimidin-4-ylamino)pyridin-4-yl)benzamide | 483.0 |

TABLE 3-continued

| | | | |
|---|---|---|---|
| 413 | 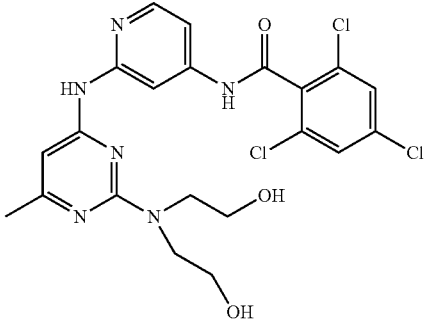 [SMILES: Cc1cc(Nc2cc(NC(=O)c3c(Cl)cc(Cl)cc3Cl)ccn2)nc(N(CCO)CCO)n1] | N-(2-(2-(bis(2-hydroxyethyl)amino)-6-methylpyrimidin-4-ylamino)pyridin-4-yl)-2,4,6-trichlorobenzamide | 511.1 |
| 414 | 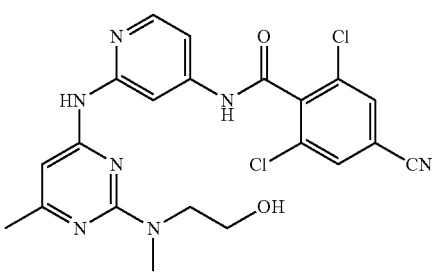 [SMILES: Cc1cc(Nc2cc(NC(=O)c3c(Cl)cc(C#N)cc3Cl)ccn2)nc(N(C)CCO)n1] | 2,6-dichloro-4-cyano-N-(2-(2-((2-hydroxyethyl)(methyl)-amino)-6-methylpyrimidin-4-ylamino)pyridin-4-yl)benzamide | 458.0 |
| 415 | 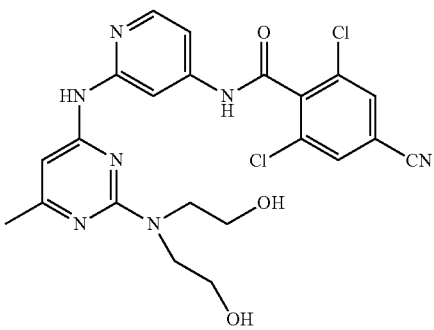 [SMILES: Cc1cc(Nc2cc(NC(=O)c3c(Cl)cc(C#N)cc3Cl)ccn2)nc(N(CCO)CCO)n1] | N-(2-(2-(bis(2-hydroxyethyl)amino)-6-methylpyrimidin-4-ylamino)pyridin-4-yl)-2,6-dichloro-4-cyanobenzamide | 502.1 |
| 416 | 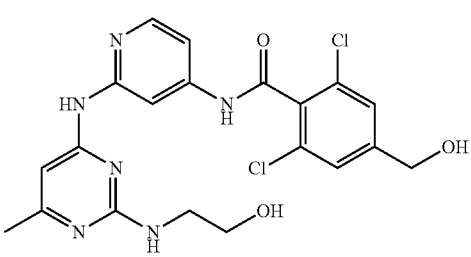 [SMILES: Cc1cc(Nc2cc(NC(=O)c3c(Cl)cc(CO)cc3Cl)ccn2)nc(NCCO)n1] | 2,6-dichloro-N-(2-(2-(2-hydroxyethylamino)-6-methylpyrimidin-4-ylamino)pyridin-4-yl)-4-(hydroxymethyl)-benzamide | 463.1 |
| 417 | 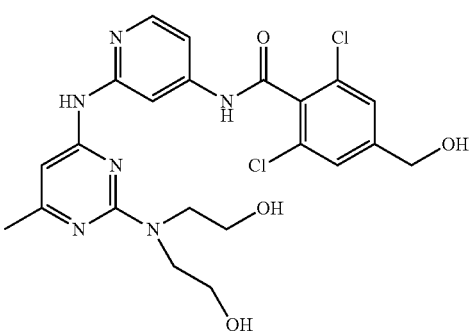 [SMILES: Cc1cc(Nc2cc(NC(=O)c3c(Cl)cc(CO)cc3Cl)ccn2)nc(N(CCO)CCO)n1] | N-(2-(2-(bis(2-hydroxyethyl)amino)-6-methylpyrimidin-4-ylamino)pyridin-4-yl)-2,6-dichloro-4-(hydroxymethyl)benz-amide | 507.1 |

TABLE 3-continued

| | | | |
|---|---|---|---|
| 418 | 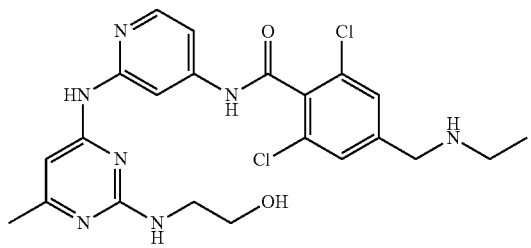 [SMILES: CCNCc1cc(Cl)c(C(=O)Nc2ccnc(Nc3cc(C)nc(NCCO)n3)c2)c(Cl)c1] | 2,6-dichloro-4-(ethylamino)methyl)-N-(2-(2-(2-hydroxyethylamino)-6-methylpyrimidin-4-ylamino)pyridin-4-yl)benzamide | 490.1 |
| 419 | 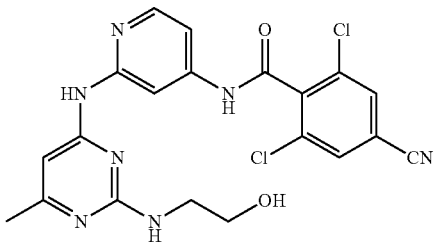 [SMILES: Cc1cc(Nc2cc(NC(=O)c3c(Cl)cc(C#N)cc3Cl)ccn2)nc(NCCO)n1] | 2,6-dichloro-4-cyano-N-(2-(2-(2-hydroxyethylamino)-6-methylpyrimidin-4-ylamino)pyridin-4-yl)benzamide | 458.0 |
| 420 | 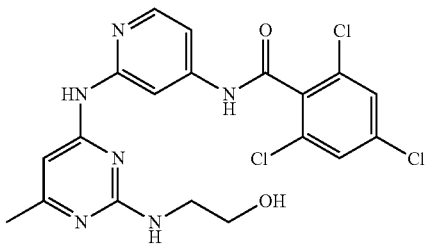 [SMILES: Cc1cc(Nc2cc(NC(=O)c3c(Cl)cc(Cl)cc3Cl)ccn2)nc(NCCO)n1] | 2,4,6-trichloro-N-(2-(2-(2-hydroxyethylamino)-6-methylpyrimidin-4-ylamino)pyridin-4-yl)benzamide | 469.0 |
| 421 | 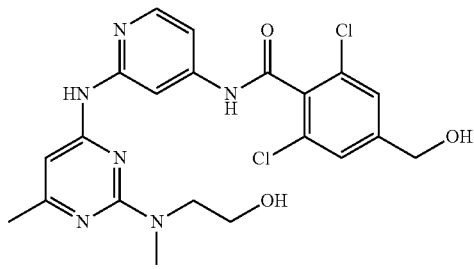 [SMILES: Cc1cc(Nc2cc(NC(=O)c3c(Cl)cc(CO)cc3Cl)ccn2)nc(N(C)CCO)n1] | 2,6-dichloro-N-(2-(2-((2-hydroxyethyl)(methyl)-amino)-6-methylpyrimidin-4-ylamino)pyridin-4-yl)-4-(hydroxymethyl)benzamide | 477.1 |
| 422 | 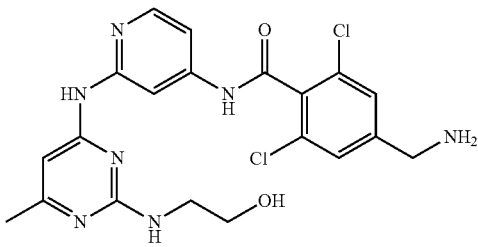 [SMILES: Cc1cc(Nc2cc(NC(=O)c3c(Cl)cc(CN)cc3Cl)ccn2)nc(NCCO)n1] | 4-(aminomethyl)-2,6-dichloro-N-(2-(2-(2-hydroxyethylamino)-6-methylpyrimidin-4-ylamino)pyridin-4-yl)benzamide | 462.1 |
| 423 | 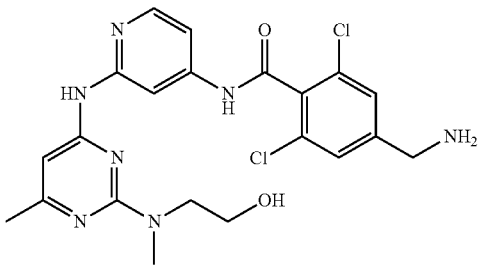 [SMILES: Cc1cc(Nc2cc(NC(=O)c3c(Cl)cc(CN)cc3Cl)ccn2)nc(N(C)CCO)n1] | 4-(aminomethyl)-2,6-dichloro-N-(2-(2-((2-hydroxyethyl)(methyl)-amino)-6-methylpyrimidin-4-ylamino)pyridin-4-yl)benzamide | 476.1 |

TABLE 3-continued

| | | | |
|---|---|---|---|
| 424 | 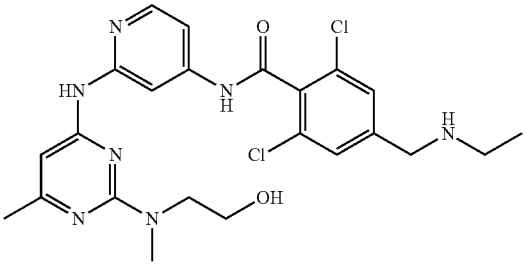 [SMILES: CCNCc1cc(Cl)c(C(=O)Nc2ccnc(Nc3cc(C)nc(N(C)CCO)n3)c2)c(Cl)c1] | 2,6-dichloro-4-((ethylamino)methyl)-N-(2-(2-((2-hydroxyethyl)(methyl)-amino)-6-methylpyrimidin-4-ylamino)pyridin-4-yl)benzamide | 504.1 |
| 425 | 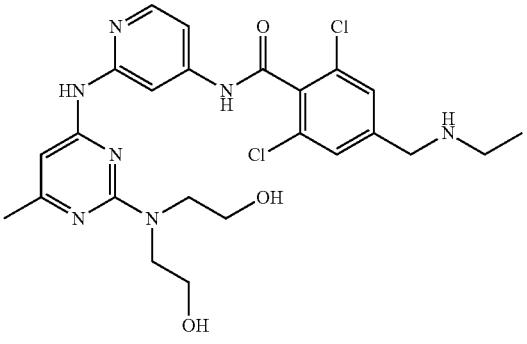 [SMILES: CCNCc1cc(Cl)c(C(=O)Nc2ccnc(Nc3cc(C)nc(N(CCO)CCO)n3)c2)c(Cl)c1] | N-(2-(2-(bis(2-hydroxyethyl)amino)-6-methylpyrimidin-4-ylamino)pyridin-4-yl)-2,6-dichloro-4-((ethylamino)methyl)benz-amide | 534.2 |
| 426 | 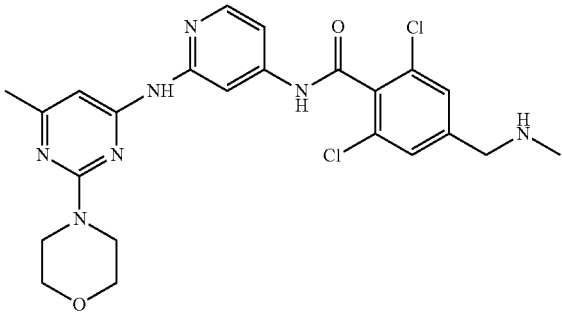 | 4-((tert-butylamino)methyl)-2,6-dichloro-N-(2-(6-methyl-2-morpholinopyrimidin-4-ylamino)pyridin-4-yl)benzamide | 544.2 |
| 427 | 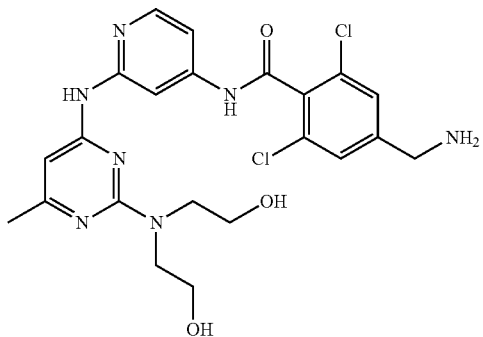 [SMILES: Cc1cc(Nc2cc(NC(=O)c3c(Cl)cc(CN)cc3Cl)ccn2)nc(N(CCO)CCO)n1] | 4-(aminomethyl)-N-(2-(2-(bis(2-hydroxyethyl)amino)-6-methylpyrimidin-4-ylamino)pyridin-4-yl)-2,6-dichlorobenzamide | 506.1 |
| 428 | 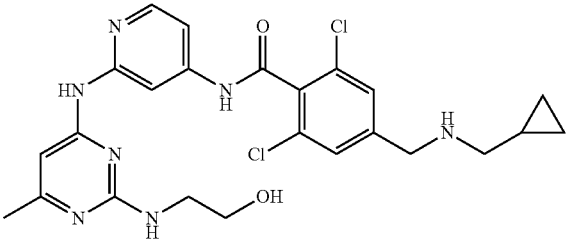 [SMILES: Cc1cc(Nc2cc(NC(=O)c3c(Cl)cc(CNCC4CC4)cc3Cl)ccn2)nc(NCCO)n1] | 2,6-dichloro-4-((cyclopropylmethylamino)-methyl)-N-(2-(2-(2-hydroxyethylamino)-6-methylpyrimidin-4-ylamino)pyridin-4-yl)benzamide | 516.2 |

TABLE 3-continued

| | | | |
|---|---|---|---|
| 429 | 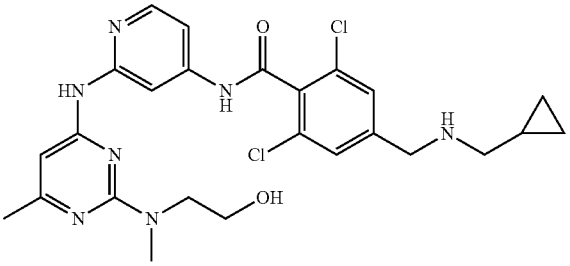 [SMILES: Cc1cc(Nc2cc(NC(=O)c3c(Cl)cc(CNCC4CC4)cc3Cl)ccn2)nc(N(C)CCO)n1] | 2,6-dichloro-4-((cyclopropylmethylamino)-methyl)-N-(2-(2-((2-hydroxyethyl)(methyl)-amino)-6-methylpyrimidin-4-ylamino)pyridin-4-yl)benzamide | 530.2 |
| 430 | 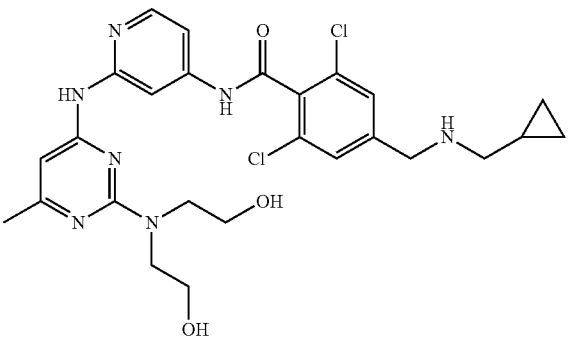 [SMILES: Cc1cc(Nc2cc(NC(=O)c3c(Cl)cc(CNCC4CC4)cc3Cl)ccn2)nc(N(CCO)CCO)n1] | N-(2-(2-(bis(2-hydroxyethyl)amino)-6-methylpyrimidin-4-ylamino)pyridin-4-yl)-2,6-dichloro-4-((cyclopropylmethylamino)-methyl)benzamide | 560.2 |
| 431 | 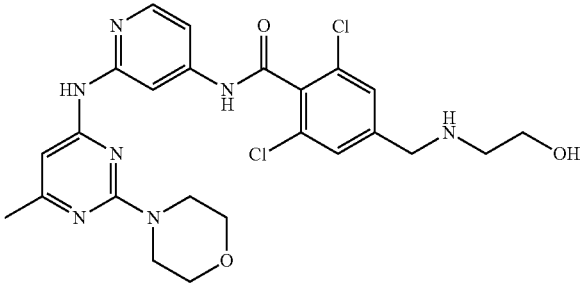 [SMILES: Cc1cc(Nc2cc(NC(=O)c3c(Cl)cc(CNCCO)cc3Cl)ccn2)nc(N2CCOCC2)n1] | 2,6-dichloro-4-((2-hydroxyethylamino)-methyl)-N-(2-(6-methyl-2-morpholinopyrimidin-4-ylamino)pyridin-4-yl)benzamide | 532.1 |
| 432 | 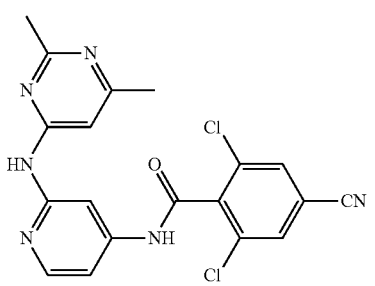 [SMILES: Cc1cc(Nc2cc(NC(=O)c3c(Cl)cc(C#N)cc3Cl)ccn2)nc(C)n1] | 2,6-dichloro-4-cyano-N-(2-(2,6-dimethylpyrimidin-4-ylamino)pyridin-4-yl)benzamide | 412.9 |
| 433 | 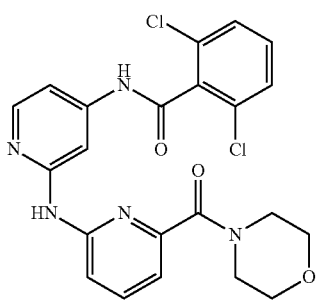 [SMILES: O=C(Nc1ccnc(Nc2cccc(C(=O)N3CCOCC3)n2)c1)c1c(Cl)cccc1Cl] | 2,6-dichloro-N-(2-(6-(morpholine-4-carbonyl)pyridin-2-ylamino)pyridin-4-yl)benzamide | 472.1 |

TABLE 3-continued

| | | | |
|---|---|---|---|
| 434 | | 2,6-dichloro-N-(2-(5-(morpholinomethyl)-pyridin-2-ylamino)pyridin-4-yl)benzamide | 458.1 |
| 435 | | 2,6-dichloro-N-(2-(2-(4-methyl-1,4-diazepan-1-yl)pyrimidin-4-ylamino)pyridin-4-yl)benzamide | 472.1 |
| 436 | | 2,6-dichloro-N-(2-(5-((4-methylpiperazin-1-yl)methyl)pyridin-2-ylamino)pyridin-4-yl)benzamide | 471.1 |
| 437 | | 2,6-dichloro-N-(2-(6-methyl-2-morpholinopyrimidin-4-ylamino)pyridin-4-yl)benzamide | 459.1 |

TABLE 3-continued
| | | | |
|---|---|---|---|
| 438 | 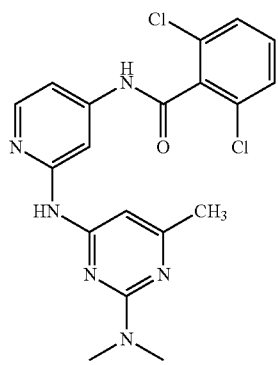 | 2,6-dichloro-N-(2-(2-(dimethylamino)-6-methylpyrimidin-4-ylamino)pyridin-4-yl)benzamide | 417.1 |
| 439 | 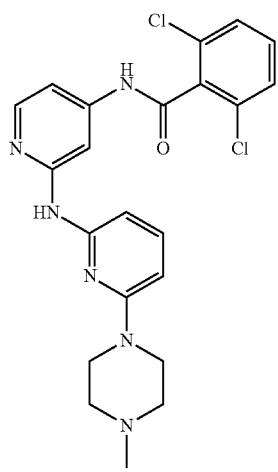 [SMILES: CN1CCN(c2cccc(Nc3cc(NC(=O)c4c(Cl)cccc4Cl)ccn3)n2)CC1] | 2,6-dichloro-N-(2-(6-(4-methylpiperazin-1-yl)pyridin-2-ylamino)pyridin-4-yl)benzamide | 457.1 |
| 440 | 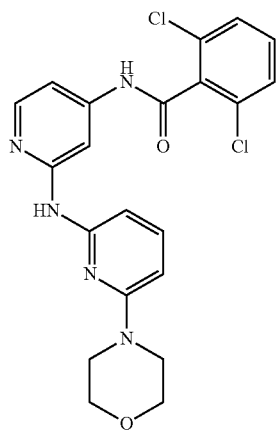 | 2,6-dichloro-N-(2-(6-morpholinopyridin-2-ylamino)pyridin-4-yl)benzamide | 444.1 |
| 441 | 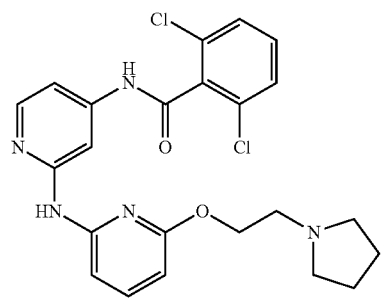 [SMILES: O=C(Nc1ccnc(Nc2cccc(OCCN3CCCC3)n2)c1)c1c(Cl)cccc1Cl] | 2,6-dichloro-N-(2-(6-(2-(pyrrolidin-1-yl)ethoxy)pyridin-2-ylamino)pyridin-4-yl)benzamide | 472.1 |

| | | | |
|---|---|---|---|
| 442 | 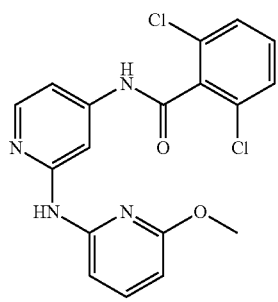 [SMILES: COc1cccc(Nc2cc(NC(=O)c3c(Cl)cccc3Cl)ccn2)n1] | 2,6-dichloro-N-(2-(6-methoxypyridin-2-ylamino)pyridin-4-yl)benzamide | 389.1 |
| 443 | 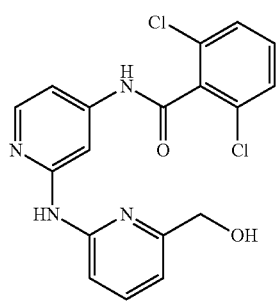 | 2,6-dichloro-N-(2-(6-(hydroxymethyl)pyridin-2-ylamino)pyridin-4-yl)benzamide | 389.0 |
| 444 | 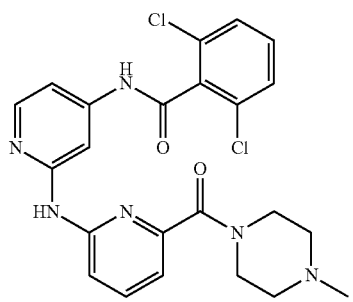 [SMILES: CN1CCN(C(=O)c2cccc(Nc3cc(NC(=O)c4c(Cl)cccc4Cl)ccn3)n2)CC1] | 2,6-dichloro-N-(2-(6-(4-methylpiperazine-1-carbonyl)pyridin-2-ylamino)pyridin-4-yl)benzamide | 485.1 |
| 445 | 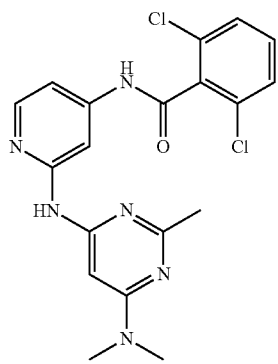 [SMILES: Cc1nc(Nc2cc(NC(=O)c3c(Cl)cccc3Cl)ccn2)cc(N(C)C)n1] | 2,6-dichloro-N-(2-(6-(dimethylamino)-2-methylpyrimidin-4-ylamino)pyridin-4-yl)benzamide | 417.1 |

TABLE 3-continued

| | | | |
|---|---|---|---|
| 446 | | 2,6-dichloro-N-(2-(2-methyl-6-morpholinopyrimidin-4-ylamino)pyridin-4-yl)benzamide | 459.1 |
| 447 | | 2,6-dichloro-N-(2-(5-(dimethylamino)pyridin-2-ylamino)pyridin-4-yl)benzamide | 402.0 |
| 448 | | 2,6-dichloro-N-(2-(4-morpholinopyridin-2-ylamino)pyridin-4-yl)benzamide | 444.1 |
| 449 | | (R)-2,6-dichloro-N-(2-(1-(2-hydroxypropyl)-1H-pyrazol-4-ylamino)pyridin-4-yl)benzamide | 406.0 |

TABLE 3-continued
| | | | |
|---|---|---|---|
| 450 | 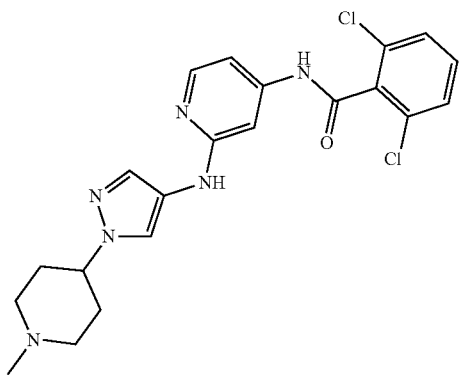 [SMILES: CN1CCC(n2cc(Nc3cc(NC(=O)c4c(Cl)cccc4Cl)ccn3)cn2)CC1] | 2,6-dichloro-N-(2-(1-(1-methylpiperidin-4-yl)-1H-pyrazol-4-ylamino)pyridin-4-yl)benzamide | 445.1 |
| 451 | 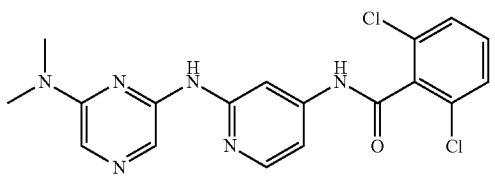 [SMILES: CN(C)c1cncc(Nc2cc(NC(=O)c3c(Cl)cccc3Cl)ccn2)n1] | 2,6-dichloro-N-(2-(6-(dimethylamino)pyrazin-2-ylamino)pyridin-4-yl)benzamide | 403.1 |
| 452 | 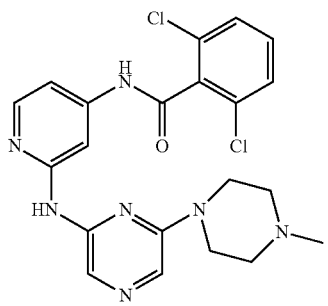 [SMILES: CN1CCN(c2cncc(Nc3cc(NC(=O)c4c(Cl)cccc4Cl)ccn3)n2)CC1] | 2,6-dichloro-N-(2-(6-(4-methylpierazin-1-yl)pyrazin-2-ylamino)pyridin-4-yl)benzamide | 458.1 |
| 453 | 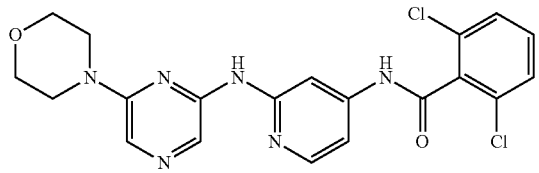 [SMILES: O=C(Nc1ccnc(Nc2cncc(N3CCOCC3)n2)c1)c1c(Cl)cccc1Cl] | 2,6-dichloro-N-(2-(6-morpholinopyrazin-2-ylamino)pyridin-4-yl)benzamide | 445.1 |
| 454 | 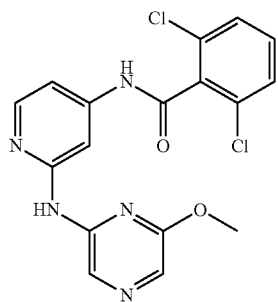 [SMILES: COc1cncc(Nc2cc(NC(=O)c3c(Cl)cccc3Cl)ccn2)n1] | 2,6-dichloro-N-(2-(6-methoxypyrazin-2-ylamino)pyridin-4-yl)benzamide | 390.0 |

| | | | |
|---|---|---|---|
| 455 | 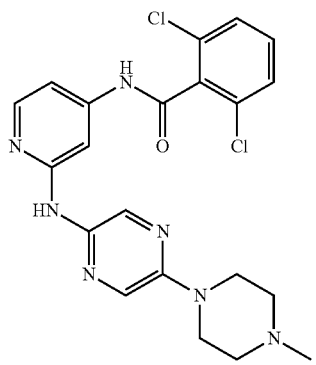 [SMILES: CN1CCN(c2cnc(Nc3cc(NC(=O)c4c(Cl)cccc4Cl)ccn3)cn2)CC1] | 2,6-dichloro-N-(2-(5-(4-methylpiperazin-1-yl)pyrazin-2-ylamino)pyridin-4-yl)benzamide | 458.0 |
| 456 | 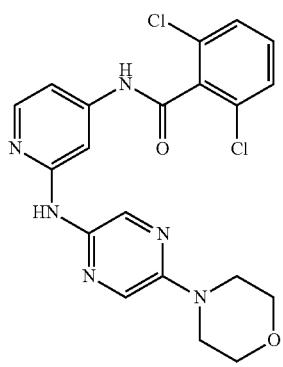 [SMILES: O=C(Nc1ccnc(Nc2cnc(N3CCOCC3)cn2)c1)c1c(Cl)cccc1Cl] | 2,6-dichloro-N-(2-(5-morpholinopyrazin-2-ylamino)pyridin-4-yl)benzamide | 445.0 |
| 457 | 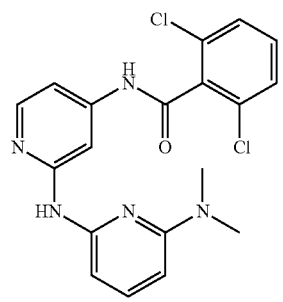 [SMILES: CN(C)c1cccc(Nc2cc(NC(=O)c3c(Cl)cccc3Cl)ccn2)n1] | 2,6-dichloro-N-(2-(6-(dimethylamino)pyridin-2-ylamino)pyridin-4-yl)benzamide | 402.1 |
| 458 | 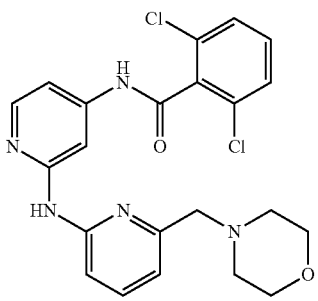 [SMILES: O=C(Nc1ccnc(Nc2cccc(CN3CCOCC3)n2)c1)c1c(Cl)cccc1Cl] | 2,6-dichloro-N-(2-(6-(morpholinomethyl)pyridin-2-ylamino)pyridin-4-yl)benzamide | 458.1 |

TABLE 3-continued
| | | | |
|---|---|---|---|
| 459 | 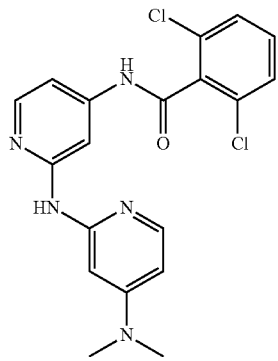 [SMILES: CN(C)c1ccnc(Nc2cc(NC(=O)c3c(Cl)cccc3Cl)ccn2)c1] | 2,6-dichloro-N-(2-(4-(dimethylamino)pyridin-2-ylamino)pyridin-4-yl)benzamide | 402.0 |
| 460 | 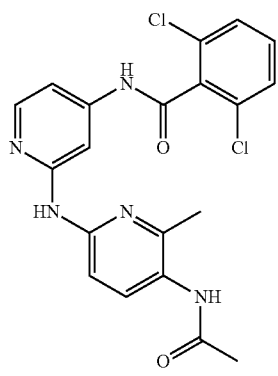 [SMILES: CC(=O)Nc1ccc(Nc2cc(NC(=O)c3c(Cl)cccc3Cl)ccn2)nc1C] | N-(2-(5-acetamido-6-methylpyridin-2-ylamino)pyridin-4-yl)-2,6-dichlorobenzamide | 430.1 |
| 461 | 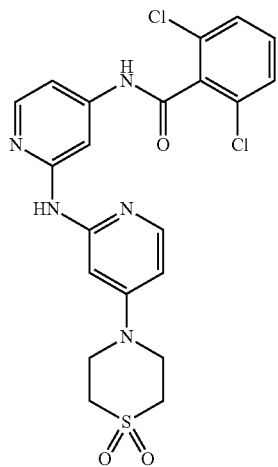 [SMILES: O=C(Nc1ccnc(Nc2cc(N3CCS(=O)(=O)CC3)ccn2)c1)c1c(Cl)cccc1Cl] | 2,6-dichloro-N-(2-(4-(S-dioxa-thiomorpholino)pyridin-2-ylamino)pyridin-4-yl)benzamide | 492.0 |
| 462 | 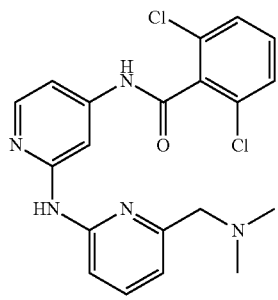 [SMILES: CN(C)Cc1cccc(Nc2cc(NC(=O)c3c(Cl)cccc3Cl)ccn2)n1] | 2,6-dichloro-N-(2-(6-((dimethylamino)methyl)-pyridin-2-ylamino)pyridin-4-yl)benzamide | 416.0 |

| | | | |
|---|---|---|---|
| 463 | 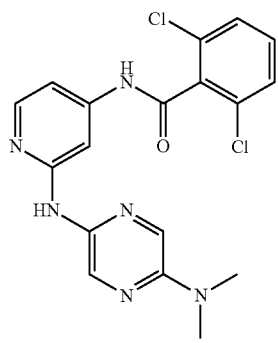 [SMILES: CN(C)c1cnc(Nc2cc(NC(=O)c3c(Cl)cccc3Cl)ccn2)cn1] | 2,6-dichloro-N-(2-(5-(dimethylamino)pyrazin-2-ylamino)pyridin-4-yl)benzamide | 403.0 |
| 464 | 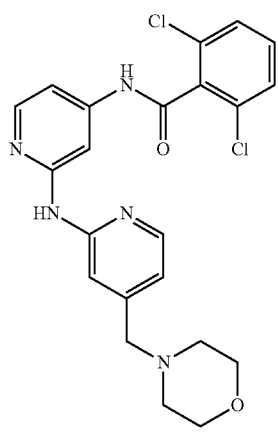 [SMILES: O=C(Nc1ccnc(Nc2cc(CN3CCOCC3)ccn2)c1)c1c(Cl)cccc1Cl] | 2,6-dichloro-N-(2-(4-(morpholinomethyl)-pyridin-2-ylamino)pyridin-4-yl)benzamide | 458.0 |
| 465 | 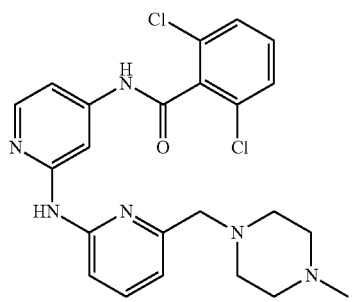 | 2,6-dichloro-N-(2-(6-((4-methylpiperazin-1-yl)methyl)pyridin-2-ylamino)pyridin-4-yl)benzamide | 471.1 |
| 466 | 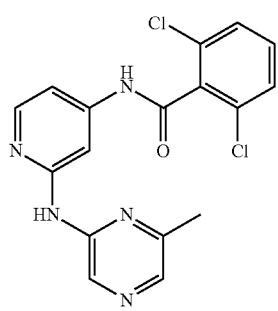 [SMILES: Cc1cncc(Nc2cc(NC(=O)c3c(Cl)cccc3Cl)ccn2)n1] | 2,6-dichloro-N-(2-(6-methylpyrazin-2-ylamino)pyridin-4-yl)benzamide | 374.1 |

TABLE 3-continued
| 467 | 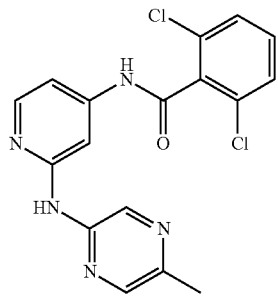 [SMILES: Cc1cnc(Nc2cc(NC(=O)c3c(Cl)cccc3Cl)ccn2)cn1] | 2,6-dichloro-N-(2-(5-methylpyrazin-2-ylamino)pyridin-4-yl)benzamide | 374.1 |
| 468 | 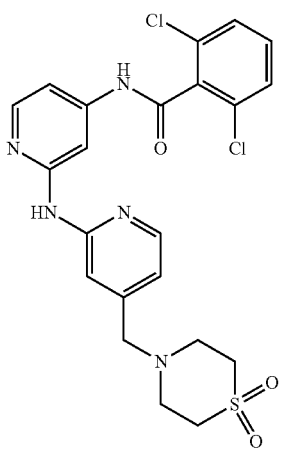 [SMILES: O=C(Nc1ccnc(Nc2cc(CN3CCS(=O)(=O)CC3)ccn2)c1)c1c(Cl)cccc1Cl] | 2,6-dichloro-N-(2-(4-(S-dioxa-thiomorpholinomethyl)-pyridin-2-ylamino)pyridin-4-yl)benzamide | 506.1 |
| 469 | 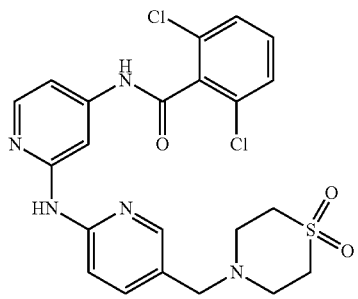 [SMILES: O=C(Nc1ccnc(Nc2ccc(CN3CCS(=O)(=O)CC3)cn2)c1)c1c(Cl)cccc1Cl] | 2,6-dichloro-N-(2-(5-(S-dioxa-thiomorpholinomethyl)-pyridin-2-ylamino)pyridin-4-yl)benzamide | 506.0 |
| 470 | 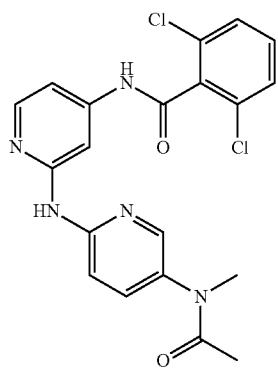 [SMILES: CC(=O)N(C)c1ccc(Nc2cc(NC(=O)c3c(Cl)cccc3Cl)ccn2)nc1] | 2,6-dichloro-N-(2-(5-(N-methylacetamido)pyridin-2-ylamino)pyridin-4-yl)benzamide | 430.1 |

| | | | |
|---|---|---|---|
| 471 | 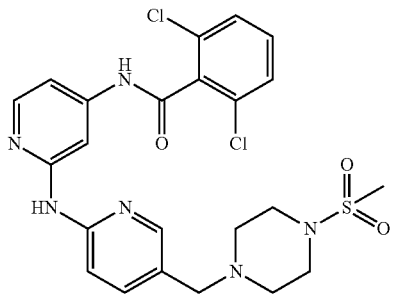 [SMILES: CS(=O)(=O)N1CCN(Cc2ccc(Nc3cc(NC(=O)c4c(Cl)cccc4Cl)ccn3)nc2)CC1] | 2,6-dichloro-N-(2-(5-((4-(methylsulfonyl)piperazin-1-yl)methyl)pyridin-2-ylamino)pyridin-4-yl)benzamide | 535.2 |
| 472 | 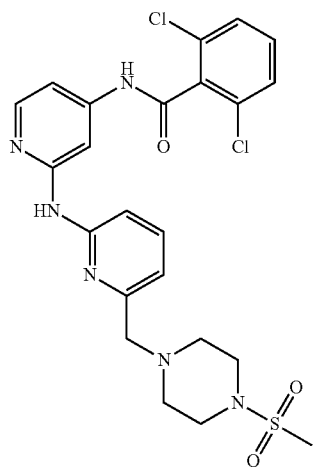 [SMILES: CS(=O)(=O)N1CCN(Cc2cccc(Nc3cc(NC(=O)c4c(Cl)cccc4Cl)ccn3)n2)CC1] | 2,6-dichloro-N-(2-(6-((4-(methylsulfonyl)piperazin-1-yl)methyl)pyridin-2-ylamino)pyridin-4-yl)benzamide | 535.1 |
| 473 | 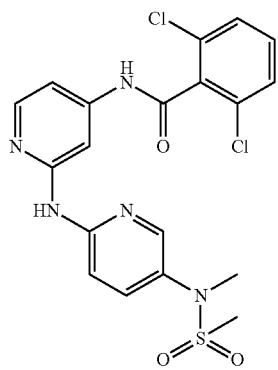 [SMILES: CN(c1ccc(Nc2cc(NC(=O)c3c(Cl)cccc3Cl)ccn2)nc1)S(C)(=O)=O] | 2,6-dichloro-N-(2-(5-(N-methylmethylsulfonamido)-pyridin-2-ylamino)pyridin-4-yl)benzamide | 466.0 |
| 474 | 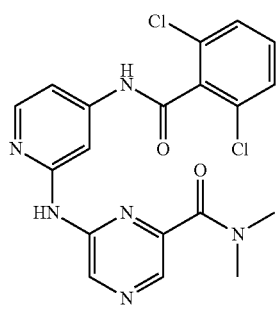 [SMILES: CN(C)C(=O)c1cncc(Nc2cc(NC(=O)c3c(Cl)cccc3Cl)ccn2)n1] | 6-(4-(2,6-dichlorobenzamido)-pyridin-2-ylamino)-N,N-dimethylpyrazine-2-carboxamide | 431.0 |

TABLE 3-continued
| | | | |
|---|---|---|---|
| 475 | 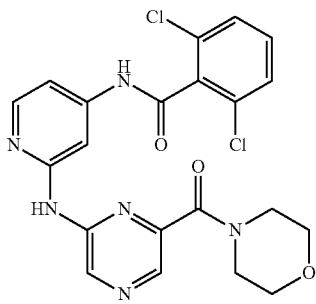 [SMILES: O=C(Nc1ccnc(Nc2cncc(C(=O)N3CCOCC3)n2)c1)c1c(Cl)cccc1Cl] | 2,6-dichloro-N-(2-(6-(morpholin-4-carbonyl)pyrazin-2-ylamino)pyridin-4-yl)benzamide | 473.1 |
| 476 | 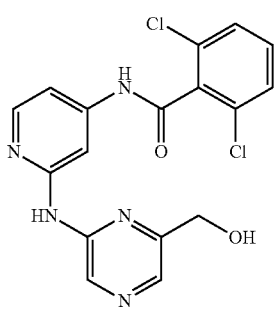 [SMILES: O=C(Nc1ccnc(Nc2cncc(CO)n2)c1)c1c(Cl)cccc1Cl] | 2,6-dichloro-N-(2-(6-(hydroxymethyl)pyrazin-2-ylamino)pyridin-4-yl)benzamide | 390.1 |
| 477 | 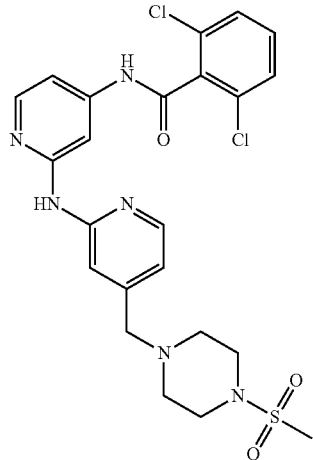 [SMILES: CS(=O)(=O)N1CCN(Cc2ccnc(Nc3cc(NC(=O)c4c(Cl)cccc4Cl)ccn3)c2)CC1] | 2,6-dichloro-N-(2-(4-((4-(methylsulfonyl)piperazin-1-yl)methyl)pyridin-2-ylamino)pyridin-4-yl)benzamide | 535.1 |
| 478 | 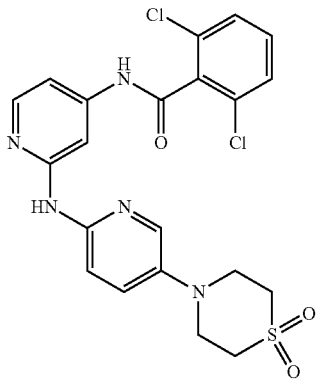 [SMILES: O=C(Nc1ccnc(Nc2ccc(N3CCS(=O)(=O)CC3)cn2)c1)c1c(Cl)cccc1Cl] | 2,6-dichloro-N-(2-(5-(S-dioxa-thiomorpholino)pyridin-2-ylamino)pyridin-4-yl)benzamide | 492.1 |

TABLE 3-continued
| | | | |
|---|---|---|---|
| 479 | 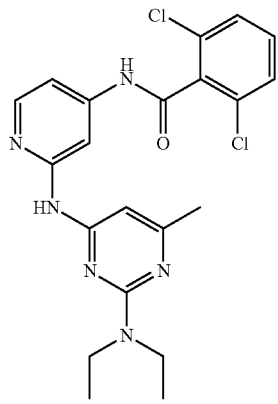 [SMILES: CCN(CC)c1nc(C)cc(Nc2cc(NC(=O)c3c(Cl)cccc3Cl)ccn2)n1] | 2,6-dichloro-N-(2-(2-(diethylamino)-6-methylpyrimidin-4-ylamino)pyridin-4-yl)benzamide | 445.1 |
| 480 | 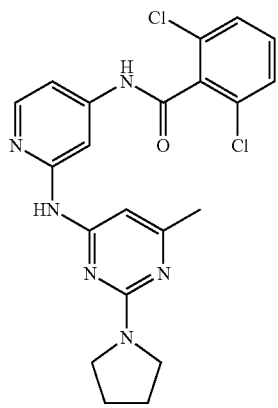 [SMILES: Cc1cc(Nc2cc(NC(=O)c3c(Cl)cccc3Cl)ccn2)nc(N2CCCC2)n1] | 2,6-dichloro-N-(2-(6-methyl-2-(pyrrolidin-1-yl)pyrimidin-4-ylamino)pyridin-4-yl)benzamide | 443.1 |
| 481 | 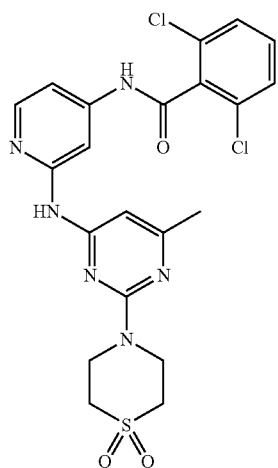 [SMILES: Cc1cc(Nc2cc(NC(=O)c3c(Cl)cccc3Cl)ccn2)nc(N2CCS(=O)(=O)CC2)n1] | 2,6-dichloro-N-(2-(6-methyl-2-(S-dioxa-thiomorpholino)pyrimidin-4-ylamino)pyridin-4-yl)benzamid | 507.0 |

TABLE 3-continued
| | | | |
|---|---|---|---|
| 482 | 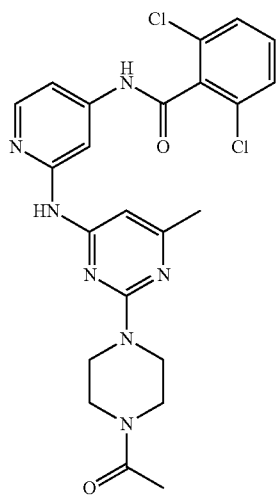 [SMILES: CC(=O)N1CCN(c2nc(C)cc(Nc3cc(NC(=O)c4c(Cl)cccc4Cl)ccn3)n2)CC1] | N-(2-(2-(4-acetylpiperazin-1-yl)-6-methylpyrimidin-4-ylamino)pyridin-4-yl)-2,6-dichlorobenzamide | 500.1 |
| 483 | 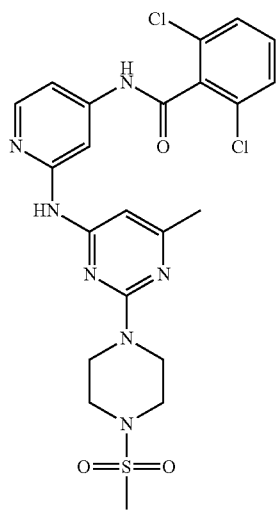 [SMILES: Cc1cc(Nc2cc(NC(=O)c3c(Cl)cccc3Cl)ccn2)nc(N2CCN(S(C)(=O)=O)CC2)n1] | 2,6-dichloro-N-(2-(6-methyl-2-(4-(methylsulfonyl)piperazin-1-yl)pyrimidin-4-ylamino)pyridin-4-yl)benzamide | 536.1 |
| 484 | 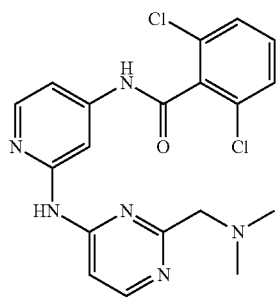 [SMILES: CN(C)Cc1nccc(Nc2cc(NC(=O)c3c(Cl)cccc3Cl)ccn2)n1] | 2,6-dichloro-N-(2-(2-((dimethylamino)methyl)-pyrimidin-4-ylamino)pyridin-4-yl)benzamide | 417.1 |
| 485 | 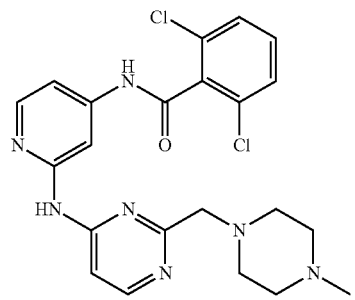 [SMILES: CN1CCN(Cc2nccc(Nc3cc(NC(=O)c4c(Cl)cccc4Cl)ccn3)n2)CC1] | 2,6-dichloro-N-(2-(2-((4-methylpiperazin-1-yl)methyl)pyrimidin-4-ylamino)pyridin-4-yl)benzamide | 472.1 |

TABLE 3-continued

| | | | |
|---|---|---|---|
| 486 | | 2,6-dichloro-N-(2-(2-(morpholinomethyl)-pyrimidin-4-ylamino)pyridin-4-yl)benzamide | 459.1 |
| 487 | | 2,6-dichloro-N-(2-(2-(4-hydroxypiperidin-1-yl)-6-methylpyrimidin-4-ylamino)pyridin-4-yl)benzamide | 473.1 |
| 488 | | 2,6-dichloro-N-(2-(2-(S-dioxa-thiomorpholinomethyl)-pyrimidin-4-ylamino)pyridin-4-yl)benzamide | 507.0 |
| 489 | | N-(2-(2-(azetidin-1-yl)-6-methylpyrimidin-4-ylamino)pyridin-4-yl)-2,6-dichlorobenzamide | 429.1 |

| | | | |
|---|---|---|---|
| 490 | 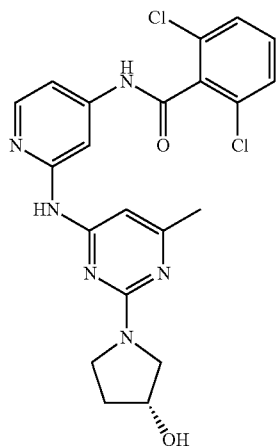 [SMILES: Cc1cc(Nc2cc(NC(=O)c3c(Cl)cccc3Cl)ccn2)nc(N2CC[C@@H](O)C2)n1] | (R)-2,6-dichloro-N-(2-(2-(3-hydroxypyrrolidin-1-yl)-6-methylpyrimidin-4-ylamino)pyridin-4-yl)benzamide | 459.1 |
| 491 | 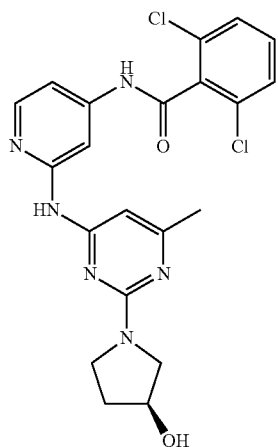 [SMILES: Cc1cc(Nc2cc(NC(=O)c3c(Cl)cccc3Cl)ccn2)nc(N2CC[C@H](O)C2)n1] | (S)-2,6-dichloro-N-(2-(2-(3-hydroxypyrrolidin-1-yl)-6-methylpyrimidin-4-ylamino)pyridin-4-yl)benzamide | 459.1 |
| 492 | 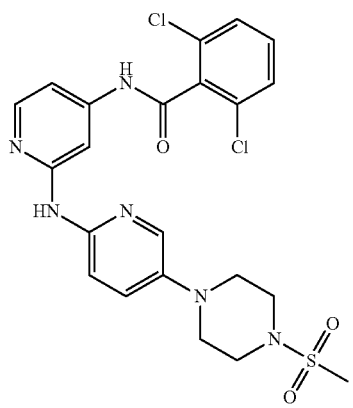 [SMILES: CS(=O)(=O)N1CCN(c2ccc(Nc3cc(NC(=O)c4c(Cl)cccc4Cl)ccn3)nc2)CC1] | 2,6-dichloro-N-(2-(5-(4-(methylsulfonyl)piperazin-1-yl)pyridin-2-ylamino)pyridin-4-yl)benzamide | 521.1 |

TABLE 3-continued
| | | | |
|---|---|---|---|
| 493 | 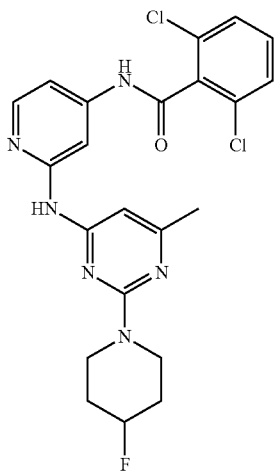 [SMILES: Cc1cc(Nc2cc(NC(=O)c3c(Cl)cccc3Cl)ccn2)nc(N2CCC(F)CC2)n1] | 2,6-dichloro-N-(2-(2-(4-fluoropiperidin-1-yl)-6-methylpyrimidin-4-ylamino)pyridin-4-yl)benzamide | 475.1 |
| 494 | 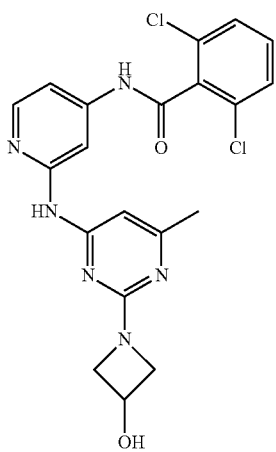 [SMILES: Cc1cc(Nc2cc(NC(=O)c3c(Cl)cccc3Cl)ccn2)nc(N2CC(O)C2)n1] | 2,6-dichloro-N-(2-(2-(3-hydroxyazetidin-1-yl)-6-methylpyrimidin-4-ylamino)pyridin-4-yl)benzamide | 445.1 |
| 495 | 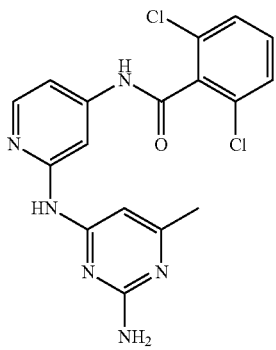 [SMILES: Cc1cc(Nc2cc(NC(=O)c3c(Cl)cccc3Cl)ccn2)nc(N)n1] | N-(2-(2-amino-6-methylpyrimidin-4-ylamino)pyridin-4-yl)-2,6-dichlorobenzamide | 389.1 |
| 496 | 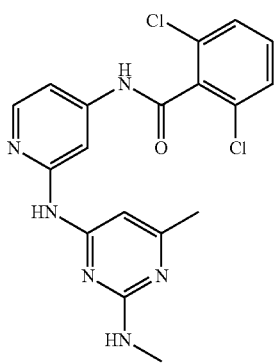 [SMILES: CNc1nc(C)cc(Nc2cc(NC(=O)c3c(Cl)cccc3Cl)ccn2)n1] | 2,6-dichloro-N-(2-(6-methyl-2-(methylamino)pyrimidin-4-ylamino)pyridin-4-yl)benzamide | 403.0 |

TABLE 3-continued
| | | | |
|---|---|---|---|
| 497 | 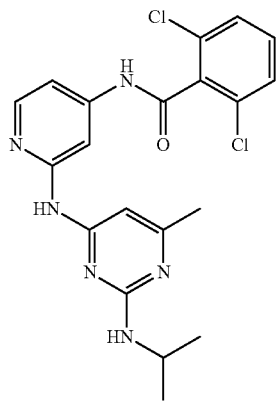 [SMILES: Cc1cc(Nc2cc(NC(=O)c3c(Cl)cccc3Cl)ccn2)nc(NC(C)C)n1] | 2,6-dichloro-N-(2-(2-(isopropylamino)-6-methylpyrimidin-4-ylamino)pyridin-4-yl)benzamide | 431.1 |
| 498 | 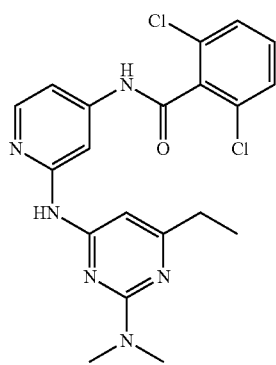 [SMILES: CCc1cc(Nc2cc(NC(=O)c3c(Cl)cccc3Cl)ccn2)nc(N(C)C)n1] | 2,6-dichloro-N-(2-(2-(dimethylamino)-6-ethylpyrimidin-4-ylamino)pyridin-4-yl)benzamide | 431.1 |
| 499 | 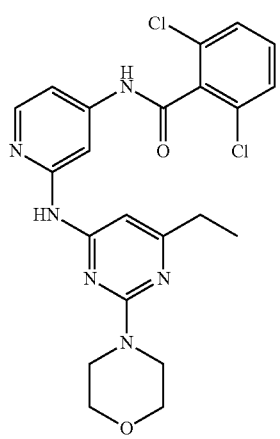 [SMILES: CCc1cc(Nc2cc(NC(=O)c3c(Cl)cccc3Cl)ccn2)nc(N2CCOCC2)n1] | 2,6-dichloro-N-(2-(6-ethyl-2-morpholinopyrimidin-4-ylamino)pyridin-4-yl)benzamide | 473.1 |
| 500 | 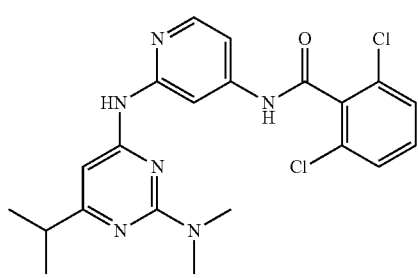 [SMILES: CC(C)c1cc(Nc2cc(NC(=O)c3c(Cl)cccc3Cl)ccn2)nc(N(C)C)n1] | 2,6-dichloro-N-(2-(2-(dimethylamino)-6-isopropylpyrimidin-4-ylamino)pyridin-4-yl)benzamide | 445.1 |

TABLE 3-continued
| | | | |
|---|---|---|---|
| 501 | 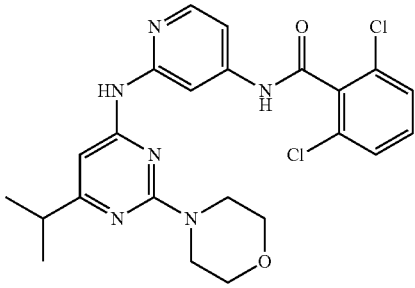 [SMILES: CC(C)c1cc(Nc2cc(NC(=O)c3c(Cl)cccc3Cl)ccn2)nc(N2CCOCC2)n1] | 2,6-dichloro-N-(2-(2-(dimethylamino)-6-isopropylpyrimidin-4-ylamino)pyridin-4-yl)benzamide | 487.0 |
| 502 | 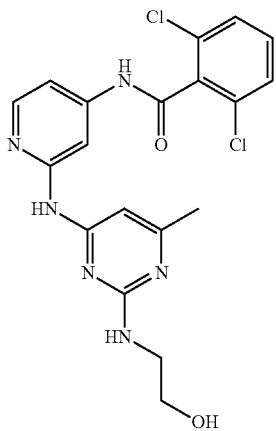 [SMILES: Cc1cc(Nc2cc(NC(=O)c3c(Cl)cccc3Cl)ccn2)nc(NCCO)n1] | 2,6-dichloro-N-(2-(2-(2-hydroxyethylamino)-6-methylpyrimidin-4-ylamino)pyridin-4-yl)benzamide | 433.1 |
| 503 | 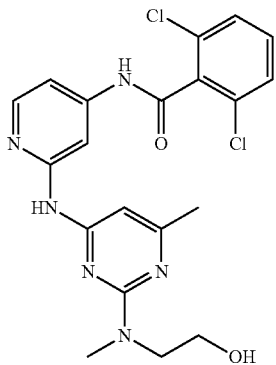 [SMILES: Cc1cc(Nc2cc(NC(=O)c3c(Cl)cccc3Cl)ccn2)nc(N(C)CCO)n1] | 2,6-dichloro-N-(2-(2-((2-hydroxyethyl)(methyl)-amino)-6-methylpyrimidin-4-ylamino)pyridin-4-yl)benzamide | 447.1 |
| 504 | 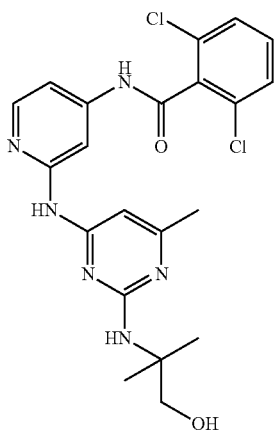 [SMILES: Cc1cc(Nc2cc(NC(=O)c3c(Cl)cccc3Cl)ccn2)nc(NC(C)(C)CO)n1] | 2,6-dichloro-N-(2-(2-(1-hydroxy-2-methylpropan-2-ylamino)-6-methylpyrimidin-4-ylamino)pyridin-4-yl)benzamide | 461.1 |

TABLE 3-continued
| 505 | 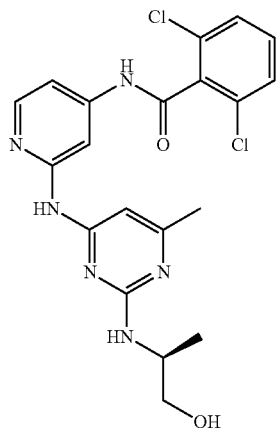 [SMILES: Cc1cc(Nc2cc(NC(=O)c3c(Cl)cccc3Cl)ccn2)nc(N[C@@H](C)CO)n1] | (S)-2,6-dichloro-N-(2-(2-(1-hydroxypropan-2-ylamino)-6-methylpyrimidin-4-ylamino)pyridin-4-yl)benzamide | 447.1 |
| --- | --- | --- | --- |
| 506 | 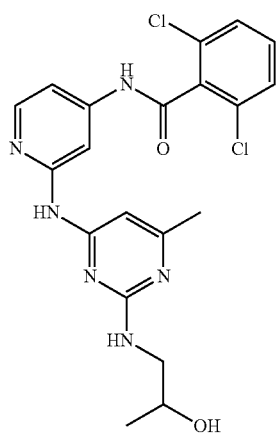 [SMILES: Cc1cc(Nc2cc(NC(=O)c3c(Cl)cccc3Cl)ccn2)nc(NCC(C)O)n1] | 2,6-dichloro-N-(2-(2-(2-hydroxypropylamino)-6-methylpyrimidin-4-ylamino)pyridin-4-yl)benzamide | 447.1 |
| 507 | 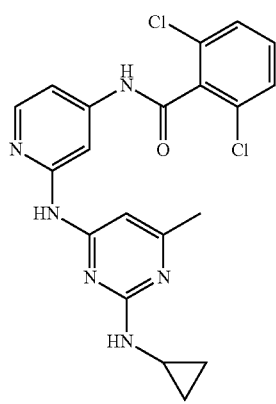 [SMILES: Cc1cc(Nc2cc(NC(=O)c3c(Cl)cccc3Cl)ccn2)nc(NC2CC2)n1] | 2,6-dichloro-N-(2-(2-(cyclopropylamino)-6-methylpyrimidin-4-ylamino)pyridin-4-yl)benzamide | 429.1 |

TABLE 3-continued
| | | | |
|---|---|---|---|
| 508 | 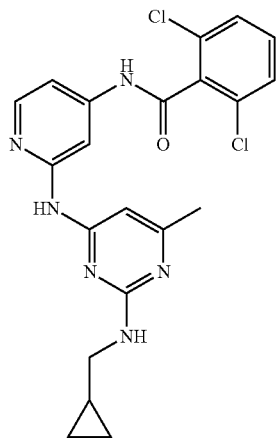 [SMILES: Cc1cc(Nc2cc(NC(=O)c3c(Cl)cccc3Cl)ccn2)nc(NCC2CC2)n1] | 2,6-dichloro-N-(2-(2-(cyclopropylmethyl-amino)-6-methylpyrimidin-4-ylamino)pyridin-4-yl)benzamide | 443.1 |
| 509 | 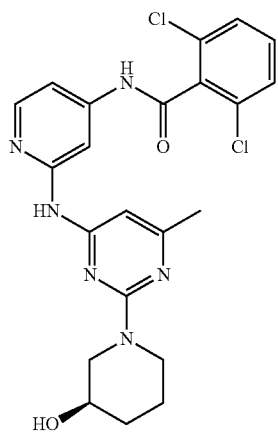 [SMILES: Cc1cc(Nc2cc(NC(=O)c3c(Cl)cccc3Cl)ccn2)nc(N2CCC[C@@H](O)C2)n1] | (R)-2,6-dichloro-N-(2-(2-(3-hydroxypiperidin-1-yl)-6-methylpyrimidin-4-ylamino)pyridin-4-yl)benzamide | 473.1 |
| 510 | 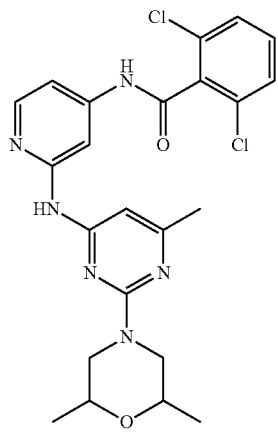 [SMILES: Cc1cc(Nc2cc(NC(=O)c3c(Cl)cccc3Cl)ccn2)nc(N2CC(C)OC(C)C2)n1] | 2,6-dichloro-N-(2-(2-(2,6-dimethylmorpholino)-6-methylpyrimidin-4-ylamino)pyridin-4-yl)benzamide | 487.1 |

TABLE 3-continued
| | | | |
|---|---|---|---|
| 511 | 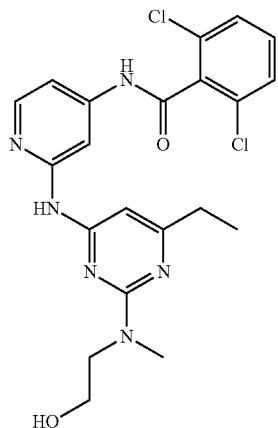 [SMILES: CCc1cc(Nc2cc(NC(=O)c3c(Cl)cccc3Cl)ccn2)nc(N(C)CCO)n1] | 2,6-dichloro-N-(2-(6-ethyl-2-((2-hydroxyethyl)(methyl)-amino)pyrimidin-4-ylamino)pyridin-4-yl)benzamide | 461.1 |
| 512 | 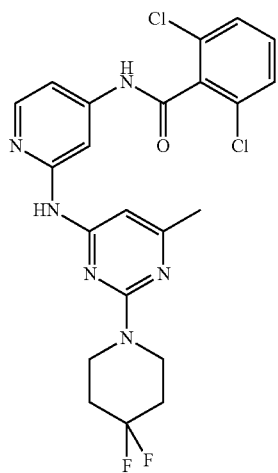 [SMILES: Cc1cc(Nc2cc(NC(=O)c3c(Cl)cccc3Cl)ccn2)nc(N2CCC(F)(F)CC2)n1] | 2,6-dichloro-N-(2-(2-(4,4-difluoropiperidin-1-yl)-6-methylpyrimidin-4-ylamino)pyridin-4-yl)benzamide | 493.1 |
| 513 | 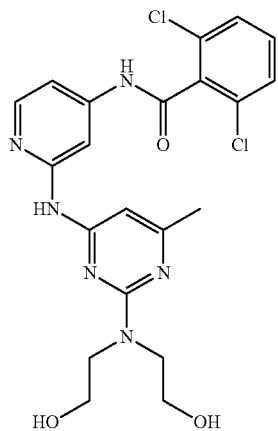 [SMILES: Cc1cc(Nc2cc(NC(=O)c3c(Cl)cccc3Cl)ccn2)nc(N(CCO)CCO)n1] | N-(2-(2-(bis(2-hydroxyethyl)amino)-6-methylpyrimidin-4-ylamino)pyridin-4-yl)-2,6-dichlorobenzamide | 477.1 |

| | | | |
|---|---|---|---|
| 514 | 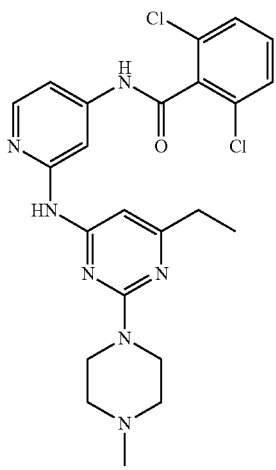 [SMILES: CCc1cc(Nc2cc(NC(=O)c3c(Cl)cccc3Cl)ccn2)nc(N2CCN(C)CC2)n1] | 2,6-dichloro-N-(2-(6-ethyl-2-(4-methylpiperazin-1-yl)pyrimidin-4-ylamino)pyridin-4-yl)benzamide | 486.2 |
| 515 | 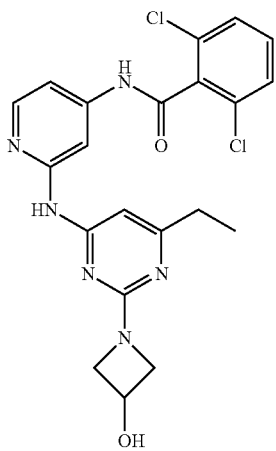 [SMILES: CCc1cc(Nc2cc(NC(=O)c3c(Cl)cccc3Cl)ccn2)nc(N2CC(O)C2)n1] | 2,6-dichloro-N-(2-(6-ethyl-2-(3-hydroxyazetidin-1-yl)pyrimidin-4-ylamino)pyridin-4-yl)benzamide | 459.1 |
| 516 | 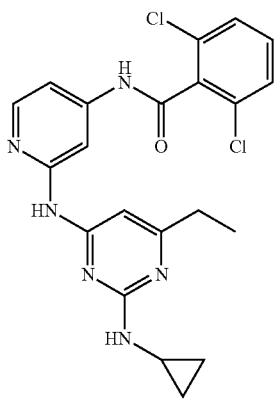 [SMILES: CCc1cc(Nc2cc(NC(=O)c3c(Cl)cccc3Cl)ccn2)nc(NC2CC2)n1] | 2,6-dichloro-N-(2-(2-(cyclopropylamino)-6-ethylpyrimidin-4-ylamino)pyridin-4-yl)benzamide | 443.1 |
| 517 | 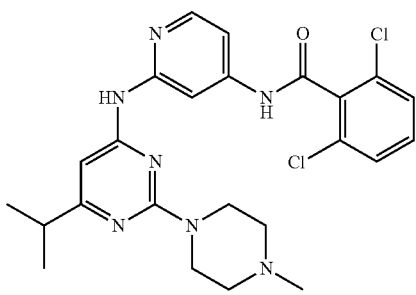 [SMILES: CC(C)c1cc(Nc2cc(NC(=O)c3c(Cl)cccc3Cl)ccn2)nc(N2CCN(C)CC2)n1] | 2,6-dichloro-N-(2-(6-isopropyl-2-(4-methylpiperazin-1-yl)pyrimidin-4-ylamino)pyridin-4-yl)benzamide | 500.1 |

TABLE 3-continued

| | | | |
|---|---|---|---|
| 518 | 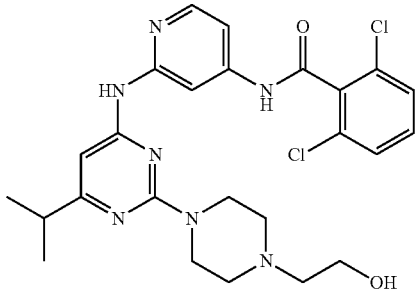 [SMILES: CC(C)c1cc(Nc2cc(NC(=O)c3c(Cl)cccc3Cl)ccn2)nc(N2CCN(CCO)CC2)n1] | 2,6-dichloro-N-(2-(2-(4-(2-hydroxyethyl)piperazin-1-yl)-6-isopropylpyrimidin-4-ylamino)pyridin-4-yl)benzamide | 530.2 |
| 519 | 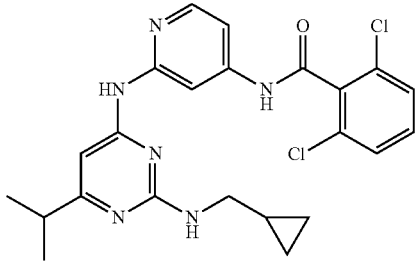 [SMILES: CC(C)c1cc(Nc2cc(NC(=O)c3c(Cl)cccc3Cl)ccn2)nc(NCC2CC2)n1] | 2,6-dichloro-N-(2-(2-(cyclopropylmethylamino)-6-isopropylpyrimidin-4-ylamino)pyridin-4-yl)benzamide | 471.1 |
| 520 | 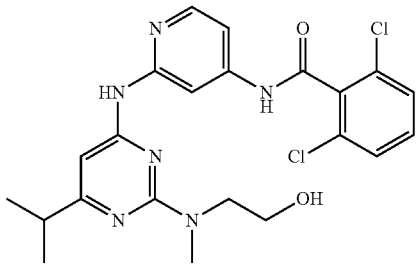 [SMILES: CC(C)c1cc(Nc2cc(NC(=O)c3c(Cl)cccc3Cl)ccn2)nc(N(C)CCO)n1] | 2,6-dichloro-N-(2-(2-((2-hydroxyethyl)(methyl)-amino)-6-issopropylpyrimidin-4-ylamino)pyridin-4-yl)benzamide | 475.1 |
| 521 | 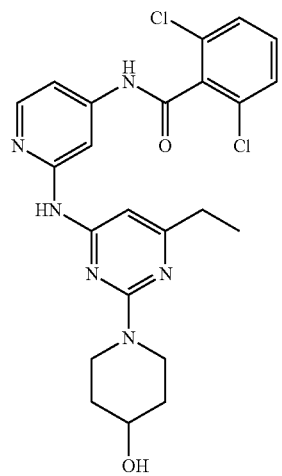 [SMILES: CCc1cc(Nc2cc(NC(=O)c3c(Cl)cccc3Cl)ccn2)nc(N2CCC(O)CC2)n1] | 2,6-dichloro-N-(2-(6-ethyl-2-(4-hydroxypiperidin-1-yl)pyrimidin-4-ylamino)pyridin-4-yl)benzamide | 487.1 |

TABLE 3-continued
| | | | |
|---|---|---|---|
| 522 | 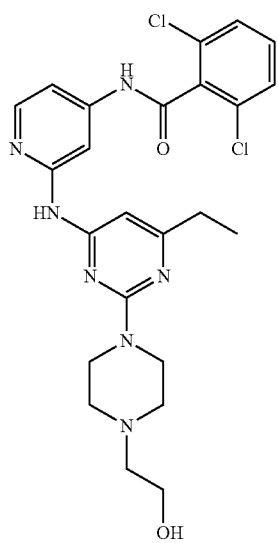 [SMILES: CCc1cc(Nc2cc(NC(=O)c3c(Cl)cccc3Cl)ccn2)nc(N2CCN(CCO)CC2)n1] | 2,6-dichloro-N-(2-(6-ethyl-2-(4-(2-hydroxyethyl)piperazin-1-yl)pyrimidin-4-ylamino)pyridin-4-yl)benzamide | 516.2 |
| 523 | 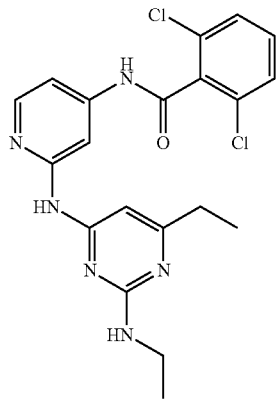 [SMILES: CCNc1nc(CC)cc(Nc2cc(NC(=O)c3c(Cl)cccc3Cl)ccn2)n1] | 2,6-dichloro-N-(2-(6-ethyl-2-(ethylamino)pyrimidin-4-ylamino)pyridin-4-yl)benzamide | 431.1 |
| 524 | 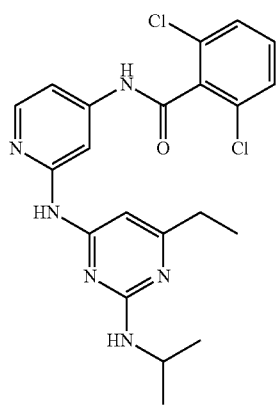 [SMILES: CCc1cc(Nc2cc(NC(=O)c3c(Cl)cccc3Cl)ccn2)nc(NC(C)C)n1] | 2,6-dichloro-N-(2-(6-ethyl-2-(isopropylamino)pyrimidin-4-ylamino)pyridin-4-yl)benzamide | 445.1 |

TABLE 3-continued

| 525 | 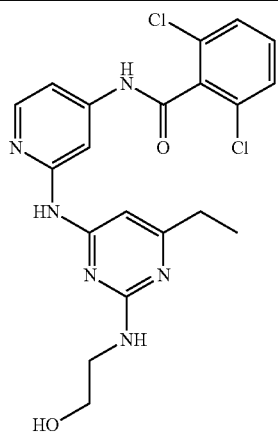 | 2,6-dichloro-N-(2-(6-ethyl-2-(2-hydroxyethylamino)-pyrimidin-4-ylamino)pyridin-4-yl)benzamide | 447.1 |
| 526 | 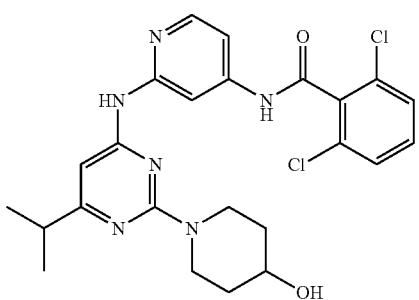 [SMILES: CC(C)c1cc(Nc2cc(NC(=O)c3c(Cl)cccc3Cl)ccn2)nc(N2CCC(O)CC2)n1] | 2,6-dichloro-N-(2-(2-(4-hydroxypiperidin-1-yl)-6-isopropylpyrimidin-4-ylamino)pyridin-4-yl)benzamide | 501.1 |
| 527 | 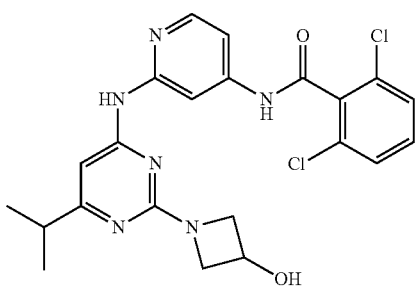 [SMILES: CC(C)c1cc(Nc2cc(NC(=O)c3c(Cl)cccc3Cl)ccn2)nc(N2CC(O)C2)n1] | 2,6-dichloro-N-(2-(2-(3-hydroxyazetidin-1-yl)-6-isopropylpyrimidin-4-ylamino)pyridin-4-yl)benzamide | 473.1 |
| 528 | 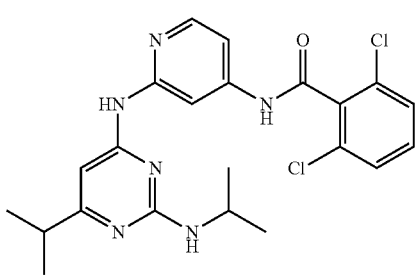 [SMILES: CC(C)Nc1nc(Nc2cc(NC(=O)c3c(Cl)cccc3Cl)ccn2)cc(C(C)C)n1] | 2,6-dichloro-N-(2-(6-isopropyl-2-(isopropylamino)pyrimidin-4-ylamino)pyridin-4-yl)benzamide | 459.1 |
| 529 | 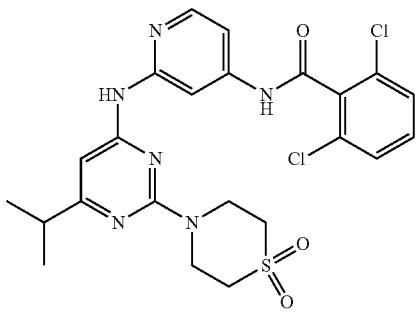 [SMILES: CC(C)c1cc(Nc2cc(NC(=O)c3c(Cl)cccc3Cl)ccn2)nc(N2CCS(=O)(=O)CC2)n1] | 2,6-dichloro-N-(2-(6-issopropyl-2-(S-dioxa-thiomorpholino)pyrimidin-4-ylamino)pyridin-4-yl)benzamide | 535.0 |

TABLE 3-continued
| | | | |
|---|---|---|---|
| 530 | 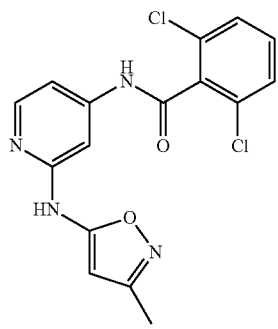 [SMILES: Cc1cc(Nc2cc(NC(=O)c3c(Cl)cccc3Cl)ccn2)on1] | 2,6-dichloro-N-(2-(3-methylisoxazol-5-ylamino)pyridin-4-yl)benzamide | 363.0 |
| 531 | 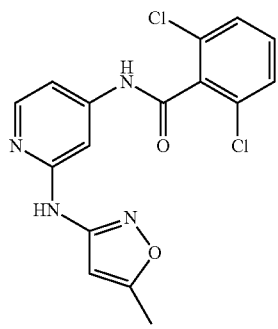 [SMILES: Cc1cc(Nc2cc(NC(=O)c3c(Cl)cccc3Cl)ccn2)no1] | 2,6-dichloro-N-(2-(5-methylisoxazol-3-ylamino)pyridin-4-yl)benzamide | 363.0 |
| 532 | 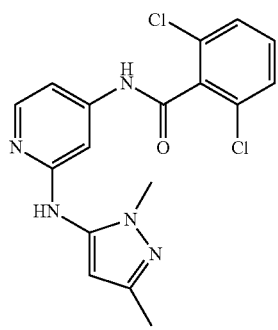 [SMILES: Cc1cc(Nc2cc(NC(=O)c3c(Cl)cccc3Cl)ccn2)n(C)n1] | 2,6-dichloro-N-(2-(1,3-dimethyl-1H-pyrazol-5-ylamino)pyridin-4-yl)benzamide | 376.0 |
| 533 | 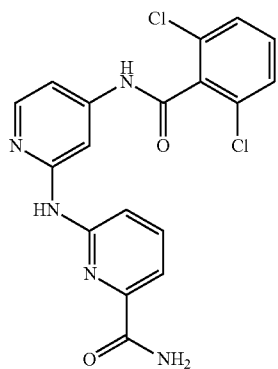 [SMILES: NC(=O)c1cccc(Nc2cc(NC(=O)c3c(Cl)cccc3Cl)ccn2)n1] | 6-(4-(2,6-dichlorobenzamido)pyridin-2-ylamino)picolinamide | 402.0 |

TABLE 3-continued
| 534 | 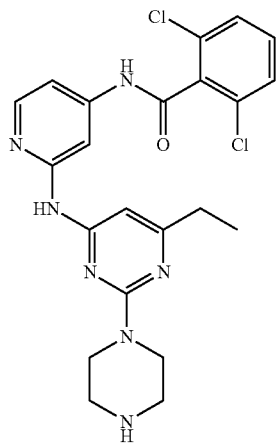 [SMILES: CCc1cc(Nc2cc(NC(=O)c3c(Cl)cccc3Cl)ccn2)nc(N2CCNCC2)n1] | 2,6-dichloro-N-(2-(6-ethyl-2-(piperazin-1-yl)pyrimidin-4-ylamino)pyridin-4-yl)benzamide | 472.1 |
| --- | --- | --- | --- |
| 535 | 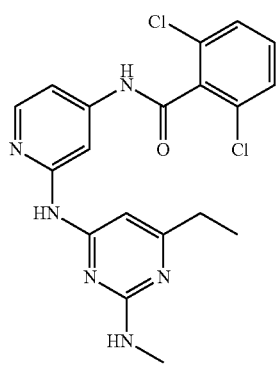 [SMILES: CCc1cc(Nc2cc(NC(=O)c3c(Cl)cccc3Cl)ccn2)nc(NC)n1] | 2,6-dichloro-N-(2-(6-ethyl-2-(methylamino)pyrimidin-4-ylamino)pyridin-4-yl)benzamide | 417.1 |
| 536 | 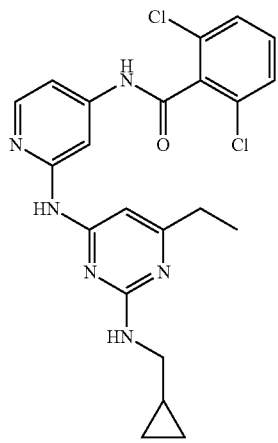 [SMILES: CCc1cc(Nc2cc(NC(=O)c3c(Cl)cccc3Cl)ccn2)nc(NCC2CC2)n1] | 2,6-dichloro-N-(2-(2-(cyclopropylmethylamino)-6-ethylpyrimidin-4-ylamino)pyridin-4-yl)benzamide | 457.1 |
| 537 | 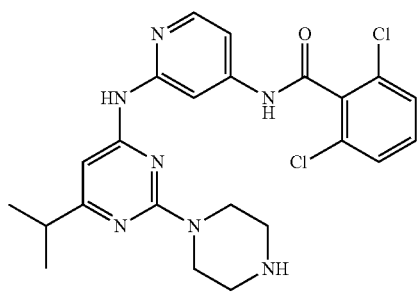 [SMILES: CC(C)c1cc(Nc2cc(NC(=O)c3c(Cl)cccc3Cl)ccn2)nc(N2CCNCC2)n1] | 2,6-dichloro-N-(2-(6-isopropyl-2-(piperazin-1-yl)pyrimidin-4-ylamino)pyridin-4-yl)benzamide | 486.1 |

| | | | |
|---|---|---|---|
| 538 | 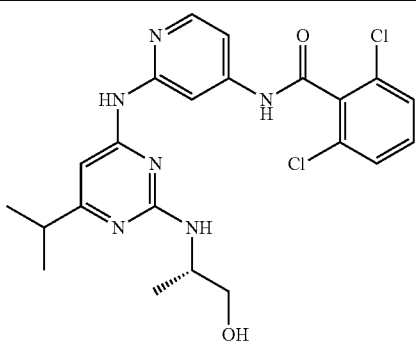 | (S)-2,6-dichloro-N-(2-(2-(1-hydroxypropan-2-ylamino)-6-isopropylpyrimidin-4-ylamino)pyridin-4-yl)benzamide | 475.1 |
| 539 | 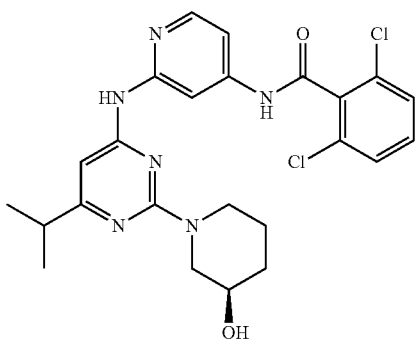 [SMILES: CC(C)c1cc(Nc2cc(NC(=O)c3c(Cl)cccc3Cl)ccn2)nc(N2CCC[C@@H](O)C2)n1] | (R)-2,6-dichloro-N-(2-(2-(3-hydroxypiperidin-1-yl)-6-isopropylpyrimidin-4-ylamino)pyridin-4-yl)benzamide | 501.1 |
| 540 | 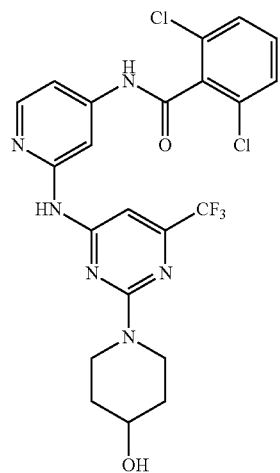 [SMILES: O=C(Nc1ccnc(Nc2cc(C(F)(F)F)nc(N3CCC(O)CC3)n2)c1)c1c(Cl)cccc1Cl] | 2,6-dichloro-N-(2-(2-(4-hydroxypiperidin-1-yl)-6-(trifluoromethyl)pyrimidin-4-ylamino)pyridin-4-yl)benzamide | 527.0 |
| 541 | 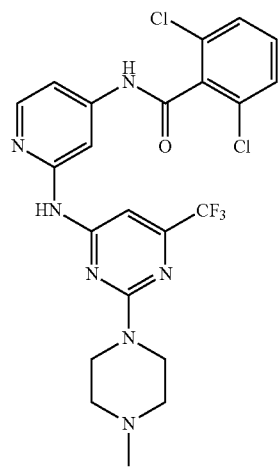 [SMILES: CN1CCN(c2nc(Nc3cc(NC(=O)c4c(Cl)cccc4Cl)ccn3)cc(C(F)(F)F)n2)CC1] | 2,6-dichloro-N-(2-(2-(4-methylpiperazin-1-yl)-6-(trifluoromethyl)pyrimidin-4-ylamino)pyridin-4-yl)benzamide | 526.1 |

TABLE 3-continued
| | | | |
|---|---|---|---|
| 542 | 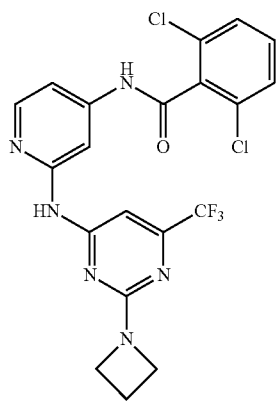 [SMILES: O=C(Nc1ccnc(Nc2cc(C(F)(F)F)nc(N3CCC3)n2)c1)c1c(Cl)cccc1Cl] | N-(2-(2-(azetidin-1-yl)-6-(trifluoromethyl)pyrimidin-4-ylamino)pyridin-4-yl)-2,6-dichlorobenzamide | 483.0 |
| 543 | 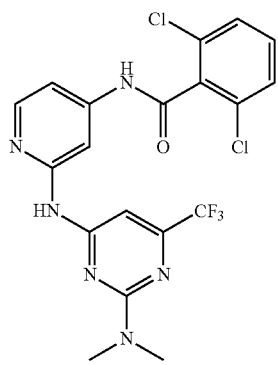 [SMILES: CN(C)c1nc(Nc2cc(NC(=O)c3c(Cl)cccc3Cl)ccn2)cc(C(F)(F)F)n1] | 2,6-dichloro-N-(2-(2-(dimethylamino)-6-(trifluoromethyl)pyrimidin-4-ylamino)pyridin-4-yl)benzamide | 471.0 |
| 544 | 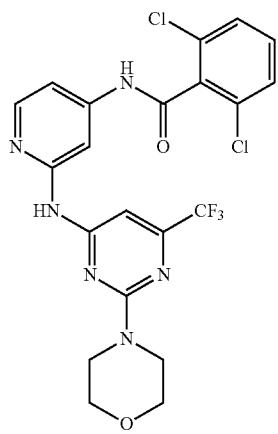 [SMILES: O=C(Nc1ccnc(Nc2cc(C(F)(F)F)nc(N3CCOCC3)n2)c1)c1c(Cl)cccc1Cl] | 2,6-dichloro-N-(2-(2-morpholino-6-(trifluoromethyl)pyrimidin-4-ylamino)pyridin-4-yl)benzamide | 513.1 |
| 545 | 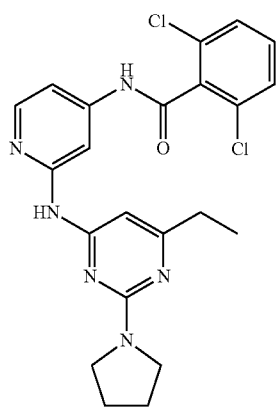 [SMILES: CCc1cc(Nc2cc(NC(=O)c3c(Cl)cccc3Cl)ccn2)nc(N2CCCC2)n1] | 2,6-dichloro-N-(2-(6-ethyl-2-(pyrrolidin-1-yl)pyrimidin-4-ylamino)pyridin-4-yl)benzamide | 457.1 |

TABLE 3-continued
| | | | |
|---|---|---|---|
| 546 | 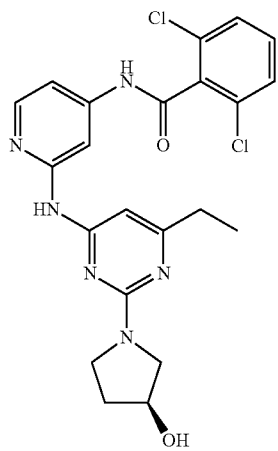 [SMILES: CCc1cc(Nc2cc(NC(=O)c3c(Cl)cccc3Cl)ccn2)nc(N2CC[C@H](O)C2)n1] | (S)-2,6-dichloro-N-(2-(6-ethyl-2-(3-hydroxypyrrolidin-1-yl)pyrimidin-4-ylamino)pyridin-4-yl)benzamide | 473.1 |
| 547 | 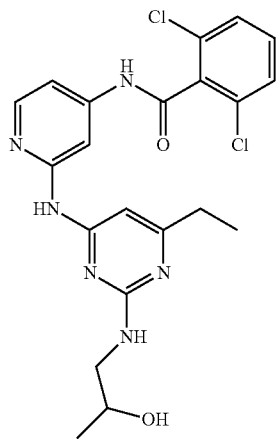 [SMILES: CCc1cc(Nc2cc(NC(=O)c3c(Cl)cccc3Cl)ccn2)nc(NCC(C)O)n1] | 2,6-dichloro-N-(2-(6-ethyl-2-(2-hydroxypropylamino)-pyrimidin-4-ylamino)pyridin-4-yl)benzamide | 461.1 |
| 548 | 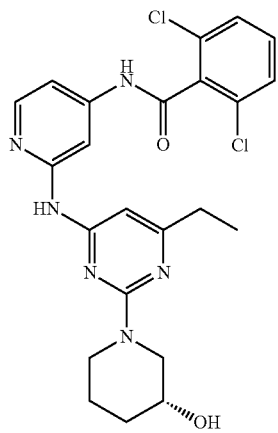 [SMILES: CCc1cc(Nc2cc(NC(=O)c3c(Cl)cccc3Cl)ccn2)nc(N2CCC[C@@H](O)C2)n1] | (R)-2,6-dichloro-N-(2-(6-ethyl-2-(3-hydroxypiperidin-1-yl)pyrimidin-4-ylamino)pyridin-4-yl)benzamide | 487.1 |

| | | | |
|---|---|---|---|
| 549 | 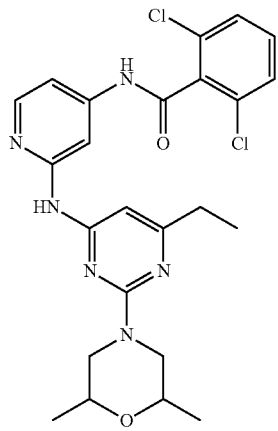 | 2,6-dichloro-N-(2-(2-(2,6-dimethylmorpholino)-6-ethylpyrimidin-4-ylamino)pyridin-4-yl)benzamide | 501.1 |
| 550 | 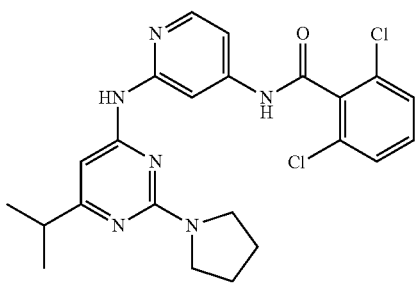 [SMILES: CC(C)c1cc(Nc2cc(NC(=O)c3c(Cl)cccc3Cl)ccn2)nc(N2CCCC2)n1] | 2,6-dichloro-N-(2-(6-issopropyl-2-(pyrrolidin-1-yl)pyrimidin-4-ylamino)pyridin-4-yl)benzamide | 471.1 |
| 551 | 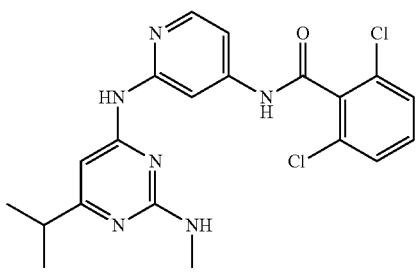 [SMILES: CNc1nc(Nc2cc(NC(=O)c3c(Cl)cccc3Cl)ccn2)cc(C(C)C)n1] | 2,6-dichloro-N-(2-(6-isopropyl-2-(methylamino)pyrimidin-4-ylamino)pyridin-4-yl)benzamide | 431.1 |
| 552 | 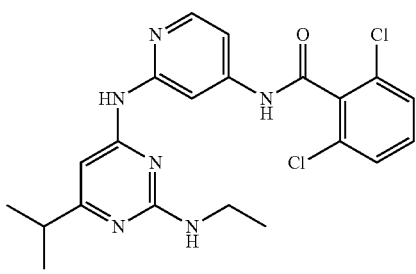 [SMILES: CCNc1nc(Nc2cc(NC(=O)c3c(Cl)cccc3Cl)ccn2)cc(C(C)C)n1] | 2,6-dichloro-N-(2-(2-(ethylamino)-6-issopropylpyrimidin-4-ylamino)pyridin-4-yl)benzamide | 445.1 |
| 553 | 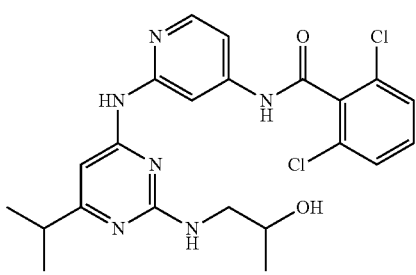 [SMILES: CC(O)CNc1nc(Nc2cc(NC(=O)c3c(Cl)cccc3Cl)ccn2)cc(C(C)C)n1] | 2,6-dichloro-N-(2-(2-(2-hydroxypropylamino)-6-isopropylpyrimidin-4-ylamino)pyridin-4-yl)benzamide | 475.1 |

TABLE 3-continued

| 554 | 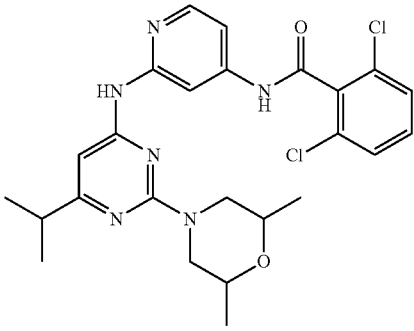 [SMILES: CC1CN(c2nc(Nc3cc(NC(=O)c4c(Cl)cccc4Cl)ccn3)cc(C(C)C)n2)CC(C)O1] | 2,6-dichloro-N-(2-(2-(2,6-dimethylmorpholino)-6-isopropylpyrimidin-4-ylamino)pyridin-4-yl)benzamide | 515.0 |
| --- | --- | --- | --- |
| 555 | 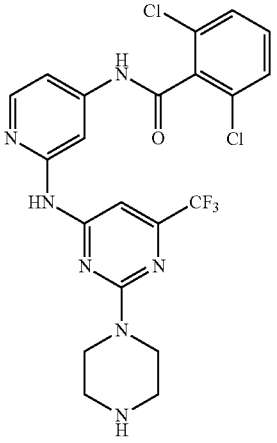 [SMILES: O=C(Nc1ccnc(Nc2cc(C(F)(F)F)nc(N3CCNCC3)n2)c1)c1c(Cl)cccc1Cl] | 2,6-dichloro-N-(2-(2-(piperazin-1-yl)-6-(trifluoromethyl)pyrimidin-4-ylamino)pyridin-4-yl)benzamide | 512.1 |
| 556 | 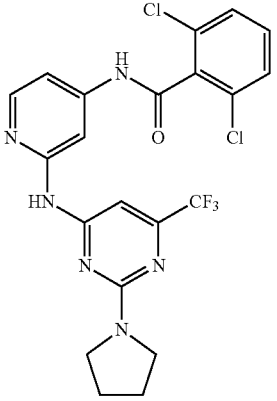 [SMILES: O=C(Nc1ccnc(Nc2cc(C(F)(F)F)nc(N3CCCC3)n2)c1)c1c(Cl)cccc1Cl] | 2,6-dichloro-N-(2-(2-(pyrrolidin-1-yl)-6-(trifluoromethyl)pyrimidin-4-ylamino)pyridin-4-yl)benzamide | 497.0 |
| 557 | 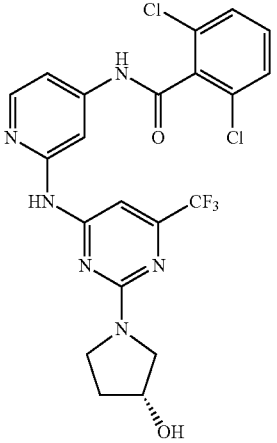 [SMILES: O=C(Nc1ccnc(Nc2cc(C(F)(F)F)nc(N3CC[C@@H](O)C3)n2)c1)c1c(Cl)cccc1Cl] | (R)-2,6-dichloro-N-(2-(2-(3-hydroxypyrrolidin-1-yl)-6-(trifluoromethyl)pyrimidin-4-ylamino)pyridin-4-yl)benzamide | 513.0 |

TABLE 3-continued

| | | | |
|---|---|---|---|
| 558 | | (S)-2,6-dichloro-N-(2-(2-(3-hydroxypyrrolidin-1-yl)-6-(trifluoromethyl)pyrimidin-4-ylamino)pyridin-4-yl)benzamide | 513.0 |
| 559 | | 2,6-dichloro-N-(2-(2-(2,6-dimethylmorpholino)-6-(trifluoromethyl)pyrimidin-4-ylamino)pyridin-4-yl)benzamide | 541.2 |
| 560 | | 2,6-dichloro-N-(2-(5-methyl-1H-pyrazol-3-ylamino)pyridin-4-yl)benzamide | 362.1 |
| 561 | | 2,6-dichloro-N-(2-(5-cyclopropyl-1H-pyrazol-3-ylamino)pyridin-4-yl)benzamide | 388.0 |
| 562 | | 2,6-dichloro-N-(2-(2-(1,2-dihydroxyethyl)-6-methylpyrimidin-4-ylamino)pyridin-4-yl)benzamide | 434.0 |

TABLE 3-continued

| | | | |
|---|---|---|---|
| 563 | 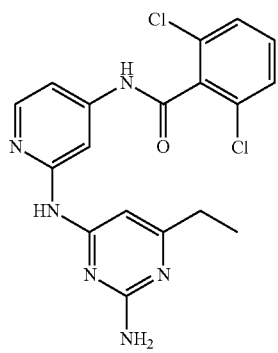 [SMILES: CCc1cc(Nc2cc(NC(=O)c3c(Cl)cccc3Cl)ccn2)nc(N)n1] | N-(2-(2-amino-6-ethylpyrimidin-4-ylamino)pyridin-4-yl)-2,6-dichlorobenzamide | 403.0 |
| 564 | 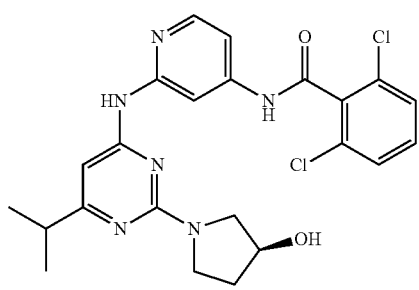 [SMILES: CC(C)c1cc(Nc2cc(NC(=O)c3c(Cl)cccc3Cl)ccn2)nc(N2CC[C@H](O)C2)n1] | (S)-2,6-dichloro-N-(2-(2-(3-hydroxypyrrolidin-1-yl)-6-isopropylpyrimidin-4-ylamino)pyridin-4-yl)benzamide | 487.1 |
| 565 | 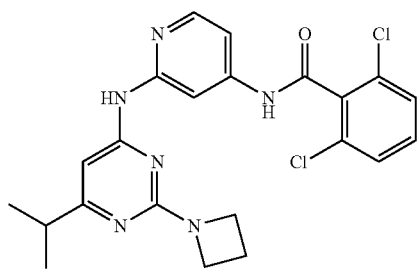 [SMILES: CC(C)c1cc(Nc2cc(NC(=O)c3c(Cl)cccc3Cl)ccn2)nc(N2CCC2)n1] | N-(2-(2-(azetidin-1-yl)-6-isopropylpyrimidin-4-ylamino)pyridin-4-yl)-2,6-dichlorobenzamide | 457.0 |
| 566 | 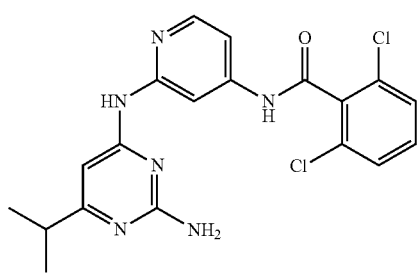 [SMILES: CC(C)c1cc(Nc2cc(NC(=O)c3c(Cl)cccc3Cl)ccn2)nc(N)n1] | N-(2-(2-amino-6-isopropylpyrimidin-4-ylamino)pyridin-4-yl)-2,6-dichlorobenzamide | 417.1 |
| 567 | 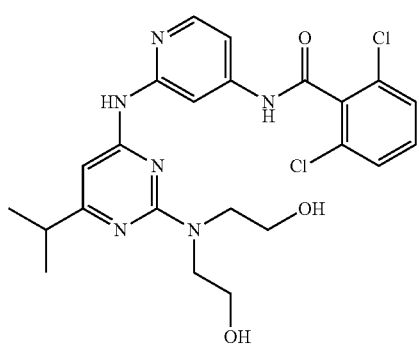 [SMILES: CC(C)c1cc(Nc2cc(NC(=O)c3c(Cl)cccc3Cl)ccn2)nc(N(CCO)CCO)n1] | N-(2-(2-(bis(2-hydroxyethyl)amino)-6-isopropylpyrimidin-4-ylamino)pyridin-4-yl)-2,6-dichlorobenzamide | 505.1 |

TABLE 3-continued
| 568 | 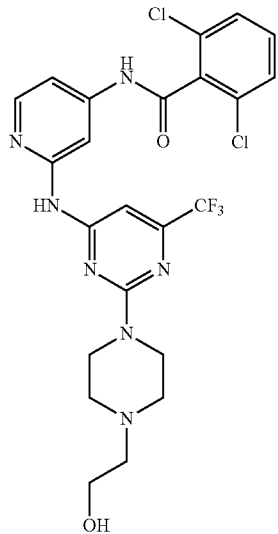 [SMILES: O=C(Nc1ccnc(Nc2cc(C(F)(F)F)nc(N3CCN(CCO)CC3)n2)c1)c1c(Cl)cccc1Cl] | 2,6-dichloro-N-(2-(2-(4-(2-hydroxyethyl)piperazin-1-yl)-6-(trifluoromethyl)pyrimidin-4-ylamino)pyridin-4-yl)benzamide | 556.1 |
| 569 | 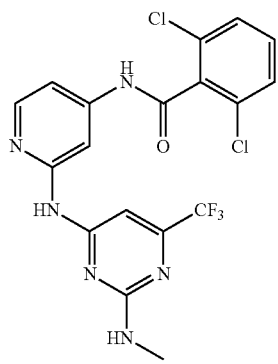 | 2,6-dichloro-N-(2-(2-(methylamino)-6-(trifluoromethyl)pyrimidin-4-ylamino)pyridin-4-yl)benzamide | 457.0 |
| 570 | 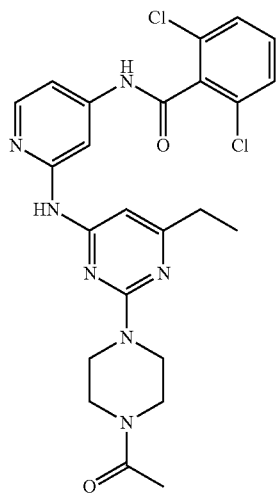 [SMILES: CCc1cc(Nc2cc(NC(=O)c3c(Cl)cccc3Cl)ccn2)nc(N2CCN(C(C)=O)CC2)n1] | N-(2-(2-(4-acetylpiperazin-1-yl)-6-ethylpyrimidin-4-ylamino)pyridin-4-yl)-2,6-dichlorobenzamide | 514.1 |

TABLE 3-continued
| 571 | 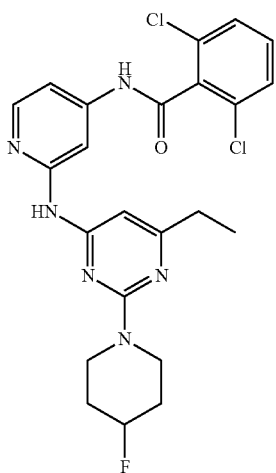 [SMILES: CCc1cc(Nc2cc(NC(=O)c3c(Cl)cccc3Cl)ccn2)nc(N2CCC(F)CC2)n1] | 2,6-dichloro-N-(2-(6-ethyl-2-(4-fluoropiperidin-1-yl)pyrimidin-4-ylamino)pyridin-4-yl)benzamide | 489.1 |
| 572 | 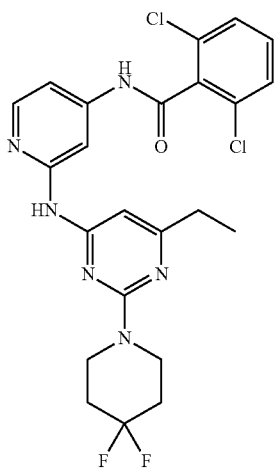 [SMILES: CCc1cc(Nc2cc(NC(=O)c3c(Cl)cccc3Cl)ccn2)nc(N2CCC(F)(F)CC2)n1] | 2,6-dichloro-N-(2-(2-(4,4-difluoropiperidin-1-yl)-6-ethylpyrimidin-4-ylamino)pyridin-4-yl)benzamide | 507.1 |
| 573 | 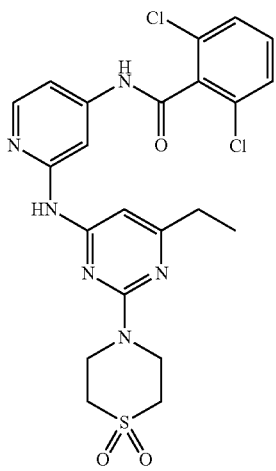 [SMILES: CCc1cc(Nc2cc(NC(=O)c3c(Cl)cccc3Cl)ccn2)nc(N2CCS(=O)(=O)CC2)n1] | 2,6-dichloro-N-(2-(6-ethyl-2-(S-dioxa-thiomorpholino)pyrimidin-4-ylamino)pyridin-4-yl)benzamide | 521.1 |

TABLE 3-continued
| | | | |
|---|---|---|---|
| 574 | 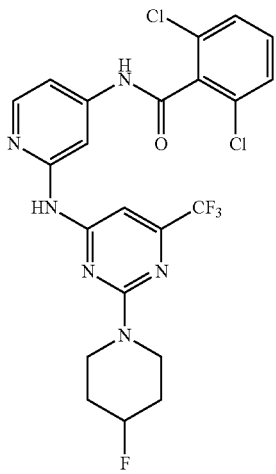 [SMILES: O=C(Nc1ccnc(Nc2cc(C(F)(F)F)nc(N3CCC(F)CC3)n2)c1)c1c(Cl)cccc1Cl] | 2,6-dichloro-N-(2-(2-(4-fluoropiperidin-1-yl)-6-(trifluoromethyl)pyrimidin-4-ylamino)pyridin-4-yl)benzamide | 529.0 |
| 575 | 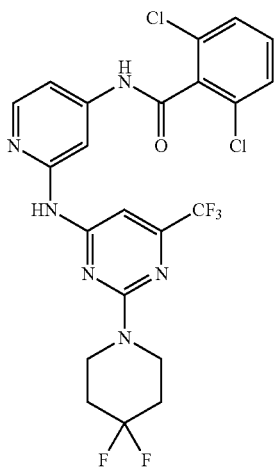 [SMILES: O=C(Nc1ccnc(Nc2cc(C(F)(F)F)nc(N3CCC(F)(F)CC3)n2)c1)c1c(Cl)cccc1Cl] | 2,6-dichloro-N-(2-(2-(4,4-difluoropiperidin-1-yl)-6-(trifluoromethyl)pyrimidin-4-ylamino)pyridin-4-yl)benzamide | 547.0 |
| 576 | 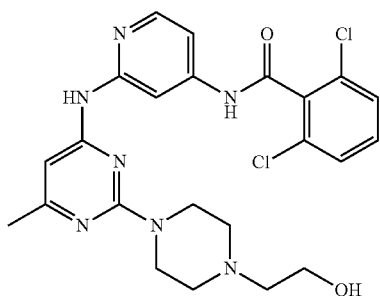 [SMILES: Cc1cc(Nc2cc(NC(=O)c3c(Cl)cccc3Cl)ccn2)nc(N2CCN(CCO)CC2)n1] | 2,6-dichloro-N-(2-(2-(4-(2-hydroxyethyl)piperazin-1-yl)-6-methylpyrimidin-4-ylamino)pyridin-4-yl)benzamide | 502.1 |

TABLE 3-continued

| | | | |
|---|---|---|---|
| 577 | | (R)-2,6-dichloro-N-(2-(6-ethyl-2-(3-hydroxypyrrolidin-1-yl)pyrimidin-4-ylamino)pyridin-4-yl)benzamide | 473.1 |
| 578 | | N-(2-(2-(azetidin-1-yl)-6-ethylpyrimidin-4-ylamino)pyridin-4-yl)-2,6-dichlorobenzamide | 443.1 |
| 579 | | N-(2-(2-(bis(2-hydroxyethyl)amino)-6-ethylpyrimidin-4-ylamino)pyridin-4-yl)-2,6-dichlorobenzamide | 491.1 |
| 580 | | 2,6-dichloro-N-(2-(2-ethyl-6-methylpyrimidin-4-ylamino)pyridin-4-yl)benzamide | 402.1 |

TABLE 3-continued
| | | | |
|---|---|---|---|
| 581 | 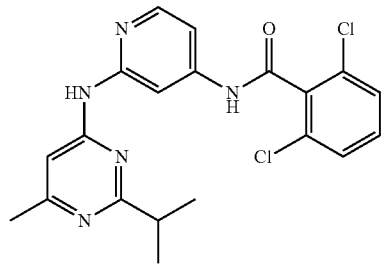 [SMILES: Cc1cc(Nc2cc(NC(=O)c3c(Cl)cccc3Cl)ccn2)nc(C(C)C)n1] | 2,6-dichloro-N-(2-(2-isopropyl-6-methylpyrimidin-4-ylamino)pyridin-4-yl)benzamide | 416.1 |
| 582 | 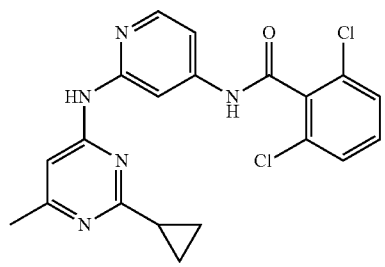 [SMILES: Cc1cc(Nc2cc(NC(=O)c3c(Cl)cccc3Cl)ccn2)nc(C2CC2)n1] | 2,6-dichloro-N-(2-(2-cyclopropyl-6-methylpyrimidin-4-ylamino)pyridin-4-yl)benzamide | 414.1 |
| 583 | 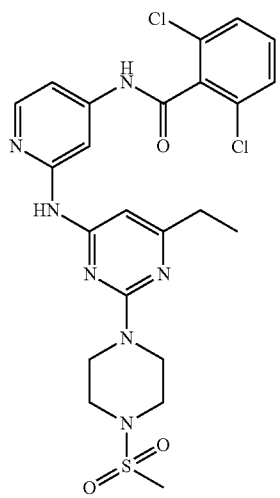 [SMILES: CCc1cc(Nc2cc(NC(=O)c3c(Cl)cccc3Cl)ccn2)nc(N2CCN(S(C)(=O)=O)CC2)n1] | 2,6-dichloro-N-(2-(6-ethyl-2-(4-(methylsulfonyl)piperazin-1-yl)pyrimidin-4-ylamino)pyridin-4-yl)benzamide | 550.1 |
| 584 | 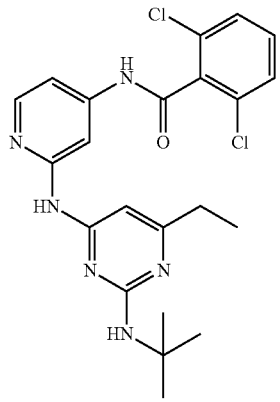 [SMILES: CCc1cc(Nc2cc(NC(=O)c3c(Cl)cccc3Cl)ccn2)nc(NC(C)(C)C)n1] | N-(2-(2-(tert-butylamino)-6-ethylpyrimidin-4-ylamino)pyridin-4-yl)-2,6-dichlorobenzamide | 459.1 |

TABLE 3-continued
| 585 | 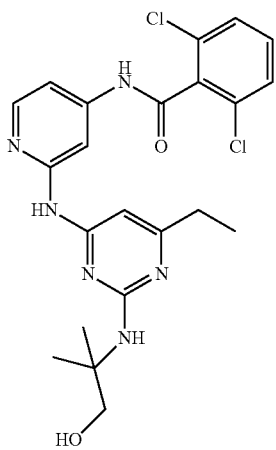 [SMILES: CCc1cc(Nc2cc(NC(=O)c3c(Cl)cccc3Cl)ccn2)nc(NC(C)(C)CO)n1] | 2,6-dichloro-N-(2-(6-ethyl-2-(1-hydroxy-2-methylpropan-2-ylamino)pyrimidin-4-ylamino)pyridin-4-yl)benzamide | 475.1 |
| --- | --- | --- | --- |
| 586 | 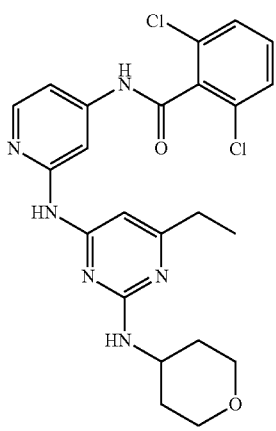 [SMILES: CCc1cc(Nc2cc(NC(=O)c3c(Cl)cccc3Cl)ccn2)nc(NC2CCOCC2)n1] | 2,6-dichloro-N-(2-(6-ethyl-2-(tetrahydro-2H-pyran-4-ylamino)pyrimidin-4-ylamino)pyridin-4-yl)benzamide | 487.1 |
| 587 | 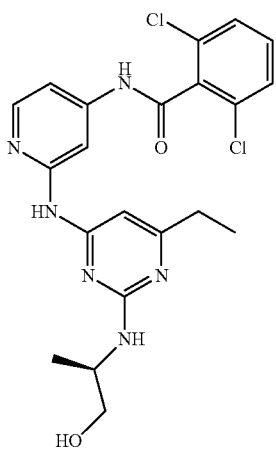 [SMILES: CCc1cc(Nc2cc(NC(=O)c3c(Cl)cccc3Cl)ccn2)nc(N[C@H](C)CO)n1] | (R)-2,6-dichloro-N-(2-(6-ethyl-2-(1-hydroxypropan-2-ylamino)pyrimidin-4-ylamino)pyridin-4-yl)benzamide | 461.1 |
| 588 | 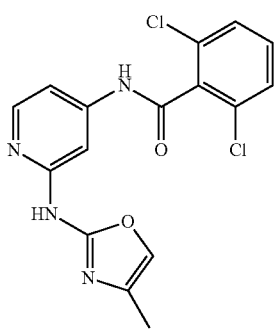 [SMILES: Cc1coc(Nc2cc(NC(=O)c3c(Cl)cccc3Cl)ccn2)n1] | 2,6-dichloro-N-(2-(4-methyloxazol-2-ylamino)pyridin-4-yl)benzamide | 363.0 |

TABLE 3-continued
| | | | |
|---|---|---|---|
| 589 | 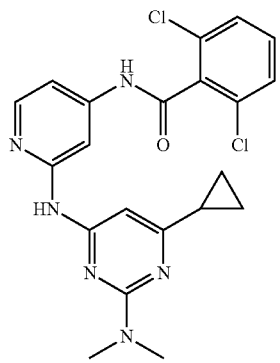 [SMILES: CN(C)c1nc(Nc2cc(NC(=O)c3c(Cl)cccc3Cl)ccn2)cc(C2CC2)n1] | 2,6-dichloro-N-(2-(6-cyclopropyl-2-(dimethylamino)pyrimidin-4-ylamino)pyridin-4-yl)benzamide | 443.1 |
| 590 | 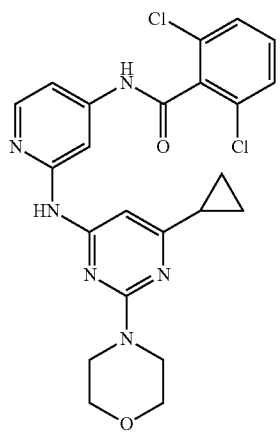 [SMILES: O=C(Nc1ccnc(Nc2cc(C3CC3)nc(N3CCOCC3)n2)c1)c1c(Cl)cccc1Cl] | 2,6-dichloro-N-(2-(6-cyclopropyl-2-morpholinopyrimidin-4-ylamino)pyridin-4-yl)benzamide | 485.1 |
| 591 | 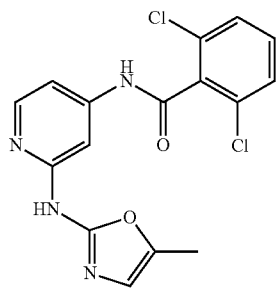 [SMILES: Cc1cnc(Nc2cc(NC(=O)c3c(Cl)cccc3Cl)ccn2)o1] | 2,6-dichloro-N-(2-(5-methyloxazol-2-ylamino)pyridin-4-yl)benzamide | 363.0 |
| 592 | 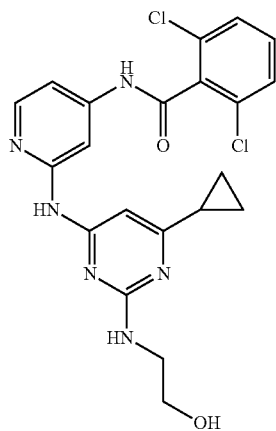 [SMILES: O=C(Nc1ccnc(Nc2cc(C3CC3)nc(NCCO)n2)c1)c1c(Cl)cccc1Cl] | 2,6-dichloro-N-(2-(6-cyclopropyl-2-(2-hydroxyethylamino)-pyrimidin-4-ylamino)pyridin-4-yl)benzamide | 459.1 |

| | | | |
|---|---|---|---|
| 593 | 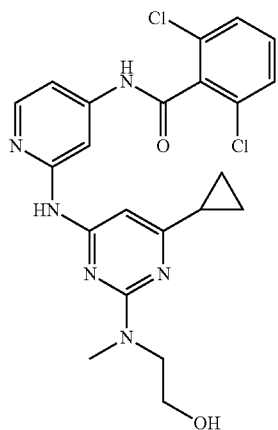 [SMILES: CN(CCO)c1nc(Nc2cc(NC(=O)c3c(Cl)cccc3Cl)ccn2)cc(C2CC2)n1] | 2,6-dichloro-N-(2-(6-cyclopropyl-2-((2-hydroxyethyl)(methyl)-amino)pyrimidin-4-ylamino)pyridin-4-yl)benzamide | 473.1 |
| 594 | 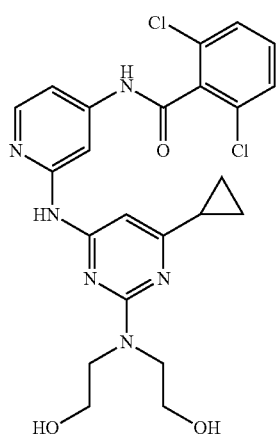 [SMILES: O=C(Nc1ccnc(Nc2cc(C3CC3)nc(N(CCO)CCO)n2)c1)c1c(Cl)cccc1Cl] | N-(2-(2-bis(2-hydroxyethyl)amino)-6-cyclopropylpyrimidin-4-ylamino)pyridin-4-yl)-2,6-dichlorobenzamide | 503.1 |
| 595 | 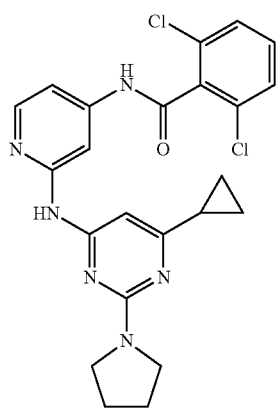 [SMILES: O=C(Nc1ccnc(Nc2cc(C3CC3)nc(N3CCCC3)n2)c1)c1c(Cl)cccc1Cl] | 2,6-dichloro-N-(2-(6-cyclopropyl-2-(pyrrolidin-1-yl)pyrimidin-4-ylamino)pyridin-4-yl)benzamide | 469.1 |

TABLE 3-continued
| | | | |
|---|---|---|---|
| 596 | 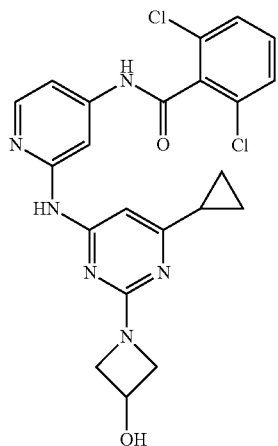 [SMILES: O=C(Nc1ccnc(Nc2cc(C3CC3)nc(N3CC(O)C3)n2)c1)c1c(Cl)cccc1Cl] | 2,6-dichloro-N-(2-(6-cyclopropyl-2-(3-hydroxyazetidin-1-yl)pyrimidin-4-ylamino)pyridin-4-yl)benzamide | 471.1 |
| 597 | 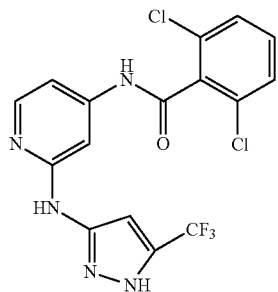 [SMILES: O=C(Nc1ccnc(Nc2cc(C(F)(F)F)[nH]n2)c1)c1c(Cl)cccc1Cl] | 2,6-dichloro-N-(2-(5-(trifluoromethyl)-1H-pyrazol-3-ylamino)pyridin-4-yl)benzamide | 416.0 |
| 598 | 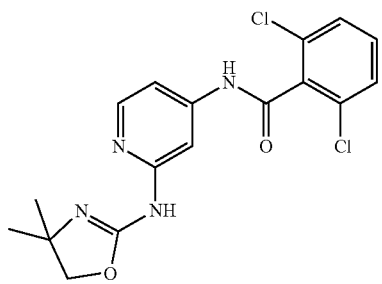 [SMILES: CC1(C)COC(Nc2cc(NC(=O)c3c(Cl)cccc3Cl)ccn2)=N1] | 2,6-dichloro-N-(2-(4,4-dimethyl-4,5-dihydrooxazol-2-ylamino)pyridin-4-yl)benzamide | 379.0 |
| 599 | 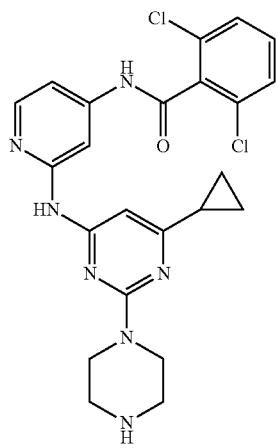 [SMILES: O=C(Nc1ccnc(Nc2cc(C3CC3)nc(N3CCNCC3)n2)c1)c1c(Cl)cccc1Cl] | 2,6-dichloro-N-(2-(6-cyclopropyl-2-(piperazin-1-yl)pyrimidin-4-ylamino)pyridin-4-yl)benzamide | 484.1 |

TABLE 3-continued
| | | | |
|---|---|---|---|
| 600 | 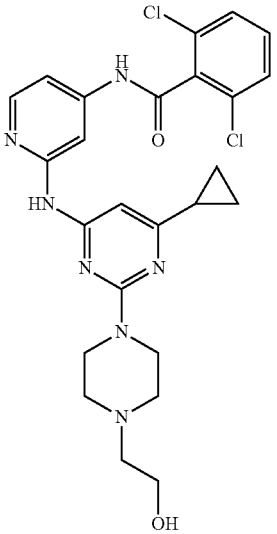 [SMILES: O=C(Nc1ccnc(Nc2cc(C3CC3)nc(N3CCN(CCO)CC3)n2)c1)c1c(Cl)cccc1Cl] | 2,6-dichloro-N-(2-(6-cyclopropyl-2-(4-(2-hydroxyethyl)piperazin-1-yl)pyrimidin-4-ylamino)pyridin-4-yl)benzamide | 528.2 |
| 601 | 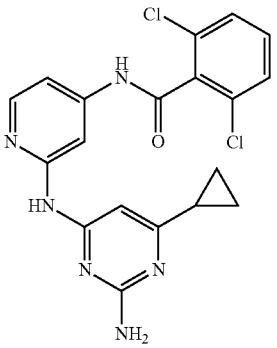 [SMILES: Nc1nc(Nc2cc(NC(=O)c3c(Cl)cccc3Cl)ccn2)cc(C2CC2)n1] | N-(2-(2-amino-6-cyclopropylpyrimidin-4-ylamino)pyridin-4-yl)-2,6-dichlorobenzamide | 415.0 |
| 602 | 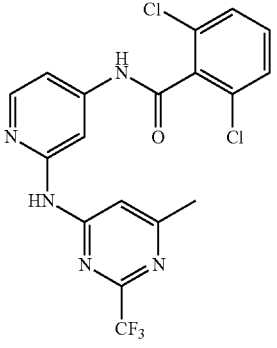 [SMILES: Cc1cc(Nc2cc(NC(=O)c3c(Cl)cccc3Cl)ccn2)nc(C(F)(F)F)n1] | 2,6-dichloro-N-(2-(6-methyl-2-(trifluoromethyl)pyrimidin-4-ylamino)pyridin-4-yl)benzamide | 442.0 |
| 603 | 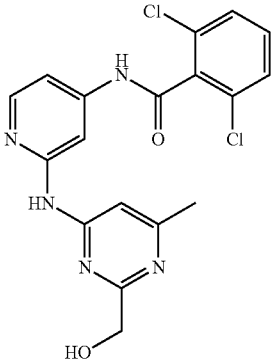 [SMILES: Cc1cc(Nc2cc(NC(=O)c3c(Cl)cccc3Cl)ccn2)nc(CO)n1] | 2,6-dichloro-N-(2-(2-(hydroxymethyl)-6-methylpyrimidin-4-ylamino)pyridin-4-yl)benzamide | 404.0 |

TABLE 3-continued

| | | | |
|---|---|---|---|
| 604 | 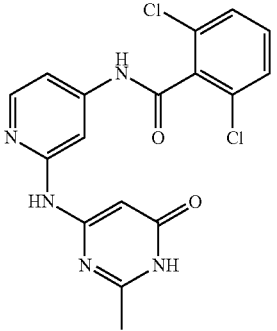 [SMILES: Cc1nc(Nc2cc(NC(=O)c3c(Cl)cccc3Cl)ccn2)cc(=O)[nH]1] | 2,6-dichloro-N-(2-(2-methyl-6-oxo-1,6-dihydropyrimidin-4-ylamino)pyridin-4-yl)benzamide | 390.1 |
| 605 | 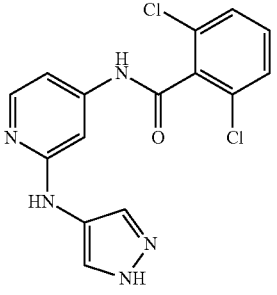 [SMILES: O=C(Nc1ccnc(Nc2cn[nH]c2)c1)c1c(Cl)cccc1Cl] | N-(2-(1H-pyrazol-4-ylamino)pyridin-4-yl)-2,6-dichlorobenzamide | 348.0 |
| 606 | 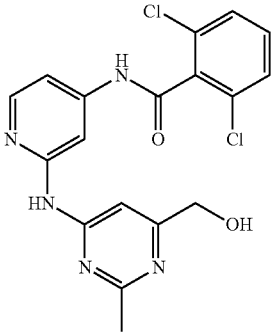 [SMILES: Cc1nc(CO)cc(Nc2cc(NC(=O)c3c(Cl)cccc3Cl)ccn2)n1] | 2,6-dichloro-N-(2-(6-(hydroxymethyl)-2-methylpyrimidin-4-ylamino)pyridin-4-yl)benzamide | 404.0 |
| 607 | 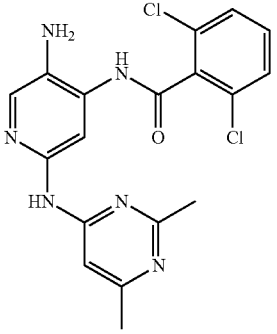 [SMILES: Cc1cc(Nc2cc(NC(=O)c3c(Cl)cccc3Cl)c(N)cn2)nc(C)n1] | N-(5-amino-2-(2,6-dimethylpyrimidin-4-ylamino)pyridin-4-yl)-2,6-dichlorobenzamide | 403.0 |
| 608 | 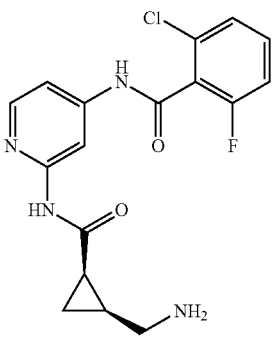 [SMILES: NC[C@H]1C[C@H]1C(=O)Nc1cc(NC(=O)c2c(F)cccc2Cl)ccn1] | cis-N-(2-(2-(aminomethyl)cyclopropanecarboxamido)pyridin-4-yl)-2-chloro-6-fluorobenzamide | 363.0 |

TABLE 3-continued
| 609 | 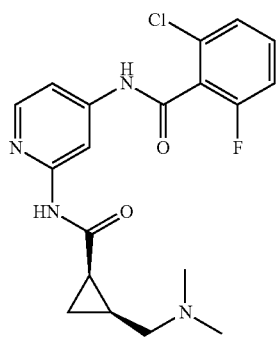 [SMILES: CN(C)C[C@H]1C[C@H]1C(=O)Nc1cc(NC(=O)c2c(F)cccc2Cl)ccn1] | cis-2-chloro-N-(2-(2-((dimethylamino)methyl)-cyclopropanecarbox-amido)pyridin-4-yl)-6-fluorobenzamide | 391.0 |
| --- | --- | --- | --- |
| 610 | 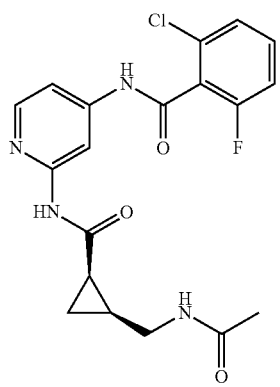 [SMILES: CC(=O)NC[C@H]1C[C@H]1C(=O)Nc1cc(NC(=O)c2c(F)cccc2Cl)ccn1] | cis-N-(2-(2-(acetamidomethyl)cyclo-propanecarboxamido)-pyridin-4-yl)-2-chloro-6-fluorobenzamide | 405.0 |
| 611 | 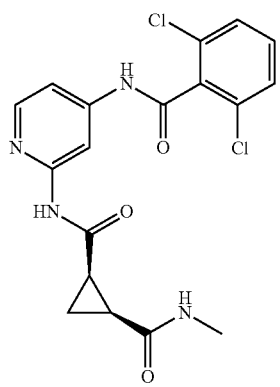 [SMILES: CNC(=O)[C@H]1C[C@H]1C(=O)Nc1cc(NC(=O)c2c(Cl)cccc2Cl)ccn1] | (1R,2S)-N1-(4-(2,6-dichlorobenzamido)-pyridin-2-yl)-N2-methylcyclopropane-1,2-dicarboxamide | 408.0 |
| 612 | 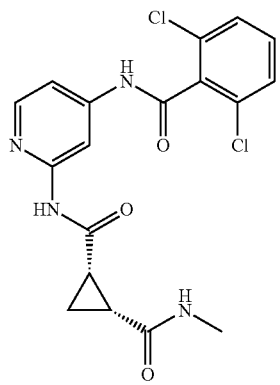 [SMILES: CNC(=O)[C@@H]1C[C@@H]1C(=O)Nc1cc(NC(=O)c2c(Cl)cccc2Cl)ccn1] | (1S,2R)-N1-(4-(2,6-dichlorobenzamido)-pyridin-2-yl)-N2-methylcyclopropane-1,2-dicarboxamide | 408.0 |

TABLE 3-continued
| 613 | 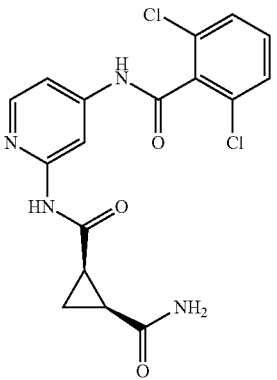 [SMILES: NC(=O)[C@H]1C[C@H]1C(=O)Nc1cc(NC(=O)c2c(Cl)cccc2Cl)ccn1] | (1R,2S)-N1-(4-(2,6-dichlorobenzamido)-pyridin-2-yl)cyclopropane-1,2-dicarboxamide | 394.0 |
| 614 | 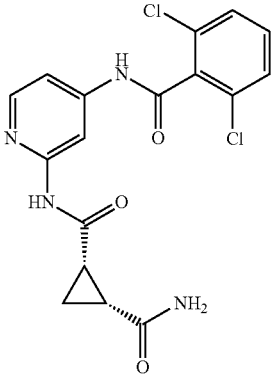 [SMILES: NC(=O)[C@@H]1C[C@@H]1C(=O)Nc1cc(NC(=O)c2c(Cl)cccc2Cl)ccn1] | (1S,2R)-N1-(4-(2,6-dichlorobenzamido)-pyridin-2-yl)cyclopropane-1,2-dicarboxamide | 394.0 |
| 615 | 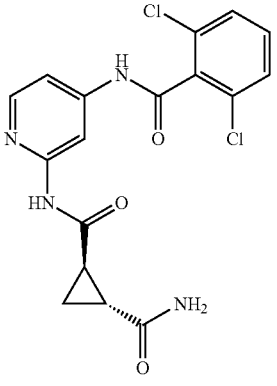 [SMILES: NC(=O)[C@@H]1C[C@H]1C(=O)Nc1cc(NC(=O)c2c(Cl)cccc2Cl)ccn1] | (1R,2R)-N1-(4-(2,6-dichlorobenzamido)-pyridin-2-yl)cyclopropane-1,2-dicarboxamide | 394.0 |
| 616 | 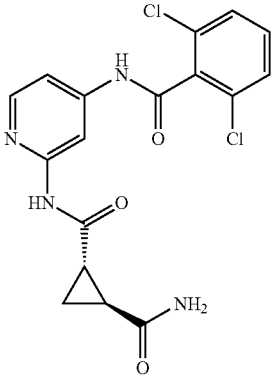 [SMILES: NC(=O)[C@H]1C[C@@H]1C(=O)Nc1cc(NC(=O)c2c(Cl)cccc2Cl)ccn1] | (1S,2S)-N1-(4-(2,6-dichlorobenzamido)-pyridin-2-yl)cyclopropane-1,2-dicarboxamide | 394.0 |

TABLE 3-continued

| | | | |
|---|---|---|---|
| 617 | | (1S,2S)-N1-(4-(2,6-dichlorobenzamido)-pyridin-2-yl)-N2-methylcyclopropane-1,2-dicarboxamide | 408.1 |
| 618 | | (1R,2R)-N1-(4-(2,6-dichlorobenzamido)-pyridin-2-yl)-N2-methylcyclopropane-1,2-dicarboxamide | 408.0 |

Specific reference is made to U.S. Patent Application Ser. No. 61/186,322, filed Jun. 11, 2009, which is incorporated herein by reference in its entirety for all purposes. Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:

1. A compound of Formula I:

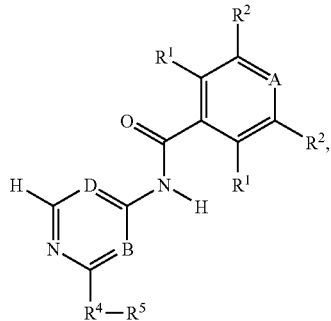

stereoisomers or a pharmaceutically acceptable salt thereof, wherein:

A is $CR^3$;

B and D are independently $CR^{15}$;

$R^1$ is independently H, halogen, $C_1$-$C_3$ alkyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein both $R^1$ cannot be H at the same time, and wherein said alkyl and cycloalkyl are optionally substituted by halogen, $OR^6$, —$NR^6R^7$ or phenyl;

$R^2$ and $R^3$ are independently H, $C_1$-$C_6$ alkyl, $C_2$-$C_6$ alkenyl, $C_2$-$C_6$ alkynyl, halogen, —$(C_0$-$C_3$ alkyl)CN, —$(C_0$-$C_3$ alkyl)$OR^8$, —$(C_0$-$C_3$ alkyl)$SR^8$, —$(C_0$-$C_3$ alkyl)$NR^8R^9$, —$(C_0$-$C_3$ alkyl)$CF_3$, —$O(C_0$-$C_3$ alkyl)$CF_3$, —$(C_0$-$C_3$ alkyl)$NO_2$, —$(C_0$-$C_3$ alkyl)$C(O)R^8$, —$(C_0$-$C_3$ alkyl)$C(O)OR^8$, —$(C_0$-$C_3$ alkyl)$C(O)NR^8R^9$, —$(C_0$-$C_3$ alkyl)$NR^8C(O)R^9$, —$(C_0$-$C_3$ alkyl)$S(O)_{1-2}R^8$, —$(C_0$-$C_3$ alkyl)$NR^8S(O)_{1-2}R^9$, —$(C_0$-$C_3$ alkyl)$S(O)_{1-2}NR^8R^9$, —$(C_0$-$C_3$ alkyl)($C_3$-$C_6$ cycloalkyl), —$(C_0$-$C_3$ alkyl)(3-6-membered heterocyclyl), —$(C_0$-$C_3$ alkyl)(5-6-membered heteroaryl) or —$(C_0$-$C_3$ alkyl)phenyl, wherein $R^2$ and $R^3$ are independently optionally substituted by $R^{10}$;

$R^4$ is —$NH_2$, —NH—, —$NR^6C(O)$—, —$NR^6C(O)O$— or —$NR^6C(O)NR^7$—;

$R^5$ is absent, $C_1$-$C_6$ alkyl, $C_3$-$C_6$ cycloalkyl, phenyl, 3-7-membered heterocyclyl or 5-6-membered heteroaryl, wherein $R^5$ is optionally substituted by $R^{10}$;

$R^6$ and $R^7$ are each independently H or $C_1$-$C_3$ alkyl, optionally substituted by halogen, oxo or —$NR^{11}R^{12}$; or $R^6$ and $R^7$ are independently taken together with the atom to which they are attached to form a 3-6 membered heterocyclyl, optionally substituted by halogen, oxo, —$NR^{11}R^{12}$ or $C_1$-$C_3$ alkyl;

$R^8$ and $R^9$ are each independently H, $C_1$-$C_3$ alkyl, $C_3$-$C_6$ cycloalkyl, phenyl, 3-6-membered heterocyclyl or 5-6-membered heteroaryl, optionally substituted by $R^{10}$; or $R^8$ and $R^9$ are independently taken together with the atom to which they are attached to form a 3-6 membered heterocyclyl, optionally substituted by halogen, oxo, —$NR^{11}R^{12}$ or $C_1$-$C_3$ alkyl;

$R^{10}$ is independently H, oxo, $C_1$-$C_6$ alkyl, $C_2$-$C_6$ alkenyl, $C_2$-$C_6$ alkynyl, halogen, —$(C_0$-$C_3$ alkyl)CN, —$(C_0$-$C_3$ alkyl)$OR^{11}$, —$(C_0$-$C_3$ alkyl)$SR^{11}$, —$(C_0$-$C_3$ alkyl)$NR^{11}R^{12}$, —$(C_0$-$C_3$ alkyl)$CF_3$, —$(C_0$-$C_3$ alkyl)$NO_2$, —$(C_0$-$C_3$ alkyl)$C(O)R^{11}$, —$(C_0$-$C_3$ alkyl)$C(O)OR^{11}$, —$(C_0$-$C_3$ alkyl)$C(O)NR^{11}R^{12}$, —$(C_0$-$C_3$ alkyl)$NR^{11}C(O)R^{12}$, —$(C_0$-$C_3$ alkyl)$S(O)_{1-2}R^{11}$, —$(C_0$-$C_3$ alkyl)$NR^{11}S(O)_{1-2}R^{12}$, —$(C_0$-$C_3$ alkyl)$S(O)_{1-2}NR^{11}R^{12}$, —$(C_0$-$C_3$ alkyl)($C_3$-$C_6$ cycloalkyl), —$(C_0$-$C_3$ alkyl)(3-6-membered heterocyclyl), —$(C_0$-$C_3$ alkyl)$C(O)$(3-6-membered heterocyclyl), —$(C_0$-$C_3$ alkyl)(5-6-membered heteroaryl) or —$(C_0$-$C_3$ alkyl)phenyl, wherein $R^{10}$ is independently optionally substituted by halogen, $C_1$-$C_3$ alkyl, oxo, —$CF_3$, —$(C_0$-$C_3$ alkyl)$OR^{13}$, —$(C_0$-$C_3$ alkyl)$NR^{13}R^{14}$, —$(C_0$-$C_3$ alkyl)$C(O)R^{13}$ or —$(C_0$-$C_3$ alkyl)$S(O)_{1-2}R^{13}$;

$R^{11}$ and $R^{12}$ are independently H, $C_1$-$C_6$ alkyl, —$(C_0$-$C_3$ alkyl)($C_3$-$C_6$ cycloalkyl), —$(C_0$-$C_3$ alkyl)(3-6-membered heterocyclyl), —$(C_0$-$C_3$ alkyl)(5-6-membered heteroaryl) or —$(C_0$-$C_3$ alkyl)phenyl, optionally substituted by halogen, oxo, —$OR^{13}$, —$SR^{13}$, —$NR^{13}R^{14}$, $C_1$-$C_3$ alkyl, —$(C_0$-$C_3$ alkyl)($C_3$-$C_6$ cycloalkyl), —$(C_0$-$C_3$ alkyl)phenyl, —$(C_0$-$C_3$ alkyl)(3-6-membered heterocyclyl) or —$(C_0$-$C_3$ alkyl)(5-6-membered heteroaryl); or $R^{11}$ and $R^{12}$ are taken together with the atom to which they attached to form a 3-6 membered heterocyclyl, optionally substituted by halogen, oxo, —$NR^{13}R^{14}$ or $C_1$-$C_3$ alkyl;

$R^{13}$ and $R^{14}$ are independently H, $C_1$-$C_6$ alkyl, OH or $OCH_3$, optionally substituted by halogen, —$NH_2$, —$N(CH_3)_2$, phenyl or oxo, wherein said phenyl is optionally substituted by halogen, $C_1$-$C_6$ alkyl, $CF_3$, —$NR^aR^b$ or $OR^a$ or $R^{13}$ and $R^{14}$ are taken together with the atom to which they attached to form a 3-6 membered heterocyclyl, optionally substituted by halogen, oxo, —$NH_2$, —$N(CH_3)_2$ or $C_1$-$C_3$ alkyl;

$R^{15}$ is H; and $R^a$ and $R^b$ are independently H or $C_1$-$C_6$ alkyl optionally substituted by halogen or oxo; or $R^a$ and $R^b$ are taken together with the atom to which they are attached to form a 3-6 membered heterocyclyl, optionally substituted by halogen, oxo or $C_1$-$C_3$ alkyl.

2. The compound claim 1, wherein one $R^1$ is halogen and the other $R^1$ is halogen, $C_1$-$C_3$ alkyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^6$, —$NR^6R^7$ or phenyl.

3. The compound of claim 2, wherein $R^2$ is H and $R^3$ is H, $C_1$-$C_6$ alkyl, $C_2$-$C_6$ alkenyl, $C_2$-$C_6$ alkynyl, halogen, —CN, —$OR^8$, —$SR^8$, —$NR^8R^9$, —$CF_3$, —$OCF_3$, —$NO_2$, —$C(O)R^8$, —$C(O)OR^8$, —$C(O)NR^8R^9$, —$NR^8C(O)R^9$, —$S(O)_{1-2}R^8$, —$NR^8S(O)_{1-2}R^9$, —$S(O)_{1-2}NR^8R^9$, $C_3$-$C_6$ cycloalkyl, 3-6-membered heterocyclyl, 5-6-membered heteroaryl or phenyl, wherein $R^3$ is optionally substituted by 0, 1, 2 or 3 $R^{10}$.

4. The compound of claim 1, wherein the portion of Formula I having the structure:

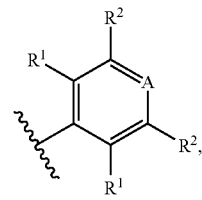

is selected from:

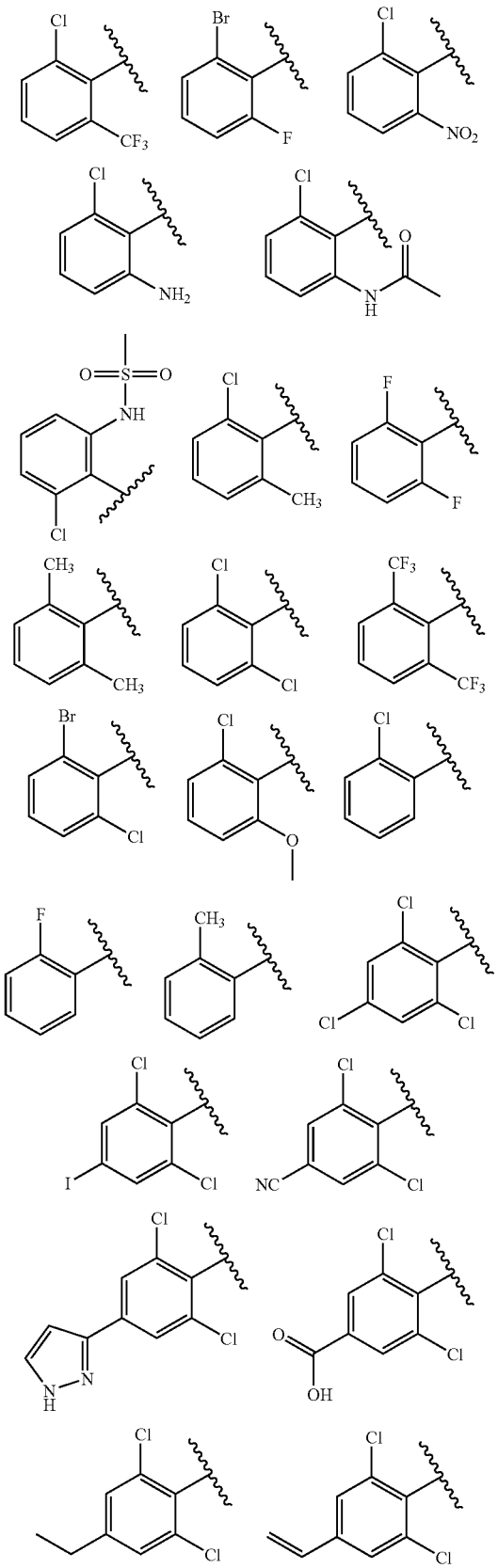

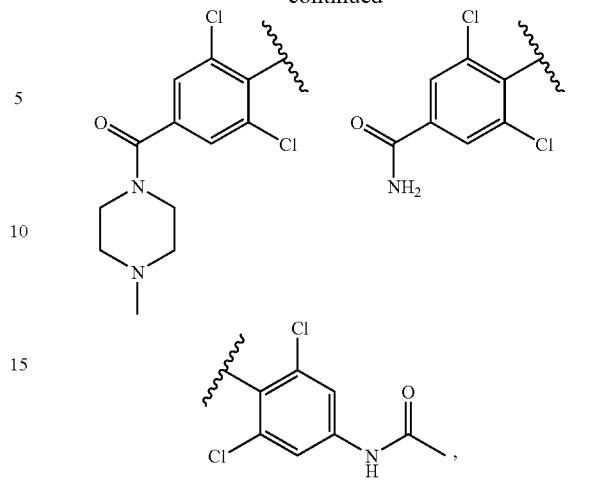

wherein the wavy lines represent the point of attachment in Formula I.

5. The compound of claim 1, wherein $R^5$ is $C_1$-$C_6$ alkyl, $C_3$-$C_6$ cycloalkyl, 3-7-membered heterocyclyl, phenyl, 5-6-membered heteroaryl, optionally substituted by $R^{10}$, and wherein $R^{10}$ is oxo, $C_1$-$C_6$ alkyl, halogen, —CN, —OR$^{11}$, —SR$^{11}$, —NR$^{11}$R$^{12}$, —CF$_3$, —C(O)R$^{11}$, —C(O)OR$^{11}$, —C(O)NR$^{11}$R$^{12}$, —NR$^{11}$C(O)R$^{12}$, —S(O)$_{1-2}$R$^{11}$, —NR$^{11}$S(O)$_{1-2}$R$^{12}$, —S(O)$_{1-2}$NR$^{11}$R$^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —CF$_3$, —OR$^{13}$, —NR$^{13}$R$^{14}$, —C(O)R$^{13}$ or —S(O)$_{1-2}$R$^{13}$.

6. The compound of claim 5, wherein $R^5$ is selected from:

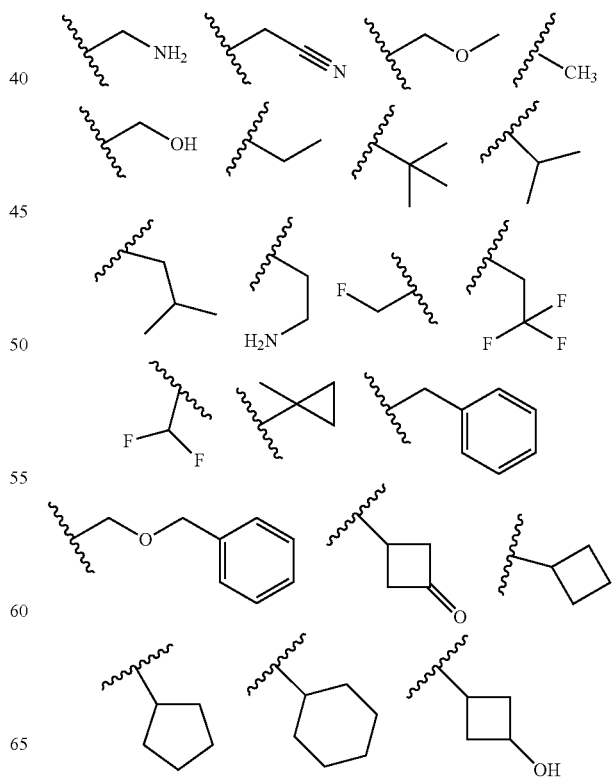

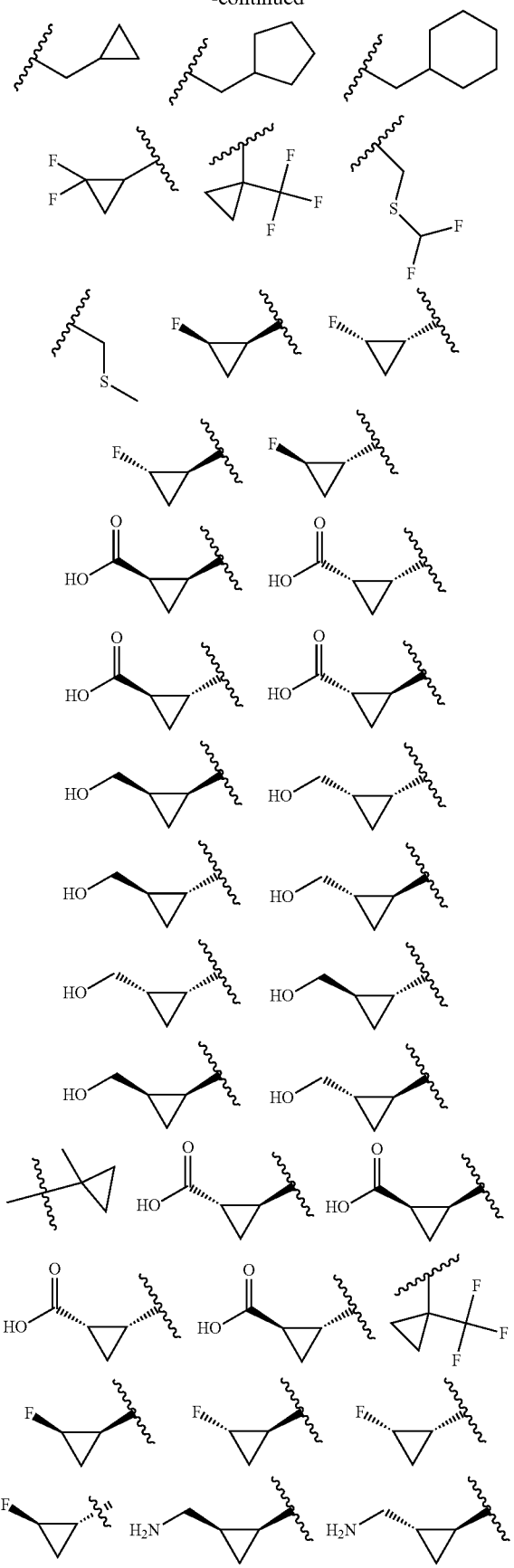
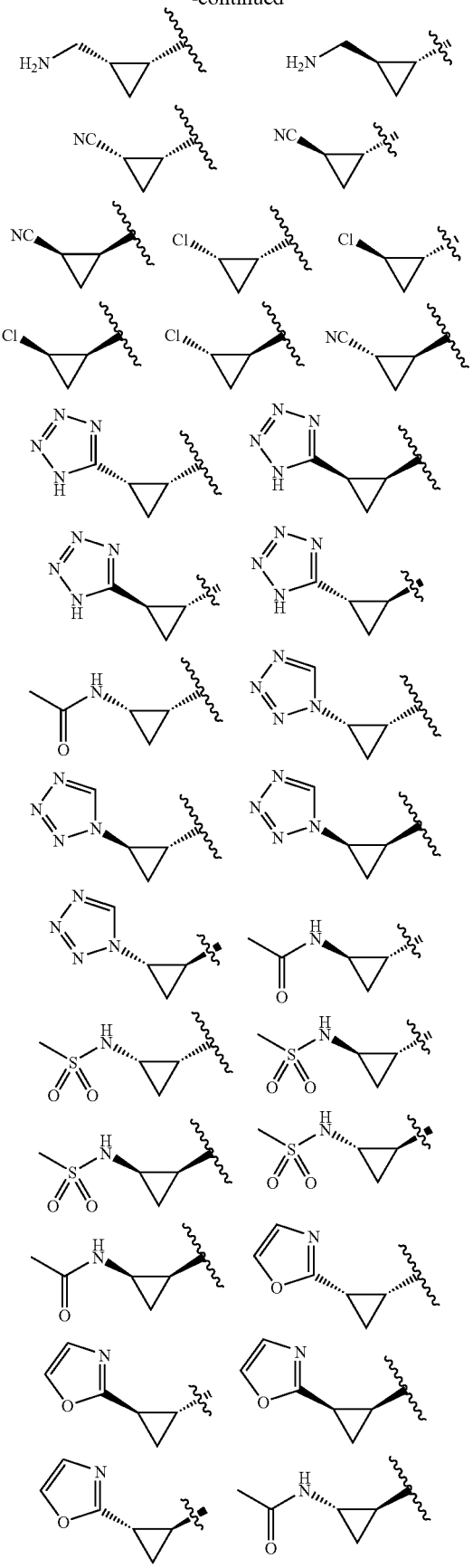

-continued
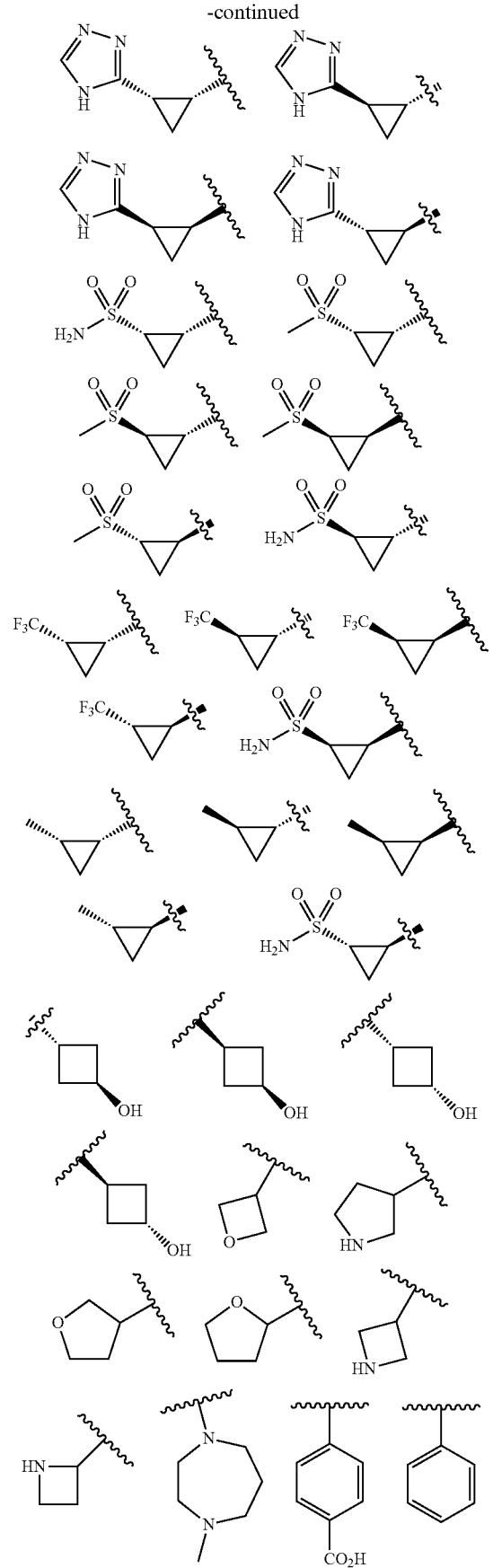
-continued
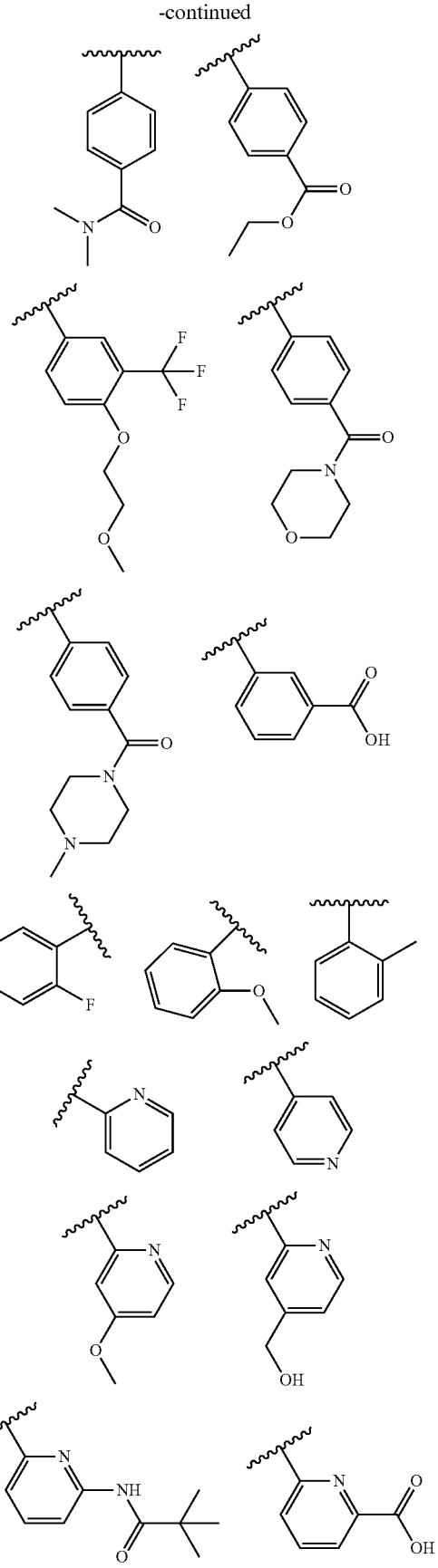

371
-continued
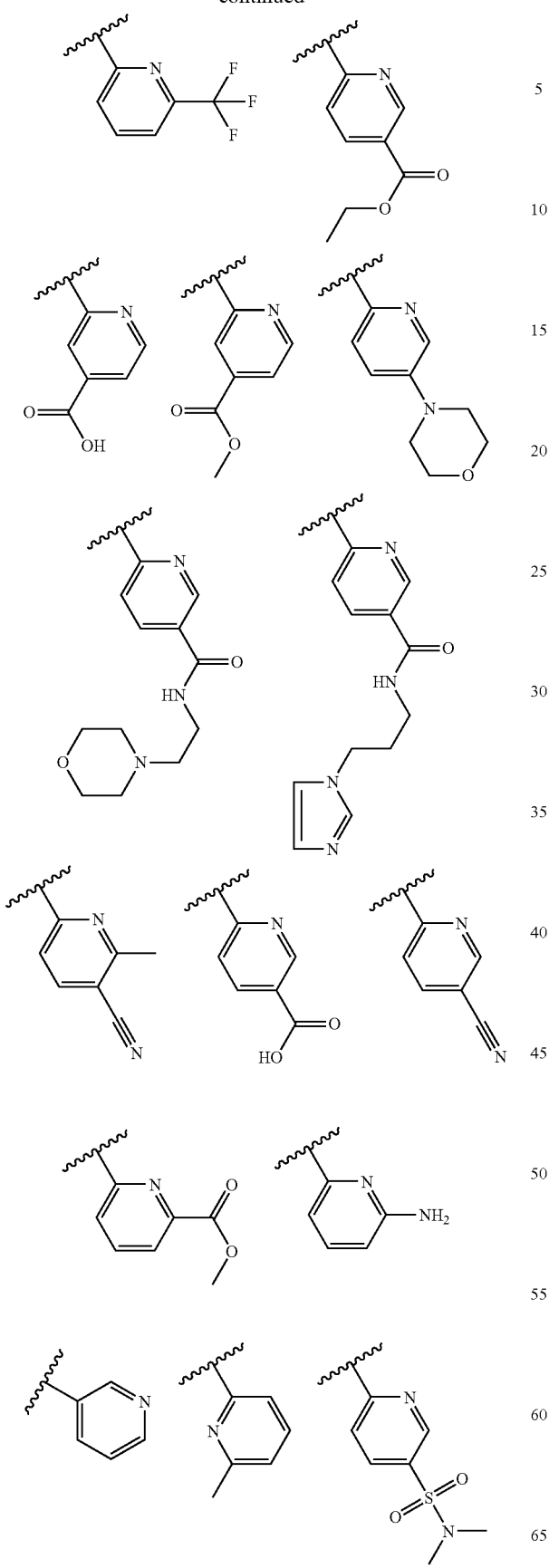
372
-continued
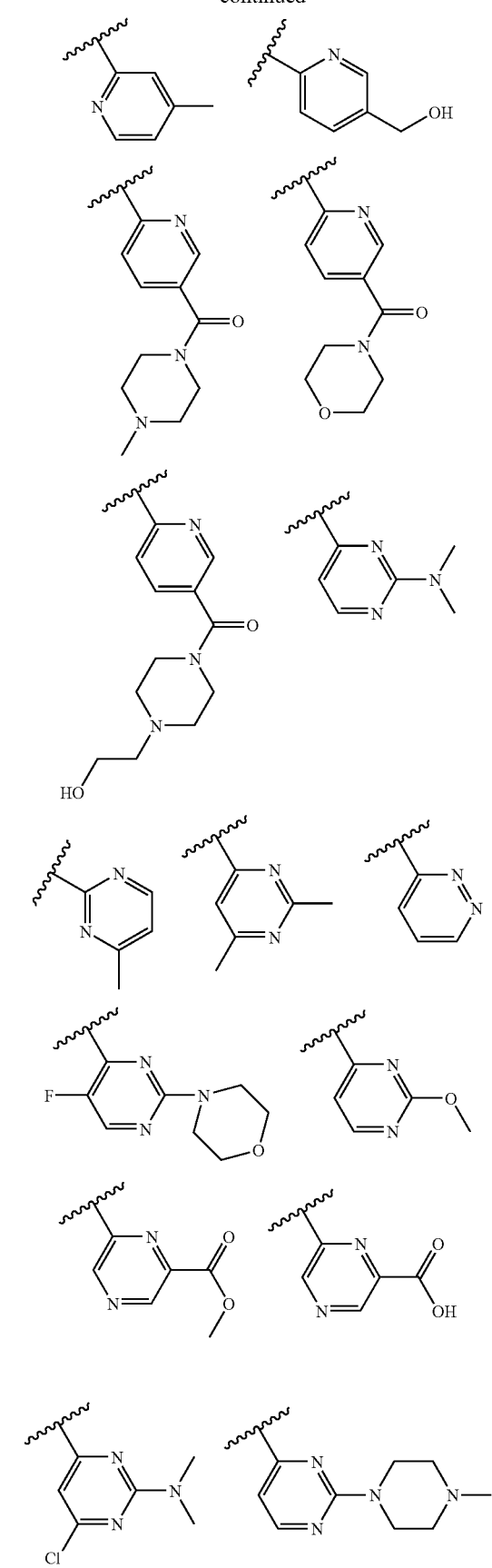

373
-continued
374
-continued
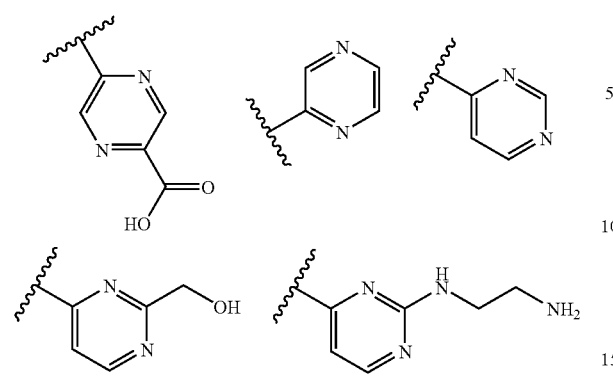
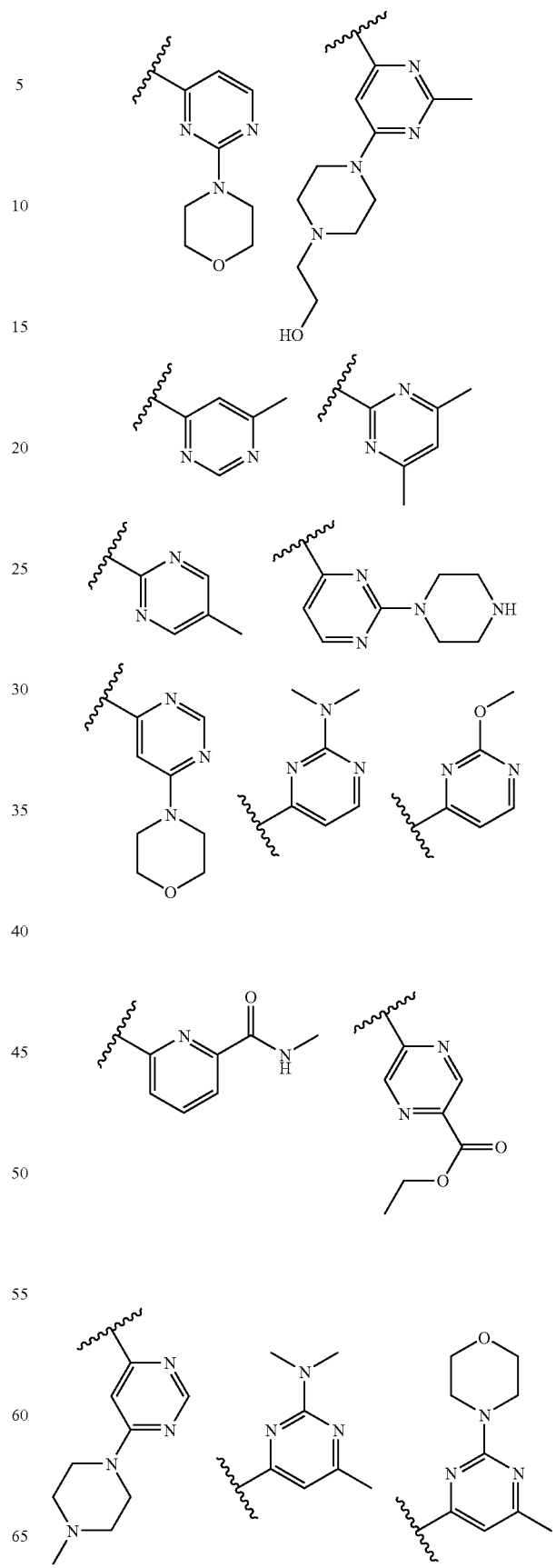

375
-continued
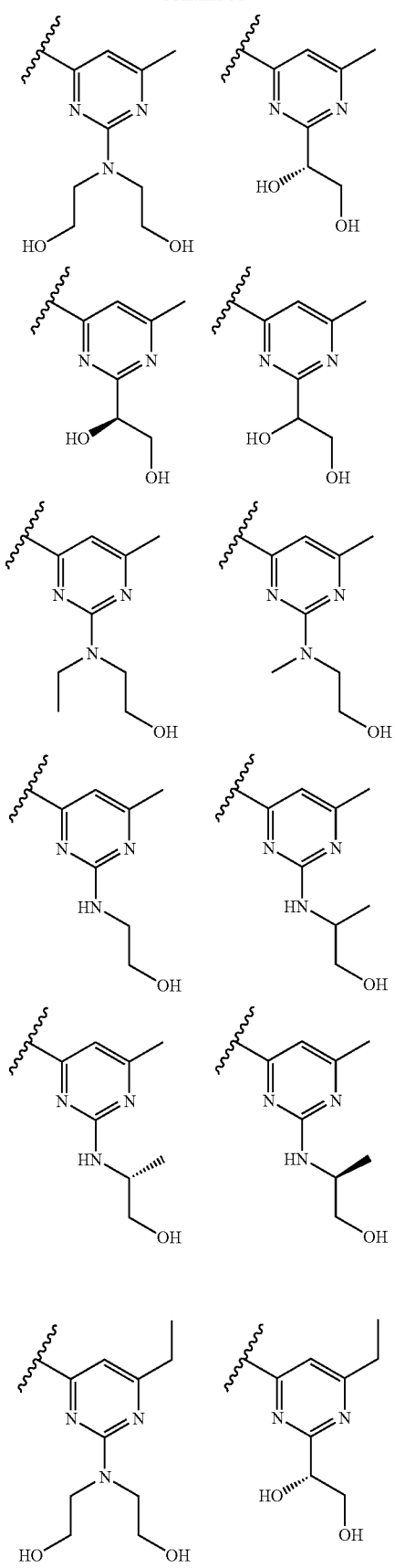
376
-continued
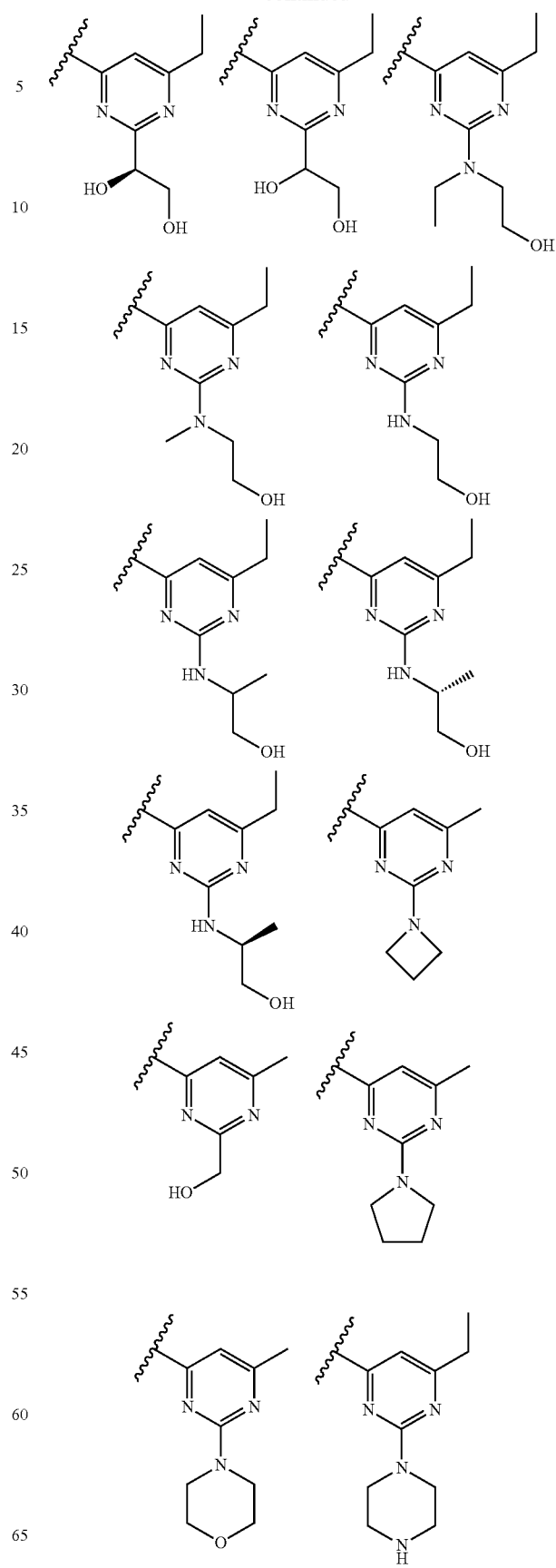

377
-continued
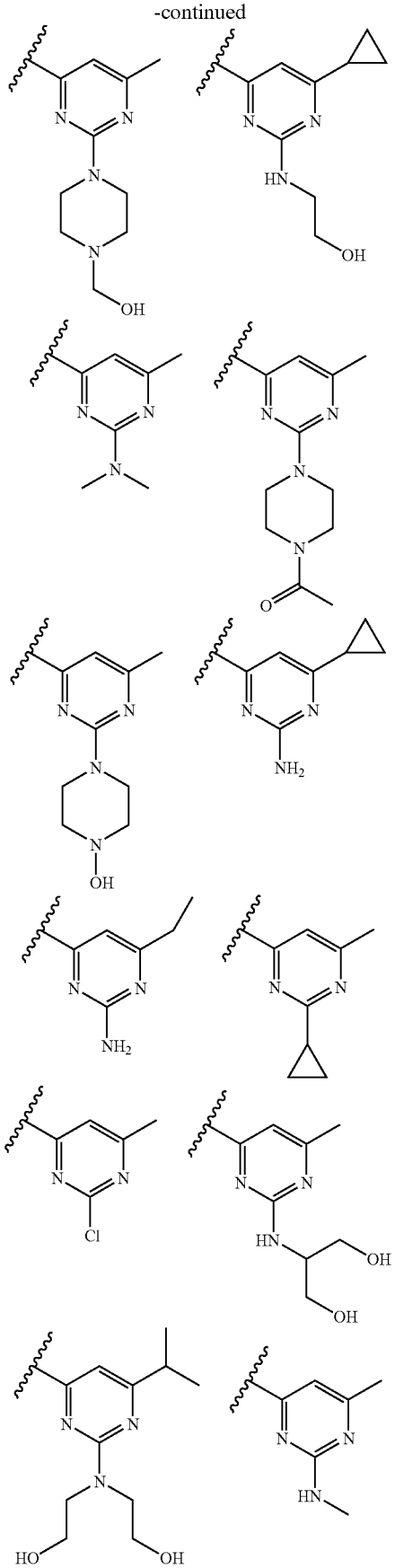
378
-continued
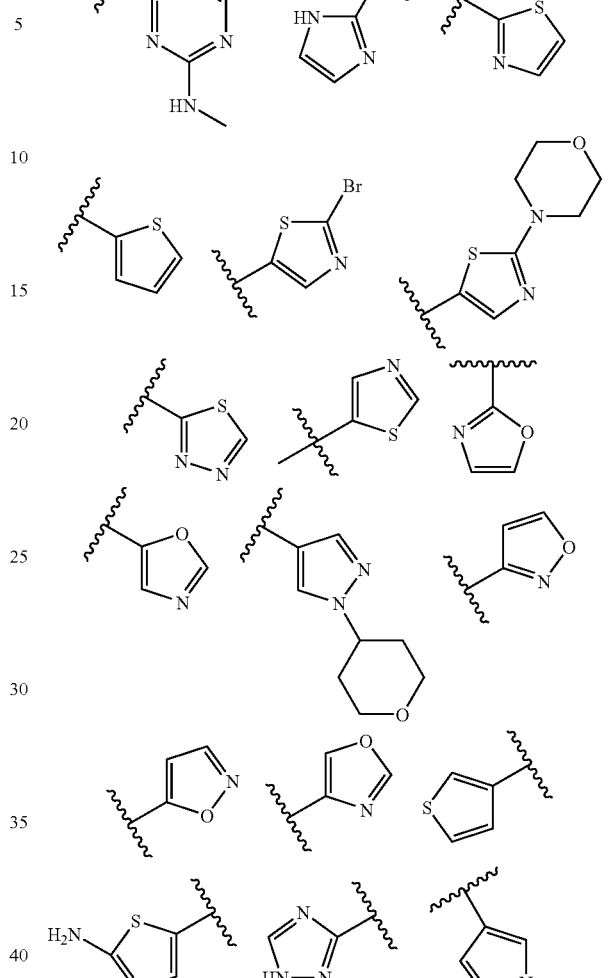
wherein the wavy lines represent the point of attachment in Formula I.
7. The compound of claim 1 selected from formula IIb:
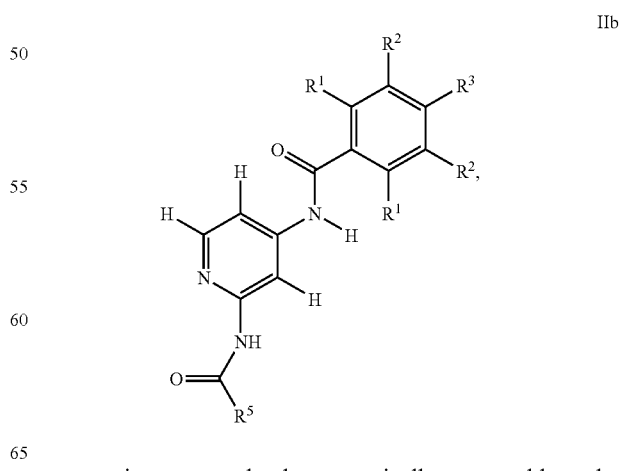
stereoisomers and pharmaceutically acceptable salts thereof.

8. The compound of claim 7, wherein one $R^1$ is halogen and the other $R^1$ is halogen, $C_1$-$C_3$ alkyl, $C_3$-$C_4$ cycloalkyl, —$CF_3$, —$OR^6$, —$SR^6$, —$OCF_3$, —CN, —$NO_2$, —$NR^6SO_2R^7$, —$NR^6C(O)R^7$ or —$NR^6R^7$, wherein said alkyl and cycloalkyl are optionally substituted by halogen, $OR^6$, —$NR^6R^7$ or phenyl.

9. The compound of claim 8, wherein $R^2$ is H and $R^3$ is H, $C_1$-$C_6$ alkyl, $C_2$-$C_6$ alkenyl, $C_2$-$C_6$ alkynyl, halogen, —CN, —$OR^8$, —$SR^8$, —$NR^8R^9$, —$CF_3$, —$OCF_3$, —$NO_2$, —$C(O)R^8$, —$C(O)OR^8$, —$C(O)NR^8R^9$, —$NR^8C(O)R^9$, —$S(O)_{1-2}R^8$, —$NR^8S(O)_{1-2}R^9$, —$S(O)_{1-2}NR^8R^9$, $C_3$-$C_6$ cycloalkyl, 3-6-membered heterocyclyl, 5-6-membered heteroaryl or phenyl, wherein $R^3$ is optionally substituted by 0, 1, 2 or 3 $R^{10}$.

10. The compound of claim 9, wherein $R^5$ is $C_1$-$C_6$ alkyl or $C_3$-$C_6$ cycloalkyl, wherein $R^5$ is optionally substituted by $R^{10}$, wherein $R^{10}$ is oxo, $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$.

11. The compound of claim 10, wherein $R^5$ is cyclopropyl optionally substituted by 1, 2 or 3 $R^{10}$.

12. The compound of claim 1 selected from formula Vb:

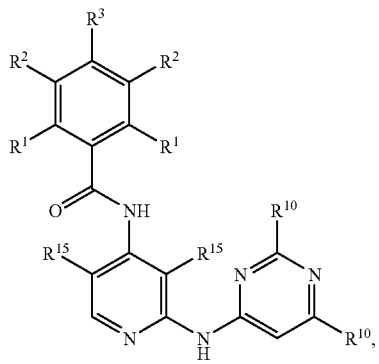

stereoisomers and pharmaceutically acceptable salts thereof.

13. The compound of claim 12, wherein $R^1$ is independently halogen.

14. The compound of claim 13, wherein $R^2$ is hydrogen; $R^3$ is hydrogen, $C_1$-$C_3$ alkyl, halogen, —CN, —OH, or —$NH_2$; $R^{10}$ is independently $C_1$-$C_6$ alkyl, halogen, —CN, —$OR^{11}$, —$SR^{11}$, —$NR^{11}R^{12}$, —$CF_3$, —$C(O)R^{11}$, —$C(O)OR^{11}$, —$C(O)NR^{11}R^{12}$, —$NR^{11}C(O)R^{12}$, —$S(O)_{1-2}R^{11}$, —$NR^{11}S(O)_{1-2}R^{12}$, —$S(O)_{1-2}NR^{11}R^{12}$, $C_3$-$C_6$ cycloalkyl, 3-6-membered heterocyclyl, —C(O)(3-6-membered heterocyclyl), 5-6-membered heteroaryl or phenyl, wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$; and $R^{15}$ is independently H, halogen, $C_1$-$C_3$ alkyl, $C_1$-$C_3$ alkenyl, $C_1$-$C_3$ alkynyl, $C_3$-$C_4$ cycloalkyl, —$CF_3$, —$OR^a$, —$SR^a$, —CN, —$NO_2$ or —$NR^aR^b$.

15. The compound of claim 14, wherein $R^{10}$ is independently $C_1$-$C_6$ alkyl, —$NR^{11}R^{12}$, $C_3$-$C_6$ cycloalkyl, 3-6-membered heterocyclyl, or —C(O)(3-6-membered heterocyclyl), wherein $R^{10}$ is independently optionally substituted by halogen, $C_1$-$C_3$ alkyl, oxo, —$CF_3$, —$OR^{13}$, —$NR^{13}R^{14}$, —$C(O)R^{13}$ or —$S(O)_{1-2}R^{13}$.

16. A pharmaceutical composition comprising a compound of claim 1, a stereoisomer or pharmaceutically acceptable salt thereof, and a pharmaceutically acceptable carrier, adjuvant or vehicle.

17. A method of manufacturing a compound of claim 1, comprising reacting a compound of formula iii:

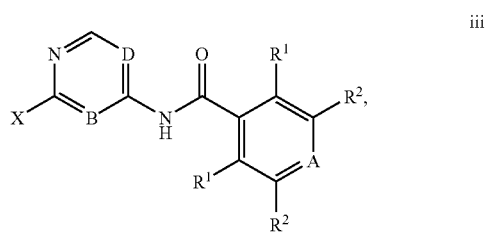

wherein X is halogen or leaving group, with a compound of the formula Y—$R^4$-$R^5$, wherein Y is H or is absent, under conditions sufficient to form a compound of Formula I.

18. The method of claim 17, further comprising reacting a compound of formula i:

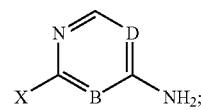

wherein X is independently hydrogen, halogen or a leaving group with a compound of formula ii:

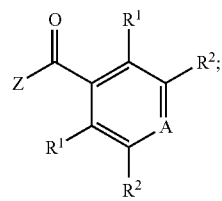

wherein Z is halogen or a leaving group, to prepare said compound of formula iii.

19. The method of claim 17, further comprising contacting a compound of formula iii with a compound of formula Y—$R^4$-$R^5$ under basic conditions and at a temperature in the range of about 50-250° C.

* * * * *

```
SEQUENCE LISTING

<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

Val Ala Leu Val Asp Gly Tyr Phe Arg Leu Thr Thr
 1               5                  10

<210> SEQ ID NO 2
<211> LENGTH: 11
<212> TYPE: PRT
<213> ORGANISM: Homo sapiens

<400> SEQUENCE: 2

Leu Pro Leu Asp Lys Asp Tyr Tyr Val Val Arg
 1               5                  10
```